(12) United States Patent
Jenkins et al.

(10) Patent No.: US 10,524,869 B2
(45) Date of Patent: *Jan. 7, 2020

(54) APPARATUS AND METHOD FOR TREATMENT OF ETHMOID SINUSITIS

(71) Applicant: Acclarent, Inc., Irvine, CA (US)

(72) Inventors: Thomas R. Jenkins, Alameda, CA (US); Jessica M. Liberatore, San Mateo, CA (US); Randy J. Kesten, Mountain View, CA (US)

(73) Assignee: Acclarent, Inc., Irvine, CA (US)

( * ) Notice: Subject to any disclaimer, the term of this patent is extended or adjusted under 35 U.S.C. 154(b) by 300 days.

This patent is subject to a terminal disclaimer.

(21) Appl. No.: 15/484,542

(22) Filed: Apr. 11, 2017

(65) Prior Publication Data

US 2017/0273747 A1    Sep. 28, 2017

Related U.S. Application Data

(63) Continuation of application No. 14/197,436, filed on Mar. 5, 2014, now Pat. No. 9,629,684, which is a
(Continued)

(51) Int. Cl.
*A61B 17/24* (2006.01)
*A61B 17/16* (2006.01)
(Continued)

(52) U.S. Cl.
CPC ............ *A61B 34/30* (2016.02); *A61B 17/24* (2013.01); *A61B 17/3205* (2013.01);
(Continued)

(58) Field of Classification Search
CPC . A61B 17/1604; A61B 17/1615; A61B 17/24; A61B 17/320016; A61B 17/32002;
(Continued)

(56) References Cited

U.S. PATENT DOCUMENTS

| 446,173 A | 2/1891 | Hancock |
|---|---|---|
| 504,424 A | 9/1893 | De Pezzer |

(Continued)

FOREIGN PATENT DOCUMENTS

| CH | 668188 | 12/1988 |
|---|---|---|
| CN | 2151720 | 1/1994 |

(Continued)

OTHER PUBLICATIONS

Argon Medical. Maxxim Medical. Ad for Sniper EliteTM Hydrophilic Ni—Ti Allow Guidewire (2001).
(Continued)

*Primary Examiner* — Adam Marcetich
(74) *Attorney, Agent, or Firm* — Frost Brown Todd LLC

(57) ABSTRACT

An apparatus may be used to form an opening in a sinus wall. The apparatus comprises a first cutting member and a second cutting member. The first cutting member comprises a helical blade. The second cutting member is slidably disposed about the first cutting member. The second cutting member comprises a sharp distal edge. An outer sheath is slidably disposed about the first and second cutting member. The sheath may be retracted to uncover the helical blade. The second cutting member may be advanced over the first cutting member to form a circular opening in the sinus wall. The sheath may include an obliquely angled distal edge. A cleaning instrument may be used to clean debris from the first cutting member.

20 Claims, 90 Drawing Sheets

Related U.S. Application Data continuation-in-part of application No. 14/038,867, filed on Sep. 27, 2013, now abandoned, which is a continuation-in-part of application No. 13/837,104, filed on Mar. 15, 2013, now Pat. No. 9,433,437.

(51) Int. Cl.

| | |
|---|---|
| *A61B 17/32* | (2006.01) |
| *A61B 17/34* | (2006.01) |
| *A61B 90/70* | (2016.01) |
| *A61B 34/30* | (2016.01) |
| *A61B 17/3205* | (2006.01) |
| *A61B 17/3207* | (2006.01) |
| *A61B 17/00* | (2006.01) |
| *A61B 90/00* | (2016.01) |

(52) U.S. Cl.
CPC .......... *A61B 17/320016* (2013.01); *A61B 17/32053* (2013.01); *A61B 17/3478* (2013.01); *A61B 90/70* (2016.02); *A61B 17/1604* (2013.01); *A61B 17/1615* (2013.01); *A61B 17/32002* (2013.01); *A61B 17/320758* (2013.01); *A61B 2017/00685* (2013.01); *A61B 2017/320064* (2013.01); *A61B 2017/320775* (2013.01); *A61B 2090/033* (2016.02); *A61B 2090/08021* (2016.02)

(58) Field of Classification Search
CPC .......... A61B 17/3205; A61B 17/32053; A61B 17/320758; A61B 17/3478; A61B 2017/00685; A61B 2017/320064; A61B 2017/320775; A61B 2090/033; A61B 2090/08021; A61B 34/30; A61B 90/70

See application file for complete search history.

(56) References Cited

U.S. PATENT DOCUMENTS

| | | | |
|---|---|---|---|
| 513,667 A | 1/1894 | Buckingham | |
| 705,346 A | 7/1902 | Hamilton | |
| 798,775 A | 9/1905 | Forsyth | |
| 816,792 A | 4/1906 | Green et al. | |
| 1,080,934 A | 12/1913 | Shackleford | |
| 1,200,267 A | 10/1916 | Sunnergren | |
| 1,650,959 A | 11/1927 | Pitman | |
| 1,735,519 A | 11/1929 | Vance | |
| 1,828,986 A | 10/1931 | Stevens | |
| 1,878,671 A | 9/1932 | Cantor | |
| 2,201,749 A | 5/1940 | Vandegrift | |
| 2,525,183 A | 3/1947 | Robinson | |
| 2,493,326 A | 1/1950 | Trinder | |
| 2,526,662 A * | 10/1950 | Hipps | A61B 17/1635 606/80 |
| 2,847,997 A | 8/1958 | Tibone | |
| 2,899,227 A | 8/1959 | Gschwend | |
| 2,906,179 A | 9/1959 | Bower | |
| 2,995,832 A | 8/1961 | Alderson | |
| 3,009,265 A | 11/1961 | Bexark | |
| 3,037,286 A | 6/1962 | Bower | |
| 3,076,637 A | 2/1963 | Moziek et al. | |
| 3,173,418 A | 3/1965 | baran | |
| 3,347,061 A | 10/1967 | Stuemky | |
| 3,376,659 A | 4/1968 | Asin et al. | |
| 3,384,970 A | 5/1968 | Avalear | |
| 3,393,073 A | 7/1968 | Reutenauer et al. | |
| 3,435,826 A | 4/1969 | Fogarty | |
| 3,469,578 A | 9/1969 | Bierman | |
| 3,481,043 A | 12/1969 | Esch | |
| 3,486,539 A | 12/1969 | Jacuzzi | |
| 3,506,005 A | 4/1970 | Gilio et al. | |
| 3,509,638 A | 5/1970 | Macleod | |
| 3,515,888 A | 6/1970 | Lewis | |
| 3,527,220 A | 9/1970 | Summers | |
| 3,531,868 A | 10/1970 | Stevenson | |
| 3,552,384 A | 1/1971 | Pierie et al. | |
| 3,624,661 A | 11/1971 | Shebanow et al. | |
| 3,731,963 A | 5/1973 | Pond | |
| 3,792,391 A | 2/1974 | Ewing | |
| 3,800,788 A | 4/1974 | White | |
| 3,802,096 A | 4/1974 | Matern | |
| 3,804,081 A | 4/1974 | Kinoshita | |
| 3,834,394 A | 9/1974 | Hunter et al. | |
| 3,850,176 A | 11/1974 | Gottschalk | |
| 3,856,000 A | 12/1974 | Chikama | |
| 3,859,993 A | 1/1975 | Bitner | |
| 3,871,365 A | 3/1975 | Chikama | |
| 3,894,538 A | 7/1975 | Richter | |
| 3,903,893 A | 9/1975 | Scheer | |
| 3,910,617 A | 10/1975 | Scalza et al. | |
| 3,921,636 A | 11/1975 | Zaffaroni | |
| 3,948,254 A | 4/1976 | Zaffaroni | |
| 3,948,262 A | 4/1976 | Zaffaroni | |
| 3,967,618 A | 7/1976 | Zaffaroni | |
| 3,968,846 A | 7/1976 | Brenner | |
| 3,976,077 A | 8/1976 | Kerfoot | |
| 3,993,069 A | 11/1976 | Buckles et al. | |
| 3,993,072 A | 11/1976 | Zaffaroni | |
| 3,993,073 A | 11/1976 | Zaffaroni | |
| 4,016,251 A | 4/1977 | Higuchi et al. | |
| 4,052,505 A | 10/1977 | Higuchi et al. | |
| 4,053,975 A | 10/1977 | Olbrich et al. | |
| 4,069,307 A | 1/1978 | Higuchi et al. | |
| 4,102,342 A | 7/1978 | Akiyama et al. | |
| 4,111,208 A * | 9/1978 | Leuenberger | A61B 17/1624 606/80 |
| 4,138,151 A | 2/1979 | Nakao | |
| 4,177,797 A | 12/1979 | Baylis et al. | |
| 4,184,497 A | 1/1980 | Kolff et al. | |
| 4,191,191 A | 3/1980 | Auburn | |
| 4,198,766 A | 4/1980 | Camin et al. | |
| 4,207,890 A | 6/1980 | Mamajek et al. | |
| 4,209,919 A | 7/1980 | Kirikae et al. | |
| 4,213,095 A | 7/1980 | Falconer | |
| 4,217,898 A | 8/1980 | Theeuwes | |
| 4,248,248 A | 2/1981 | De Busscher | |
| 4,268,115 A | 5/1981 | Slemon et al. | |
| 4,299,226 A | 11/1981 | Banka | |
| 4,299,227 A | 11/1981 | Lincoff | |
| 4,312,353 A | 1/1982 | Shahbabian | |
| 4,332,322 A | 6/1982 | Jaeschke et al. | |
| 4,338,941 A | 7/1982 | Payton | |
| D269,204 S | 5/1983 | Trepp | |
| 4,388,941 A | 6/1983 | Reidhammer | |
| RE31,351 E | 8/1983 | Falconer | |
| 4,435,716 A | 3/1984 | Zandbergen | |
| 4,437,856 A | 3/1984 | Valli | |
| 4,450,150 A | 5/1984 | Sidman | |
| 4,459,977 A | 7/1984 | Pizon et al. | |
| 4,464,175 A | 8/1984 | Altman et al. | |
| 4,471,779 A | 9/1984 | Antoshkiw et al. | |
| 4,499,899 A | 2/1985 | Lyons, III | |
| 4,554,929 A | 11/1985 | Samson et al. | |
| 4,564,364 A | 1/1986 | Zaffaroni et al. | |
| 4,571,239 A | 2/1986 | Heyman | |
| 4,571,240 A | 2/1986 | Samson et al. | |
| 4,581,017 A | 4/1986 | Sahota | |
| 4,585,000 A | 4/1986 | Hershenson | |
| D283,921 S | 5/1986 | Dyak | |
| 4,589,868 A | 5/1986 | Dretler | |
| 4,596,528 A | 6/1986 | Lewis et al. | |
| D284,892 S | 7/1986 | Glassman | |
| 4,603,564 A | 8/1986 | Kleinhany et al. | |
| 4,606,346 A | 8/1986 | Berg et al. | |
| 4,607,622 A | 8/1986 | Fritch et al. | |
| 4,637,389 A | 1/1987 | Heyden | |
| 4,639,244 A | 1/1987 | Rizk et al. | |
| 4,645,495 A | 2/1987 | Vaillancourt | |
| 4,669,469 A | 6/1987 | Gifford, III | |
| 4,672,961 A | 6/1987 | Davies | |
| 4,675,613 A | 6/1987 | Naegeli et al. | |
| 4,691,948 A | 9/1987 | Austin, Jr. et al. | |

(56) References Cited

U.S. PATENT DOCUMENTS

| | | |
|---|---|---|
| 4,708,434 A | 11/1987 | Tsuno |
| 4,708,834 A | 11/1987 | Cohen et al. |
| 4,726,772 A | 2/1988 | Amplatz |
| 4,736,970 A | 4/1988 | McGourty et al. |
| 4,737,141 A | 4/1988 | Spits |
| 4,748,869 A | 6/1988 | Ohtsuka |
| 4,748,969 A | 6/1988 | Wardle |
| 4,748,986 A | 6/1988 | Morrison et al. |
| 4,755,171 A | 7/1988 | Tennant |
| 4,771,776 A | 9/1988 | Powell et al. |
| 4,793,359 A | 12/1988 | Sharrow |
| 4,795,439 A | 1/1989 | Guest |
| 4,796,629 A | 1/1989 | Grayzel |
| 4,803,076 A | 2/1989 | Ranade |
| 4,807,710 A | 2/1989 | Greeley |
| 4,811,743 A | 3/1989 | Stevens |
| 4,815,478 A | 3/1989 | Buchbinder et al. |
| 4,819,619 A | 4/1989 | Augustine et al. |
| 4,846,186 A | 7/1989 | Box et al. |
| 4,847,258 A | 7/1989 | Sturm et al. |
| 4,851,228 A | 7/1989 | Zenter et al. |
| 4,854,330 A | 8/1989 | Evans, III et al. |
| 4,862,874 A | 9/1989 | Kellner |
| 4,867,138 A | 9/1989 | Kubota et al. |
| 4,883,465 A | 11/1989 | Brennan |
| 4,897,651 A | 1/1990 | DeMonte |
| 4,898,577 A | 2/1990 | Badger et al. |
| 4,917,419 A | 4/1990 | Mora, Jr. et al. |
| 4,917,667 A | 4/1990 | Jackson |
| 4,919,112 A | 4/1990 | Siegmund |
| 4,920,967 A | 5/1990 | Cottonaro et al. |
| 4,925,445 A | 5/1990 | Sakamoto et al. |
| 4,940,062 A | 7/1990 | Hampton et al. |
| 4,943,275 A | 7/1990 | Stricker |
| 4,946,466 A | 8/1990 | Pinchuk et al. |
| 4,961,433 A | 10/1990 | Christian |
| 4,966,163 A | 10/1990 | Kraus et al. |
| 4,984,581 A | 1/1991 | Stice |
| 4,994,033 A | 2/1991 | Shockey et al. |
| 4,998,916 A | 3/1991 | Hammerslag et al. |
| 4,998,917 A | 3/1991 | Gaiser et al. |
| 5,001,825 A | 3/1991 | Halpern |
| 5,002,322 A | 3/1991 | Fukumoto |
| 5,019,075 A | 5/1991 | Spears et al. |
| 5,019,372 A | 5/1991 | Folkman et al. |
| 5,020,514 A | 6/1991 | Heckele |
| 5,021,043 A | 6/1991 | Becker et al. |
| 5,024,650 A | 6/1991 | Hagiwara et al. |
| 5,024,658 A | 6/1991 | Kozlov et al. |
| 5,026,384 A | 6/1991 | Farr et al. |
| 5,030,227 A | 7/1991 | Rosenbluth et al. |
| 5,041,089 A | 8/1991 | Mueller et al. |
| 5,044,678 A | 9/1991 | Detweiler |
| 5,047,040 A | 9/1991 | Simpson et al. |
| 5,053,007 A | 10/1991 | Euteneuer |
| 5,055,051 A | 10/1991 | Duncan |
| 5,060,660 A | 10/1991 | Gambale et al. |
| 5,067,489 A | 11/1991 | lind |
| 5,069,226 A | 12/1991 | Yamauchi et al. |
| 5,087,244 A | 2/1992 | Wolinsky et al. |
| 5,087,246 A | 2/1992 | Smith |
| 5,090,595 A | 2/1992 | Vandeninck |
| 5,090,910 A | 2/1992 | Narlo |
| 5,112,228 A | 5/1992 | Zouras |
| 5,116,311 A | 5/1992 | Lofstedt |
| 5,127,393 A | 7/1992 | McFarlin et al. |
| 5,137,517 A | 8/1992 | Loney et al. |
| 5,139,510 A | 8/1992 | Goldsmith, III et al. |
| 5,139,832 A | 8/1992 | Hayashi et al. |
| D329,496 S | 9/1992 | Wotton |
| 5,152,747 A | 10/1992 | Oliver |
| 5,156,595 A | 10/1992 | Adams |
| 5,163,989 A | 11/1992 | Campbell et al. |
| 5,167,220 A | 12/1992 | Brown |
| 5,168,864 A | 12/1992 | Shockey |
| 5,169,043 A | 12/1992 | Catania |
| 5,169,386 A | 12/1992 | Becker et al. |
| 5,171,233 A | 12/1992 | Amplatz et al. |
| 5,180,368 A | 1/1993 | Garrison |
| 5,183,470 A | 2/1993 | Wttermann |
| 5,189,110 A | 2/1993 | Ikematu et al. |
| 5,195,168 A | 3/1993 | Yong |
| 5,197,457 A | 3/1993 | Adair |
| 5,207,695 A | 5/1993 | Trout, III |
| 5,211,952 A | 5/1993 | Spicer et al. |
| 5,215,105 A | 6/1993 | Kizelshteyn et al. |
| 5,221,260 A | 6/1993 | Burns et al. |
| 5,226,302 A | 7/1993 | Anderson |
| 5,230,348 A | 7/1993 | Ishibe et al. |
| 5,236,422 A | 8/1993 | Eplett, Jr. |
| 5,243,996 A | 9/1993 | Hall |
| D340,111 S | 10/1993 | Yoshikawa |
| 5,250,059 A | 10/1993 | Andreas et al. |
| 5,251,092 A | 10/1993 | Brady et al. |
| 5,252,183 A | 10/1993 | Shaban et al. |
| 5,255,679 A | 10/1993 | Imran |
| 5,256,144 A | 10/1993 | Kraus et al. |
| 5,258,003 A | 11/1993 | Ciaglia et al. |
| 5,263,926 A | 11/1993 | Wilk |
| 5,264,260 A | 11/1993 | Saab |
| 5,267,965 A | 12/1993 | Deniega |
| 5,270,086 A | 12/1993 | Hamlin |
| 5,273,052 A | 12/1993 | Kraus et al. |
| 5,275,593 A | 1/1994 | Easley et al. |
| 5,286,254 A | 2/1994 | Shapland et al. |
| 5,290,310 A | 3/1994 | Makower et al. |
| 5,295,694 A | 3/1994 | Levin |
| 5,300,085 A | 4/1994 | Yock |
| 5,304,123 A | 4/1994 | Atala et al. |
| 5,308,326 A | 5/1994 | Zimmon |
| 5,313,967 A | 5/1994 | Lieber et al. |
| 5,314,417 A | 5/1994 | Stephens et al. |
| 5,315,618 A | 5/1994 | Yoshida |
| 5,324,306 A | 6/1994 | Makower et al. |
| 5,333,620 A | 8/1994 | Moutafis et al. |
| 5,334,167 A | 8/1994 | Cocanower |
| 5,336,163 A | 8/1994 | DeMane et al. |
| 5,341,818 A | 8/1994 | Abrams et al. |
| 5,342,296 A | 8/1994 | Persson et al. |
| 5,343,865 A | 9/1994 | Gardineer et al. |
| 5,345,945 A | 9/1994 | Hodgson et al. |
| 5,346,075 A | 9/1994 | Nichols et al. |
| 5,346,508 A | 9/1994 | Hastings |
| 5,348,537 A | 9/1994 | Wiesner et al. |
| 5,350,396 A | 9/1994 | Eliachar |
| 5,353,804 A | 10/1994 | Kornberg et al. |
| 5,356,418 A | 10/1994 | Shturman |
| 5,368,049 A | 11/1994 | Raman et al. |
| 5,368,558 A | 11/1994 | Nita |
| 5,368,566 A | 11/1994 | Crocker |
| 5,372,138 A | 12/1994 | Crowley et al. |
| 5,372,584 A | 12/1994 | Zink et al. |
| D355,031 S | 1/1995 | Yoshikawa |
| 5,386,817 A | 2/1995 | Jones |
| 5,391,147 A | 2/1995 | Imran et al. |
| 5,391,179 A | 2/1995 | Mezzoli |
| 5,402,799 A | 4/1995 | Colon et al. |
| 5,403,338 A | 4/1995 | Milo |
| 5,409,444 A | 4/1995 | Kensey |
| 5,411,475 A | 5/1995 | Atala et al. |
| 5,411,476 A | 5/1995 | Abrams et al. |
| 5,411,477 A | 5/1995 | Saab |
| 5,415,633 A | 5/1995 | Lazarus |
| 5,425,370 A | 6/1995 | Vilkomerson |
| 5,439,446 A | 8/1995 | Barry |
| 5,441,494 A | 8/1995 | Ortiz |
| 5,441,497 A | 8/1995 | Narciso, Jr. |
| 5,450,853 A | 9/1995 | Hastings et al. |
| 5,451,221 A | 9/1995 | Cho et al. |
| 5,454,817 A | 10/1995 | Katz |
| 5,458,572 A | 10/1995 | Campbell et al. |
| 5,465,717 A | 11/1995 | Imran et al. |
| 5,465,733 A | 11/1995 | Hinohara et al. |
| 5,478,565 A | 12/1995 | Geria |

(56) References Cited

U.S. PATENT DOCUMENTS

| | | |
|---|---|---|
| 5,486,181 A | 1/1996 | Cohen et al. |
| 5,496,338 A | 3/1996 | Miyagi et al. |
| 5,497,783 A | 3/1996 | Urick et al. |
| 5,507,301 A | 4/1996 | Wasicek et al. |
| 5,507,725 A | 4/1996 | Savage et al. |
| 5,507,766 A | 4/1996 | Kugo et al. |
| 5,512,055 A | 4/1996 | Domb et al. |
| 5,514,128 A | 5/1996 | Hillsman et al. |
| 5,519,532 A | 5/1996 | Broome |
| 5,531,676 A | 7/1996 | Edwards et al. |
| 5,533,985 A | 7/1996 | Wang |
| 5,538,008 A | 7/1996 | Crowe |
| 5,546,964 A | 8/1996 | Stangerup |
| 5,549,542 A | 8/1996 | Kovalcheck |
| 5,558,073 A | 9/1996 | Pomeranz et al. |
| 5,558,652 A | 9/1996 | Henke |
| 5,562,619 A | 10/1996 | Mirarchi et al. |
| 5,568,809 A | 10/1996 | Ben-Haim |
| 5,571,086 A | 11/1996 | Kaplan et al. |
| 5,575,804 A * | 11/1996 | Yoon ............... A61B 10/0233 604/165.02 |
| 5,578,007 A | 11/1996 | Imran |
| 5,578,048 A | 11/1996 | Pasqualucci et al. |
| 5,584,827 A | 12/1996 | Korteweg et al. |
| 5,591,194 A | 1/1997 | Berthiaume |
| 5,599,284 A | 2/1997 | Shea |
| 5,599,304 A | 2/1997 | Shaari |
| 5,599,576 A | 2/1997 | Opolski |
| 5,601,087 A | 2/1997 | Gunderson et al. |
| 5,601,594 A | 2/1997 | Best |
| 5,607,386 A | 3/1997 | Flam |
| 5,615,839 A | 4/1997 | Hartwig |
| 5,617,870 A | 4/1997 | Hastings et al. |
| 5,626,374 A | 5/1997 | Kim |
| 5,633,000 A | 5/1997 | Grossman et al. |
| 5,634,908 A | 6/1997 | Loomas |
| 5,638,819 A | 6/1997 | Manwaring et al. |
| 5,643,251 A | 7/1997 | Hillsman et al. |
| 5,645,789 A | 7/1997 | Roucher, Jr. |
| 5,647,361 A | 7/1997 | Damadian |
| 5,656,030 A | 8/1997 | Hunjan et al. |
| 5,662,674 A | 9/1997 | Debbas |
| 5,664,567 A | 9/1997 | Linder |
| 5,664,580 A | 9/1997 | Erickson et al. |
| 5,665,052 A | 9/1997 | Bullard |
| 5,669,388 A | 9/1997 | Vilkomerson |
| 5,673,707 A | 10/1997 | Chandrasekaran |
| 5,676,673 A | 10/1997 | Ferre et al. |
| 5,679,400 A | 10/1997 | Tuch |
| 5,682,199 A | 10/1997 | Lankford |
| 5,685,838 A | 11/1997 | Peters et al. |
| 5,685,847 A | 11/1997 | Barry |
| 5,690,373 A | 11/1997 | Luker |
| 5,693,065 A | 12/1997 | Rains, III |
| 5,694,945 A | 12/1997 | Ben-Haim |
| 5,697,159 A | 12/1997 | Linden |
| 5,700,286 A | 12/1997 | Tartaglia et al. |
| 5,707,389 A | 1/1998 | Louw et al. |
| 5,708,175 A | 1/1998 | Loyanagi et al. |
| 5,711,315 A | 1/1998 | Jerusalmy |
| 5,713,839 A | 2/1998 | Shea |
| 5,713,946 A | 2/1998 | Ben-Haim |
| 5,718,702 A | 2/1998 | Edwards |
| 5,720,300 A | 2/1998 | Fagan et al. |
| 5,722,401 A | 3/1998 | Pietroski et al. |
| 5,722,984 A | 3/1998 | Fischell et al. |
| 5,729,129 A | 3/1998 | Acker |
| 5,730,128 A | 3/1998 | Pomeranz et al. |
| 5,733,248 A | 3/1998 | Adams et al. |
| 5,752,513 A | 5/1998 | Acker et al. |
| 5,762,604 A | 6/1998 | Kieturakis |
| 5,766,158 A | 6/1998 | Opolski |
| 5,775,327 A | 7/1998 | Randolph et al. |
| 5,776,158 A | 7/1998 | Chou |
| 5,779,699 A | 7/1998 | Lipson |
| 5,789,391 A | 8/1998 | Jacobus et al. |
| 5,792,100 A | 8/1998 | Shantha |
| 5,797,878 A | 8/1998 | Bleam |
| 5,803,089 A | 9/1998 | Ferre et al. |
| 5,814,016 A | 9/1998 | Valley et al. |
| 5,819,723 A | 10/1998 | Joseph |
| 5,820,568 A | 10/1998 | Willis |
| 5,824,044 A | 10/1998 | Quiachon et al. |
| 5,824,048 A | 10/1998 | Tuch |
| 5,824,173 A | 10/1998 | Fontirroche et al. |
| 5,827,224 A | 10/1998 | Shippert |
| 5,830,188 A | 11/1998 | Abouleish |
| 5,833,608 A | 11/1998 | Acker |
| 5,833,645 A | 11/1998 | Lieber et al. |
| 5,833,650 A | 11/1998 | Imran |
| 5,833,682 A | 11/1998 | Amplatz et al. |
| 5,836,638 A | 11/1998 | Slocum |
| 5,836,935 A | 11/1998 | Ashton et al. |
| 5,837,313 A | 11/1998 | Ding et al. |
| 5,843,089 A | 12/1998 | Sahatjian et al. |
| 5,843,113 A | 12/1998 | High |
| 5,846,259 A | 12/1998 | Berthiaume |
| 5,857,998 A | 1/1999 | Barry |
| 5,862,693 A | 1/1999 | Myers et al. |
| 5,865,767 A | 2/1999 | Frechette et al. |
| 5,872,879 A | 2/1999 | Hamm |
| 5,873,835 A | 2/1999 | Hastings |
| 5,887,467 A | 3/1999 | Butterweck et al. |
| 5,902,247 A | 5/1999 | Coe et al. |
| 5,902,333 A | 5/1999 | Roberts et al. |
| 5,904,701 A | 5/1999 | Daneshvar |
| 5,908,407 A | 6/1999 | Frazee et al. |
| 5,916,193 A | 6/1999 | Stevens et al. |
| 5,928,192 A | 7/1999 | Maahs |
| 5,931,811 A | 8/1999 | Haissaguerre et al. |
| 5,931,818 A | 8/1999 | Werp et al. |
| 5,932,035 A | 8/1999 | Koger et al. |
| 5,935,061 A | 8/1999 | Acker et al. |
| 5,941,816 A | 8/1999 | Barthel et al. |
| D413,629 S | 9/1999 | Wolff et al. |
| 5,947,988 A | 9/1999 | Smith |
| 5,949,929 A | 9/1999 | Hamm |
| 5,954,693 A | 9/1999 | Barry |
| 5,954,694 A | 9/1999 | Sunseri |
| 5,957,842 A | 9/1999 | Littmann et al. |
| 5,968,085 A | 10/1999 | Morris et al. |
| 5,971,975 A | 10/1999 | Mills et al. |
| 5,979,290 A | 11/1999 | Simeone |
| 5,980,503 A | 11/1999 | Chin |
| 5,980,551 A | 11/1999 | Summers et al. |
| 5,984,945 A | 11/1999 | Sirhan |
| 5,985,307 A | 11/1999 | Hanson et al. |
| 5,997,562 A | 12/1999 | Zadno-Azizi |
| 6,006,126 A | 12/1999 | Cosman |
| 6,006,130 A | 12/1999 | Higo et al. |
| 6,007,516 A | 12/1999 | Burbank et al. |
| 6,007,991 A | 12/1999 | Sivaraman et al. |
| 6,010,511 A | 1/2000 | Murphy |
| 6,013,019 A | 1/2000 | Fischell et al. |
| 6,015,414 A | 1/2000 | Werp et al. |
| 6,016,429 A | 1/2000 | Khafizov et al. |
| 6,016,439 A | 1/2000 | Acker |
| 6,019,736 A | 2/2000 | Avellanet et al. |
| 6,019,777 A | 2/2000 | Mackenzie |
| 6,021,340 A | 2/2000 | Randolph et al. |
| 6,022,313 A | 2/2000 | Ginn et al. |
| 6,027,461 A | 2/2000 | Walker et al. |
| 6,027,478 A | 2/2000 | Katz |
| 6,030,402 A | 2/2000 | Thompson et al. |
| 6,039,699 A | 3/2000 | Viera |
| 6,042,561 A | 3/2000 | Ash et al. |
| 6,048,299 A | 4/2000 | von Hoffmann |
| 6,048,358 A | 4/2000 | Barak |
| 6,053,172 A | 4/2000 | Hovda et al. |
| 6,056,702 A | 5/2000 | Lorenzo |
| 6,059,752 A | 5/2000 | Segal |
| 6,071,233 A | 6/2000 | Ishikawa et al. |
| 6,079,755 A | 6/2000 | Chang |
| 6,080,190 A | 6/2000 | Schwartz |

(56) References Cited

U.S. PATENT DOCUMENTS

| | | | |
|---|---|---|---|
| 6,083,148 A | 7/2000 | Williams | |
| 6,083,188 A | 7/2000 | Becker et al. | |
| 6,086,585 A | 7/2000 | Hovda et al. | |
| 6,092,846 A | 7/2000 | Fuss et al. | |
| 6,093,150 A | 7/2000 | Chandler et al. | |
| 6,093,195 A | 7/2000 | Ouchi | |
| 6,106,538 A | 8/2000 | Shiber | |
| 6,109,268 A | 8/2000 | Thapliyal et al. | |
| 6,110,178 A * | 8/2000 | Zech | A61B 17/1635 606/96 |
| 6,113,567 A | 9/2000 | becker | |
| 6,117,105 A | 9/2000 | Bresnaham et al. | |
| 6,122,541 A | 9/2000 | Cosman et al. | |
| 6,123,697 A | 9/2000 | Shippert | |
| 6,136,006 A | 10/2000 | Johnson et al. | |
| 6,139,510 A | 10/2000 | Palermo | |
| 6,142,957 A | 11/2000 | Diamond et al. | |
| 6,148,823 A | 11/2000 | Hastings | |
| 6,149,213 A | 11/2000 | Sokurenko et al. | |
| 6,159,170 A | 12/2000 | Borodulin et al. | |
| 6,171,298 B1 | 1/2001 | Matsuura et al. | |
| 6,171,303 B1 | 1/2001 | Ben-Haim | |
| 6,174,280 B1 | 1/2001 | Oneda et al. | |
| 6,176,829 B1 | 1/2001 | Vilkomerson | |
| 6,179,788 B1 | 1/2001 | Sullivan | |
| 6,179,811 B1 | 1/2001 | Fugoso et al. | |
| 6,183,461 B1 | 2/2001 | Matsuura et al. | |
| 6,183,464 B1 | 2/2001 | Sharp et al. | |
| 6,190,353 B1 | 2/2001 | Makower et al. | |
| 6,190,381 B1 | 2/2001 | Olsen et al. | |
| 6,193,650 B1 | 2/2001 | Ryan, Jr. | |
| 6,195,225 B1 | 2/2001 | Komatsu et al. | |
| 6,200,257 B1 | 3/2001 | Winkler | |
| 6,206,870 B1 | 3/2001 | Kanner | |
| 6,213,975 B1 | 4/2001 | Laksin | |
| 6,221,042 B1 | 4/2001 | Adams | |
| 6,231,543 B1 | 5/2001 | Hegde et al. | |
| 6,234,958 B1 | 5/2001 | Snoke et al. | |
| 6,238,355 B1 * | 5/2001 | Daum | A61B 10/0266 600/567 |
| 6,238,364 B1 | 5/2001 | Becker | |
| 6,238,391 B1 | 5/2001 | Olsen et al. | |
| 6,241,519 B1 | 6/2001 | Sedleemayer | |
| 6,249,180 B1 | 6/2001 | Maalej et al. | |
| 6,254,550 B1 | 7/2001 | McNamara et al. | |
| 6,268,574 B1 | 7/2001 | Edens | |
| 6,293,957 B1 | 9/2001 | Peters et al. | |
| 6,302,875 B1 | 10/2001 | Makower et al. | |
| 6,306,105 B1 | 10/2001 | Rooney et al. | |
| 6,306,124 B1 | 10/2001 | Jones et al. | |
| D450,382 S | 11/2001 | Nestenborg | |
| 6,322,495 B1 | 11/2001 | Snow et al. | |
| 6,328,564 B1 | 12/2001 | Thurow | |
| 6,332,089 B1 | 12/2001 | Acker et al. | |
| 6,332,891 B1 | 12/2001 | Himes | |
| 6,340,360 B1 | 1/2002 | Lyles et al. | |
| 6,348,041 B1 | 2/2002 | Klint | |
| 6,352,503 B1 | 3/2002 | Matsui et al. | |
| 6,375,615 B1 | 4/2002 | Flaherty et al. | |
| 6,375,629 B1 | 4/2002 | Muni et al. | |
| 6,383,146 B1 | 5/2002 | Klint | |
| 6,386,197 B1 | 5/2002 | Miller | |
| 6,389,313 B1 | 5/2002 | Marchitto et al. | |
| 6,390,993 B1 | 5/2002 | Cornish et al. | |
| 6,394,093 B1 | 5/2002 | Lethi | |
| 6,398,758 B1 | 6/2002 | Jacobsen et al. | |
| 6,409,863 B1 | 6/2002 | Williams et al. | |
| 6,419,653 B2 | 7/2002 | Edwards et al. | |
| 6,423,012 B1 | 7/2002 | Kato et al. | |
| 6,425,877 B1 | 7/2002 | Edwards | |
| 6,432,986 B2 | 8/2002 | Levin | |
| 6,440,061 B1 | 8/2002 | Wenner et al. | |
| 6,443,947 B1 | 9/2002 | Marko et al. | |
| 6,445,939 B1 | 9/2002 | Swanson et al. | |
| 6,450,975 B1 | 9/2002 | Brennan et al. | |
| 6,450,989 B2 | 9/2002 | Dubrul et al. | |
| 6,464,650 B2 | 10/2002 | Jafari et al. | |
| 6,468,202 B1 | 10/2002 | Irion et al. | |
| 6,468,297 B1 | 10/2002 | Williams et al. | |
| 6,485,475 B1 | 11/2002 | Chelly | |
| 6,491,940 B1 | 12/2002 | Levin | |
| 6,494,894 B2 | 12/2002 | Mirarchi | |
| 6,500,130 B2 | 12/2002 | Kinsella et al. | |
| 6,500,189 B1 | 12/2002 | Lang et al. | |
| 6,503,087 B1 | 1/2003 | Eggert et al. | |
| 6,503,185 B1 | 1/2003 | Waksman et al. | |
| 6,503,263 B2 | 1/2003 | Adams | |
| 6,511,418 B2 | 1/2003 | Shahidi et al. | |
| 6,514,249 B1 | 2/2003 | Maguire et al. | |
| 6,517,478 B2 | 2/2003 | Khadem | |
| 6,524,299 B1 | 2/2003 | Tran et al. | |
| 6,526,302 B2 | 2/2003 | Hassett | |
| 6,527,753 B2 | 3/2003 | Sekine et al. | |
| 6,529,756 B1 | 3/2003 | Phan et al. | |
| 6,533,754 B1 | 3/2003 | Hisamatsu et al. | |
| 6,536,437 B1 | 3/2003 | Dragisic | |
| 6,537,294 B1 | 3/2003 | Boyle et al. | |
| 6,543,452 B1 | 4/2003 | Lavigne | |
| 6,544,230 B1 | 4/2003 | Flaherty et al. | |
| 6,549,800 B1 | 4/2003 | Atalar et al. | |
| 6,551,239 B2 | 4/2003 | Renner et al. | |
| 6,569,146 B1 | 5/2003 | Werner et al. | |
| 6,569,147 B1 | 5/2003 | Evans et al. | |
| 6,571,131 B1 | 5/2003 | Nguyen | |
| 6,572,538 B2 | 6/2003 | Takase | |
| 6,572,590 B1 | 6/2003 | Stevens et al. | |
| 6,579,285 B2 | 6/2003 | Sinofsky | |
| 6,585,639 B1 | 7/2003 | Kotmel et al. | |
| 6,585,717 B1 | 7/2003 | Wittenberger et al. | |
| 6,585,794 B2 | 7/2003 | Shimoda et al. | |
| 6,589,237 B2 | 7/2003 | Woloszko et al. | |
| 6,591,130 B2 | 7/2003 | Shahidi | |
| 6,596,009 B1 | 7/2003 | Jelic | |
| 6,607,546 B1 | 8/2003 | Murken | |
| 6,612,999 B2 | 9/2003 | Brennan et al. | |
| 6,613,066 B1 | 9/2003 | Fukaya et al. | |
| 6,616,601 B2 | 9/2003 | Hayakawa | |
| 6,616,659 B1 | 9/2003 | de la Torre et al. | |
| 6,616,678 B2 | 9/2003 | Nishtala et al. | |
| 6,616,913 B1 | 9/2003 | Mautone | |
| 6,619,085 B1 | 9/2003 | Hsieh | |
| 6,634,684 B2 | 10/2003 | Spiessl | |
| 6,638,233 B2 | 10/2003 | Corvi et al. | |
| 6,638,268 B2 | 10/2003 | Niazi | |
| 6,638,291 B1 | 10/2003 | Ferrera et al. | |
| 6,645,193 B2 | 11/2003 | Mangosong | |
| 6,652,472 B2 | 11/2003 | Jafari et al. | |
| 6,652,480 B1 | 11/2003 | Imran et al. | |
| 6,656,166 B2 | 12/2003 | Lurie et al. | |
| 6,663,589 B1 | 12/2003 | Halevy | |
| 6,669,689 B2 | 12/2003 | Lehmann et al. | |
| 6,669,711 B1 | 12/2003 | Noda | |
| 6,672,773 B1 | 1/2004 | Glenn et al. | |
| 6,673,025 B1 | 1/2004 | Richardson et al. | |
| 6,679,871 B2 | 1/2004 | Hahnen | |
| 6,685,648 B2 | 2/2004 | Flaherty et al. | |
| 6,689,096 B1 | 2/2004 | Loubens et al. | |
| 6,689,146 B1 | 2/2004 | Himes | |
| 6,702,735 B2 | 3/2004 | Kelly | |
| 6,712,757 B2 | 3/2004 | Becker et al. | |
| 6,714,809 B2 | 3/2004 | Lee et al. | |
| 6,716,216 B1 | 4/2004 | Boucher et al. | |
| 6,716,813 B2 | 4/2004 | Lim et al. | |
| 6,719,749 B1 | 4/2004 | Schweikert et al. | |
| 6,719,763 B2 | 4/2004 | Chung et al. | |
| 6,726,701 B2 | 4/2004 | Gilson et al. | |
| 6,755,812 B2 | 6/2004 | Peterson et al. | |
| 6,776,772 B1 | 8/2004 | de Vrijer et al. | |
| 6,780,168 B2 | 8/2004 | Jellie | |
| 6,783,522 B2 | 8/2004 | Fischell | |
| 6,783,536 B2 | 8/2004 | Vilsmeier et al. | |
| 6,786,864 B2 | 9/2004 | Matsuura et al. | |
| 6,796,960 B2 | 9/2004 | Cioanta et al. | |
| 6,811,544 B2 | 11/2004 | Schaer | |

(56) References Cited

U.S. PATENT DOCUMENTS

| | | |
|---|---|---|
| 6,814,743 B2 | 11/2004 | Chin et al. |
| 6,817,364 B2 | 11/2004 | Garibaldi et al. |
| 6,817,976 B2 | 11/2004 | Rovegno |
| 6,827,683 B2 | 12/2004 | Otawara |
| 6,827,701 B2 | 12/2004 | MacMahon et al. |
| 6,832,715 B2 | 12/2004 | Eungard et al. |
| D501,677 S | 2/2005 | Becker |
| 6,851,290 B1 | 2/2005 | Meier et al. |
| 6,860,264 B2 | 3/2005 | Christopher |
| 6,860,849 B2 | 3/2005 | Matsushita et al. |
| 6,878,106 B1 | 4/2005 | Herrmann |
| 6,890,329 B2 | 5/2005 | Carroll et al. |
| 6,899,672 B2 | 5/2005 | Chin et al. |
| 6,902,556 B2 | 6/2005 | Grimes et al. |
| 6,913,763 B2 | 7/2005 | Lerner |
| 6,927,478 B2 | 8/2005 | Paek |
| 6,939,361 B1 | 9/2005 | Kleshinski |
| 6,939,374 B2 | 9/2005 | Banik et al. |
| 6,955,657 B1 | 10/2005 | Webler |
| 6,966,906 B2 | 11/2005 | Brown |
| 6,971,998 B2 | 12/2005 | Rosenman et al. |
| 6,979,290 B2 | 12/2005 | Mourlas et al. |
| 6,984,203 B2 | 1/2006 | Tartaglia et al. |
| 6,991,597 B2 | 1/2006 | Gellman et al. |
| 6,997,931 B2 | 2/2006 | Sauer et al. |
| 6,997,941 B2 | 2/2006 | Sharkey et al. |
| 7,004,173 B2 | 2/2006 | Sparks et al. |
| 7,008,381 B2 | 3/2006 | Janssens |
| 7,008,412 B2 | 3/2006 | Maginot |
| 7,011,654 B2 | 3/2006 | Dubrul et al. |
| 7,022,105 B1 | 4/2006 | Edwards |
| 7,043,961 B2 | 5/2006 | Pandey |
| 7,052,474 B2 | 5/2006 | Castell et al. |
| 7,056,284 B2 | 6/2006 | Martone et al. |
| 7,056,303 B2 | 6/2006 | Dennis et al. |
| 7,074,197 B2 | 7/2006 | Reynolds et al. |
| 7,074,426 B2 | 7/2006 | Kochinke |
| 7,097,612 B2 | 8/2006 | Bertolero et al. |
| 7,108,677 B2 | 9/2006 | Courtney et al. |
| 7,108,706 B2 | 9/2006 | Hogle |
| 7,125,252 B2 | 10/2006 | Rouiller et al. |
| 7,128,718 B2 | 10/2006 | Hojeibane et al. |
| 7,131,969 B1 | 11/2006 | Hovda et al. |
| 7,140,480 B2 | 11/2006 | Drussel et al. |
| D534,216 S | 12/2006 | Makower et al. |
| 7,160,255 B2 | 1/2007 | Saadat |
| 7,169,140 B1 | 1/2007 | Kume |
| 7,169,163 B2 | 1/2007 | Becker |
| 7,172,562 B2 | 2/2007 | McKinley |
| 7,174,774 B2 | 2/2007 | Pawar et al. |
| 7,182,735 B2 | 2/2007 | Shireman et al. |
| 7,184,827 B1 | 2/2007 | Edwards |
| 7,214,201 B2 | 5/2007 | Burmeister et al. |
| 7,233,820 B2 | 6/2007 | Gilboa |
| 7,235,088 B2 | 6/2007 | Pintor et al. |
| 7,235,099 B1 | 6/2007 | Duncavage et al. |
| 7,237,313 B2 | 7/2007 | Skujins et al. |
| 7,252,677 B2 | 8/2007 | Burwell et al. |
| 7,258,694 B1 | 8/2007 | Choi et al. |
| 7,282,057 B2 | 10/2007 | Surti et al. |
| 7,294,345 B2 | 11/2007 | Haapakumpu et al. |
| 7,294,365 B2 | 11/2007 | Hayakawa et al. |
| 7,313,430 B2 | 12/2007 | Urquhart et al. |
| 7,316,168 B2 | 1/2008 | van der Knokke et al. |
| 7,316,656 B2 | 1/2008 | Shireman et al. |
| 7,318,831 B2 | 1/2008 | Alvarez et al. |
| 7,322,934 B2 | 1/2008 | Miyake et al. |
| 7,326,235 B2 | 2/2008 | Edwards |
| 7,338,467 B2 | 3/2008 | Lutter |
| 7,343,920 B2 | 3/2008 | Toby et al. |
| 7,359,755 B2 | 4/2008 | Jones et al. |
| 7,361,168 B2 | 4/2008 | Makower et al. |
| 7,366,562 B2 | 4/2008 | Dukesherer |
| 7,371,210 B2 | 5/2008 | Brock et al. |
| 7,381,205 B2 | 6/2008 | Thommen |
| 7,410,480 B2 | 8/2008 | Muni et al. |
| 7,419,497 B2 | 9/2008 | Muni et al. |
| 7,438,701 B2 | 10/2008 | Theeuwes et al. |
| 7,442,191 B2 | 10/2008 | Hovda et al. |
| 7,452,351 B2 | 11/2008 | Miller et al. |
| 7,454,244 B2 | 11/2008 | Kassab et al. |
| 7,462,175 B2 | 12/2008 | Chang et al. |
| 7,471,994 B2 | 12/2008 | Ford et al. |
| 7,481,218 B2 | 1/2009 | Djupesland |
| 7,481,800 B2 | 1/2009 | Jacques |
| D586,465 S | 2/2009 | Faulkner et al. |
| D586,916 S | 2/2009 | Faulkner et al. |
| 7,485,125 B2 | 2/2009 | Sjostrom |
| 7,488,313 B2 | 2/2009 | Segal et al. |
| 7,488,337 B2 | 2/2009 | Saab et al. |
| 7,493,156 B2 | 2/2009 | Manning et al. |
| 7,500,971 B2 | 3/2009 | Chang et al. |
| D590,502 S | 4/2009 | Geisser et al. |
| 7,520,876 B2 | 4/2009 | Ressemann et al. |
| 7,532,920 B1 | 5/2009 | Ainsworth et al. |
| 7,544,192 B2 | 6/2009 | Eaton et al. |
| 7,559,925 B2 | 7/2009 | Goldfarb et al. |
| 7,569,056 B2 | 8/2009 | Cragg et al. |
| 7,610,104 B2 | 10/2009 | Kaplan et al. |
| 7,615,005 B2 | 11/2009 | Stefanchik et al. |
| 7,618,450 B2 | 11/2009 | Zarowski et al. |
| 7,625,335 B2 | 12/2009 | Deichmann et al. |
| 7,632,291 B2 | 12/2009 | Stephens et al. |
| 7,634,233 B2 | 12/2009 | Deng et al. |
| 7,641,644 B2 | 1/2010 | Chang et al. |
| 7,641,668 B2 | 1/2010 | Perry et al. |
| 7,645,272 B2 | 1/2010 | Chang et al. |
| 7,648,367 B1 | 1/2010 | Makower et al. |
| 7,654,997 B2 | 2/2010 | Makower et al. |
| 7,680,244 B2 | 3/2010 | Gertner et al. |
| 7,686,798 B2 | 3/2010 | Eaton et al. |
| 7,691,120 B2 | 4/2010 | Shluzas et al. |
| 7,717,933 B2 | 5/2010 | Becker |
| 7,720,521 B2 | 5/2010 | Chang et al. |
| 7,727,186 B2 | 6/2010 | Makower et al. |
| 7,727,226 B2 | 6/2010 | Chang et al. |
| 7,736,301 B1 | 6/2010 | Webler et al. |
| 7,740,642 B2 | 6/2010 | Becker |
| 7,753,929 B2 | 7/2010 | Becker |
| 7,753,930 B2 | 7/2010 | Becker |
| 7,771,409 B2 | 8/2010 | Chang et al. |
| 7,771,482 B1 | 8/2010 | Karmon |
| 7,775,968 B2 | 8/2010 | Mathis |
| 7,799,048 B2 | 9/2010 | Hudson et al. |
| 7,803,150 B2 | 9/2010 | Chang et al. |
| 7,806,871 B2 | 10/2010 | Li et al. |
| 7,833,282 B2 | 11/2010 | Mandpe |
| 7,837,672 B2 | 11/2010 | Intoccia |
| 7,840,254 B2 | 11/2010 | Glossop |
| 7,849,938 B1 | 12/2010 | Maier |
| 7,854,744 B2 | 12/2010 | Becker |
| D630,321 S | 1/2011 | Hamilton, Jr. |
| 7,875,050 B2 | 1/2011 | Samson et al. |
| D632,791 S | 2/2011 | Murner |
| 7,883,717 B2 | 2/2011 | Varner et al. |
| 7,896,891 B2 | 3/2011 | Catanese, III et al. |
| 7,905,896 B2 | 3/2011 | Straub |
| 7,951,132 B2 | 5/2011 | Eaton et al. |
| 7,988,705 B2 | 8/2011 | Galdonik et al. |
| 7,993,353 B2 | 8/2011 | Roβner et al. |
| 8,002,740 B2 | 8/2011 | Willink et al. |
| 8,014,849 B2 | 9/2011 | Peckham |
| 8,016,752 B2 | 9/2011 | Armstrong et al. |
| 8,025,635 B2 | 9/2011 | Eaton et al. |
| 8,080,000 B2 | 12/2011 | Makower et al. |
| 8,088,063 B2 | 1/2012 | Fujikura et al. |
| 8,088,101 B2 | 1/2012 | Chang et al. |
| 8,090,433 B2 | 1/2012 | Makower et al. |
| 8,100,933 B2 | 1/2012 | Becker |
| 8,104,483 B2 | 1/2012 | Taylor |
| 8,197,552 B2 | 1/2012 | Mandpe |
| 8,114,062 B2 | 2/2012 | Muni et al. |
| 8,114,113 B2 | 2/2012 | Becker |
| 8,116,875 B2 | 2/2012 | Osypka et al. |

(56) References Cited

U.S. PATENT DOCUMENTS

| | | |
|---|---|---|
| 8,123,722 B2 | 2/2012 | Chang et al. |
| 8,142,422 B2 | 3/2012 | Makower et al. |
| 8,147,545 B2 | 4/2012 | Avior |
| 8,167,821 B2 | 5/2012 | Sharrow |
| 8,172,863 B2 | 5/2012 | Robinson et al. |
| 8,187,254 B2 | 5/2012 | Hissink et al. |
| 8,190,389 B2 | 5/2012 | Kim et al. |
| 8,197,433 B2 | 6/2012 | Cohen |
| 8,239,001 B2 | 8/2012 | Verard et al. |
| 8,241,266 B2 | 8/2012 | Keith et al. |
| 8,249,700 B2 | 8/2012 | Clifford et al. |
| 8,277,386 B2 | 10/2012 | Ahmed et al. |
| 8,317,816 B2 | 11/2012 | Becker |
| 8,337,454 B2 | 12/2012 | Eaton et al. |
| 8,348,969 B2 | 1/2013 | Keith et al. |
| 8,388,642 B2 | 3/2013 | Muni et al. |
| 8,403,954 B2 | 3/2013 | Santin et al. |
| 8,439,687 B1 | 5/2013 | Morriss et al. |
| 8,454,603 B2 | 6/2013 | Webb et al. |
| 8,480,696 B2 | 7/2013 | Clague et al. |
| 8,535,707 B2 | 9/2013 | Arensdorf et al. |
| 8,585,728 B2 | 11/2013 | Keith et al. |
| 8,585,753 B2 | 11/2013 | Scanlon et al. |
| 8,608,360 B2 | 12/2013 | Nath |
| 8,642,631 B2 | 2/2014 | Anderson et al. |
| 8,647,256 B2 | 2/2014 | Carrillo |
| 8,882,697 B2 | 11/2014 | Celermajer et al. |
| 2001/0001124 A1 | 5/2001 | Mueller |
| 2001/0004644 A1 | 6/2001 | Levin |
| 2001/0034530 A1 | 10/2001 | Malackowski et al. |
| 2002/0006961 A1 | 1/2002 | Katz et al. |
| 2002/0055746 A1 | 5/2002 | Burke et al. |
| 2002/0090388 A1 | 7/2002 | Humes et al. |
| 2002/0111603 A1 | 8/2002 | Cheikh |
| 2002/0138021 A1* | 9/2002 | Pflueger ............ A61B 10/0266 600/565 |
| 2002/0138091 A1 | 9/2002 | Pflueger |
| 2003/0013985 A1 | 1/2003 | Saadat |
| 2003/0017111 A1 | 1/2003 | Rabito |
| 2003/0018291 A1 | 1/2003 | Hill et al. |
| 2003/0040697 A1 | 2/2003 | Pass et al. |
| 2003/0078608 A1 | 4/2003 | Shiu |
| 2003/0083608 A1 | 5/2003 | Evans et al. |
| 2003/0114732 A1 | 6/2003 | Webler et al. |
| 2003/0114773 A1 | 6/2003 | Janssens |
| 2003/0163154 A1 | 8/2003 | Miyata et al. |
| 2004/0015150 A1 | 1/2004 | Zadno-Azizi |
| 2004/0018980 A1 | 1/2004 | Gurney et al. |
| 2004/0034311 A1 | 2/2004 | Mihalcik |
| 2004/0043052 A1 | 3/2004 | Hunter et al. |
| 2004/0058992 A1 | 3/2004 | Marinello et al. |
| 2004/0064105 A1 | 4/2004 | Capes et al. |
| 2004/0116958 A1 | 6/2004 | Gopferich et al. |
| 2004/0127820 A1 | 7/2004 | Clayman et al. |
| 2004/0158229 A1 | 8/2004 | Quinn |
| 2004/0181175 A1 | 9/2004 | Clayman et al. |
| 2004/0193073 A1 | 9/2004 | DeMello et al. |
| 2004/0230156 A1 | 11/2004 | Schreck et al. |
| 2004/0236231 A1 | 11/2004 | Knighton et al. |
| 2004/0249243 A1 | 12/2004 | Kleiner |
| 2004/0265082 A1 | 12/2004 | Abrams |
| 2004/0267347 A1 | 12/2004 | Cervantes |
| 2005/0027249 A1 | 2/2005 | Reifart et al. |
| 2005/0055077 A1 | 3/2005 | Marco et al. |
| 2005/0059931 A1 | 3/2005 | Garrison et al. |
| 2005/0089670 A1 | 4/2005 | Large |
| 2005/0107738 A1 | 5/2005 | Slater et al. |
| 2005/0113687 A1 | 5/2005 | Herweck et al. |
| 2005/0113850 A1 | 5/2005 | Tagge |
| 2005/0119590 A1 | 6/2005 | Burmeister et al. |
| 2005/0131316 A1 | 6/2005 | Flagle et al. |
| 2005/0143687 A1 | 6/2005 | Rosenblatt et al. |
| 2005/0182319 A1 | 8/2005 | Glossop |
| 2005/0234507 A1 | 10/2005 | Geske et al. |
| 2005/0244472 A1 | 11/2005 | Hughes et al. |
| 2005/0283221 A1 | 12/2005 | Mann et al. |
| 2006/0004323 A1 | 1/2006 | Chang et al. |
| 2006/0004368 A1 | 1/2006 | Zaleski et al. |
| 2006/0058837 A1 | 3/2006 | Bose et al. |
| 2006/0063973 A1 | 3/2006 | Makower et al. |
| 2006/0173382 A1 | 8/2006 | Schreiner |
| 2006/0190022 A1 | 8/2006 | Beyar et al. |
| 2006/0211752 A1 | 9/2006 | Kohn et al. |
| 2006/0253069 A1 | 11/2006 | Li et al. |
| 2006/0271024 A1 | 11/2006 | Gertner et al. |
| 2007/0020196 A1 | 1/2007 | Pipkin et al. |
| 2007/0112358 A1 | 5/2007 | Abbott |
| 2007/0129751 A1 | 6/2007 | Muni et al. |
| 2007/0135789 A1 | 6/2007 | Chang et al. |
| 2007/0167682 A1 | 7/2007 | Goldfarb et al. |
| 2007/0208252 A1 | 9/2007 | Makower |
| 2007/0208301 A1 | 9/2007 | Evard et al. |
| 2007/0249896 A1 | 10/2007 | Goldfarb et al. |
| 2007/0269385 A1 | 11/2007 | Yun et al. |
| 2007/0282305 A1 | 12/2007 | Goldfarb et al. |
| 2007/0288036 A1 | 12/2007 | Seshadri et al. |
| 2007/0293727 A1 | 12/2007 | Goldfarb et al. |
| 2007/0293946 A1 | 12/2007 | Gonzales et al. |
| 2008/0015540 A1 | 1/2008 | Muni et al. |
| 2008/0033519 A1 | 2/2008 | Burwell et al. |
| 2008/0051804 A1 | 2/2008 | Cottler et al. |
| 2008/0103521 A1 | 5/2008 | Makower et al. |
| 2008/0119693 A1 | 5/2008 | Makower et al. |
| 2008/0125626 A1 | 5/2008 | Chang et al. |
| 2008/0132938 A1 | 6/2008 | Chang et al. |
| 2008/0183128 A1 | 7/2008 | Morriss et al. |
| 2008/0188870 A1 | 8/2008 | Andre et al. |
| 2008/0195041 A1 | 8/2008 | Goldfarb et al. |
| 2008/0228085 A1 | 9/2008 | Jenkins et al. |
| 2008/0228231 A1 | 9/2008 | Raphael et al. |
| 2008/0262508 A1 | 10/2008 | Clifford et al. |
| 2008/0275483 A1 | 11/2008 | Makower et al. |
| 2008/0281156 A1 | 11/2008 | Makower et al. |
| 2008/0287908 A1 | 11/2008 | Muni et al. |
| 2008/0319424 A1 | 12/2008 | Muni et al. |
| 2009/0030274 A1 | 1/2009 | Goldfarb et al. |
| 2009/0088728 A1 | 4/2009 | Dollar et al. |
| 2009/0156980 A1 | 6/2009 | Eaton et al. |
| 2009/0163890 A1 | 6/2009 | Clifford et al. |
| 2009/0187089 A1 | 7/2009 | Say et al. |
| 2009/0187098 A1 | 7/2009 | Makower et al. |
| 2009/0198216 A1 | 8/2009 | Muni et al. |
| 2009/0240112 A1 | 9/2009 | Goldfarb et al. |
| 2009/0240237 A1 | 9/2009 | Goldfarb et al. |
| 2009/0312745 A1 | 12/2009 | Goldfarb et al. |
| 2010/0030031 A1 | 2/2010 | Goldfarb et al. |
| 2010/0087811 A1 | 4/2010 | Herrin et al. |
| 2010/0114066 A1 | 5/2010 | Makower et al. |
| 2010/0125253 A1 | 5/2010 | Olson et al. |
| 2010/0174308 A1 | 7/2010 | Chang et al. |
| 2010/0198191 A1 | 8/2010 | Clifford et al. |
| 2010/0198302 A1 | 8/2010 | Shalev |
| 2010/0274188 A1 | 10/2010 | Chang et al. |
| 2011/0004057 A1 | 1/2011 | Goldfarb et al. |
| 2011/0015612 A1 | 1/2011 | Arcand et al. |
| 2011/0015645 A1 | 1/2011 | Liu et al. |
| 2011/0046682 A1 | 2/2011 | Stephan et al. |
| 2012/0053567 A1 | 3/2012 | Schreck et al. |
| 2012/0078118 A1 | 3/2012 | Jenkins et al. |
| 2012/0109111 A1 | 5/2012 | Li |
| 2012/0184983 A1 | 7/2012 | Chang et al. |
| 2012/0316572 A1 | 12/2012 | Rosenblatt et al. |
| 2014/0276328 A1 | 9/2014 | Kesten et al. |
| 2014/0277039 A1 | 9/2014 | Liberatore et al. |

FOREIGN PATENT DOCUMENTS

| | | |
|---|---|---|
| CN | 2352818 | 12/1999 |
| DE | 3202878 | 8/1983 |
| DE | 4032096 | 4/1992 |
| DE | 4406077 | 9/1994 |
| DE | 8810044 | 11/1998 |
| DE | 29923582 | 12/2000 |
| DE | 10104663 | 8/2002 |

(56) References Cited

FOREIGN PATENT DOCUMENTS

| | | |
|---|---|---|
| DE | 10105592 | 8/2002 |
| EP | 129634 | 1/1985 |
| EP | 257605 | 3/1988 |
| EP | 355996 | 2/1990 |
| EP | 418391 | 3/1991 |
| EP | 427852 | 5/1991 |
| EP | 623582 | 11/1994 |
| EP | 624349 | 11/1994 |
| EP | 744400 | 11/1996 |
| EP | 585757 | 6/1997 |
| EP | 893426 | 1/1999 |
| EP | 1042998 | 10/2000 |
| EP | 1166710 | 1/2002 |
| EP | 1413258 | 4/2004 |
| EP | 1944053 | 7/2008 |
| FR | 2859377 | 3/2005 |
| FR | 2916144 | 11/2008 |
| GB | 2125874 | 3/1984 |
| GB | 2305174 | 4/1997 |
| GB | 2318135 | 4/1998 |
| JP | 53-67935 | 6/1978 |
| JP | 10-24098 | 1/1989 |
| JP | 3-503011 | 7/1991 |
| JP | 3-504935 | 10/1991 |
| JP | 4-221313 | 8/1992 |
| JP | 5-211985 | 8/1993 |
| JP | 6-277296 | 10/1994 |
| JP | 7-327916 | 12/1995 |
| JP | 8-317989 | 12/1996 |
| JP | 11-507251 | 6/1999 |
| JP | 2000-501634 | 2/2000 |
| JP | 2001-501846 | 2/2001 |
| JP | 2001-095815 | 4/2001 |
| JP | 2001-526077 | 12/2001 |
| JP | 2002-028166 | 1/2002 |
| JP | 2002-508214 | 3/2002 |
| JP | 2002-537908 | 11/2002 |
| JP | 2002-538850 | 11/2002 |
| JP | 2003-062080 | 3/2003 |
| JP | 2003-521327 | 7/2003 |
| JP | 2004-357728 | 12/2004 |
| JP | 2005-532869 | 11/2005 |
| RU | 2213530 | 10/2003 |
| SU | 1662571 | 7/1991 |
| WO | WO 90/011053 | 10/1990 |
| WO | WO 90/014865 | 12/1990 |
| WO | WO 91/017787 | 11/1991 |
| WO | WO 92/015286 | 9/1992 |
| WO | WO 92/022350 | 12/1992 |
| WO | WO 94/012095 | 6/1994 |
| WO | WO 96/029071 | 9/1996 |
| WO | WO 97/021461 | 6/1997 |
| WO | WO 99/024106 | 5/1999 |
| WO | WO 99/030655 | 6/1999 |
| WO | WO 99/032041 | 7/1999 |
| WO | WO 00/009192 | 2/2000 |
| WO | WO 00/023009 | 4/2000 |
| WO | WO 00/051672 | 9/2000 |
| WO | WO 00/053252 | 9/2000 |
| WO | WO 01/045572 | 6/2001 |
| WO | WO 01/054558 | 8/2001 |
| WO | WO 01/056481 | 8/2001 |
| WO | WO 01/070325 | 9/2001 |
| WO | WO 01/074266 | 10/2001 |
| WO | WO 01/097895 | 12/2001 |
| WO | WO 02/047561 | 6/2002 |
| WO | WO 02/062269 | 8/2002 |
| WO | WO 03/049603 | 6/2003 |
| WO | WO 03/063703 | 8/2003 |
| WO | WO 03/105657 | 12/2003 |
| WO | WO 04/006788 | 1/2004 |
| WO | WO 04/018980 | 3/2004 |
| WO | WO 04/026391 | 4/2004 |
| WO | WO 04/082525 A2 | 9/2004 |
| WO | WO 04/082525 A3 | 9/2004 |
| WO | WO 05/018730 | 3/2005 |
| WO | WO 05/077450 | 8/2005 |
| WO | WO 05/089670 | 9/2005 |
| WO | WO 05/117755 | 12/2005 |
| WO | WO 06/034008 | 3/2006 |
| WO | WO 06/078884 | 7/2006 |
| WO | WO 06/107957 | 10/2006 |
| WO | WO 06/116597 | 11/2006 |
| WO | WO 06/118737 | 11/2006 |
| WO | WO 06/135853 | 12/2006 |
| WO | WO 07/062668 | 6/2007 |
| WO | WO 07/111636 | 10/2007 |
| WO | WO 07/124260 | 11/2007 |
| WO | WO 08/036149 | 3/2008 |
| WO | WO 08/045242 | 4/2008 |
| WO | WO 08/051918 | 5/2008 |
| WO | WO 08/134382 | 11/2008 |

OTHER PUBLICATIONS

Aust, R., et al. 'The Functional Size of the Human Maxillary Ostium in Vivo' Acta. Otolaryn. (9178) vol. 78 pp. 432-435.

Baim, D.S., MD 'Grossman's Cardiac Catheterization, Angiography, and Intervention'(2000) Lippincott Williams & Wilkins pp. 76, 84 & 214.

Barrett, S. 'Be Wary of Neurocranial Restructuring (NCR)' Chirobase; Jul. 2003; www.chirobase.org/06DD/ncr.html.

Bartal N. 'An Improved stent for Use in the Surgical Management of Congential Posterior Choanal Atresia' J. Laryngol. Otol (1988) vol. 102 pp. 146-147.

Becker, A.E. 'Restenosis After Angioplasty' The Lancet (1988) vol. 331, No. 8584 p. 532.

Bellis, M. History of the Catheter-Balloon Catheter—Thomas Fogarty. www.inventors.about.com/library/inventors/blcatheter.htm?p=1.

Benninger et al.; Adult Chronic Rhinosinusitis: Definitions, Diagnosis, Epidemiology, and Pathophysilogy Arch Otolaryngol Head and Neck Surg. vol. 129 (Sep. 2003) pp. A1-S32.

Bent et al. 'The Frontal Cell as a Cause of Frontal Sinus Obstruction' American Journal of Rhinology, vol. 8, No. 4 (1994) pp. 185-191.

Binner et al. 'Fibre-Optic Transillunination of the Sinuses: A Comparison of the Value of Radiography and Transillumination in Antral Disease' Clinical Otolaryngology. vol. 3 (1978) pp. 1-11.

Brown, C.L. et al., 'Safety and Feasibility of Balloon Catheter Dilation of Paranasal Sinus Ostia: A Preliminary Investigation' Annals of Otology, Rhinology & Laryngology (2006) vol. 115, No. 4 pp. 293-299.

Casiano et al. 'Endoscopic Lothrop Procedure: The University of Miami Experience' American Journal of Rhinology, vol. 12, No. 5 (1998) pp. 335-339.

Casserly, I.P. et al., Chapter 7. 'Guides and Wires in Percutaneous Coronary Intervention' Strategic Approaches in Coronary Intervention (2006) Lippincott Williams & Wilkins pp. 91-99.

Chien, Y.W. et al. 'Nasal Systemic Drug Delivery', Drugs and Pharmaceutical Sciences, vol. 39, pp. 60-63.

Cohen et al. 'Endoscopic Sinus Surgery: Where we are and where we're going' Current Opinion in Otolaryngology & Head and Neck Surgery, vol. 13 (2005) pp. 32-38.

Colla, A. et al., 'Trihaloacetylated Enol Ethers—General Synthetic Procedure and Heterocyclic Ring Closure Reactions with Hydroxylamine' Synthesis, (Jun. 1991) pp. 483-486.

Costa, M.N. et al. 'Endoscopic Study of the Intranasal Ostium in External Dacryocystorhinostomy Postoperative. Influence of Saline Solution and 5-Flurorouracil' Clinics (2007) vol. 62, Issue1, pp. 41-46.

Cussler, E.L. 'Diffusion: Mass transfer in Fluid Systems' Cambridge University Press (1996).

Davis, G.E. et al. 'A Complication from Neurocranial Restructuring' Arch Otolaryngol Head Neck Surg. vol. 129 (Apr. 2003) pp. 472-474.

Deutschmann, R. et al. 'A Contribution to the Topical Treatment of [Maxillary] Sinusitis Preliminary Communication' Stomat DDR 26, (1976) pp. 585-592.

(56) References Cited

OTHER PUBLICATIONS

Domb, A. et al. 'Handbook of Biodegradable Polymers' Harwood Academic Publishers (1997).
Doyle Nasal Splints, Jan 25, 2007; www.doylemedical.com/nasalsplints.htm.
Draf, W. 'Endonasal Micro-Endoscopic Frontal Sinus Surgery: the Fulda Concept' Op Tech Otolaryngol Head Neck Surg. vol. 2 (1991) pp. 234-240. .
Edmond, C. et al. 'ENT Surgical Stimulator' Nov. 1989.
ENT Checklist; Physical Examination Performance Checklist [date of publication unknown].
Eremychev, V.A. 'Needles for Puncture and Drainage of the Maxillary Sinus' Meditsinskaya Tekhnika, No. 5 (1974) pp. 54.55.
Feldman, R.L. et al., 'New Steerable, Catheter: Ultra-Low-Profile, Fixed Wire Angioplasty Catheter: Initial Experience with the Cordis OrionTM Steerable PTCA Balloon Catheter' Cathet. Cardiovasc. Diagn. (1990) vol. 19, No. 2, pp. 142-145.
Ford, C.N. 'A Multipurpose Laryngeal Injector Device' Otolaryngol. Head Neck Surg. (1990) vol. 103, No. 1 pp. 135-137.
Friedman, M., M.D., et al. 'Frontal Sinus Surgery: Endoscopic Technique' Operative Techniques in Otolarynology—Head and Neck Surgery. vol. 12, No. 2 (Jun. 2001) pp. 60-65.
Friedman, et al. 'Intraoperative and Postoperative Assessment of Frontal Sinus Patency by Transillumination' Laryngoscope. vol. 110 (Apr. 2000) pp. 683-684.
Friedman, et al 'Middle Turbinate Medialization and Preservation in Endoscopic Surgery' Otolaryngology—Head and Neck Surgery. (2000) vol. 123, No. 1, part 1, pp. 76-80.
Fung, M.K.T. 'Template for Frontal Osteoplastic Flap' Laryngoscope. vol. 96 (1986) pp. 578-579.
Gatot, A. et al. 'Early treatment of Orbital Floor Fractures with Catheter Balloon in Children' Int J. Pediatric Otorhinolaryngol (1991) vol. 21 pp. 97-101.
Gerus, I.I. et al. 'β-Ethoxyvinyl Polyfluroroalkyl Ketones—Versatile Synthones in Fluoroorganic Chemistry' Journal of Fluorine Chemistry. vol. 69 (1994) pp. 195-198. Elesvier Science S.A.
Good, R.H. 'An Intranasal Method for Opening the Frontal Sinus Establishing the Largest Possible Drainage' Laryngoscope. vol. 18 (1980) pp. 266-274.
Gopferich 'Polymer Degradation and Erosion: Mechanisms and Application' Eur. J. Parm. Biophar. vol. 42 (1996) pp. 1-11.
Gorlov, D.V. et al 'Acylation and 2-Methoxypropene with Anhydrides and Halides of Perflurocarboxylic Acids in the Presence of Teriary Amines' Russian Chemical Bulletin. vol. 48 No. 9 (Sep. 1999) pp. 1791-1792. Kluwer Academic/Plenum Publishers.
Gottmann, et al. 'Balloon Dilatation in the Nasal Cavity and Paranasal Sinuses' CIRSE. (Sep. 25, 2004) pp. 1-27.
Gottmann, et al. 'Balloon Dilatation of Recurrent Ostial Occlusion of the Frontal Sinus' CIRSE. (Mar. 2001).
Gottmann, et al. 'Successful treatment of Recurrent Post-Operative Frontal Sinus Stenoses by Balloon Dilatation' CIRSE. (Oct. 5, 2002).
Gupta, D. et al., 'Dacrystitis Secondary to an Iatrogenic Foreign Body in the Lacrimal Apparatus' Ear, Nose & Throat Journal (2009) www.findarticles.com/p/articles/mi_m0BUM/is_7_88/ai_n32428620/.
Hashim, et al. 'Balloon Compression of the Intermaxillary Sinus for Intractable Post Traumatic Bleeding from the Maxillary Artery' Scandinavia Journal of Plastic and reconsruction Sergery and Hand Surgery (1999) vol. 33 pp. 321-324.
Hojo, M. et al, 'Electrophilic Substiutions of Olefinic Hydrogens II. Acylation of Vinyle Ethers and N Vinyl Amides Chemistry Letters' (1976) pp. 499-502. Chemical Society of Japan.
Hopf, J.U.G. et al. 'Minature Endoscopes in Otorhinolaryngologic Applications' Min Invas Ther & Allied Technol. (1998) vol. 7, No. 3, pp. 209-218.
Hosemann, W. et al. A Dissection Course on Endoscopic Endonasal Sinus Surgery (2005) Endo-Press, Tuttlingen pp. 4-37.
Hosemann, W. et al. 'Endonasal Frontal Sinusotomy in Surgical Management of Chronic Sinusitis: A Critical Evaluation' American Journal of Rhinology. vol. 11, No. 1 (1997) pp. 1-9.

Hosemann, M.E. et al. 'Experimental investigations on wound healing of the paranasal sinuses. II. Spontaneous wound closure and pharmacological effects in standardized animal model.' HNO 39 (1991) pp. 48-54.
Hosemann, W.G. et al. 'Minimally Invasive Endonasal Sinus Surgery' Thieme, Stuttgart, New York (2000).
Hosemann, M.E. et al. 'Normal Wound Healing of the Paranasal Sinuses—Clinical and Experimental Investigations' Eur Arch Otorhinolaryngol. vol. 248, (1991) pp. 390-394.
Hosemann, W. et al. 'Behandlung nach Nasennebenhohleneingriffen, part 2: Theapeutische Maβnahem' HNO akutell 7 (1999) pp. 291-302.
Hospital Corpsman Sickcall Screener's Handbook. Naval Hospital Great Lakes (Apr. 1999) www.brooksidepress.org/Products/Operationa. Medicine/DATA. 2001 pp. 1-6.
Hybels, R.L. 'Transillumination Durning Osteoplastic Frontal Sinusotomy' The Laryngoscope. vol. 91 (Sep. 1981) pp. 1560.
Ijaduola, T.G.A. 'Use of a Foley Catheter for Short-Term Drainage in Frontal Sinus Surgery' Ther Journal of Laryngology and Otology. (1989) vol. 103. pp. 375.378.
Ingals, E.F. 'New Operation and Instruments for Draining the Frontal Sinus' Ann. Otol. Rhinol. Layyngol. vol. 14 (1905) pp. 644-649.
Iro, H. et al., 'A New Device for Frontal Sinus Endoscopy: First Clinical Report' Otolaryngol. Head Neck Surg. (2001) vol. 125 No. 6 pp. 613-616.
Jacobs, J.B. '100 Years of Frontal Sinus Surgery' Laryngoscope. vol. 107 (1997) pp. 1-36.
K-Splints Internal Nasal Splints; Jan. 25, 2007; www.invotec.net/rhinology/ksplint.html.
Kaiser, H. et al 'Cortizontherapie, Corticoide in Klinik und Praxis' Thieme, Stuggart (1992) pp. 390-401.
Kennedy, D.W., M.D. et al. 'Diseases of the Sinuses: Diagnosis and Management' (Copyright 2001) by B.C. Decker Inc.
Khomutov, S.M. et al. 'Dissolution of a Mixture of Steroids in Cyclodextrin Solutions: a Model Description' Pharmaceutical Chemistry Journal. vol. 35, No. 11 (Nov. 2001) pp. 627-629.
Kingdom, T.T. et al. 'Image-Guided Surgery of the Sinuses: Current Technology and Applications' Otolaryngol. Clin. North Am. vol. 37, No. 2 (Apr. 2004) pp. 381-400.
Klossek, J.M. et al. 'Local Safety of Intranasal Trimcinolone Acentonide: Clinical and Histological Aspects of Nasal Mucosa in the Long-Term Treatment of Perennial Allergic Rhinitis' Rhinology. vol. 39, No. 1 (2001) pp. 17-22.
Kozlov et al. 'Diagnosis and Treatment of Sinusitis by YAMIK Sinus Catheters' Rhinology (1996) vol. 34, pp. 123-124.
Kuhn, et al. 'The Agger Nasi Cell in Frontal Recess Obstruction: An Anatomic, Radiology and Clinical Correlation' Operative Techniques in Otolaryngology—Head and Neck Surgery. vol. 2, No. 4 (1991) pp. 226-231.
Laliberte, F. et al. 'Clinical and Pathologic Methods to Assess the Long-Term Safety of Nasal Corticosteroids' Allergy. vol. 55, No. 8 (2000) pp. 718-722.
Lang, E.V., et al., 'Access Systems for Puncture at an Acute Angle' J. Vasc. Interv. Radiol. (1995) vol. 6, No. 5, pp. 711-713.
Lanza, D.C. 'Postoperative Care and Avoiding Frontal Recess Stenosis' International Advanced Sinus Symposium (1993) Jul. 21-24.
Large, G.C. 'Crystalline Tetracycline Hydrochloride in the Treatment of Acute and Chronic Maxillary Sinusitis' Canad. M.A.J. (1958) vol. 79, pp. 15-16.
Lund, V.J. 'Maximal Medical Therapy for Chronic Rhinosinusitis' Otolaryngol Clin N. Am. vol. 38 (2005) pp. 1301-1310.
Maran, A.G.D. et al. 'The Use of the Foley Balloon Catheter in the Tripod Fracture' J. Laryngol. Otol. (1971) vol. 85, Issue 9, pp. 897-902.
May, M. et al. 'Frontal Sinus Surgery: Endonasal Drainage Instead of an External Osteopolstic Approach' Op Tech Otolaryngo Head Neck Surgery. 6 (1995) pp. 184-192.
Medtronic, xomed.com—MicroFrance Catalog Browser. www.xomcat.com/xomfrance/index.php?zone=both&cat=58&prodline=1272 (Dec. 31, 2003) pp. 1-2.

(56) References Cited

OTHER PUBLICATIONS

Mehan, V.K. et al., 'Coronary Angioplasty through 4 French Diagnostic Catheters' Cathet. Cardiovasc. Diagn. (1993) vol. 30, No. 1 pp. 22-26.
Mellor, J.M. et al 'Synthesis of Trifluoromethylnaphthalenes' Tetrahedron. vol. 56 (2000) pp. 10067-10074. Elsevier Science Ltd.
Metson, R., et al., 'Endoscopic Treatment of Sphenoid Sinusitis' Otolaryngol. Head Neck Surg. (1996) vol. 114, No. 6 pp. 736-744.
Metson, R. 'Holmium: YAG Laser Endoscopic Sinus Surgery: A Randomized Controlled Study' Laryngoscope. vol. 106, Issue 1, Supplement 77 (Jan. 1996) pp. 1-18.
Miller, et al. 'Management of Fractures of the Supraorbital Rim' Journal of Trauma. vol. 18, No. 7 (Jul. 1978) pp. 507-512.
Min, Y-G et al. 'Mucociliary Activity and Histopathology of Sinus Mucosa in Experimental Maxilary Sinusitis: A Comparison of Systemic Administration of Antibiotic and Antibiotic Delivery of Polylactic Acid Polymer' Laryngoscope. vol. 105 (Aug. 1995) pp. 835-842.
Mols, B. 'Movable Tool Tip for Keyhole Surgery' Delft Outlook, vol. 3 (2005) pp. 13-17.
Mooney, M.R., et al., 'Monorail™ Piccolino Catheter: A New Rapid Exchange/Ultralow Profile Coronary Antioplasty System' Cathet. Cardiovasc. Diagn. (1990) vol. 20, No. 2 pp. 114-119.
Moriguchi, T. et al. 'Additional-Elimination Reaction in the Trifluoroacetylation of Electron-Rich Olefins' J. Org. Chem. vol. 60, No. 11 (1995) pp. 3523-3528. American Chemical Society.
Nasal Surgery and Accessories, Jan. 25, 2007; www.technologyforlife.com.au/ent/nasal.html.
Park, K. et al. 'Biodegradable Hydrogels for Drug Delivery' (1993) Technomic Publishing Inc. Lancaster.
Piccirillo, J.F. et al. 'Physchometric and Clinimetric Validity of the 20-Item Sino-Nasal Outcome test (SNOT-20)' Copyright 1996 Washington University, St. Louis, MO.
Piers, et al. 'A Flexible Distal Tip with Two Degrees of Freedon for Enhanced Dexterity in Endoscopic Robot Surgery' Proceedings 13th Micromechanics Europe Workshop (2002) pp. 271-274.
Podoshin, L et al. 'Balloon Technique for Treatment of Frontal Sinus Fractures' The journal of Laryngology & Otology (1967), vol. 81. pp. 1157-1161.
Pownell, P.H. et al., 'Diagnostic Nasal Endoscopy' plastic & Reconstructive Surgery (1997) vol. 99, Iss5 pp. 1451-1458.
Prince, et al. 'Analysis of the Intranasal Distribution of Ointment' J Otolaryngol. vol. 26 (1997) pp. 357-360.
Ramsdale, D.R., Illustrated Coronary Intervention: A case-oriented approach, (2001) Martin Dunitz Ltd. pp. 1-5.
Ritter, F.N. et al., Atlas of Paranasal Sinus Surgery (1991) Igaku-Shoin Medical Pub. pp. 1-81.
Robison, J. Mathews, M.D. 'Pressure Treatment of Maxillary Sinusitis' J.A.M.A. (May 31, 1952) pp. 436-440.
Robison, J. Mathews, M.D. 'Pressure Treatment of Purulent Maxillary Sinusitis' Texas State Journal of Medicine (May 1952) pp. 281-288.
Sama, A., et al., 'Current Opinions on the Surgical Management of Frontal Sinus Disease' ENT News. Www.pinpointmedical.com/ent-news (2009) vol. 17, No. 6 pp. 60-63.
Sanborn, T.A. et al., 'Percutaneous Endocardial Transfer and Expression of Genes to the Myocardium Utilizing Fluropscopic Guidance' Catheter Cardiovasc. Interv. (2001) vol. 52, No. 2 pp. 260-266.
Sawbones Catalog 2001, Pacific Research Laboratories, Inc., Vashon Washington 98070 USA.
Saxon, R.R. et al., 'Technical Aspects of Accessing the Portal Vein During the TIPS Procedure' J. Vasc. Interv. Radiol. (1997) vol. 8, No. 5 pp. 733-744.
Schaefer, S.D., M.D. 'Rhinology and Sinus Disease: A Problem-Oriented Approach' (Copyright 1988) by Mosby, Inc.
Schneider, Pfizer Ad for Softip [date of publication unknown].
Shah, N.J. et al., 'Endoscopic Pituitary Surgery—A Beginner's Guide' Indian Journal of Otolaryngology and Head and Neck Surgery (2004) vol. 56, No. 1 pp. 71-78.
Shah, N.J. 'Functional Endoscopic Sinus Surgery' (1999); found at bhj.org/journal/1999_4104_oct99/sp_659.htm.
Single-Pole and Multi-Pole Lightguides for UV Spot Light Curing Systems. Www.dymax.com/products/curing_equipment/lightguids/light. (2004) pp. 1-2.
Sobol, et al. 'Sinusitis, Maxillary, Acute Surgical Treatment.' eMedicine. Retrieved from the Internet: «http://emedicine.medscape.com/article/862030-print» (Nov. 16, 2010) pp. 1-11.
St. Croix, et al., 'Genes Expressed in Human Tumor Endothelium' Science (May 15, 2000) vol. 289 pp. 1197-1202.
Stammberger, H. 'Komplikationen entzundlicher Nasennebenhohlenerkrankungen eischließ iatrogen bedingter Komlikationen' Eur Arch Oti-Rhino-Laryngol Supple. (Jan. 1993) pp. 61-102.
Stammberger, et al. Chapter 3 'Special Endoscopic Anatomy of the Lateral Nasal Wall and Ethmoidal Sinuses' Functional Endoscopic Sinus Surgery. (1991) Ch. 3, pp. 49-87.
Strom, et al. Die Behandlung von Stenosen der oberen Luftwege mittels rontgenologisch gesteurter Ballondilation (Sep. 25, 1999) pp. 1-4.
Strohm, et al. 'Treatment of Stenoses of the Upper Airways by Balloon Dilation' Sudwestdeutscher Abstract 45 (Sep. 25, 1999) pp. 1-3.
Suh, Paranasal Sinuses: Sagittal Anatomy with CT Images. http://ws.ajou.ac.kr/~ent/mew/case_topic/RHINODATA/sagittalIPNS.htm. May 18, 1998. Accessed Feb. 20, 2015.
SurgTrainer Product Information 'Incisive Human Nasal Model for ESS Training' Surg Trainer, Ltd. Ibaraki, Japan (2004) www1.accsnet.ne.jp/~juliy/st/en/partslist.html.
Tabor, M.H. et al., 'Symptomatic Bilateral Duct Cysts in a Newborn—Rhinoscopic Clinic' Ear, Nose & Throat Journal (2003) www.findarticles.com/p/articles/mi_m0BUM/is_2_82/ai_98248244 pp. 1-3.
Tarasov, D.I. et al. 'Application of Drugs Based on Polymers in the Treatment of Acute and Chronic Maxillary Sinusitis' Vestn Otorinoloaringol. vol. 6 (1978) pp. 45-47.
Terumo, Medi-Tech. Boston Scientific. (1993) Ad of Glidewire.
The Operating Theatre Journal (www.otjonline.com) 'Disposable Medical Device for Wound Disclosure/The Tristel Purple Promotion—A Collaboration between Tristel PLC and Karl Storz Ednoscopy (UK) Ltd.' p. 4.
Weber, R. et al. 'Endonasale Stirnhohlenchirugie mit Langzeiteinlage eines Platzhalters' Laryngol. Rhinol. Otol. vol. 76 (1997) pp. 728-734. (English Abstract).
Weber, R. et al., 'Videoendoscopic Analysis of Nasal Steroid Distribution' Rhinology. vol. 37 (1999) pp. 69-73.
Weiner, R.I., D.O., et al., 'Development and Application of Transseptal Left Heart Catheterization' Cathet. Cardiovasc. Diagn. (1988) vol. 15, No. 2, pp. 112-120.
Wiatrak, B.J., et al., 'Unilateral Choanal Atresia: Initial Presentation and Endoscopic Repair' International Journal of Pediatric Otorhinolaryngology (1998) vol. 46, pp. 27-35.
Woog, et al. 'Paranasal Sinus Endoscopy and Orbital Fracture Repair' Arch Ophthalmol. vol. 116 (May 1998) pp. 688-691.
Wormald, P.J., et al., 'The 'Swing-Door' Technique for Uncinectomy in Endoscopic Sinus Surgery' The Journal of Laryngology and Otology (1998) vol. 112, pp. 547-551.
Xomed-Treace. Bristol-Myers Squibb. Ad for Laser Shield II. Setting the Standards for Tomorrow. [date of publication unknown].
Yamauchi, Y. et al., 'Development of a Silicone Model for Endoscopic Sinus Surgery' Proc International Journal of Computer Assisted Radiology and Surgery vol. 99 (1999) p. 1039.
Yamauchi, Y., et al., 'A Training System for Endoscopic Sinus Surgery with Skill Evaluation' Computer Assisted Radiology and Surgery (2001) with accompanying poster presentation.
Yanagisawa et al. 'Anterior and Posterior Fontanelles.' Ear, Nose & Throat Journal (2001) vol. 80, pp. 10-12.
Zimarino, M., M.D., et al., 'Initial Experience with the EuropassTM: A new Ultra-Low Profile Monorail Balloon Catheter' Cathet. Cardiovasc. Diagn. (1994) vol. 33, No. 1, pp. 76-79.
Australian Office Action, Examiners First Report dated Apr. 8, 2010 for Application No. AU 2005274794.
European Communication dated Sep. 4, 2008 for Application No. EP 05773189.

(56) References Cited

OTHER PUBLICATIONS

European Communication dated Jun. 19, 2009 for Application No. EP 05773189.
European Exam Report dated Feb. 22, 2006 for Application No. 02716734.5.
European Exam Report dated Feb. 8, 2007 for Application No. 02716734.5.
Supplemental European Search Report and Written Opinion dated Sep. 11, 2009 for Application No. EP 06815174.
European Search Report dated Sep. 27, 2011 for Application No. EP 10182961.
European Search Report dated Sep. 29, 2011 for Application No. EP 10182893.
Partial European Search Report dated Sep. 20, 2007 for Application No. EP 07252018.
Partial European Search Report dated Mar. 25, 2008 for Application No. EP 07252018.
Supplemental European Search Report dated Jun. 2, 2008 for Application No. EP 05773189.
Supplemental Partial European Search Report dated Jul. 1, 2009 for Application No. EP 06815285.
Supplemental European Search Report dated Jan. 29, 2010 for Application No. EP 07836108.
Supplemental European Search Report dated Feb. 2, 2010 for Application No. EP 07836109.
Supplemental European Search Report dated Feb. 17, 2010 for Application No. EP 07836110.
Supplemental European Search Report dated Mar. 1, 2010 for Application No. EP 05778834.
Supplemental European Search Report dated Mar. 16, 2010 for Application No. EP 06718986.
Supplemental European Search Report dated Jun. 22, 2010 for Application No. EP 06784759.
Supplemental European Search Report dated Sep. 23, 2010 for Application No. EP 08746715.
Supplemental Partial European Search Report dated Nov. 19, 2010 for Application No. EP 06751637.
Supplemental European Search Report dated Jan. 28, 2011 for Application No. EP 07777004.
Supplemental European Search Report dated Mar. 31, 2011 for Application No. EP 05798331.
Supplemental European Search Report dated Aug. 30, 2011 for Application No. EP 06800540.
Supplemental European Search Report dated Sep. 29, 2011 for Application No. EP 07750248.
International Preliminary Report on Patentability dated Aug. 7, 2006 for Application No. PCT/US05/25371.
International Preliminary Report on Patentability and Written Opinion dated Sep. 25, 2007 for Application No. PCT/US06/002004.
International Preliminary Report on Patentability and Written Opinion dated Nov. 18, 2008 for Application No. PCT/US07/11449.
International Preliminary Report on Patentability and Written Opinion dated Apr. 7, 2009 for Application No. PCT/US07/021170.
International Preliminary Report on Patentability and Written Opinion dated May 5, 2009 for Application No. PCT/US06/36960.
International Preliminary Report on Patentability and Written Opinion dated Oct. 13, 2009 for Application No. PCT/US08/059786.
International Preliminary Report on Patentability and Written Opinion dated Oct. 27, 2009 for Application No. PCT/US08/061343.
International Search Report dated Jun. 3, 2002 for Application No. PCT/EP02/01228.
International Search Report and Written Opinion dated Apr. 10, 2006 for Application No. PCT/US05/25371.
International Search Report dated May 8, 2007 for Application No. PCT/US2006/16026.
International Search Report and Written Opinion dated Aug. 17, 2007 for Application No. PCT/US05/13617.
International Search Report dated Aug. 29, 2007 for Application No. PCT/US06/002004.
International Search Report dated Sep. 25, 2007 for Application No. PCT/US06/37167.
International Search Report dated Oct. 19, 2007 for Application No. PCT/US07/03394.
International Search Report and Written Opinion dated May 29, 2008 for Application No. PCT/US07/021170.
International Search Report dated May 29, 2008 for Application No. PCT/US07/21922.
International Search Report and Written Opinion dated Jul. 1, 2008 for Application No. PCT/US06/22745.
International Search Report dated Jul. 3, 2008 for Application No. PCT/US2006/029695.
International Search Report dated Jul. 7, 2008 for Application No. PCT/US07/16213.
International Search Report dated Jul. 8, 2008 for Application No. PCT/US07/11474.
International Search Report dated Jul. 17, 2008 for Application No. PCT/US06/36960.
International Search Report and Written Opinion dated Jul. 21, 2008 for Application No. PCT/US05/33090.
International Search Report dated Aug. 25, 2008 for Application No. PCT/US2008/000911.
International Search Report dated Sep. 10, 2008 for Application No. PCT/US07/16212.
International Search Report and Written Opinion dated Sep. 12, 2008 for Application No. PCT/US07/16214.
International Search Report and Written Opinion dated Sep. 17, 2008 for Application No. PCT/US08/059786.
International Search Report and Written Opinion dated Sep. 17, 2008 for Application No. PCT/US08/061343.
International Search Report and Written Opinion dated Oct. 1, 2008 for Application No. PCT/US07/11449.
International Search Report dated Oct. 15, 2008 for Application No. PCT/US2008/061048.
International Search Report dated Nov. 30, 2009 for Application No. PCT/US2009/057203.
International Search Report dated Dec. 10, 2009 for Application No. PCT/US2009/052236.
International Search Report dated Dec. 15, 2009 for Application No. PCT/US2009/050800.
International Search Report dated Mar. 31, 2010 for Application No. PCT/US2009/069143.
International Search Report dated Jul. 8, 2010 for Application No. PCT/US2010/027837.
International Search Report and Written Opinion dated Oct. 6, 2010 for Application No. PCT/US2010/040548.
International Search Report dated Mar. 25, 2011 for Application No. PCT/US2010/062161.
International Search Report dated Mar. 28, 2011 for Application No. PCT/US2010/061850.
International Search Report dated Mar. 31, 2011 for Application No. PCT/US2010/060898.
International Search Report dated Aug. 9, 2011 for Application No. PCT/US2011/038751.
International Search Report dated May 18, 2012 for Application No. PCT/US2011/052321.
International Search Report and Written Opinion dated May 15, 2014 for Application No. PCT/US2014/021842.
International Preliminary Report on Patentability dated Sep. 15, 2015 for Application No. PCT/US2014/021842.
USPTO Office Action dated Sep. 16, 2005 for U.S. Appl. No. 10/259,300.
USPTO Office Action dated Jul. 7, 2006 for U.S. Appl. No. 10/259,300.
USPTO Office Action dated Feb. 13, 2007 for U.S. Appl. No. 10/259,300.
USPTO Office Action dated Oct. 9, 2007 for U.S. Appl. No. 10/259,300.
USPTO Office Action dated Jan. 24, 2008 for U.S. Appl. No. 10/259,300.
USPTO Office Action dated Oct. 6, 2008 for U.S. Appl. No. 10/259,300.

(56) References Cited

OTHER PUBLICATIONS

USPTO Office Action dated May 29, 2007 for U.S. Appl. No. 10/912,578.
USPTO Office Action dated Nov. 14, 2007 for U.S. Appl. No. 10/912,578.
USPTO Office Action dated Dec. 10, 2007 for U.S. Appl. No. 10/912,578.
USPTO Office Action dated Oct. 18, 2007 for U.S. Appl. No. 11/037,548.
USPTO Office Action dated Dec. 6, 2007 for U.S. Appl. No. 11/037,548.
USPTO Office Action dated Apr. 9, 2008 for U.S. Appl. No. 11/037,548.
USPTO Office Action dated Nov. 28, 2007 for U.S. Appl. No. 11/234,395.
USPTO Office Action dated Sep. 12, 2008 for U.S. Appl. No. 10/829,917.
USPTO Office Action dated Nov. 17, 2008 for U.S. Appl. No. 10/829,917.
USPTO Office Action dated Mar. 18, 2009 for U.S. Appl. No. 10/829,917.
USPTO Office Action dated Nov. 9, 2009 for U.S. Appl. No. 10/829,917.
USPTO Office Action dated Oct. 29, 2008 for U.S. Appl. No. 11/347,147.
USPTO Office Action dated Feb. 4, 2009 for U.S. Appl. No. 11/347,147.
USPTO Office Action dated Aug. 6, 2009 for U.S. Appl. No. 11/347,147.
USPTO Office Action dated Nov. 7, 2008 for U.S. Appl. No. 10/944,270.
USPTO Office Action dated Jan. 28, 2009 for U.S. Appl. No. 10/944,270.
USPTO Office Action dated Apr. 21, 2009 for U.S. Appl. No. 10/944,270.
USPTO Office Action dated Nov. 17, 2008 for U.S. Appl. No. 12/117,582.
USPTO Office Action dated Mar. 3, 2009 for U.S. Appl. No. 12/117,582.
USPTO Office Action dated Aug. 6, 2009 for U.S. Appl. No. 12/117,582.
USPTO Office Action dated Nov. 17, 2008 for U.S. Appl. No. 12/118,931.
USPTO Office Action dated Mar. 4, 2009 for U.S. Appl. No. 12/118,931.
USPTO Office Action dated Jul. 30, 2009 for U.S. Appl. No. 12/118,931.
USPTO Office Action dated Nov. 25, 2008 for U.S. Appl. No. 12/117,961.
USPTO Office Action dated Aug. 6, 2009 for U.S. Appl. No. 12/117,961.
USPTO Office Action dated Dec. 5, 2008 for U.S. Appl. No. 12/120,902.
USPTO Office Action dated Oct. 21, 2009 for U.S. Appl. No. 12/120,902.
USPTO Office Action dated Mar. 17, 2009 for U.S. Appl. No. 11/960,127.
USPTO Office Action dated Mar. 23, 2009 for U.S. Appl. No. 11/804,309.
USPTO Office Action dated Nov. 17, 2008 for U.S. Appl. No. 11/926,326.
USPTO Office Action dated Aug. 28, 2009 for U.S. Appl. No. 11/150,847.
U.S. Appl. No. 11/789,705, filed Apr. 24, 2007.
U.S. Appl. No. 13/832,167, filed Mar. 15, 2013.
U.S. Appl. No. 13/837,104, filed Mar. 15, 2013.
U.S. Appl. No. 14/038,867, filed Sep. 27, 2013.
U.S. Appl. No. 14/197,436, filed Mar. 5, 2014.
U.S. Appl. No. 60/844,874, filed Sep. 15, 2006.
U.S. Appl. No. 60/922,730, filed Apr. 9, 2007.
U.S. Appl. No. 61/052,413, filed May 12, 2008.
U.S. Appl. No. 61/084,949, filed Jul. 30, 2008.
U.S. Appl. No. 61/725,523, filed Nov. 3, 2012.

\* cited by examiner

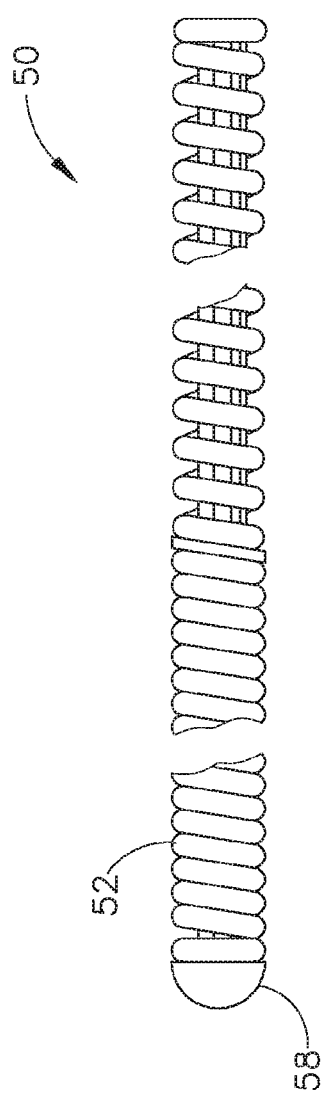
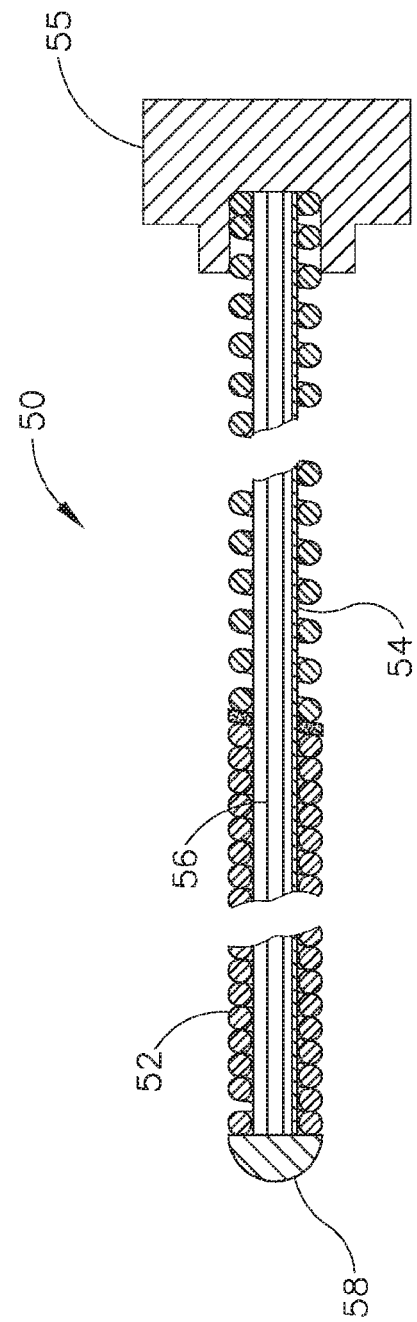
Fig.2
Fig.3

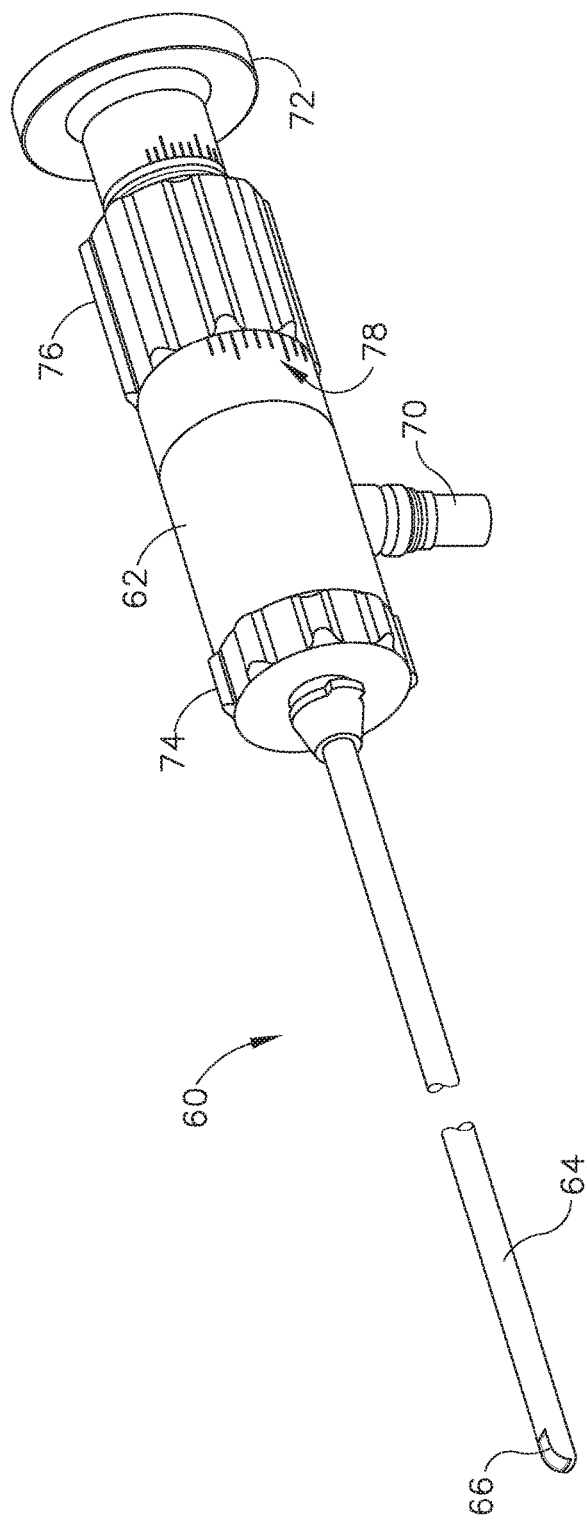
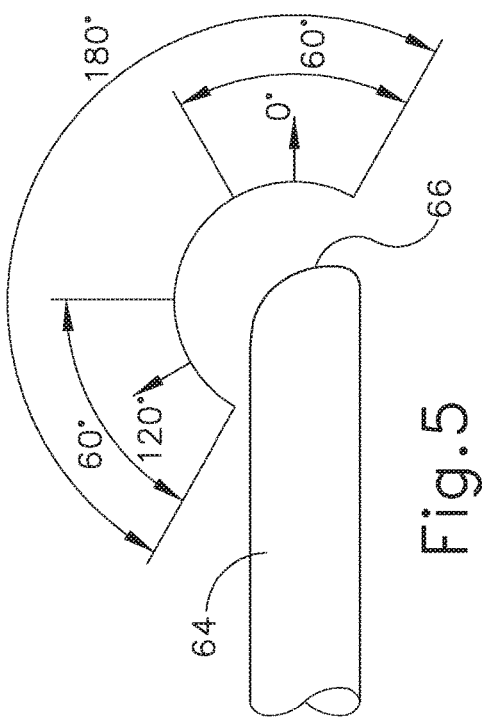
Fig.4
Fig.5

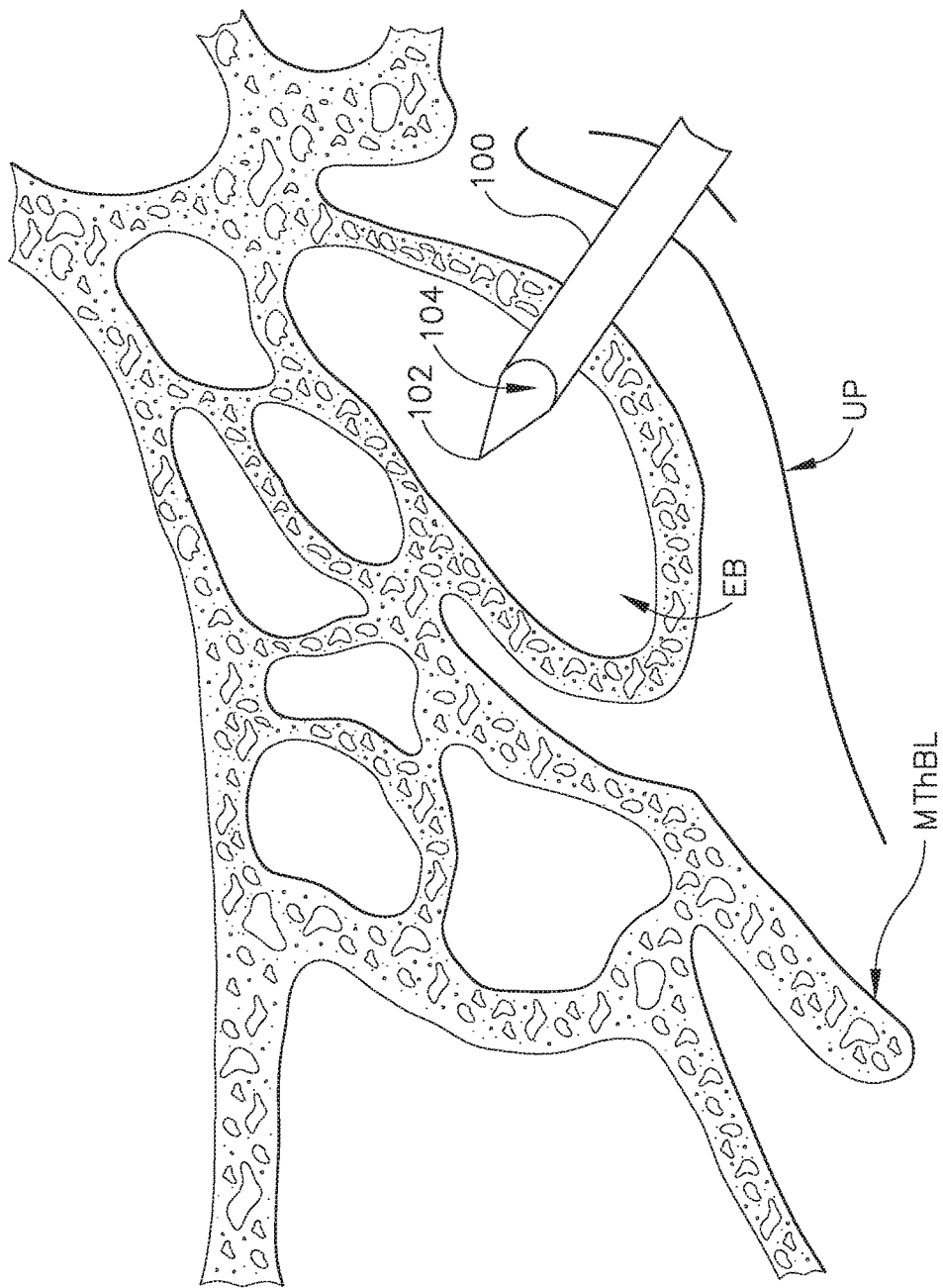

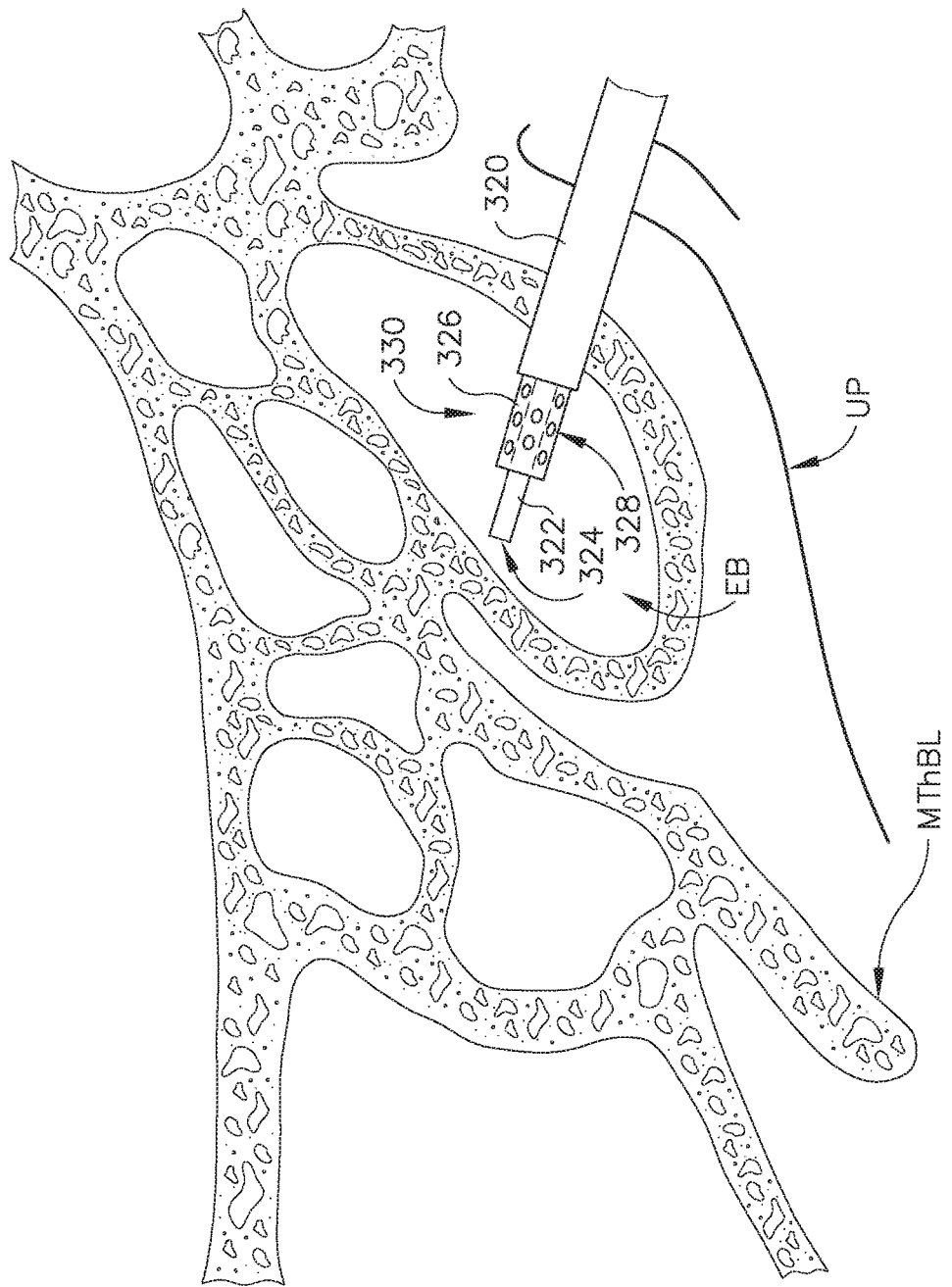

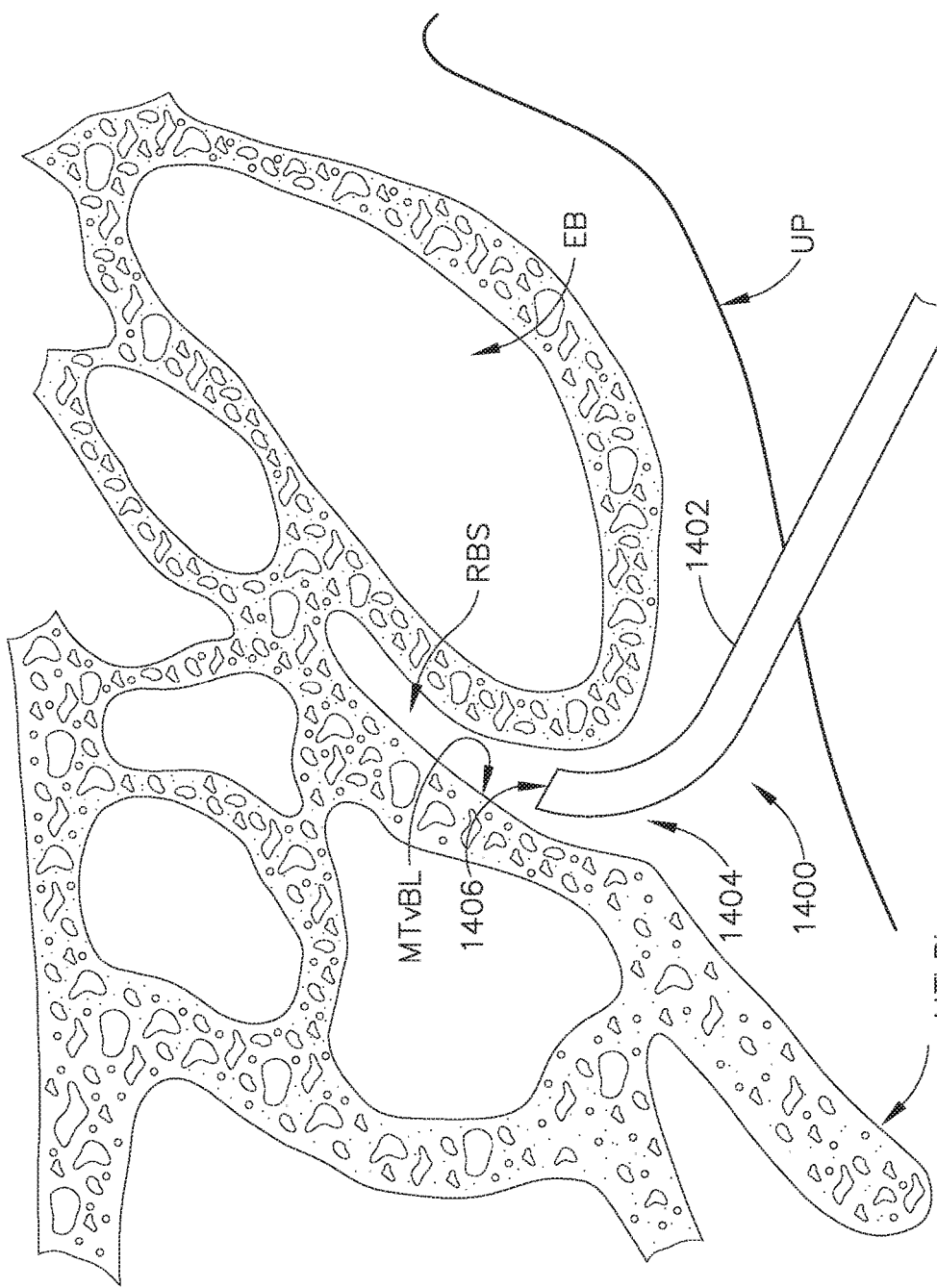

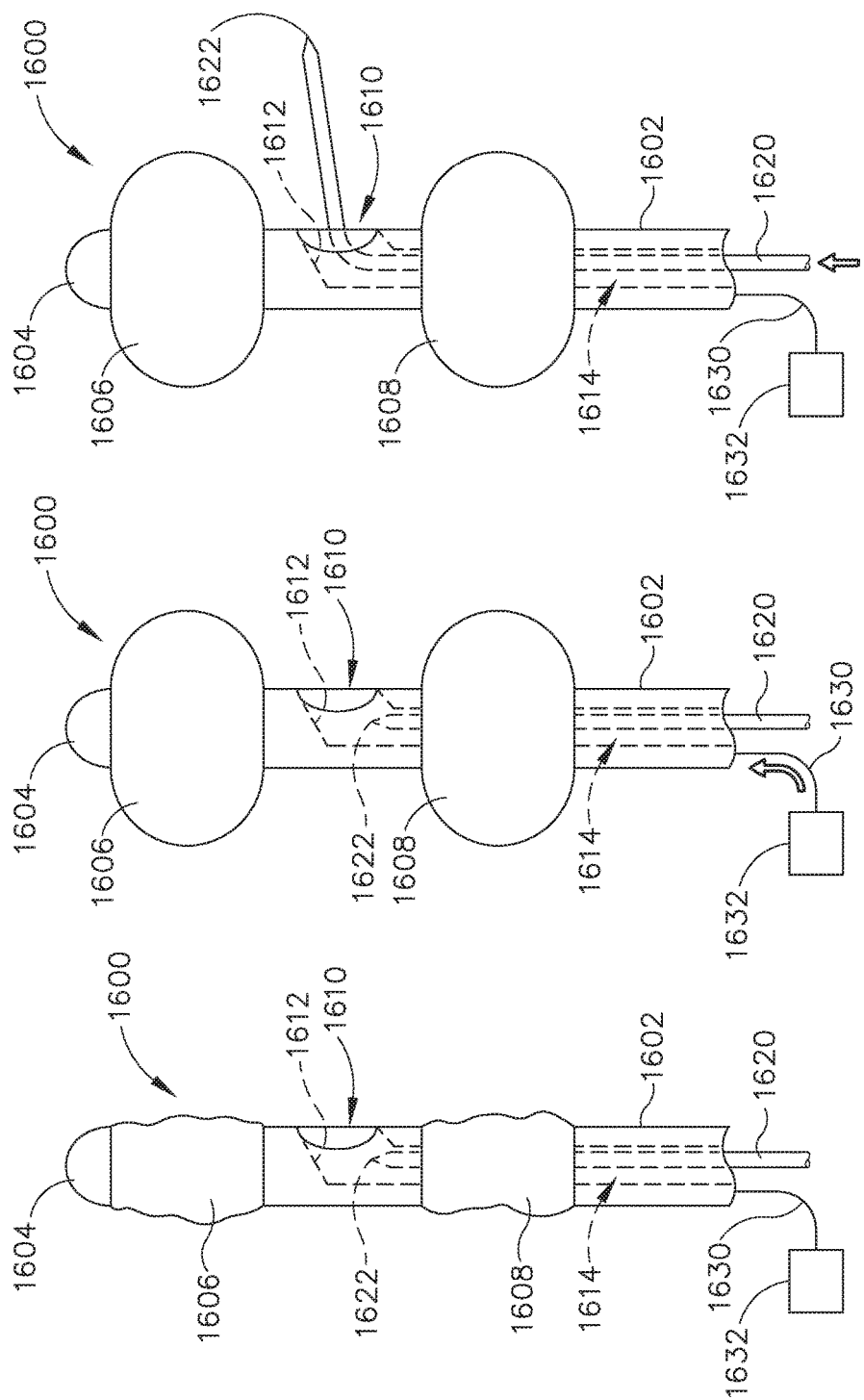

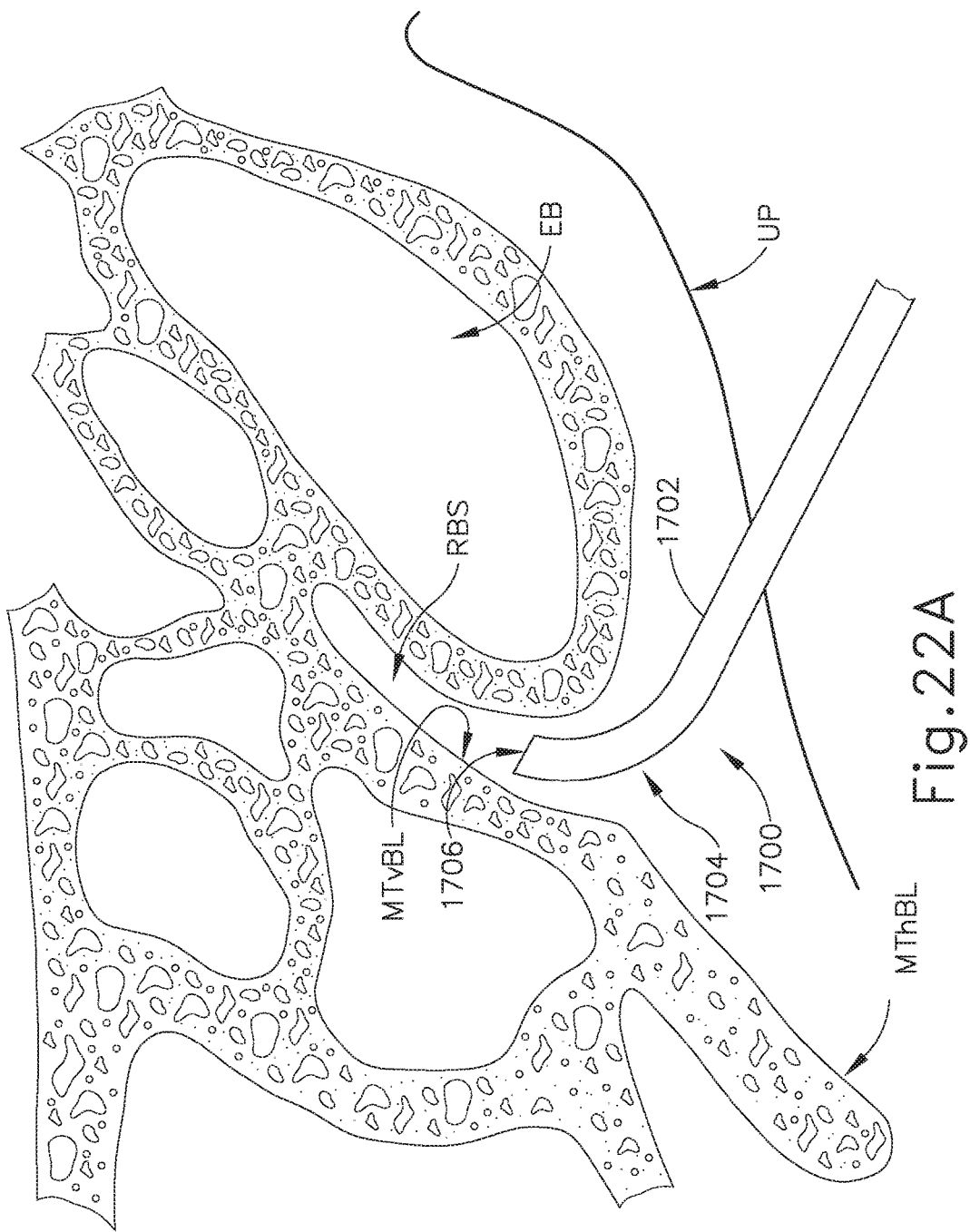

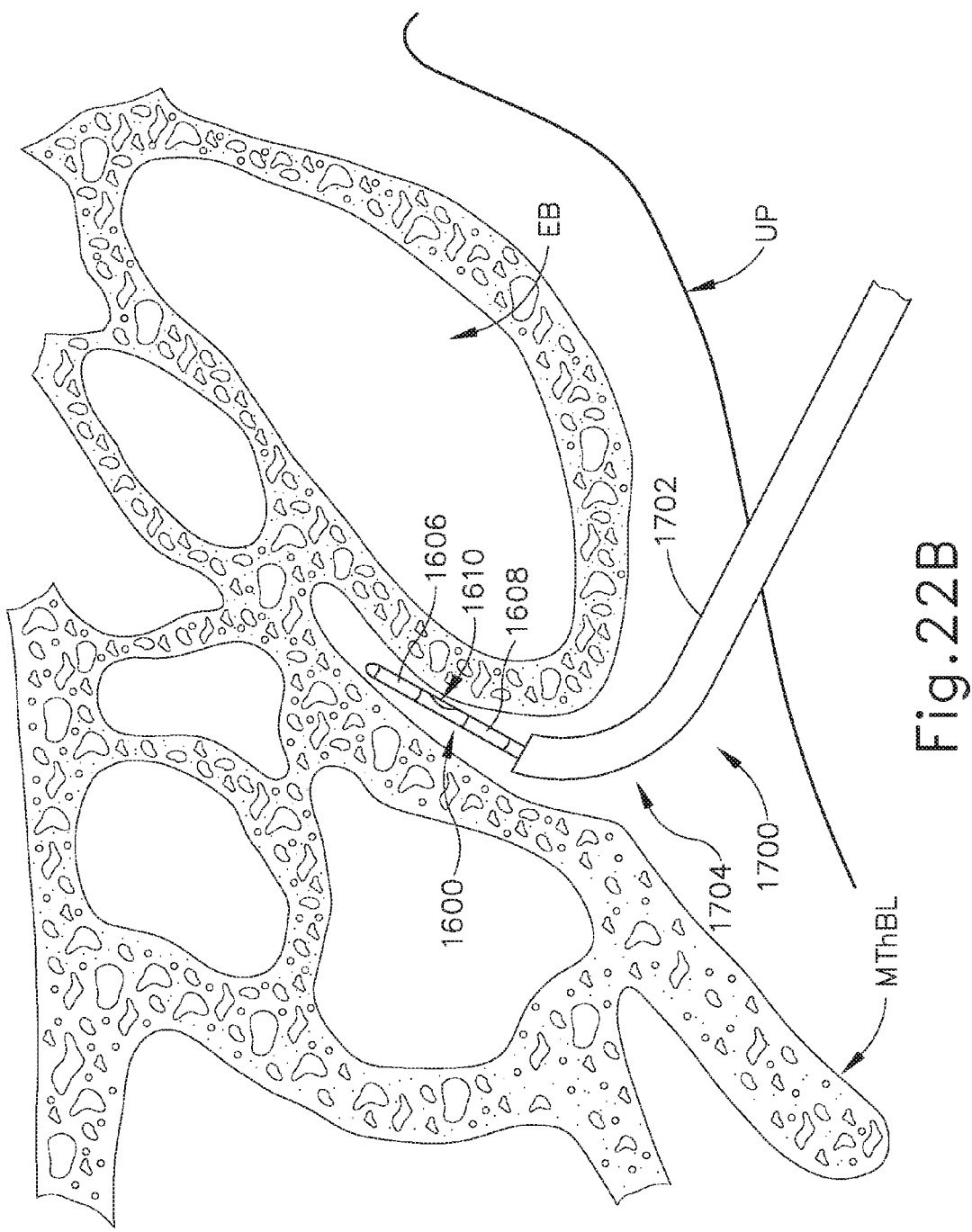

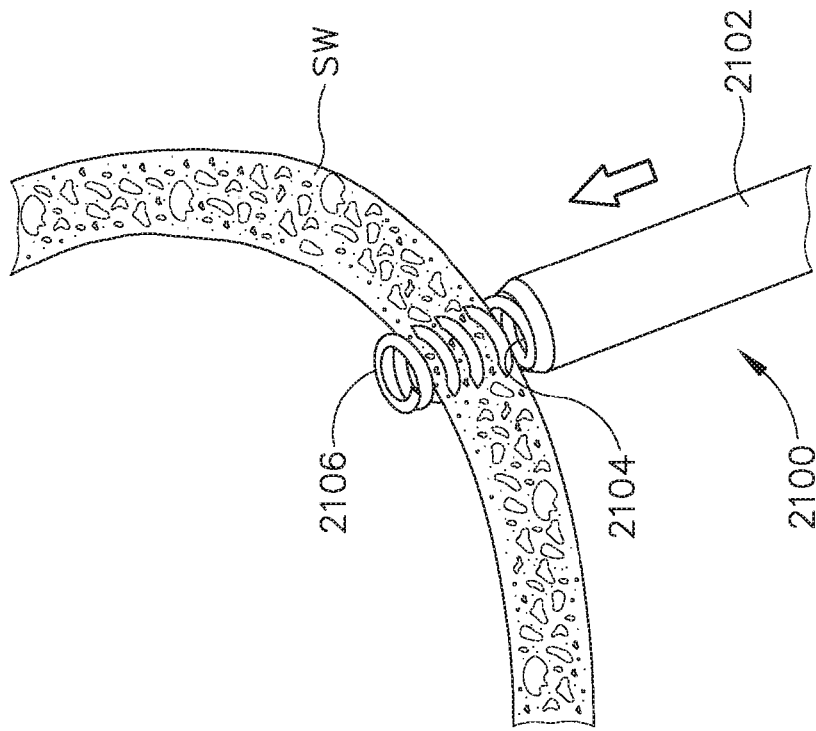
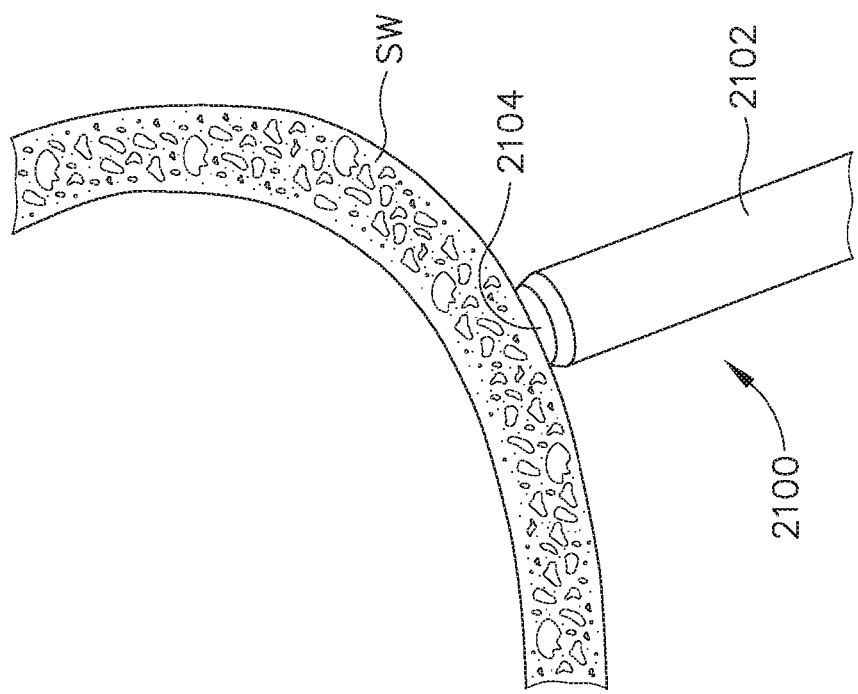

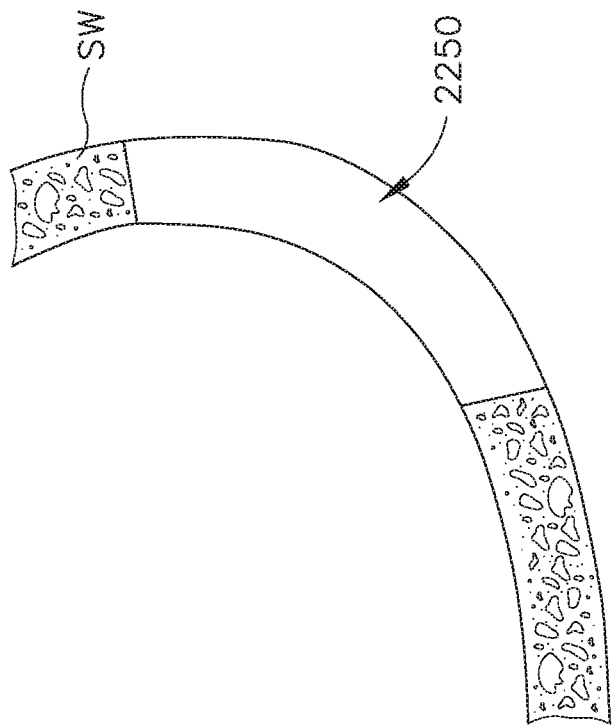
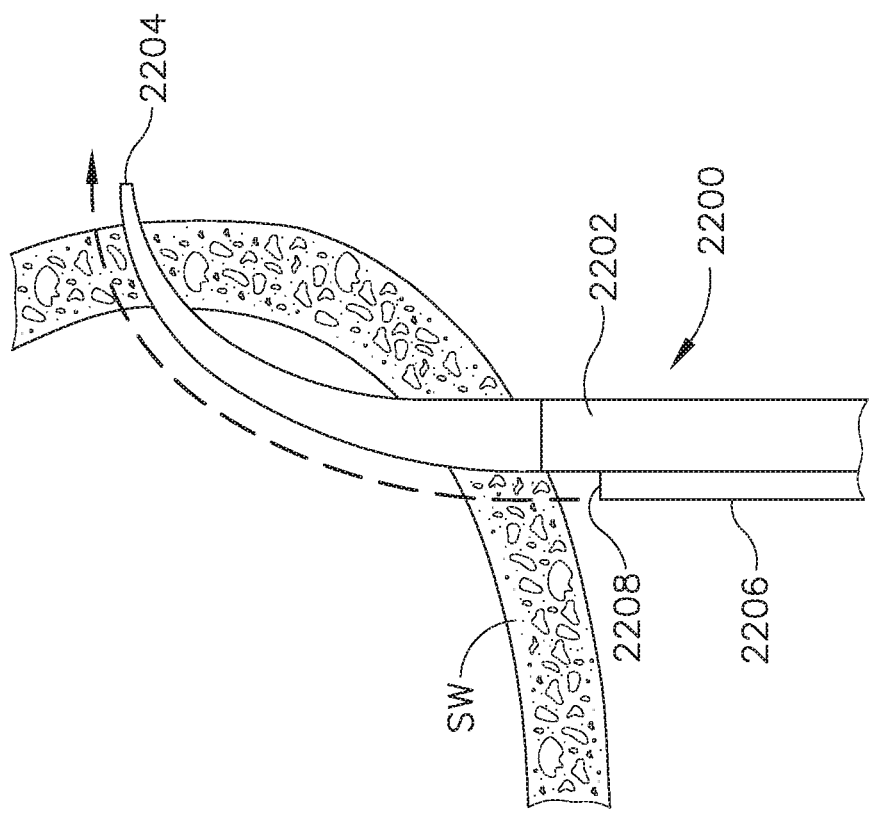

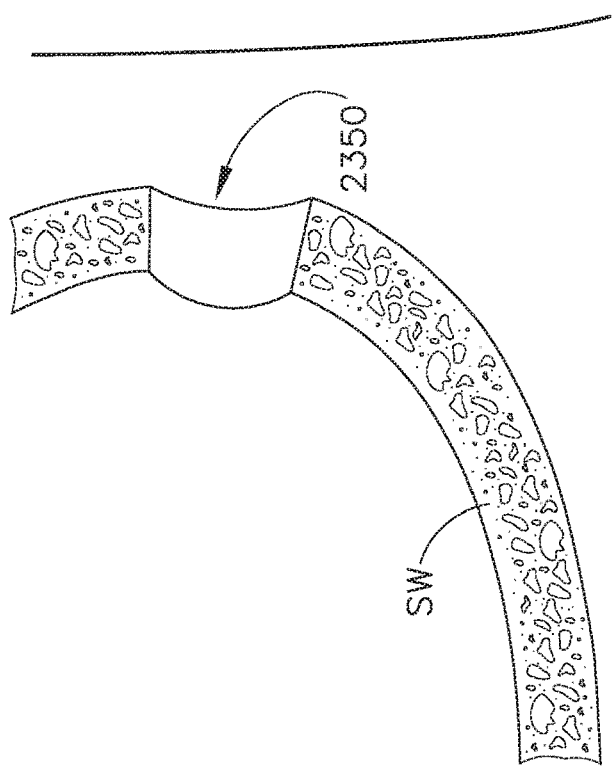
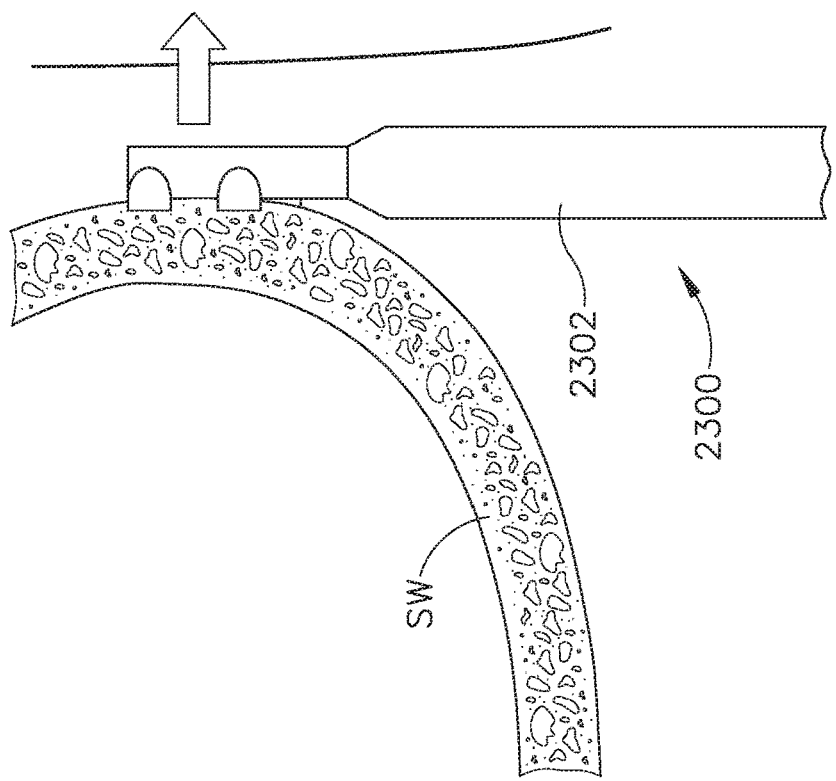
Fig.29D
Fig.29C

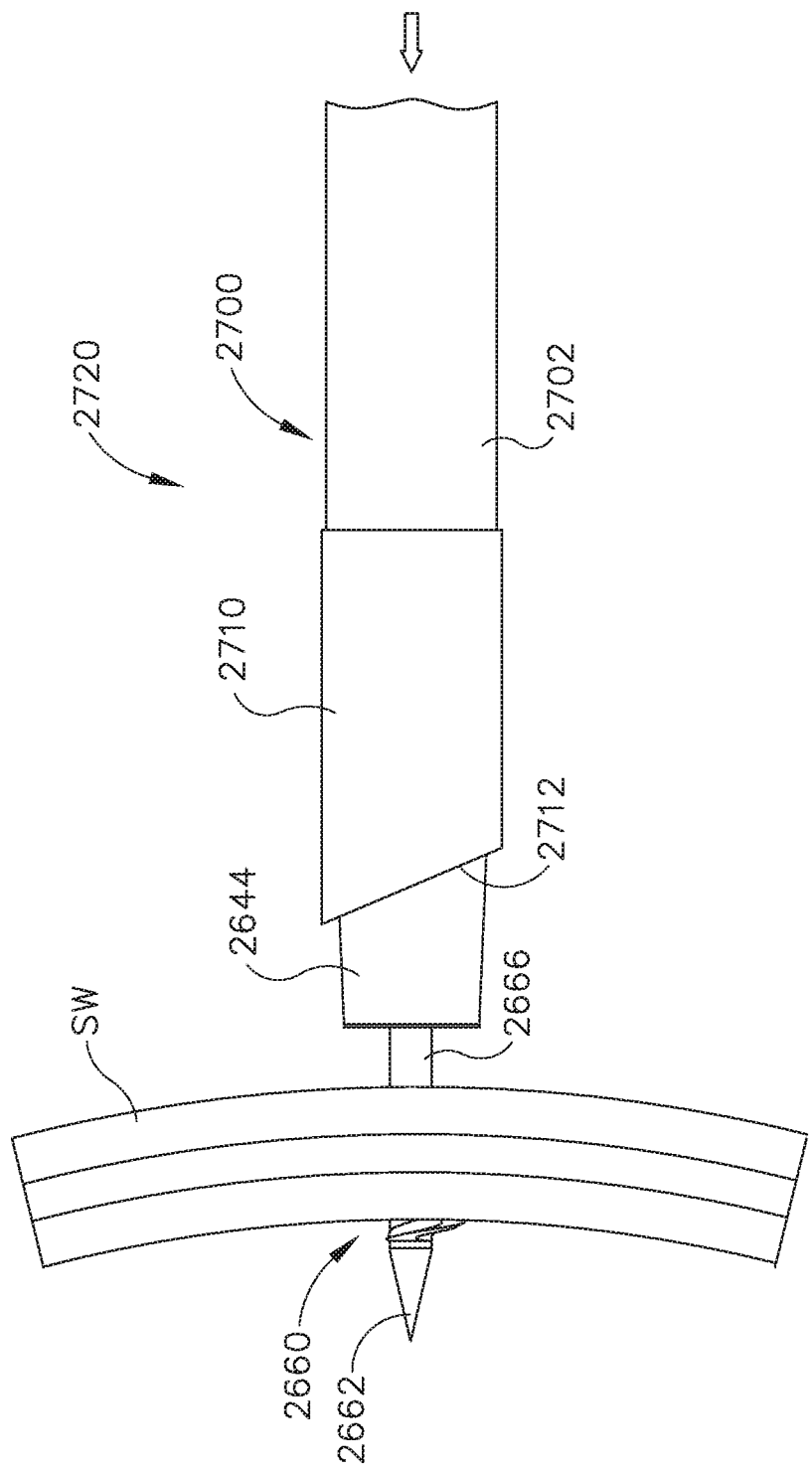

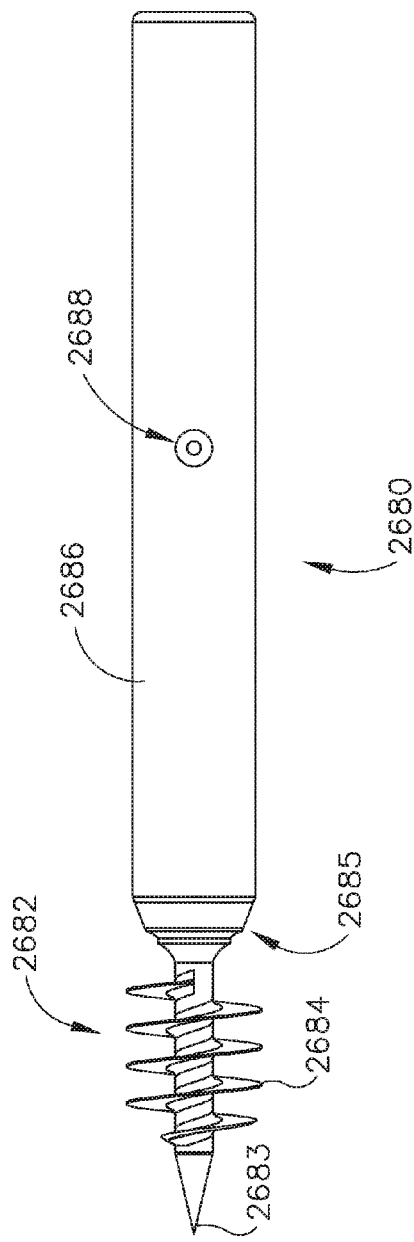
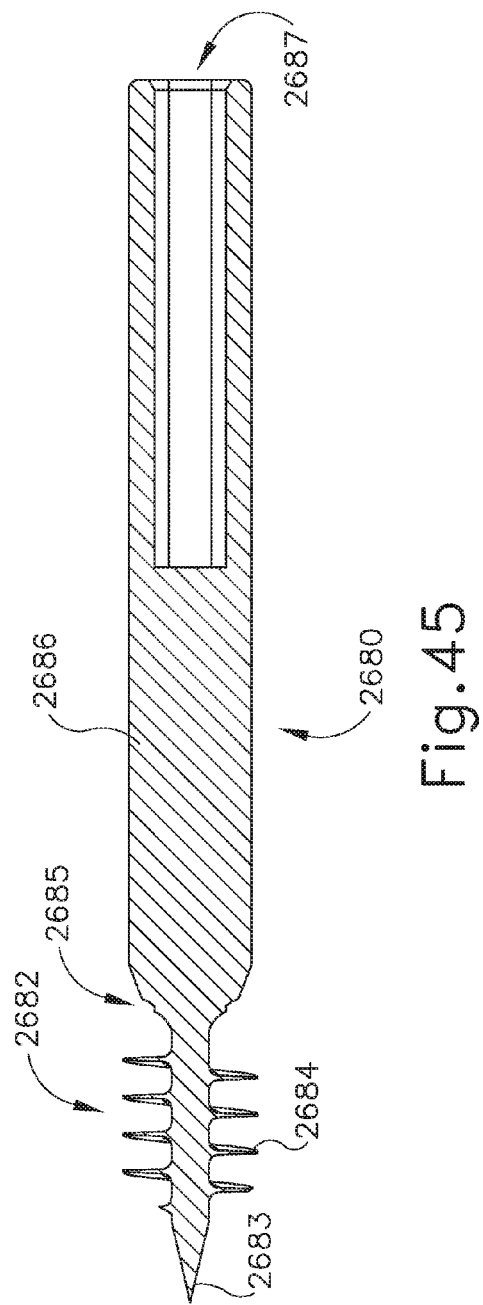

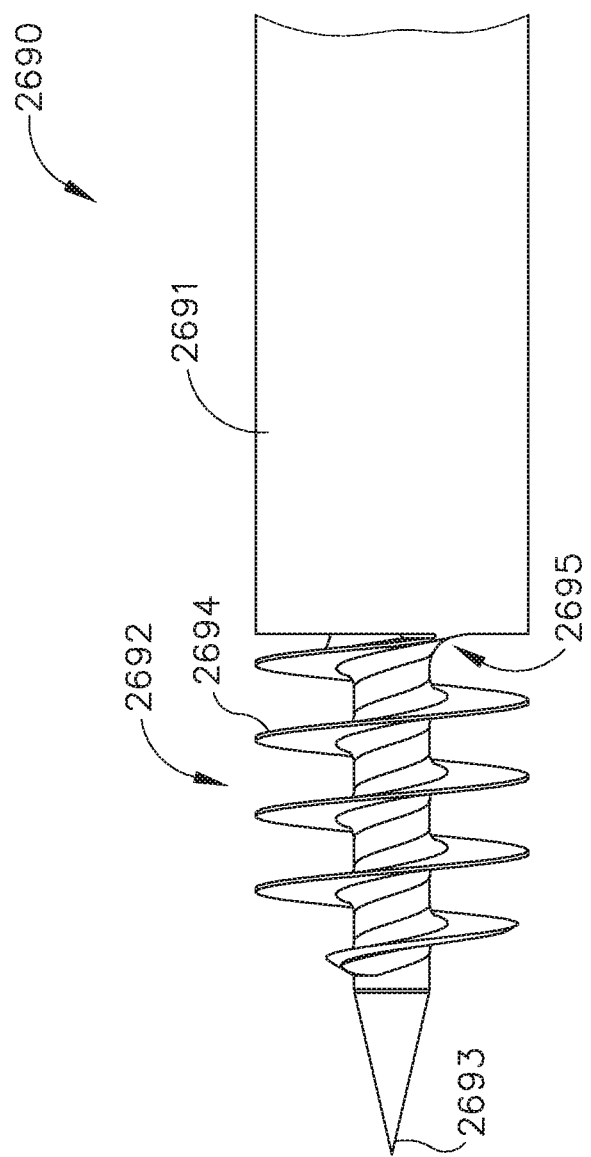

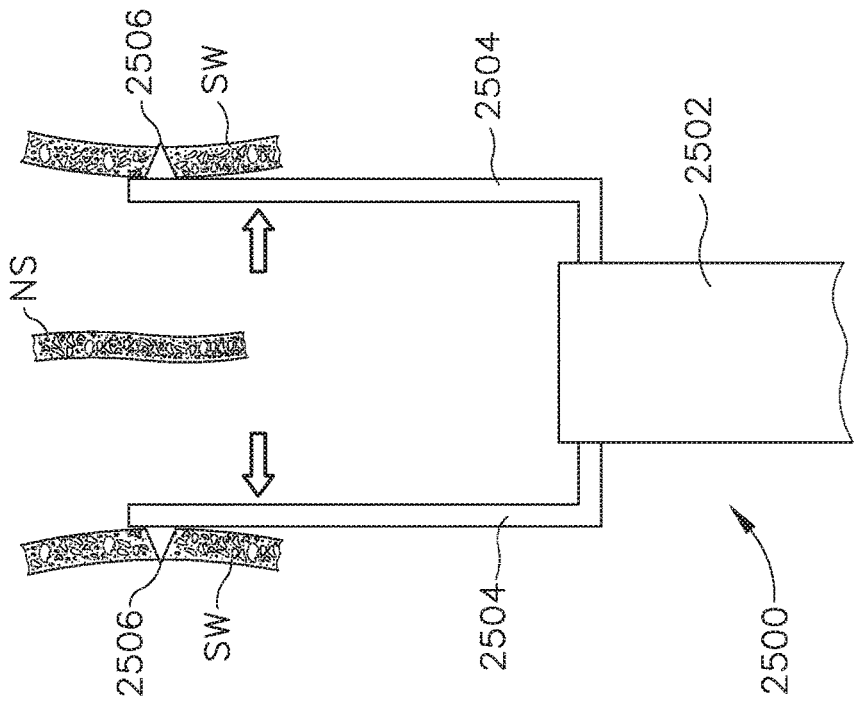
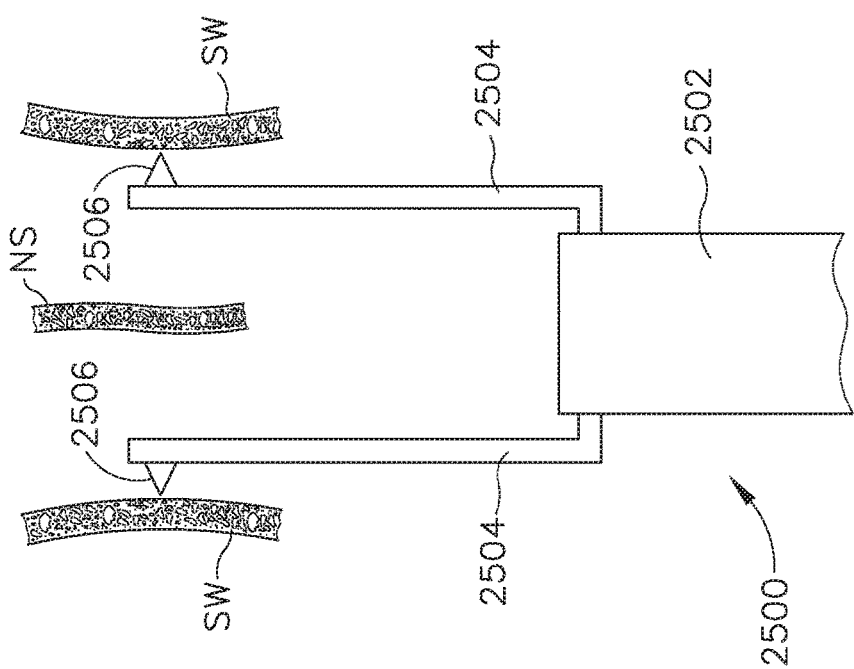

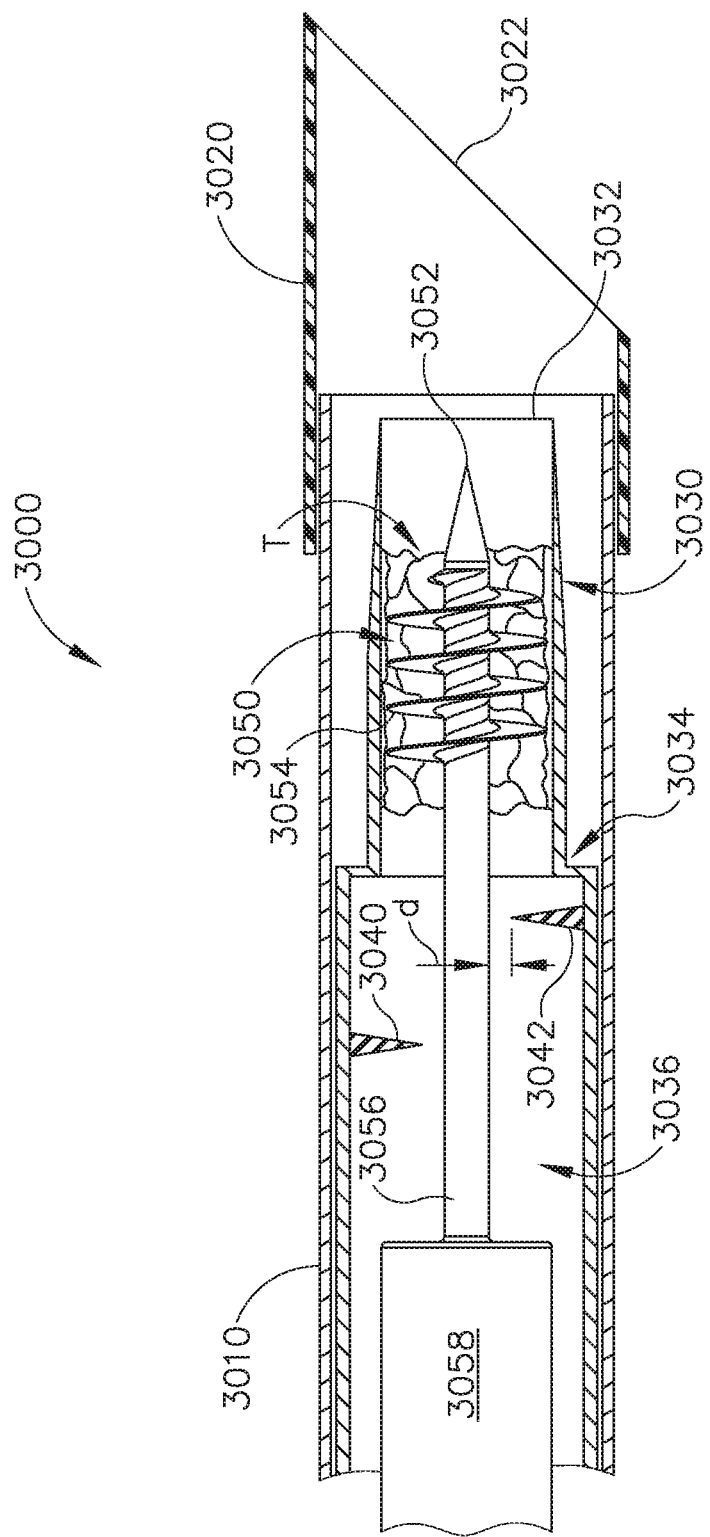

APPARATUS AND METHOD FOR TREATMENT OF ETHMOID SINUSITIS

PRIORITY

This application is a continuation of U.S. patent application Ser. No. 14/197,436, filed Mar. 5, 2014, entitled "Apparatus and Method for Treatment of Ethmoid Sinusitis," now U.S. Pat. No. 9,629,684, issued on Apr. 25, 2017, which is a continuation-in-part of U.S. patent application Ser. No. 14/038,867, filed Sep. 27, 2013, entitled "Apparatus and Method for Treatment of Ethmoid Sinusitis," published as U.S. Patent Pub. No. 2014/0277039 on Sep. 18, 2014, the disclosure of which is incorporated by reference herein, and which is a continuation-in-part of U.S. patent application Ser. No. 13/837,104, filed Mar. 15, 2013, entitled "Apparatus and Method for Treatment of Ethmoid Sinusitis," now U.S. Pat. No. 9,433,437, issued on Sep. 6, 2016, the disclosure of which is incorporated by reference herein.

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guide wire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, now abandoned, the disclosure of which is incorporated by reference herein. An example of such a system is the Relieva® Spin Balloon Sinuplasty™ System by Acclarent, Inc. of Menlo Park, Calif.

A variable direction view endoscope may be used with such a system to provide visualization within the anatomical passageway (e.g., the ear, nose, throat, paranasal sinuses, etc.) to position the balloon at desired locations. A variable direction view endoscope may enable viewing along a variety of transverse viewing angles without having to flex the shaft of the endoscope within the anatomical passageway. Such an endoscope that may be provided in accordance with the teachings of U.S. Pub. No. 2010/0030031, entitled "Swing Prism Endoscope," published Feb. 4, 2010, now abandoned, the disclosure of which is incorporated by reference herein. An example of such an endoscope is the Acclarent Cyclops™ Multi-Angle Endoscope by Acclarent, Inc. of Menlo Park, Calif.

While a variable direction view endoscope may be used to provide visualization within the anatomical passageway, it may also be desirable to provide additional visual confirmation of the proper positioning of the balloon before inflating the balloon. This may be done using an illuminating guidewire. Such a guidewire may be positioned within the target area and then illuminated, with light projecting from the distal end of the guidewire. This light may illuminate the adjacent tissue and thus be visible to the naked eye from outside the patient through transcutaneous illumination. For instance, when the distal end is positioned in the maxillary sinus, the light may be visible through the patient's cheek. Using such external visualization to confirm the position of the guidewire, the balloon may then be advanced distally along the guidewire into position at the dilation site. Such an illuminating guidewire may be provided in accordance with the teachings of U.S. Pub. No. 2012/0078118, entitled "Sinus Illumination Lightwire Device," published Mar. 29, 2012, now U.S. Pat. No. 9,155,492, issued on Oct. 13, 2015, the disclosure of which is incorporated by reference herein. An example of such an illuminating guidewire is the Relieva Luma Sentry™ Sinus Illumination System by Acclarent, Inc. of Menlo Park, Calif.

While several instruments and procedures have been made and used for treatment of anatomical passageways in a patient, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 2 depicts a side elevational view of an exemplary illuminating guidewire suitable for use with the dilation catheter system of FIG. 1:

FIG. 3 depicts a side cross-sectional view of the illuminating guidewire of FIG. 2;

FIG. 4 depicts a perspective view of an exemplary endoscope suitable for use with the dilation catheter system of FIG. 1;

FIG. 5 depicts a side elevational view of the distal end of the endoscope of FIG. 5, showing an exemplary range of viewing angles;

FIG. 7A depicts a left sagittal cross-sectional view of a portion of a human head, with an exemplary port deployment instrument piercing a wall of the ethmoid bulla;

FIG. 8C depicts a left sagittal cross-sectional view of a portion of a human head, with a suction and irrigation device positioned in the ethmoid bulla via the sheath of FIG. 8B;

FIG. 19B depicts a left sagittal cross-sectional view of a portion of a human head, with a guide catheter positioned at the retrobullar space;

FIG. 21A depicts a side elevational view of exemplary piercing catheter, with support balloons in a non-inflated state and with a piercing element in a retracted state;

FIG. 21B depicts a side elevational view of the piercing catheter of FIG. 21A, with the support balloons in an inflated state and with the piercing element in the retracted state;

FIG. 21C depicts a side elevational view of the piercing catheter of FIG. 21A, with the support balloons in an inflated state and with the piercing element in an advanced state:

FIG. 22A depicts a left sagittal cross-sectional view of a portion of a human head, with a guide catheter positioned at the retrobullar space;

FIG. 22B depicts a left sagittal cross-sectional view of a portion of a human head, with the piercing catheter of FIG. 21A advanced through the guide catheter into the retrobullar space;

FIG. 26A depicts an elevational view of the distal end of another exemplary alternative sinus wall piercing instrument positioned adjacent to a sinus wall, with the sinus wall in cross section, and with a piercing element in a retracted position;

FIG. 26B depicts an elevational view of the distal end of the piercing instrument of FIG. 26A, with the sinus wall in cross section, and with the piercing element advanced through the sinus wall;

FIG. 27C depicts an elevational view of the distal end of the piercing instrument of FIG. 27A, with the sinus wall in cross section, with the piercing element advanced through the sinus wall, and with the wall cutter being advanced toward the sinus wall;

FIG. 27D depicts a cross-sectional view of the sinus wall of FIG. 27A after completion of a procedure with the piercing instrument of FIG. 27A;

FIG. 29C depicts an elevational view of the distal end of the piercing instrument of FIG. 29A, with the sinus wall in cross section, with the instrument being pulled away from the sinus wall while the piercing elements are disposed in the sinus wall;

FIG. 29D depicts a cross-sectional view of the sinus wall of FIG. 29A after completion of a procedure with the piercing instrument of FIG. 29A;

FIG. 42D depicts a side elevational view of the shaft assembly of FIG. 36, incorporating the outer sheath assembly of FIG. 40, with the entire shaft assembly advanced to a third longitudinal position;

FIG. 44 depicts a side elevational view of an exemplary alternative auger shaft that may be used with the instrument of FIG. 32;

FIG. 45 depicts a side cross-sectional view of the auger of FIG. 44;

FIG. 46 depicts a detailed side elevational view of another exemplary alternative auger shaft that may be used with the instrument of FIG. 32;

FIG. 56A depicts an elevational view of the distal end of another exemplary alternative sinus wall piercing instrument positioned adjacent to a sinus wall, with the sinus wall in cross section, and with arms of the instrument in retracted positions;

FIG. 56B depicts an elevational view of the distal end of the piercing instrument of FIG. 43A, with the sinus wall in cross section, and with the arms of the instrument in laterally advanced positions;

FIG. 59A depicts a side cross-sectional view of the shaft assembly of FIG. 57, with tissue disposed on the auger member, and with the auger member at a distal position;

Figure 1:
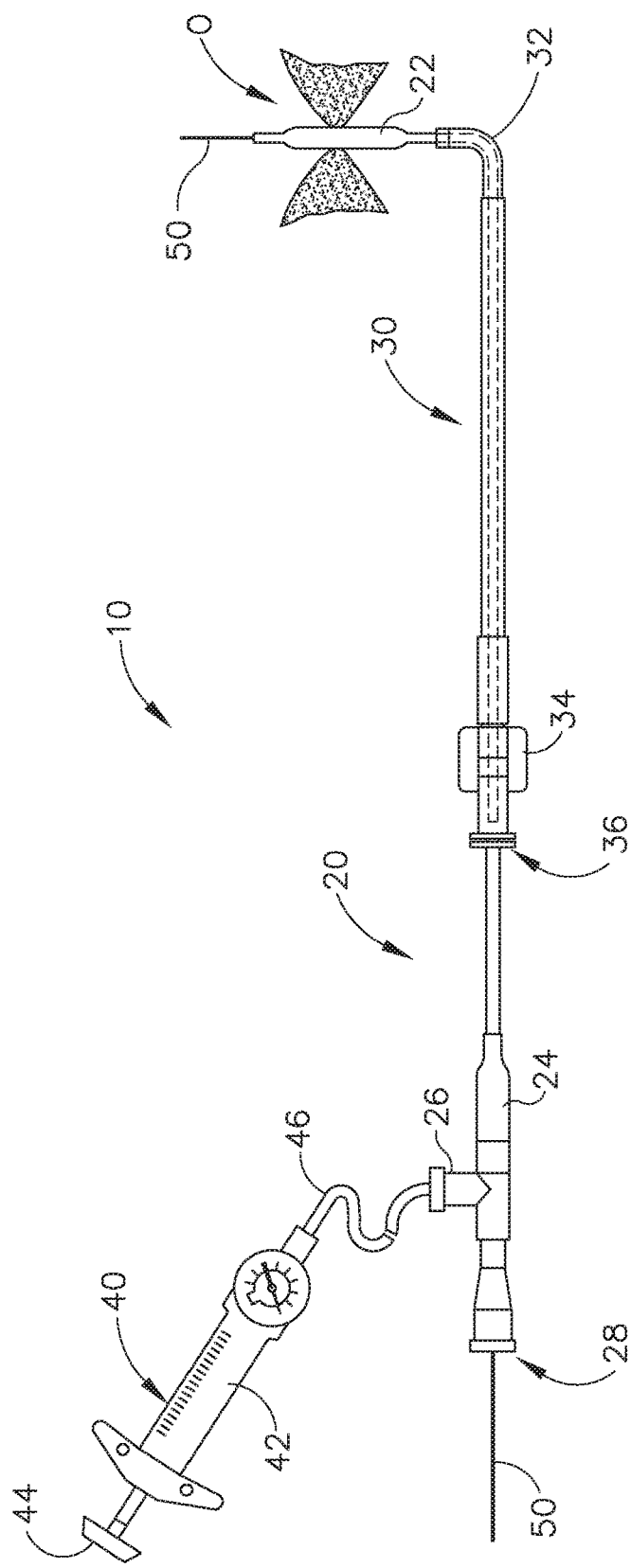
FIG. 1 depicts a side elevational view of an exemplary dilation catheter system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview of Exemplary Dilation Catheter System

FIG. 1 shows an exemplary dilation catheter system (10) that may be used to dilate the ostium of a paranasal sinus; or to dilate some other anatomical passageway (e.g., within the ear, nose, or throat, etc.). Dilation catheter system (10) of this example comprises a dilation catheter (20), a guide catheter (30), an inflator (40), and a guidewire (50). By way of example only, dilation catheter system (10) may be configured in accordance with at least some of the teachings of U.S. Patent Pub. No. 2011/0004057, now abandoned, the disclosure of which is incorporated by reference herein. In some versions, at least part of dilation catheter system (10) is configured similar to the Relieva® Spin Balloon Sinuplasty™ System by Acclarent, Inc. of Menlo Park, Calif.

The distal end of dilation catheter (20) includes an inflatable dilator (22). The proximal end of dilation catheter (20) includes a grip (24), which has a lateral port (26) and an open proximal end (28). Dilation catheter (20) includes a first lumen (not shown) that provides fluid communication between lateral port (26) and the interior of dilator (22). Dilator catheter (20) also includes a second lumen (not shown) that extends from open proximal end (28) to an open distal end that is distal to dilator (22). This second lumen is configured to slidably receive guidewire (50). The first and second lumens of dilator catheter (20) are fluidly isolated from each other. Thus, dilator (22) may be selectively inflated and deflated by communicating fluid along the first lumen via lateral port (26) while guidewire (50) is positioned within the second lumen. In some versions, dilator catheter (20) is configured similar to the Relieva Ultirra™ Sinus Balloon Catheter by Acclarent, Inc. of Menlo Park, Calif. In some other versions, dilator catheter (20) is configured similar to the Relieva Solo Pro™ Sinus Balloon Catheter by Acclarent, Inc. of Menlo Park, Calif. Other suitable forms that dilator catheter (20) may take will be apparent to those of ordinary skill in the art in view of the teachings herein.

Guide catheter (30) of the present example includes a bent distal end (32) and a grip (34) at its proximal end. Grip (34) has an open proximal end (36). Guide catheter (30) defines a lumen that is configured to slidably receive catheter (20), such that guide catheter (30) may guide dilator (22) out through bent distal end (32). In some versions, guide catheter (30) is configured similar to the Relieva Flex™ Sinus Guide Catheter by Acclarent, Inc. of Menlo Park, Calif. Other suitable forms that guide catheter (30) may take will be apparent to those of ordinary skill in the art in view of the teachings herein.

Inflator (40) of the present example comprises a barrel (42) that is configured to hold fluid and a plunger (44) that is configured to reciprocate relative to barrel (42) to selectively discharge fluid from (or draw fluid into) barrel (42). Barrel (42) is fluidly coupled with lateral port (26) via a flexible tube (46). Thus, inflator (40) is operable to add fluid to dilator (22) or withdraw fluid from dilator (22) by translating plunger (44) relative to barrel (42). In the present example, the fluid communicated by inflator (40) comprises saline, though it should be understood that any other suitable fluid may be used. In some versions, inflator (40) is configured in accordance with at least some of the teachings of U.S. Pat. App. No. 61/725,523, entitled "Inflator for Dilation of Anatomical Passageway," filed Nov. 13, 2012, the disclosure of which is incorporated by reference herein. Other suitable forms that inflator (40) may take will be apparent to those of ordinary skill in the art in view of the teachings herein.

As best seen in FIGS. 2-3, guidewire (50) of the present example comprises a coil (52) positioned about a core wire (54). An illumination wire (56) extends along the interior of core wire (54) and terminates in an atraumatic lens (58). A connector (55) at the proximal end of guidewire (50) enables optical coupling between illumination wire (56) and a light source (not shown). Illumination wire (56) may comprise one or more optical fibers. Lens (58) is configured to project light when illumination wire (56) is illuminated by the light source, such that illumination wire (56) transmits light from the light source to the lens (58). In some versions, the distal end of guidewire (50) is more flexible than the proximal end of guidewire (50). Guidewire (50) has a length enabling the distal end of guidewire (50) to be positioned distal to dilator (22) while the proximal end of guidewire (50) is positioned proximal to grip (24). Guidewire (50) may include indicia along at least part of its length (e.g., the proximal portion) to provide the operator with visual feedback indicating the depth of insertion of guidewire (50) relative to dilation catheter (20). By way of example only, guidewire (50) may be configured in accordance with at least some of the teachings of U.S. Pub. No. 2012/0078118, now U.S. Pat. No. 9,155,492, issued on Oct. 13, 2015, the disclosure of which is incorporated by reference herein. In some versions, guidewire (50) is configured similar to the Relieva Luma Sentry™ Sinus Illumination System by Acclarent, Inc. of Menlo Park, Calif. Other suitable forms that guidewire (50) may take will be apparent to those of ordinary skill in the art in view of the teachings herein.

In an exemplary dilation procedure, guide catheter (30) may first be positioned near the targeted anatomical passageway, such as a sinus ostium (O). Dilator (22) and the distal end of guidewire (50) may be positioned within or proximal to bent distal end (32) of guide catheter (30) at this stage. Guide catheter (30) is initially inserted into the nose of the patient and is advanced to a position that is within or near the ostium (O) to be dilated. This positioning of guide catheter (30) may be performed under visualization provided by an endoscope such as endoscope (60) described below. After guide catheter (30) has been positioned, the operator may advance guidewire (50) distally through guide catheter (30) such that a distal portion of the guidewire (50) passes through the sinus ostium (O) and into the sinus cavity. The operator may illuminate illumination wire (56) and lens (58), which may provide transcutaneous illumination through the patient's face to enable the operator to visually confirm positioning of the distal end of guidewire (50) with relative ease.

With guide catheter (30) and guidewire (50) suitably positioned, dilation catheter (20) is advanced along guidewire (50) and through bent distal end (32) of guide catheter (30), with dilator (22) in a non-dilated state until dilator (22) is positioned within the sinus ostium (O) (or some other targeted anatomical passageway). After dilator (22) has been positioned within the ostium (O), dilator (22) may be inflated, thereby dilating the ostium. To inflate dilator (22), plunger (44) may be actuated to push saline from barrel (42) of inflator (40) through dilation catheter (20) into dilator (22). The transfer of fluid expands dilator (22) to an expanded state to open or dilate the ostium (O), such as by remodeling the bone, etc., forming ostium (O). By way of example only, dilator (22) may be inflated to a volume sized to achieve about 10 to about 12 atmospheres. Dilator (22) may be held at this volume for a few seconds to sufficiently open the ostium (O) (or other targeted anatomical passageway). Dilator (22) may then be returned to a non-expanded state by reversing plunger (44) of inflator (40) to bring the saline back to inflator (40). Dilator (22) may be repeatedly inflated and deflated in different ostia and/or other targeted anatomical passageways. Thereafter, dilation catheter (20), guidewire (50), and guide catheter (30) may be removed from the patient.

II. Overview of Exemplary Endoscope

As noted above, an endoscope (60) may be used to provide visualization within an anatomical passageway (e.g., within the nasal cavity, etc.) during a process of using dilation catheter system (10). As shown in FIGS. 4-5, endoscope of the present example comprises a body (62) and a rigid shaft (64) extending distally from body (62). The distal end of shaft (64) includes a curved transparent window (66). A plurality of rod lenses and light transmitting fibers may extend along the length of shaft (64). A lens is positioned at the distal end of the rod lenses and a swing prism is positioned between the lens and window (66). The swing prism is pivotable about an axis that is transverse to the longitudinal axis of shaft (64). The swing prism defines a line of sight that pivots with the swing prism. The line of sight defines a viewing angle relative to the longitudinal axis of shaft (64). This line of sight may pivot from approximately 0 degrees to approximately 120 degrees, from approximately 10 degrees to approximately 90 degrees, or within any other suitable range. The swing prism and window (66) also provide a field of view spanning approximately 60 degrees (with the line of sight centered in the field of view). Thus, the field of view enables a viewing range spanning approximately 180 degrees, approximately 140 degrees, or any other range, based on the pivot range of the swing prism. Of course, all of these values are mere examples.

Body (62) of the present example includes a light post (70), an eyepiece (72), a rotation dial (74), and a pivot dial (76). Light post (70) is in communication with the light transmitting fibers in shaft (64) and is configured to couple with a source of light, to thereby illuminate the site in the patient distal to window (66). Eyepiece (72) is configured to provide visualization of the view captured through window (66) via the optics of endoscope (60). It should be understood that a visualization system (e.g., camera and display screen, etc.) may be coupled with eyepiece (72) to provide visualization of the view captured through window (66) via the optics of endoscope (60). Rotation dial (74) is configured to rotate shaft (64) relative to body (62) about the longitudinal axis of shaft (64). It should be understood that such rotation may be carried out even while the swing prism is pivoted such that the line of sight is non-parallel with the longitudinal axis of shaft (64). Pivot dial (76) is coupled with the swing prism and is thereby operable to pivot the swing prism about the transverse pivot axis. Indicia (78) on body (62) provide visual feedback indicating the viewing angle. Various suitable components and arrangements that may be used to couple rotation dial (74) with the swing prism will be apparent to those of ordinary skill in the art in view of the teachings herein. By way of example only, endoscope (60) may be configured in accordance with at least some of the teachings of U.S. Pub. No. 2010/0030031, now abandoned, the disclosure of which is incorporated by reference herein. In some versions, endoscope (60) is configured similar to the Acclarent Cyclops™ Multi-Angle Endoscope by Acclarent, Inc. of Menlo Park, Calif. Other suitable forms that endoscope (60) may take will be apparent to those of ordinary skill in the art in view of the teachings herein.

III. Exemplary Port for Ethmoid Sinus

Figure 6:
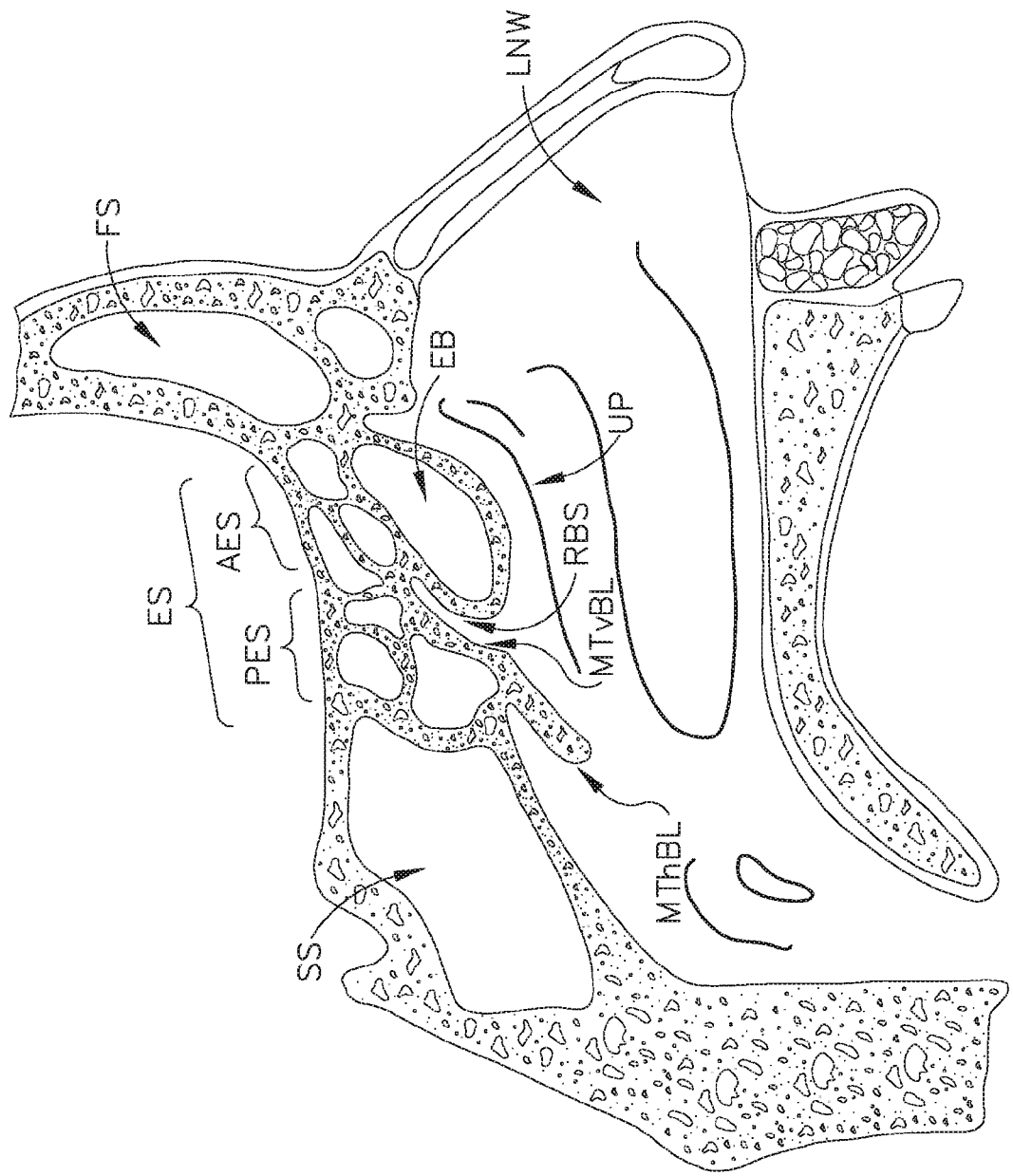
FIG. 6 depicts a left sagittal cross-sectional view of a portion of a human head, showing paranasal sinus structures.

FIG. 6 shows a left sagittal cross-sectional view of a portion of a human head, which includes a sphenoid sinus (SS), ethmoid sinus (ES), frontal sinus (FS), middle turbinate horizontal basal lamella (MThBL), middle turbinate vertical basal lamella (MTvBL), uncinate process (UP), and lateral nasal wall (LNW). The ethmoid sinus (ES) comprises a set of sinus cells that may be categorized as anterior ethmoid sinus (AES) cells and posterior ethmoid sinus (PES) cells. The ethmoid bulla (EB) is the largest ethmoid sinus (ES) cell, and is generally inferior and anterior to the other cells of the ethmoid sinus (ES). The posterior wall of the ethmoid bulla (EB) and the middle turbinate vertical basal lamella (MTvBL) together define a retrobullar space (RBS). It should be understood that anatomical variation in the human is such that this retrobullar space (RBS) may or may not be present in a given individual.

The ethmoid sinus (ES) includes ostia (not shown) for providing fluid communication to and from the cells of the ethmoid sinus (ES) and the nasal cavity. For instance, ostia may provide fluid paths for cells within the anterior ethmoid sinus (AES), cells within the posterior ethmoid sinus (PES), and the ethmoid bulla (EB). In some instances, suprabullar cells of the ethmoid sinus (ES) drain into the ethmoid bulla (EB). Some suprabullar cells may drain directly into the retrobullar space (RBS). The ethmoid bulla (EB) may itself provide fluid communication with the nasal cavity via one or more ostia, such that the ethmoid bulla (EB) may provide a fluid communication path between the other ethmoid sinus (ES) cells (that drain into the ethmoid bulla (EB)) and the nasal cavity. For instance, the ethmoid bulla (EB) may provide fluid communication through an ostium at the retrobullar space (RBS). The fluid communication paths provided by ostia may allow the entry of air and liquids (e.g., medications); while also allowing drainage of mucus. In some instances, the ostia may become blocked, may become functionally closed due to mucosal thickening, or may otherwise not provide sufficient fluid communication. In addition or in the alternative, the configuration of the retrobullar space (RBS) may impede flow through the ostium of the ethmoid bulla (EB).

The anatomy of the ethmoid sinus (ES) may make it impractical to perform a dilation procedure on ostia of the ethmoid sinus (ES) using dilation catheter system (10) to improve fluid communication within the ethmoid sinus (ES). This may lead some operators to perform an ethmoidectomy, which is an invasive procedure that involves removal of ethmoid sinus (ES) portions (e.g., tissue and bone) using an instrument such as a debriding instrument. This kind of procedure may be somewhat crude an inelegant, resulting in removal of significant amounts of mucosa that might otherwise benefit the patient. Ethmoidectomy procedures may also have risks of inadvertent damage to optic nerves, damage to orbital muscles, damage to olfactory bulbs, damage to other anatomical structures, and even leakage of cerebrospinal fluid. Even in successful ethmoidectomies, the patient may need to return for several follow-up debridements. It may therefore be desirable to improve fluid communication from within the ethmoid sinus (ES) to the nasal cavity without resorting to a procedure like an ethmoidectomy. In some instances, this may involve implantation of a port in one or more cells of the ethmoid sinus (ES). Several merely illustrative examples of such ports are described in greater detail below, while other examples will be apparent to those of ordinary skill in the art in view of the teachings herein.

A. Exemplary Port with Single Wall Deployment

FIG. 7A shows an exemplary instrument (100) that may be used to deploy a port (200) in the ethmoid bulla (EB). Instrument (100) of this example has a piercing tip (102) and an opening (104) proximal to tip (102). In some versions, the outer diameter of instrument (100) is approximately 3 mm, though other dimensions may be used. The mouth of opening (104) lies along a plane that is oblique to the longitudinal axis of instrument (100) in the present example, though it should be understood that opening (100) may instead have other configurations and orientations. Instrument (100) may be introduced through the patient's nose (in this case, the patient's right nostril) and positioned at an anterior/inferior wall of the ethmoid bulla (EB). Instrument (100) may be positioned using visualization from endoscope (60) described above and/or from some other device. A retractable sheath (not shown) may be used to shield tip (102) until instrument (100) reaches the ethmoid bulla (EB).

Once positioned at the ethmoid bulla (EB), instrument (100) may be advanced against the ethmoid bulla (EB) such that tip (102) pierces the wall of the ethmoid bulla (EB), allowing opening (104) to be positioned within the ethmoid bulla (EB) as shown in FIG. 7A. Tip (102) is configured to pierce the wall of the ethmoid bulla (EB) without shattering the wall of the ethmoid bulla (EB). In other words, the wall of the ethmoid bulla (EB) remains intact except for the opening created by instrument (100), with such an opening being approximately the same size as the outer diameter of instrument (100). In some versions, tip (102) is rotated (e.g., by hand, using a torsion spring, etc.) to assist with piercing of the ethmoid bulla (EB). Such rotation may be in one angular direction or may be in opposing angular directions (e.g., in a rocking motion). In addition or in the alternative, tip (102) may be imparted with a reciprocating longitudinal motion. Tip (102) may also have an abrasive surface/edge and/or other features that promote piercing of the ethmoid bulla (EB). Various suitable configurations for tip (102) and methods for piercing the ethmoid bulla (EB) with tip (102) will be apparent to those of ordinary skill in the art in view of the teachings herein.

Figure 7B:
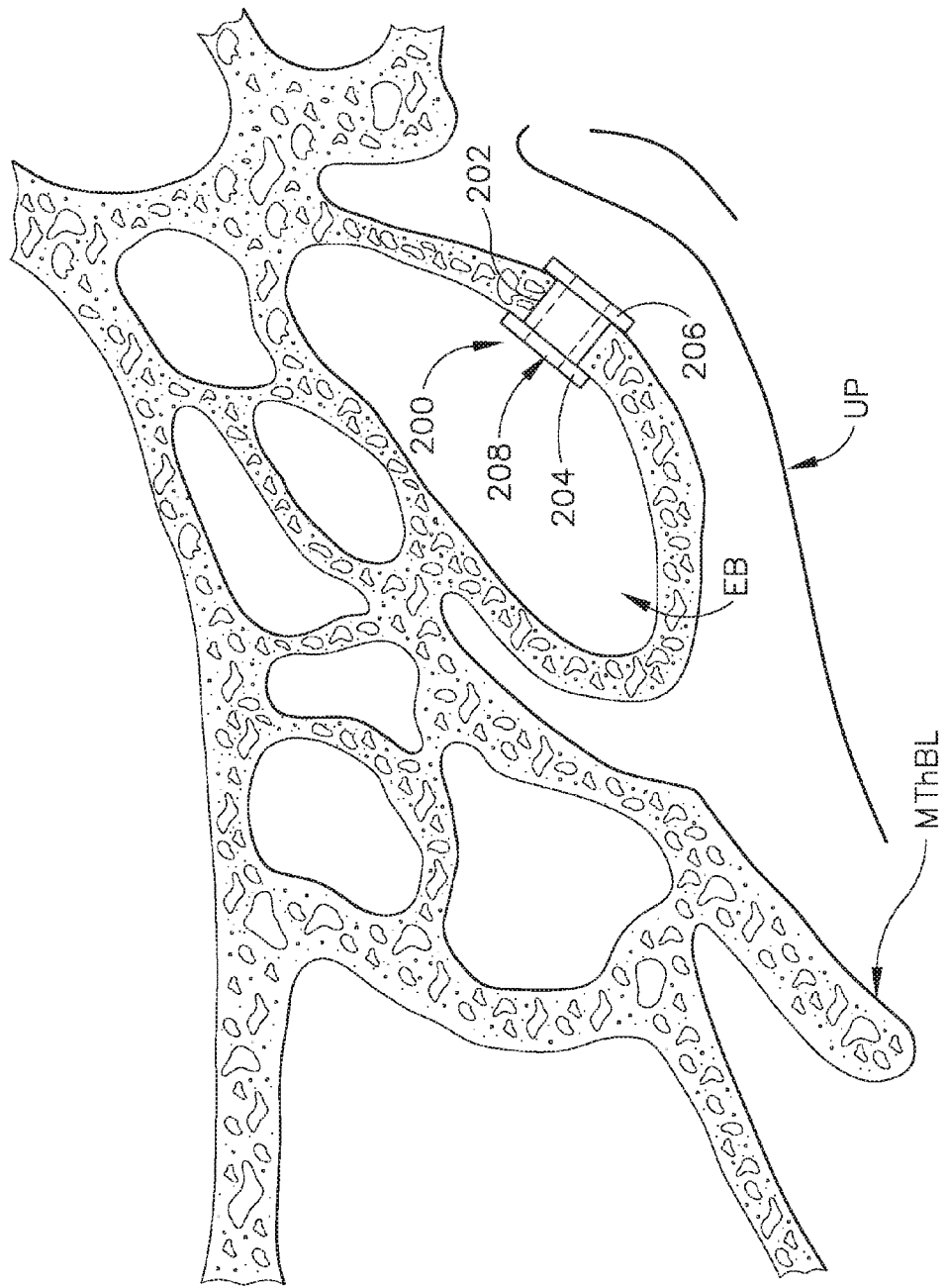
FIG. 7B depicts a left sagittal cross-sectional view of a portion of a human head, with a port disposed in the pierced wall of the ethmoid bulla.

After instrument (100) has pierced the ethmoid bulla (EB), instrument (100) may deploy a port (200) within the opening created in the wall of the ethmoid bulla (EB) by tip (102), as shown in FIG. 7B. By way of example only, instrument (100) may include a translating push-rod or other feature within instrument (100) that is able to drive port (200) out through opening (104). As another merely illustrative example, instrument (100) may be configured and operable in accordance with at least some of the teachings of U.S. Pub. No. 2011/0015645, entitled "Tympanic Membrane Pressure Equalization Tube Delivery System," published Jan. 20, 2011, now U.S. Pat. No. 8,864,774, issued on Oct. 21, 2014, the disclosure of which is incorporated by reference herein. In such versions, port (200) may be generally analogized to the pressure equalization tube deployed in a patient's tympanic membrane. Various other suitable ways in which port (200) may be deployed in the wall of the ethmoid bulla (EB) will be apparent to those of ordinary skill in the art in view of the teachings herein.

Port (200) of the present example comprises a cylindraceous body (202), a first flange (204) at one end of body (202), and a second flange (206) at the other end of body (202). Body (202) is hollow and defines a lumen (208) extending from flange (204) to flange (206). As shown in FIG. 7B, flange (204) is positioned within the interior of the ethmoid bulla (EB) while flange (206) is positioned at the exterior of the ethmoid bulla (EB). Flanges (204, 206) are configured to generally maintain the position of port (200) with respect to the ethmoid bulla (EB). Flanges (204, 206) may be separated from each other by any other suitable distance, such that body (202) may extend to any suitable length. In some versions, only one flange (204, 206) is provided. For instance, flange (206) may be omitted in some versions.

Port (200) may be formed of a resilient material, such that port (200) is compressed while port (200) is within instrument (100); with port (200) resiliently assuming the rivet like shape shown in FIG. 7B as soon as port (200) exits instrument (100). In some other versions, port (200) is formed of a malleable material. In some such versions, instrument (100) includes features that form the rivet like shape of port (200) as port (200) is deployed in the wall of ethmoid bulla (EB). It should also be understood that port (200) may be formed of a bioabsorbable or biodegradable material. In versions where port (200) is formed of a bioabsorbable material, the bioabsorbable material forming port (200) may include one or more therapeutic materials. In some versions where port (200) is formed of a non-bioabsorbable/non-biodegradable material, port (200) may eventually be removed from the patient some time after implantation. Port (200) may also be formed of a material that is configured to wick fluids. By way of example only, port (200) may be formed of semi-flexible, porous polyethylene, with a pore size selected to optimize wicking and with a surface coating/treatment to make port (200) hydrophilic. Various suitable materials that may be used to form port (200) will be apparent to those of ordinary skill in the art in view of the teachings herein.

It should be understood that, once port (200) has been deployed, lumen (208) enables the substantially free communication of air/mucus/etc. into and out of the ethmoid bulla (EB). Port (200) thus serves as a substitute or supplemental ostium for the ethmoid bulla (EB). In some instances, the patient may be instructed to periodically self-administer medications or other fluids within their nose after a port (200) has been implanted. By way of example only, such fluids/medications may include saline, a combination of saline and a surfactant, an anti-inflammatory (e.g., mometasone, etc.), an antibiotic, an anti-fungal, and/or various other kinds of fluids/medications, including combinations thereof. Lumen (208) may provide a substantially clear path for such fluids/medications to reach the mucosa within the ethmoid bulla (EB), in addition to providing a vent/drainage path for the ethmoid bulla (EB). In other words, the presence of port (200) may provide substantially greater communication of the administered fluids/medications to the ethmoid bulla (EB) than the communication that would be provided in the absence of port (200). In some variations, a sleeve (not shown) extends from flange (206) and is in fluid communication with lumen (208). Such a sleeve may be directly coupled with a fluid delivery device and/or a suction device to actively deliver fluid or suction to the ethmoid bulla (EB) via port (200). In addition or in the alternative, such a sleeve may provide a wicking function similar to the various wicks described in greater detail below.

Figure 8A:
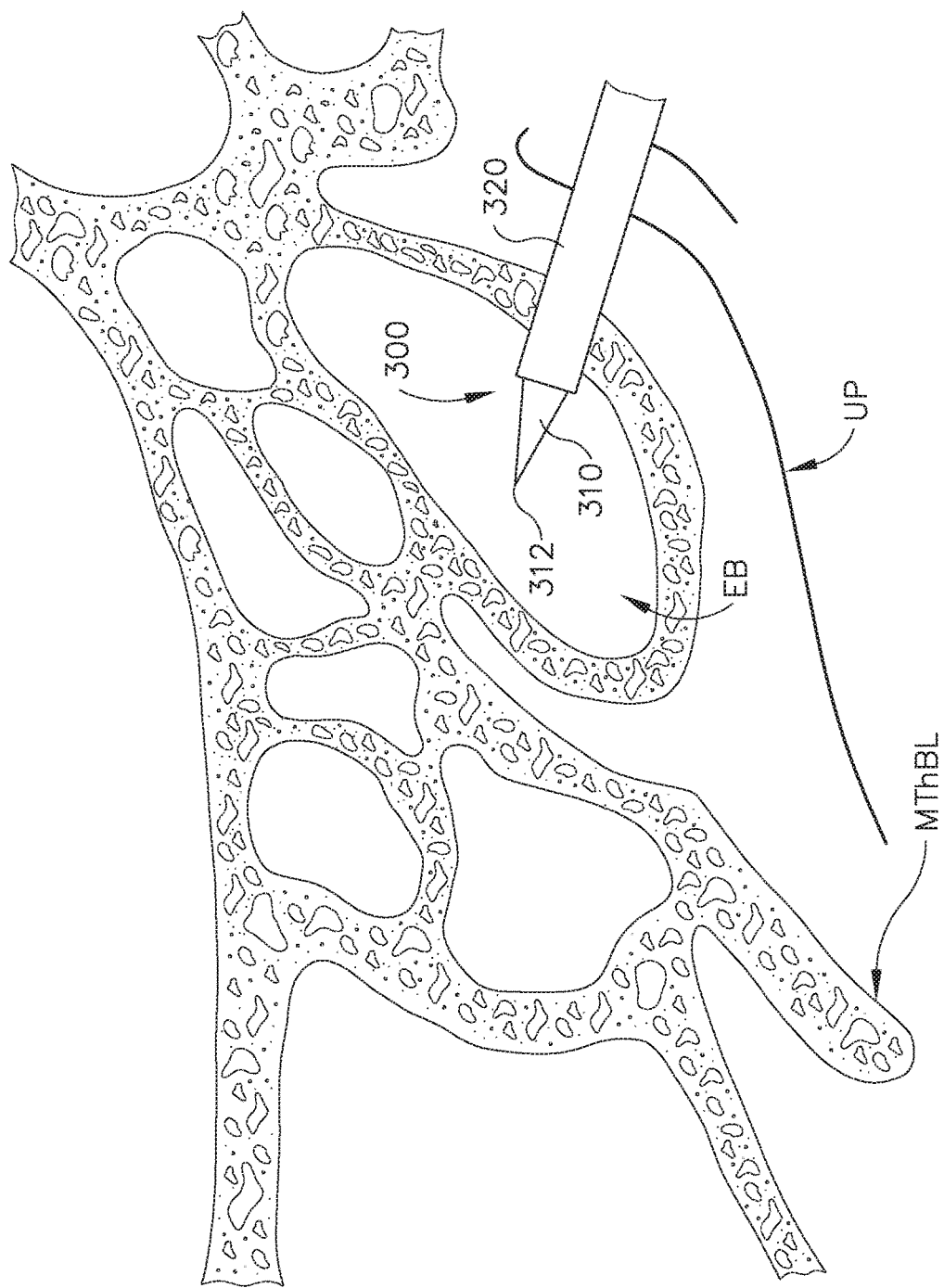
FIG. 8A depicts a left sagittal cross-sectional view of a portion of a human head, with another exemplary port deployment instrument piercing a wall of the ethmoid bulla.
Figure 8B:
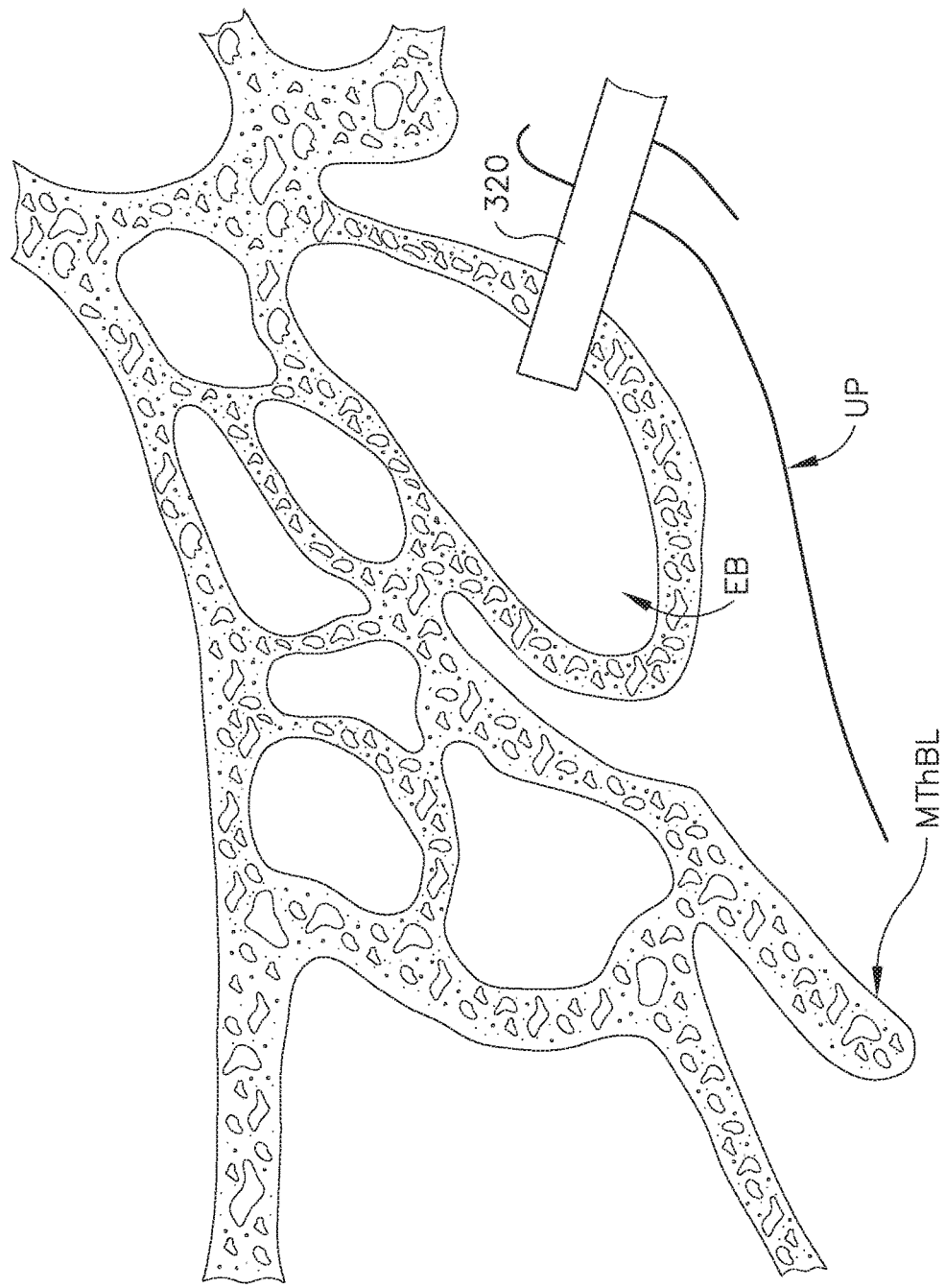
FIG. 8B depicts a left sagittal cross-sectional view of a portion of a human head, with a sheath of the instrument of FIG. 8A disposed in the pierced wall of the ethmoid bulla, and with a piercing obturator removed from the sheath.

FIGS. 8A-8D show another exemplary instrument (300) that may be used to deploy a port (200) in the ethmoid bulla (EB). Instrument (300) of this example comprises an outer cannula (320) and an obturator (310) slidably disposed within outer cannula (320). Obturator (310) has a sharp tip (312) configured to pierce the wall of the ethmoid bulla (EB), with cannula (320) trailing behind as shown in FIG. 8A. Tip (312) is configured to pierce the wall of the ethmoid bulla (EB) without shattering the wall of the ethmoid bulla (EB). In other words, the wall of the ethmoid bulla (EB) remains intact except for the opening created by tip (312), with that opening being approximately the same diameter as cannula (320). Obturator (310) may be coupled with a rotary drive, reciprocating drive, and/or any other suitable kind of drive that may assist in driving tip (312) through the wall of the ethmoid bulla (EB). Tip (312) may also have an abrasive surface/edge and/or other features that promote piercing of the ethmoid bulla (EB). By way of example only, tip (312) may be configured in accordance with any of the teachings herein relating to structures operable to pierce the wall of the ethmoid bulla (EB). Various suitable forms that tip (312) and associated drive features may take will be apparent to those of ordinary skill in the art in view of the teachings herein. It should also be understood that the wall of the ethmoid bulla (EB) may be reinforced with a backing, as taught elsewhere herein, to prevent the wall from shattering when encountered by tip (312). Furthermore, in some instances tip (312) may be passed through the wall of the ethmoid bulla (EB) so quickly that the inertia of the bone in the wall provides the effect of a backing support. Regardless of how tip (312) successfully passes through the wall of the ethmoid bulla (EB), once tip (312) and the distal end of cannula (320) are positioned within the ethmoid bulla (EB), obturator (310) may be withdrawn from cannula (320) as shown in FIG. 8B.

Next, the operator may advance a dual mode catheter (330) through cannula (320) into the ethmoid bulla (EB) as shown in FIG. 8C. Catheter (330) of this example includes a suction conduit (322) and an irrigation conduit (326). Suction conduit (322) is coaxially disposed within irrigation conduit (326). Suction conduit (324) is in fluid communication with a suction source (not shown) and has an open distal end (324), such that suction conduit (324) is operable to provide suction at distal end (324). Irrigation conduit (326) is in fluid communication with a fluid source (not shown) and has a plurality of transverse openings (328), such that irrigation conduit (326) is operable to communicate fluid (e.g. saline) through openings (328). Conduits (322, 326) may operate together within the ethmoid bulla (EB) to flush and draw out excess mucus/debris/etc. from within the ethmoid bulla (EB), thereby increasing the effective capacity of the ethmoid bulla (EB) and improving contact between the mucosa and subsequently administered medications.

Figure 8D:
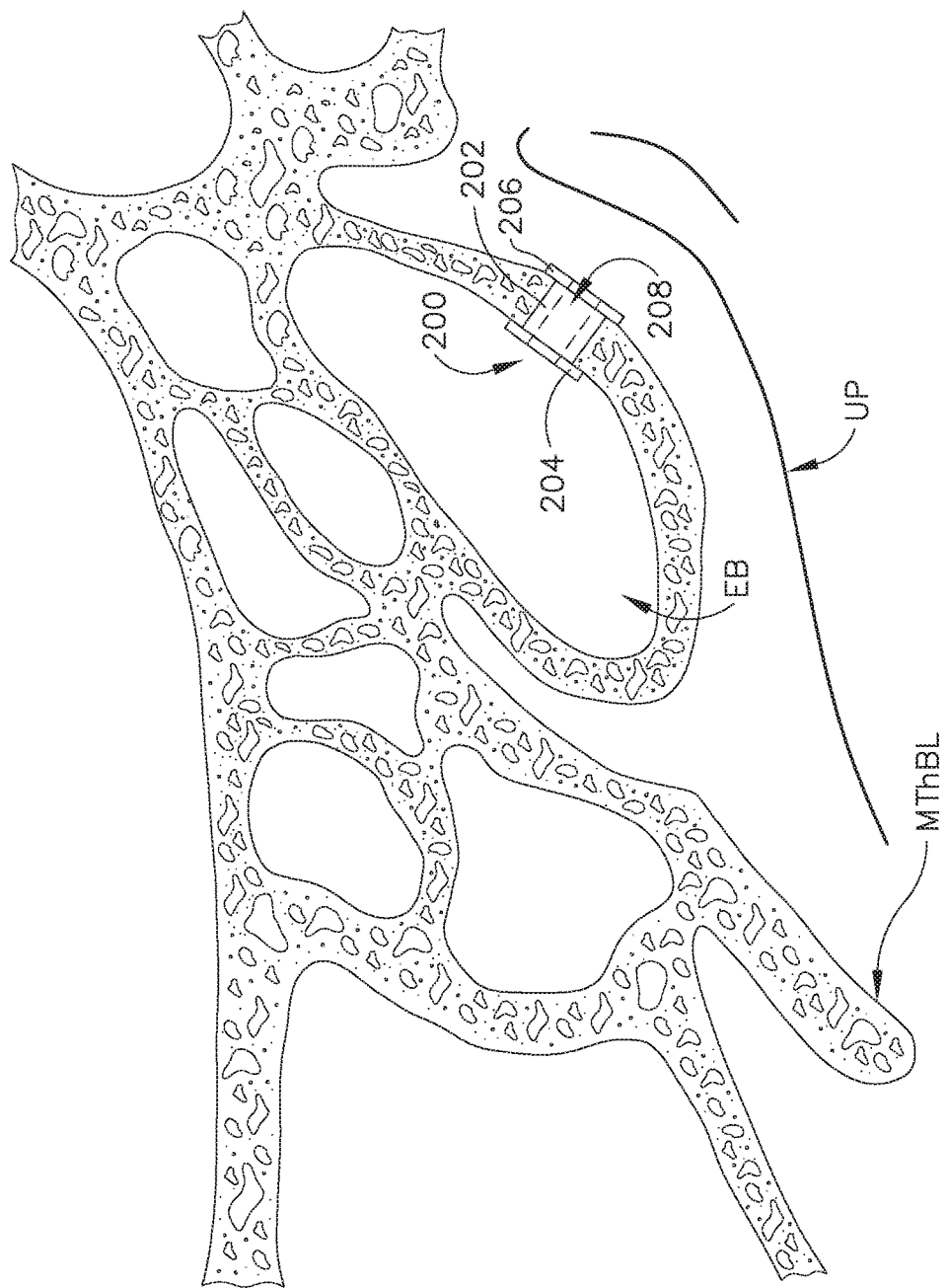
FIG. 8D depicts a left sagittal cross-sectional view of a portion of a human head, with a port disposed in the pierced wall of the ethmoid bulla.

After dual mode catheter (330) has been used to flush out the ethmoid bulla (EB), a port (200) may be deployed in the wall of the ethmoid bulla (EB) via cannula (320), as shown in FIG. 8D. Port (200) of this example is the same as port (200) shown in FIG. 7B and described above. Various suitable ways in which port (200) may be deployed via cannula (320) will be apparent to those of ordinary skill in the art in view of the teachings herein. In some other versions, cannula (320) is withdrawn from the ethmoid bulla (EB) and a separate instrument is used to deploy port (200) in the opening left by cannula (320). While instruments (100, 300) have been described above as being used to deploy port (200) in the wall of the ethmoid bulla (EB), it should be understood that the same instruments (100, 300) (or variations thereof) may be used to deploy various other devices in the wall of the ethmoid bulla (EB). By way of example only, such alternative devices may include wicks as described below, a combination of port and wick as described below, and/or various other devices. Furthermore, while port (200) is described herein as being deployed in the ethmoid bulla (EB), it should be understood that port (200) may be deployed in various other sinus cells.

B. Exemplary Port with Dual Wall Deployment

Figure 9A:
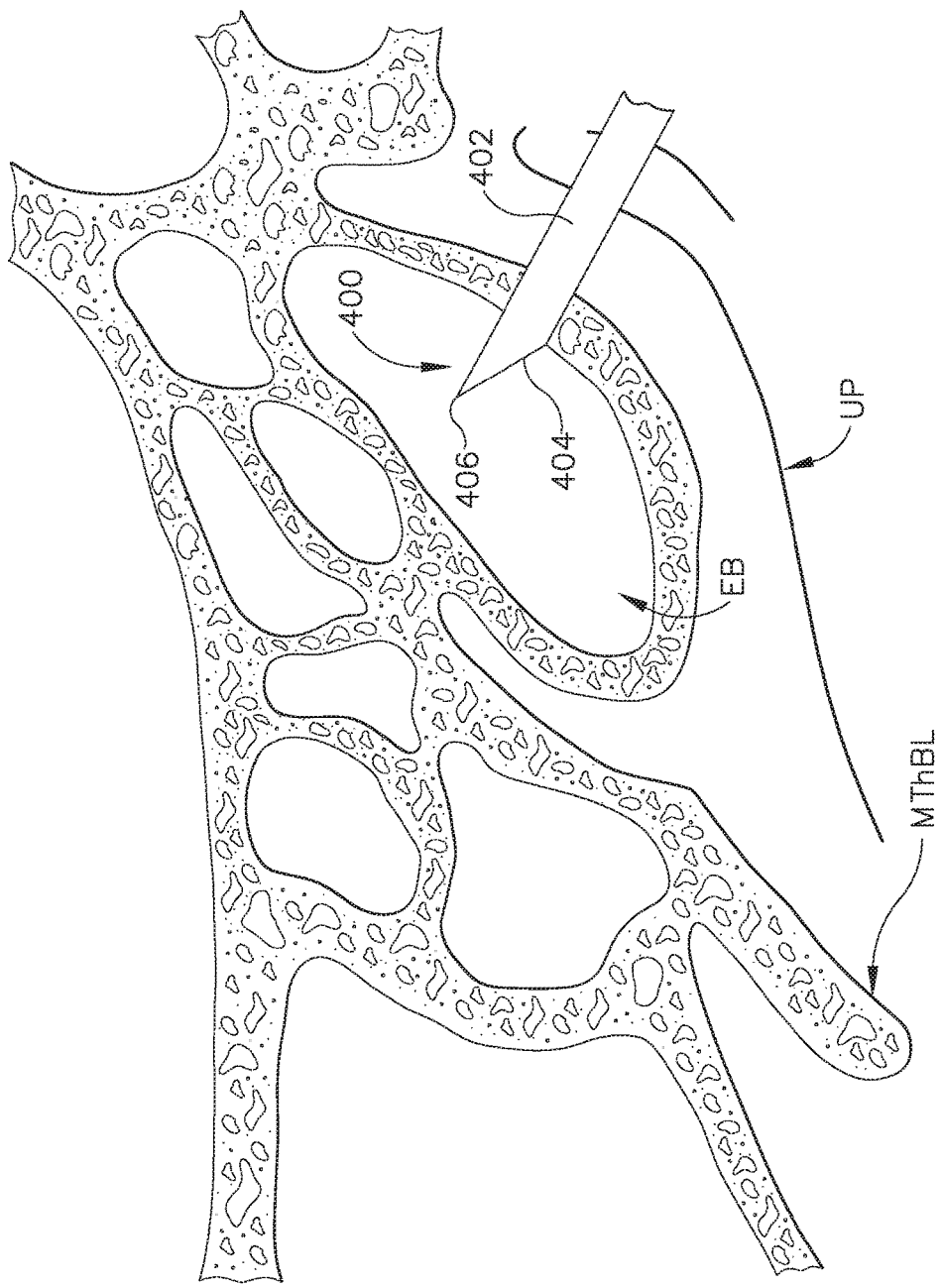
FIG. 9A depicts a left sagittal cross-sectional view of a portion of a human head, with another exemplary port deployment instrument piercing a wall of the ethmoid bulla.
Figure 9B:
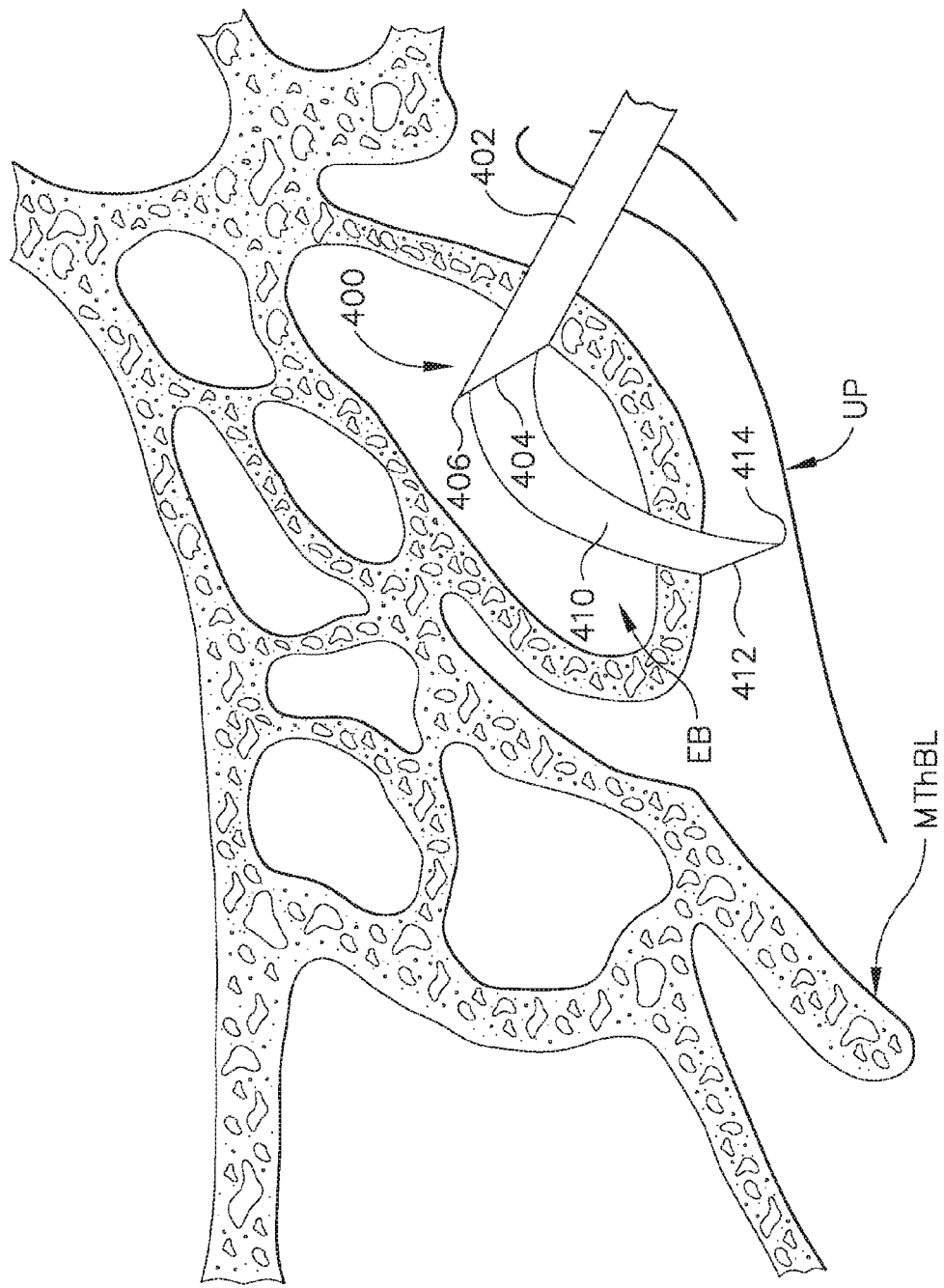
FIG. 9B depicts a left sagittal cross-sectional view of a portion of a human head, with a secondary piercing element extended from the instrument of FIG. 9A to pierce the wall of the ethmoid bulla in a second location.
Figure 9C:
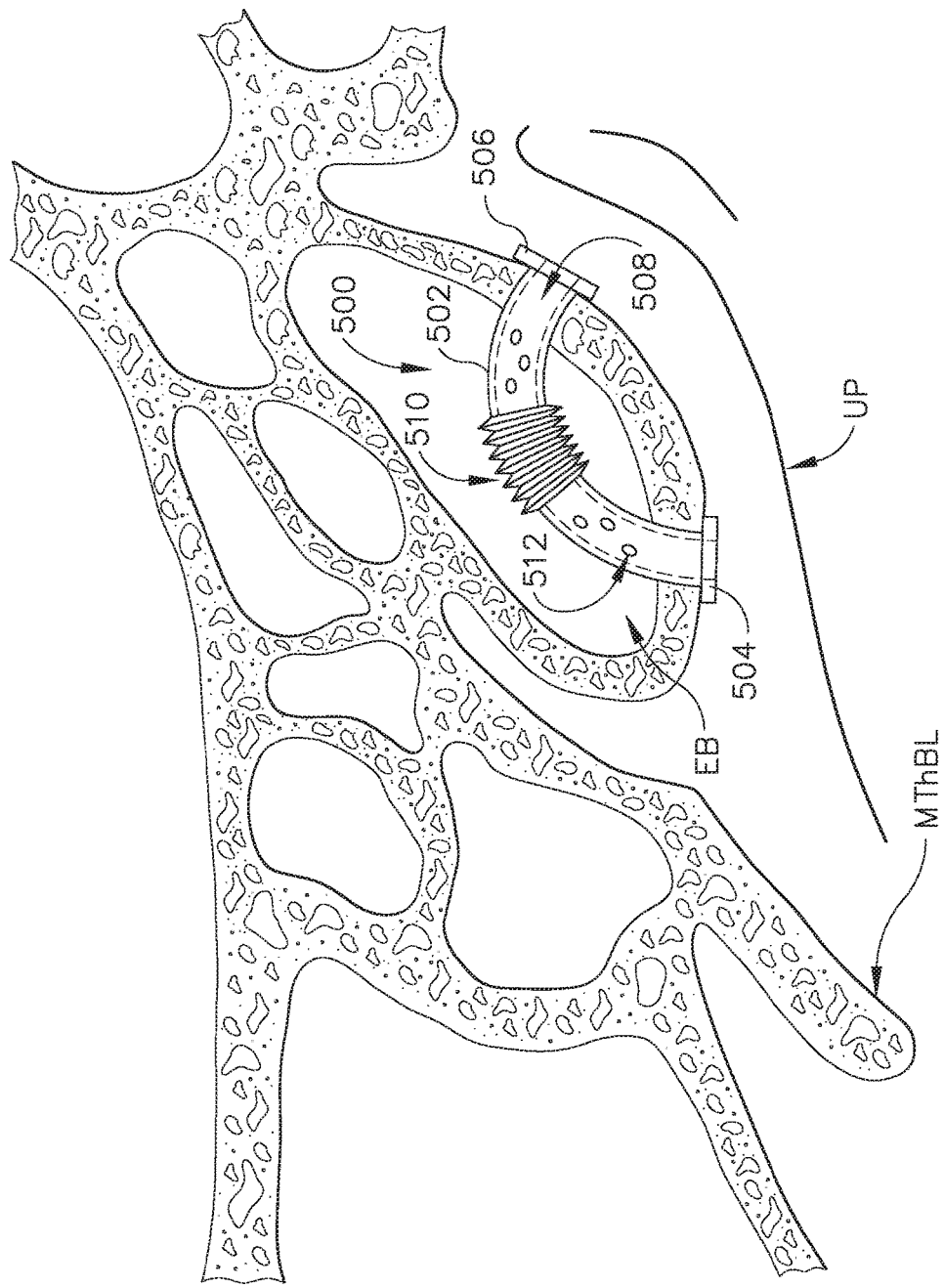
FIG. 9C depicts a left sagittal cross-sectional view of a portion of a human head, with a port disposed in both of the pierced walls of the ethmoid bulla.

In some instances, it may be desirable to provide more than one effective supplemental ostium in the ethmoid bulla (EB). Providing a plurality of effective supplemental ostia in the ethmoid bulla (EB) may further promote fluid communication into and out of the ethmoid bulla (EB). In some instances, this may be accomplished by deploying a plurality of ports (200) as described above in different locations in the ethmoid bulla (EB). Alternatively, a single port may provide a plurality of effective supplemental ostia in the ethmoid bulla (EB). FIGS. 9A-9C show one merely illustrative example of how an instrument (400) may be used to deploy a single port (500) that provides two effective supplemental ostia in the ethmoid bulla (EB). Instrument (400) of this example comprises a rigid first piercing member (402). Piercing member (402) includes a beveled, open distal end (404) that terminates in a sharp tip (406). This sharp tip (406) may be used to pierce the wall of the ethmoid bulla (EB) as shown in FIG. 9A. As noted above, a rotating and/or reciprocating motion may be imparted to tip (406) in various ways in order to assist tip (406) in piercing the wall of the ethmoid bulla (EB). Tip (406) may also have an abrasive surface/edge and/or other features that promote piercing of the ethmoid bulla (EB). Tip (406) is configured to pierce the wall of the ethmoid bulla (EB) without shattering the wall of the ethmoid bulla (EB). In other words, the wall of the ethmoid bulla (EB) remains intact except for the opening created by piercing member (402), with such an opening being approximately the same size as the outer diameter of piercing member (402).

Once distal end (404) has been positioned within the ethmoid bulla (EB), a second piercing member (410) is advanced distally out of distal end (404) as shown in FIG. 9B. Second piercing member (410) also has a beveled distal end (412) that terminates in a sharp tip (414). Sharp tip (414) is also configured to pierce the wall of the ethmoid bulla (EB). Tip (414) is configured to pierce the wall of the ethmoid bulla (EB) without shattering the wall of the ethmoid bulla (EB). In other words, the wall of the ethmoid bulla (EB) remains intact except for the opening created by second piercing member (410), with such an opening being approximately the same size as the outer diameter of second piercing member (410). Second piercing member (410) is formed of a resilient material such that second piercing member (410) is resiliently biased to assume the curved configuration shown in FIG. 9B. However, second piercing member (410) is configured to substantially straighten while fully disposed within first piercing member (402). By way of example only, second piercing member (410) may comprise nitinol. Various other suitable materials and configurations that may be used to form second piercing member (410) will be apparent to those of ordinary skill in the art in view of the teachings herein. Similarly, various suitable ways in which second piercing member (410) may be driven relative to first piercing member (402) will be apparent to those of ordinary skill in the art in view of the teachings herein. As shown in FIG. 9B, second piercing member (410) pierces the wall of ethmoid bulla (EB) when second piercing member (410) is advanced distally, due to the curved configuration of second piercing member. It should therefore be understood that first and second piercing members (402, 410) together form two separate openings in the wall of the ethmoid bulla (EB).

After second piercing member (412) has been actuated to form the second opening in the wall of the ethmoid bulla (EB), instrument (400) deploys a port (500) in the ethmoid bulla (EB), as shown in FIG. 9C. In some versions, port (500) is deployed along the exterior of second piercing member (412). Various suitable ways in which port (500) may be deployed will be apparent to those of ordinary skill in the art in view of the teachings herein. Port (500) of this example comprises a body (502) that extends between a first flange (504) and second flange (506). Flanges (504, 506) are both positioned at the exterior of the ethmoid bulla (EB) when port (500) is deployed. Body (502) is hollow and defines a lumen (508) extending from flange (504) to flange (506). Body (502) also defines a plurality of transverse openings (512) that are in fluid communication with lumen (508). Thus, fluid (e.g., air, mucus, medication, etc.) may flow through lumen (508) and openings (512), into and out of the ethmoid bulla (EB), via the effective supplemental ostia created at each flange (504, 506) of port (500).

Port (500) of this example also includes a corrugated region (510) that serves as a length absorbing feature. In particular, corrugated region (510) is resiliently biased to assume a compressed configuration, at which port (500) has a minimum length. However, corrugated region (510) is expandable to increase the effective length of port (500). In addition to providing a variable length for port (500), corrugated region (510) allows port (500) to flex such that flanges (504, 506) may be positioned at various orientations relative to each other. Thus, port (500) may be readily installed in various positions and configurations without requiring a particular predetermined distance between flanges (504, 506) or orientation of flanges (504, 506). It should be understood that port (500) may be formed of any of the various kinds of materials described above in relation to port (200).

C. Exemplary Alternative Port Configurations

Figure 10:
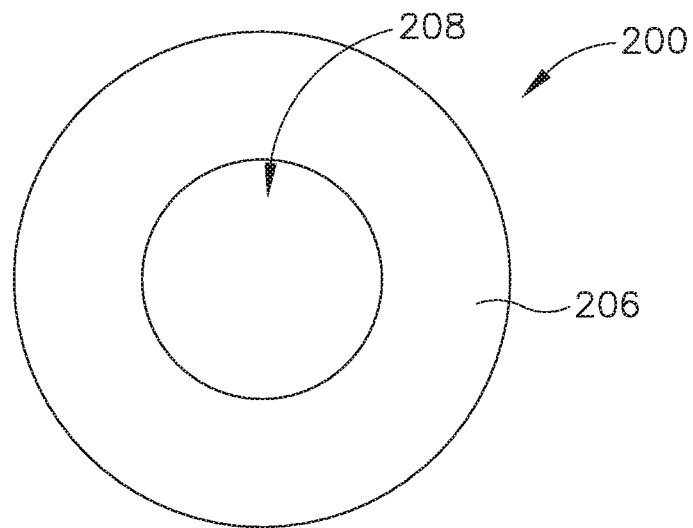
FIG. 10 depicts a top plan view of an exemplary port suitable for installation in a wall of an ethmoid bulla.
Figure 11:
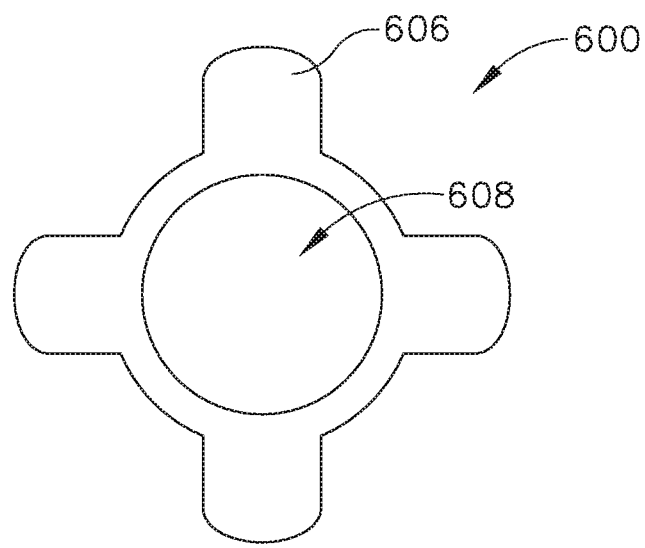
FIG. 11 depicts a top plan view of another exemplary port suitable for installation in a wall of an ethmoid bulla.
Figure 12:
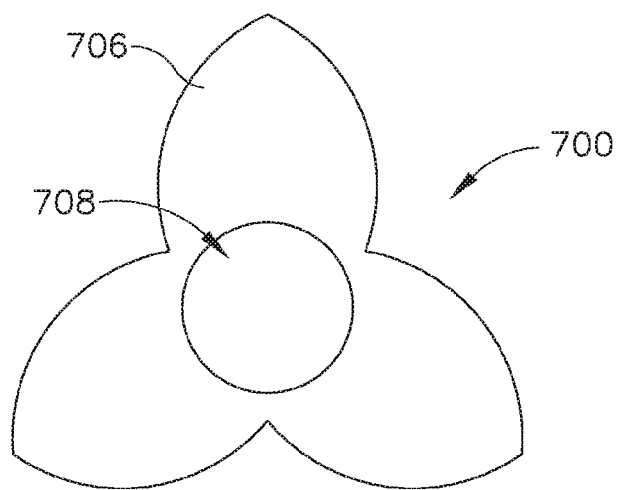
FIG. 12 depicts a top plan view of another exemplary port suitable for installation in a wall of an ethmoid bulla.

As shown in FIG. 10, flange (206) of port (200) described above has a circular shape. Flange (204) of port (200) may also have a circular shape. Alternatively, a variety of other shapes may be used. For instance, FIG. 11 shows an exemplary alternative port (600) that may be used as a substitute for port (200). Port (600) of this example that has a plurality of rounded wings or petals (606) extending outwardly relative to a lumen (608). This array of petals (606) may serve as a functional equivalent of flange (206), substantially maintaining the position of port (600) with respect to the ethmoid bulla (EB). FIG. 12 shows another exemplary alternative port (700) that may be used as a substitute for port (200). Port (700) of this example has a plurality of pointed petals (706) extending outwardly relative to a lumen (708). Again, petals (706) may serve as a functional equivalent of flange (206), substantially maintaining the position of port (700) with respect to the ethmoid bulla (EB). Other suitable variations of flanges (204, 206) and petals (606, 706) will be apparent to those of ordinary skill in the art in view of the teachings herein.

It should also be understood that flanges (204, 206) and petals (606, 706) may be deformable, such that port (200, 600, 700) may compress into a substantially cylindraceous shape before port (200, 600, 700) is deployed in the ethmoid bulla (EB). Furthermore, some versions of port (200, 600, 700) may have flange (204, 206) or petals (606, 706) only at one end of the body of port (200, 600, 700), such that the other end of port (200, 600, 700) is substantially straight without an outwardly protruding feature.

Figure 13:
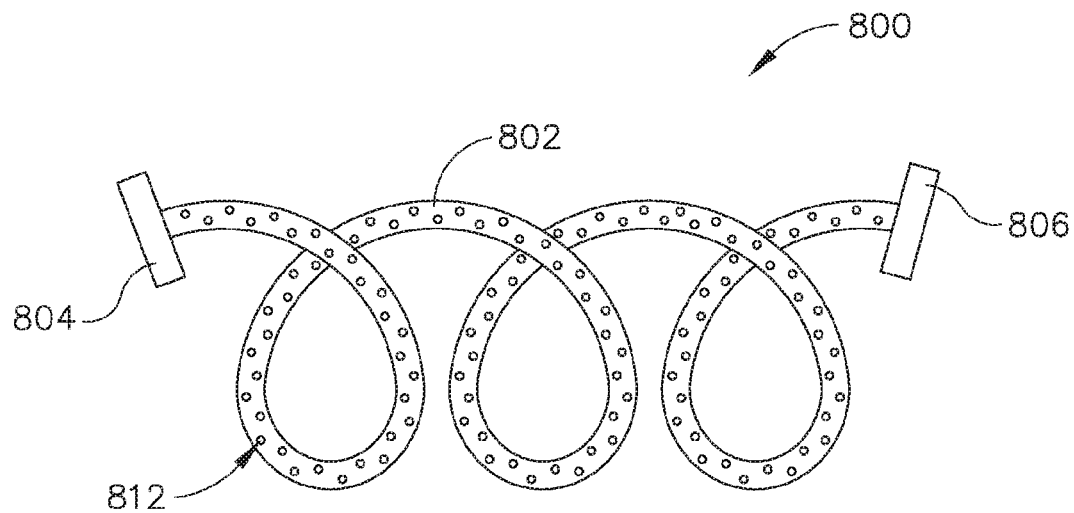
FIG. 13 depicts a side elevational view of another exemplary port suitable for installation in a wall of an ethmoid bulla.

FIG. 13 shows an exemplary port (800) that may be used as a substitute for port (500) described above. Port (800) of this example comprises a body (802) with a pair of flanges (804, 806). Body (802) defines a lumen (not shown) extending from flange (804) to flange (806). Body (802) also defines a plurality of transverse openings (812), similar to transverse openings (512) described above, that are in fluid communication with the lumen of body (802). Body (802) also has a corkscrew configuration in this example and is formed of a resilient material. In particular, body (802) is resiliently biased to form a compressed corkscrew configuration; yet may be expanded to increase the effective length of port (800). The corkscrew configuration thus serves as a length absorbing feature similar to corrugated region (510) of port (500). This facilitates deployment of port (800) installed in various positions and configurations without requiring a particular predetermined distance between flanges (804, 806). The corkscrew configuration also enables port (800) to be installed with flanges (804, 806) at various orientations relative to each other.

It should be understood that ports (600, 700, 800) may be formed of any of the various kinds of materials described above in relation to port (200). Various other suitable forms that an ethmoid port may take will be apparent to those of ordinary skill in the art in view of the teachings herein. Furthermore, while the foregoing examples are provided in the context of providing a port in the ethmoid bulla (EB), it should be understood that ports may be installed elsewhere within the sinus complex, such as in the sphenoid sinus (SS), in the posterior ethmoid sinus (PES), and/or elsewhere, without necessarily also being installed in the ethmoid bulla (EB). By way of example only, an instrument may be used to form an opening in the middle turbinate vertical basal lamella (MTvBL), medial to the posterior wall of the ethmoid bulla (EB) but lateral to the lateral wall of the vertical basal lamella (MTvBL). A port may then be deployed in that formed opening. In some instances, the port may enter the superior meatus, medial to the posterior ethmoid sinus (PES) cells. In some other instances, the port may enter the anterior-most cell of the posterior ethmoid sinus (PES). In either case, the port may serve to increase ventilation to the posterior ethmoid sinus (PES) cells and allow patient-administered substances to reach the posterior ethmoid sinus (PES) cells. Various other ways in which the above described procedures (and in some cases, instruments) may be modified to provide ports in sinus cells other than the ethmoid bulla (EB) will be apparent to those of ordinary skill in the art in view of the teachings herein.

IV. Exemplary Wick for Ethmoid Sinus

In addition to or as an alternative to deploying a port in the ethmoid bulla (EB), it may be desirable to deploy a wick in the ethmoid bulla (EB) and/or in other sinus cavities. A wick may promote communication of medical fluids to the mucosa of the ethmoid bulla (EB) through a capillary action. This capillary action may be enhanced by maximizing contact between the wick material and the mucosa in the ethmoid bulla (EB). The wick may be bioabsorbable and may itself be formed in part by a therapeutic material. Various examples of intrasinus and intersinus wicks will be described in greater detail below, while other examples will be apparent to those of ordinary skill in the art in view of the teachings herein.

Figure 14:
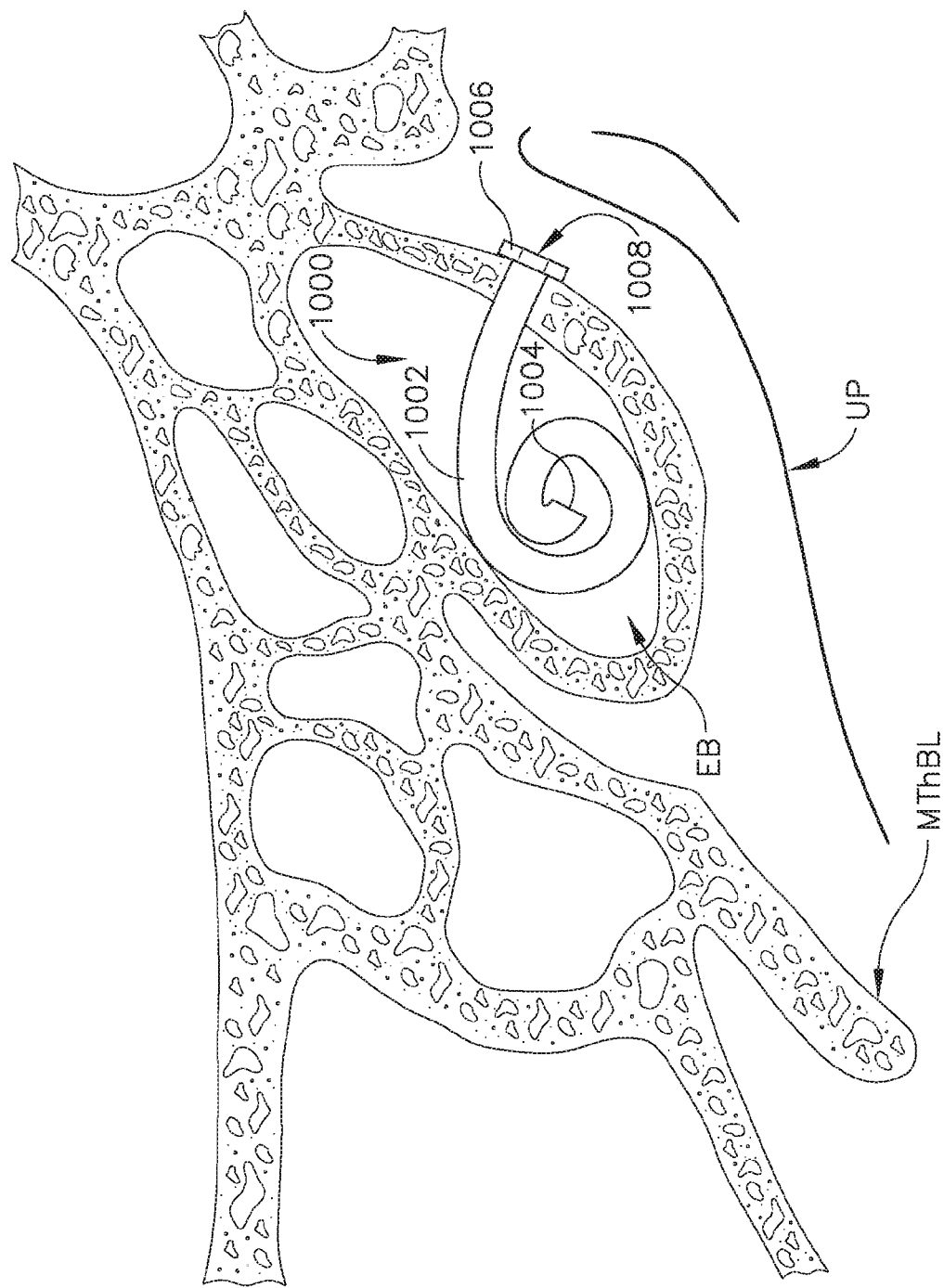
FIG. 14 depicts a left sagittal cross-sectional view of a portion of a human head, with an exemplary wick installed in the ethmoid bulla.

FIG. 14 shows one merely exemplary wick (1000) deployed in the ethmoid bulla (EB). By way of example only, an instrument similar to instrument (100) or instrument (400) may be used to deploy wick (1000). Wick (1000) of this example comprises a body (1002) having a free end (1004) and a flange (1006). The material forming body (1002) is selected to optimize the capillary action provided through body (1002). Various suitable materials that may be used to form body (1002) will be apparent to those of ordinary skill in the art in view of the teachings herein. Body (1002) is shown as being coiled within the ethmoid bulla (EB), and it should be understood that body (1002) is in contact with the mucosa of the ethmoid bulla (EB).

Flange (1006) is configured to generally secure one end of wick (1000) relative to the wall of the ethmoid bulla (EB). It should be understood that flange (1006) may be configured similar to flange (206), similar to petals (606, 706), or in any other suitable fashion. It should also be understood that flange (1006) may simply be omitted in some versions. Flange (1006) of the present example defines an opening (1008) permitting communication of fluid through flange (1006) to reach body (1002). For instance, if a patient self-administers a fluid medication into their nose while wick (1000) is deployed in the patient's ethmoid bulla (EB), that medication may wick through body (1002) to the mucosa of the ethmoid bulla (EB). Wick (1000) thus provides a path for the medication that the medication would have otherwise not had, in order to reach the mucosa of the ethmoid bulla (EB).

Figure 15:
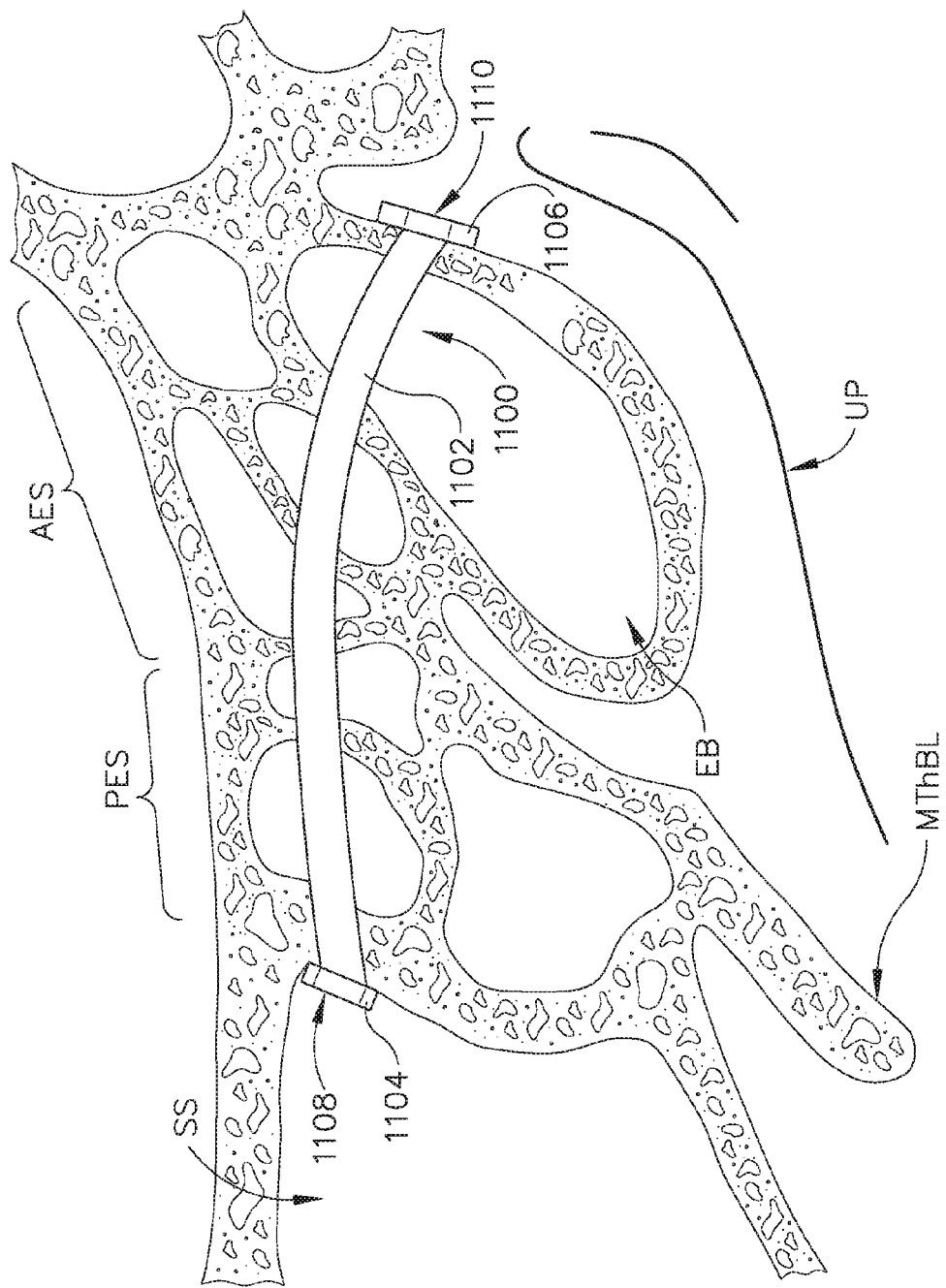
FIG. 15 depicts a left sagittal cross-sectional view of a portion of a human head, with an exemplary wick installed across a series of ethmoid sinus cells.

If desired, a wick may span across more than one sinus cell. For instance, FIG. 15 shows a wick (1100) extending along several sinus cells. In particular, wick (1100) traverses the ethmoid bulla (EB), traverses two anterior ethmoid sinus (AES) cells, traverses two posterior ethmoid sinus (PES) cells, and terminates at the sphenoid sinus (SS). Wick (1100) of this example comprises a body (1102) having a first flange (1104) at one end and a second flange (1106) at the other end. The material forming body (1102) is selected to optimize the capillary action provided through body (1102). Various suitable materials that may be used to form body (1102) will be apparent to those of ordinary skill in the art in view of the teachings herein. When installed as shown, body (1102) contacts mucosa in the ethmoid bulla (EB), the anterior ethmoid sinus (AES) cells, and the posterior ethmoid sinus (PES) cells. While body (1102) is shown as having a substantially straight configuration while spanning across the ethmoid bulla (EB), the anterior ethmoid sinus (AES) cells, and the posterior ethmoid sinus (PES) cells, it should be understood that body (1102) may be more loosely positioned in these cells such that there is substantial contact between body (1102) and the mucosa in these cells.

Flange (1106) generally secures one end of body (1102) at an exterior wall of the ethmoid bulla (EB) while flange (1104) generally secures the other end of body (1102) at an interior wall of the sphenoid sinus (SS). Flanges (1104, 1106) may each be configured similar to flange (206), similar to petals (606, 706), or in any other suitable fashion. It should also be understood that one or both of flanges (1104, 1106) may simply be omitted in some versions. Each flange (1104, 1106) of the present example defines a respective opening (1108, 1110) permitting communication of fluid through flange (1104, 1106) to reach body (1102). For instance, if a patient self-administers a fluid medication into their nose while wick (1100) is deployed, that medication may wick through body (1102) to the mucosa of the ethmoid bulla (EB), the mucosa of the anterior ethmoid sinus (AES) cells, and the mucosa of the posterior ethmoid sinus (PES) cells; and may further reach the sphenoid sinus (SS). Wick (1100) thus provides a path for the medication that the medication would not have otherwise had, in order to reach the mucosa of the ethmoid bulla (EB), the mucosa of the anterior ethmoid sinus (AES) cells, and the mucosa of the posterior ethmoid sinus (PES) cells.

It should also be understood that wick (1100) may be installed in numerous other configurations. For instance, wick (1100) need not reach all the way to the sphenoid sinus (SS), and may instead terminate in any other sinus cell (e.g., within one of the anterior ethmoid sinus (AES) cells or one of the posterior ethmoid sinus (PES) cells, etc.). Various suitable paths for wick (1100) will be apparent for those of ordinary skill in the art in view of the teachings herein. It should also be understood that various instruments may be used to deploy wick (1100). By way of example only, an instrument similar to instrument (100) or instrument (400) may be used to deploy wick (1100). Other suitable instruments that may be used to deploy wick (1100) will be apparent to those of ordinary skill in the art in view of the teachings herein.

Figure 16A:
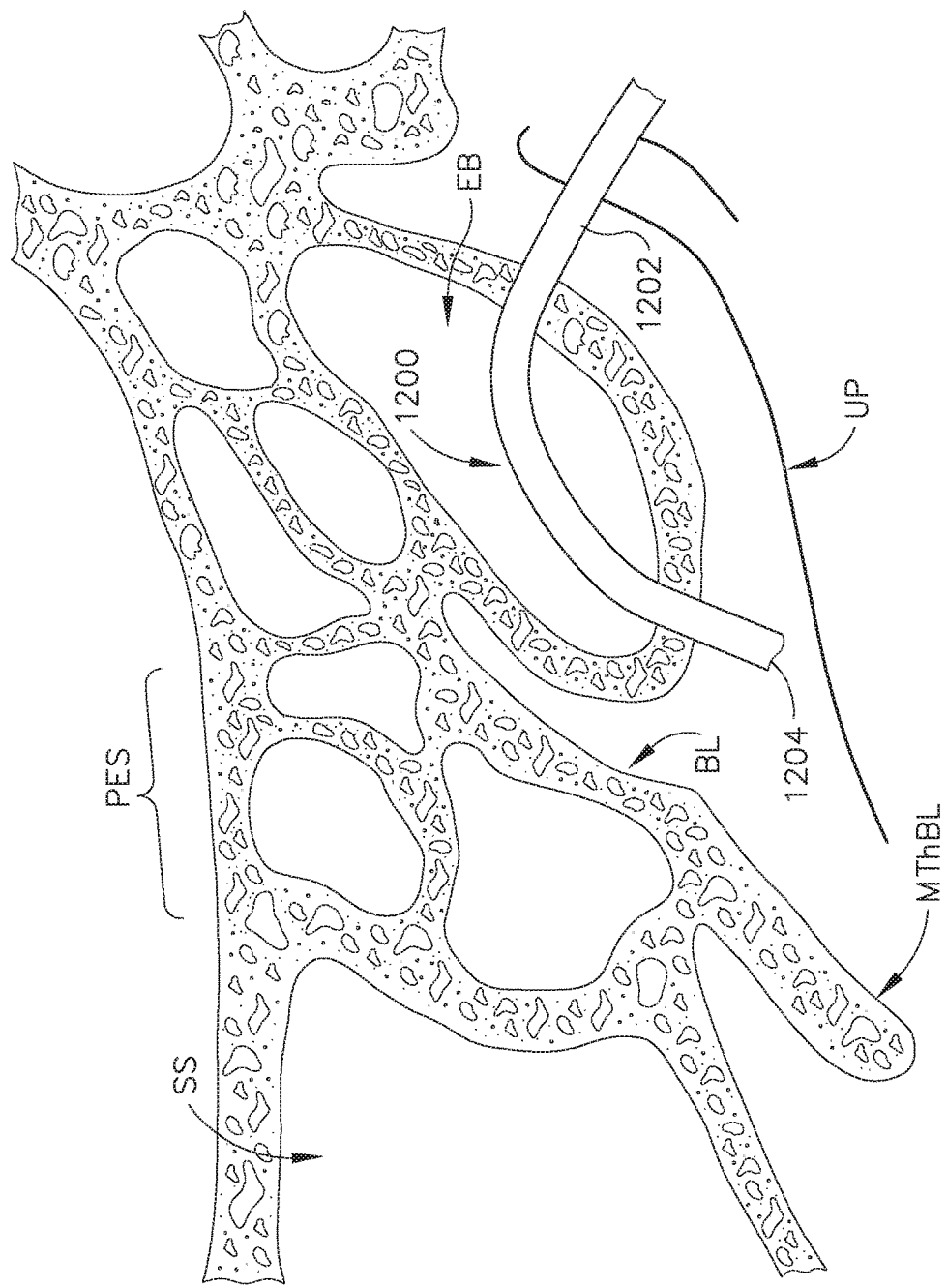
FIG. 16A depicts a left sagittal cross-sectional view of a portion of a human head, with an exemplary wick passed through the ethmoid bulla in a first stage of installation.
Figure 16B:
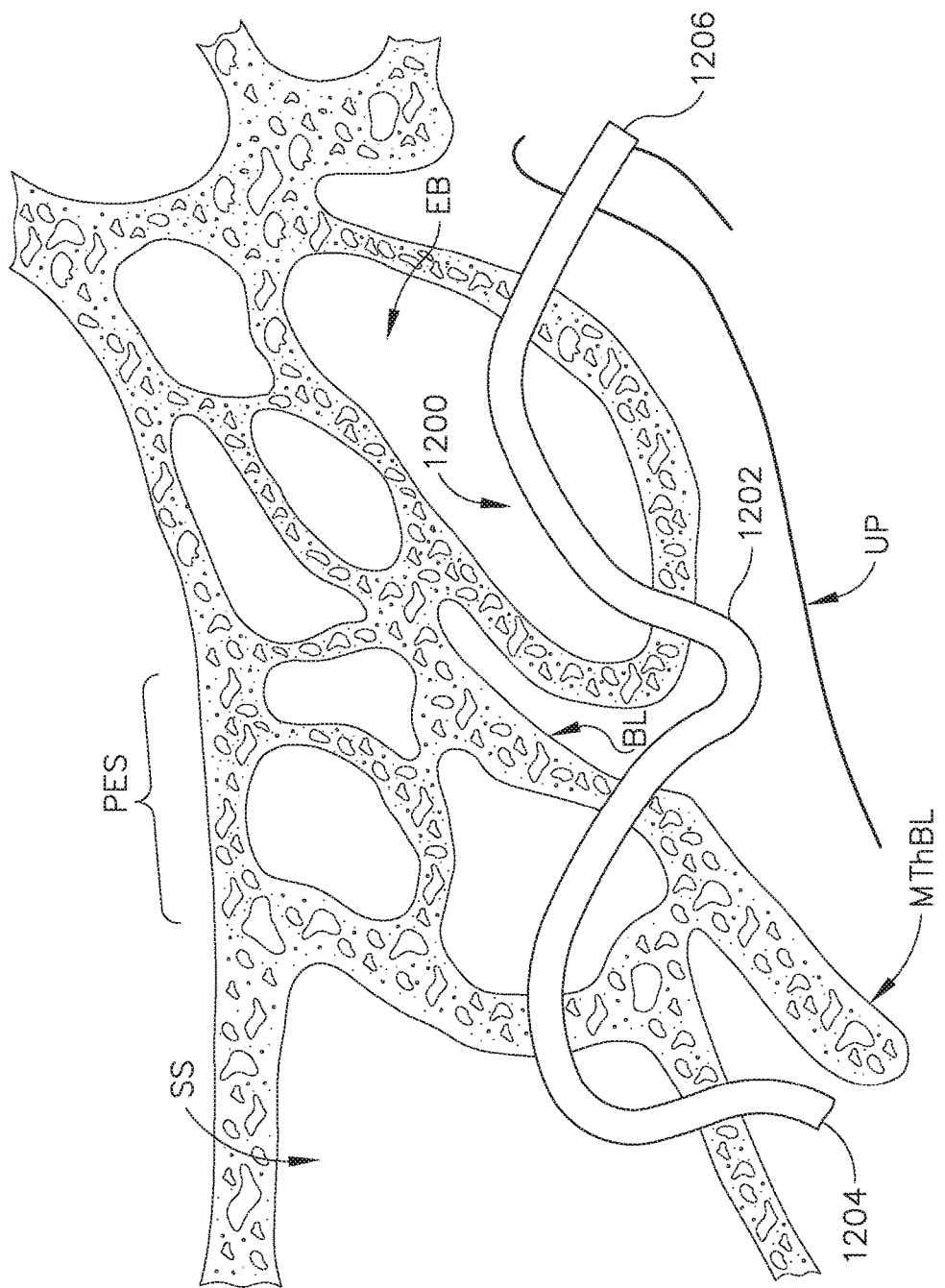
FIG. 16B depicts a left sagittal cross-sectional view of a portion of a human head, with the wick of FIG. 16A passed through an additional ethmoid sinus cell and the sphenoid sinus in a second stage of installation.

In some instances, a curved needle may be used to deploy a wick. For instance, FIG. 16A shows an example of a wick (1200) that has been driven through the ethmoid bulla (EB) with one pass of a curved needle (not shown). Wick (1200) of this example has a body (1202), a first free end (1204), and a second free end (1206). Body (1202) may be configured similar to bodies (1002, 1102) described above. The arc of the curved needle enables the needle to pierce and pass through the wall of the ethmoid bulla (EB) twice in a single pass, such that wick (1200) enters and exits the ethmoid bulla (EB). In a second pass, the curved needle pierces the middle turbinate vertical basal lamella (MTvBL) to pass through a posterior ethmoid sinus (PES) cell and then through the sphenoid sinus (SS) as shown in FIG. 16B. Thus, first free end (1204) is positioned inferior to the sphenoid sinus (SS), while second free end (1206) is positioned anterior to the ethmoid bulla (EB). Ends (1204, 1206) lack flanges, petals, or similar structures in this example. Body (1202) contacts mucosa in the ethmoid bulla (EB), the posterior ethmoid sinus (PES) cell, and the sphenoid sinus (SS), such that body (1202) is able to deliver medical fluid to these sinus cells through a capillary action. Of course, a curved needle or other device may be used to route a wick (1200) in various other routes using any desired number of passes of the needle.

Figure 17:
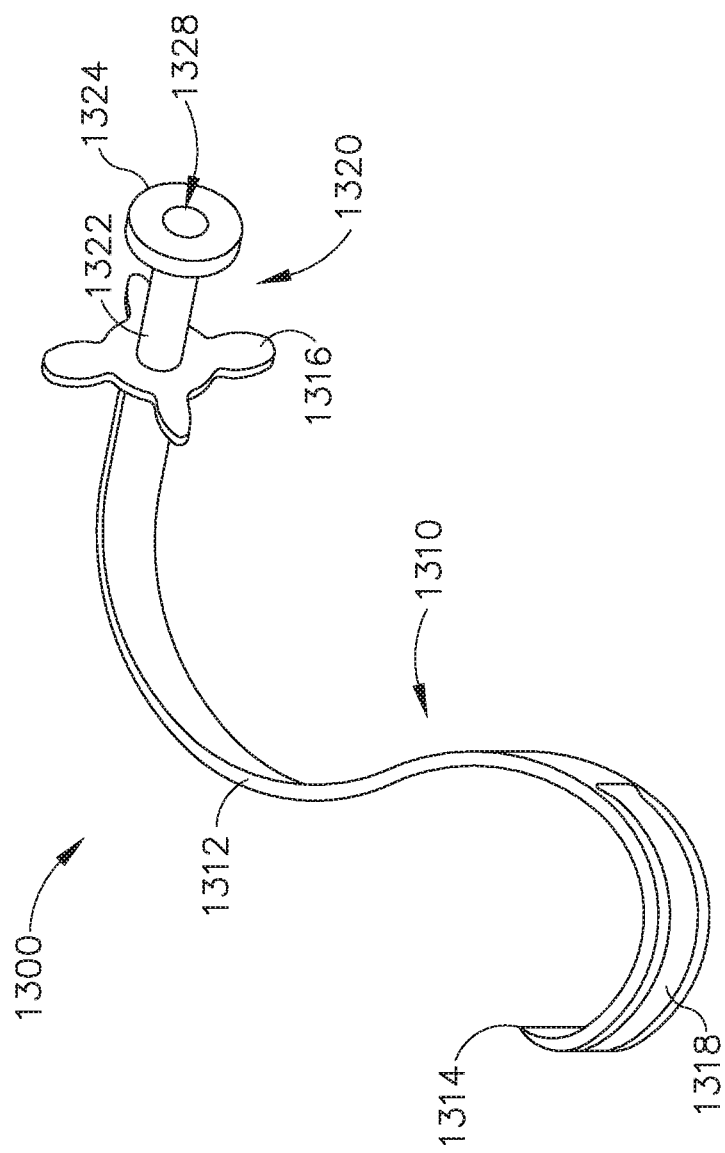
FIG. 17 depicts a perspective view of an exemplary ethmoid port with a wick having a clamping feature.

FIG. 17 depicts an example of a wicking port (1300) that is essentially a hybrid of the ports and wicks described above. Wicking port (1300) of this example includes a wick portion (1310) and a port portion (1320). As described in greater detail below, wick portion (1310) will be positioned anteriorly relative to port portion (1320) when wicking port (1300) is deployed in a patient. Wicking port (1300) is positioned in the particular orientation shown in FIG. 17 merely to illustrate the structural features of wicking port (1300), not to represent a deployed orientation. Wick portion (1310) includes a generally flat wick body (1312) that terminates in a free end (1314), with a set of wings (1316) at the other end. Body (1312) may be configured similar to bodies (1002, 1102) described above. A resilient band (1318) is integrated into wick body (1312), just proximal to free end (1314). Band (1318) is resiliently biased to assume a bent clamping configuration as described below; yet band (1318) is sufficiently compliant to flex into a substantially straight configuration. Port portion (1320) includes a cylindraceous body (1322), a flange (1324), and a lumen (1328). Port portion (1320) is substantially similar to port (200) described above, except that body (1322) is joined to wick portion (1310) where body (202) has flange (206). Lumen (1328) is in fluid communication with body (1312), such that fluid communicated through lumen (1328) may be wicked through body (1312); and such that fluid wicked through body (1312) may be communicated through lumen (1328). In some alternative versions, flange (1324) is omitted.

Figure 18:
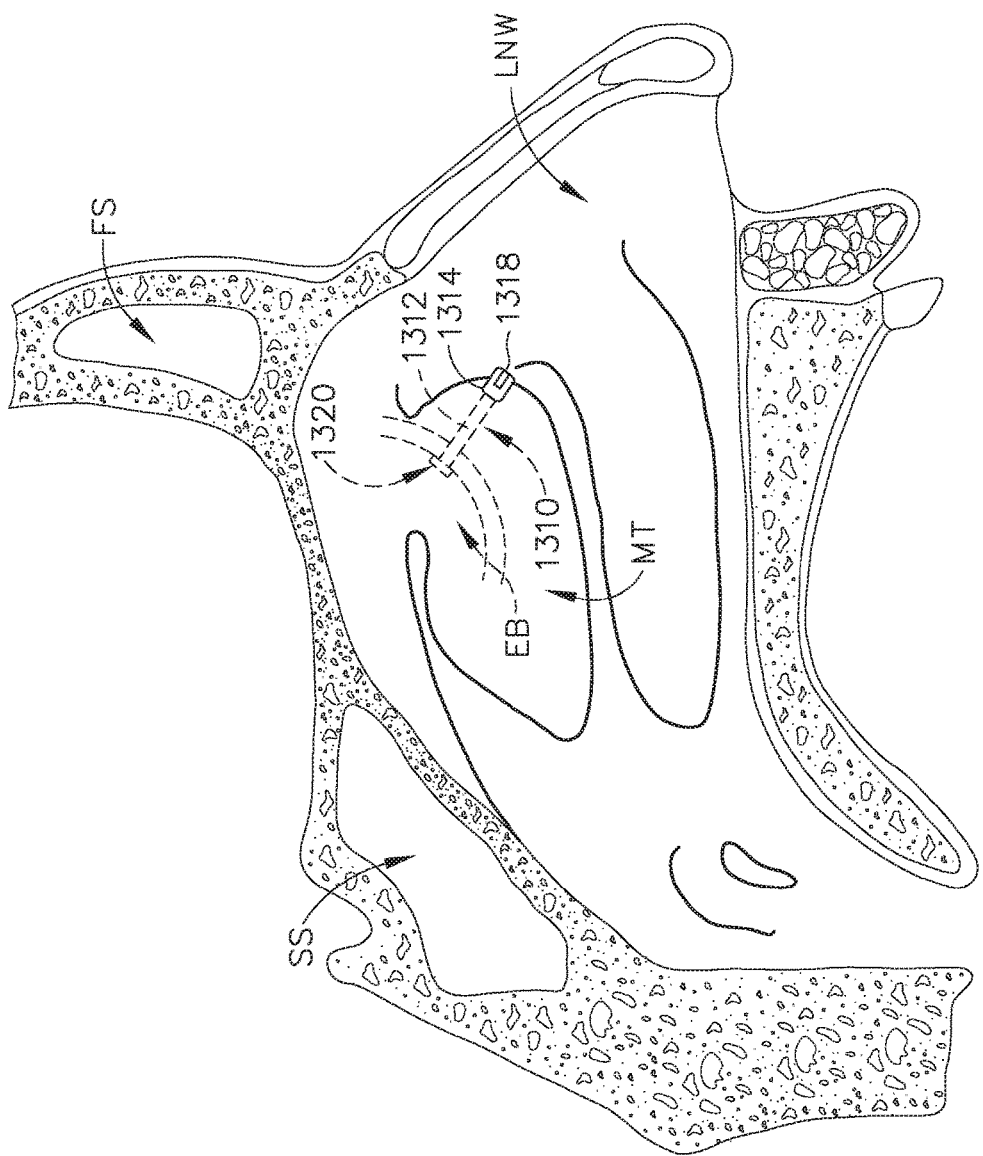
FIG. 18 depicts a left sagittal cross-sectional view of a portion of a human head, along a plane medial to the plane associated with the view of FIG. 6, with the port of FIG. 17 installed in the ethmoid bulla and with the clamping feature engaged with the middle turbinate.

FIG. 18 shows an exemplary deployment of wicking port (1300). As shown, port (1300) is positioned such that port portion (1320) is disposed through the wall of the ethmoid bulla (EB). Wings (1316) and flange (1324) cooperate to maintain the position of port portion (1320) relative to the ethmoid bulla (EB). Body (1312) spans across a portion of the nasal cavity to reach the middle turbinate (MT). Body (1312) wraps around an anterior ridge of the middle turbinate (MT) and band (1318) acts as a clip resiliently securing body (1312) to the middle turbinate (MT). Free end (1314) of body (1312) is positioned at the medial side of the middle turbinate (MT). The positioning of body (1312) may substantially increase its saturation with fluids administered through the patient's nose. Fluid from the saturated body (1312) may reach the patient's ethmoid bulla (EB) by wicking to port portion (1320), where the medical fluid crosses into the ethmoid bulla (EB).

Various suitable ways in which wicking port (1300) may be deployed will be apparent to those of ordinary skill in the art in view of the teachings herein. For instance, an instrument similar to instrument (100) or instrument (400) may be used to first deploy port portion (1320), with visualization from endoscope (60) and/or some other source of visualization. After port portion (1320) is deployed in the ethmoid bulla (EB), a pair of forceps or some other instrument may be used to wrap the free end of wick portion (1310) about the anterior ridge of the middle turbinate (MT). A mandrel or other feature may be used to hold band (1318) in a straight position before wick portion (1310) is appropriately situated in relation to the middle turbinate (MT). Various other suitable instruments and methods that may be used to deploy wicking port (1300) will be apparent to those of ordinary skill in the art in view of the teachings herein. It should also be understood that port portion (1320) may be installed in a posterior ethmoid sinus (PES) cell or some other location instead of being installed in the ethmoid bulla (EB), if desired. It should also be understood that band (1318) and/or other portions of wicking port (1300) may be formed of bioabsorbable material, if desired.

While the foregoing examples are provided in the context of providing a wick in the ethmoid bulla (EB), it should be understood that wicks may be installed elsewhere within the sinus complex, such as in the sphenoid sinus (SS), in the posterior ethmoid sinus (PES), and/or elsewhere, without necessarily also being installed in the ethmoid bulla (EB). By way of example only, an instrument may be used to form an opening in the middle turbinate vertical basal lamella (MTvBL), medial to the posterior wall of the ethmoid bulla (EB) but lateral to the lateral wall of the vertical basal lamella (MTvBL). A wick may then be deployed in that formed opening. In some instances, the wick may enter the superior meatus, medial to the posterior ethmoid sinus (PES) cells. In some other instances, the wick may enter the anterior-most cell of the posterior ethmoid sinus (PES). In either case, the wick may allow patient-administered substances to reach the posterior ethmoid sinus (PES) cells. Various other ways in which the above described procedures (and in some cases, instruments) may be modified to provide wicks in sinus cells other than the ethmoid bulla (EB) will be apparent to those of ordinary skill in the art in view of the teachings herein.

V. Exemplary Expansion of Retrobullar Space

Figure 19A:
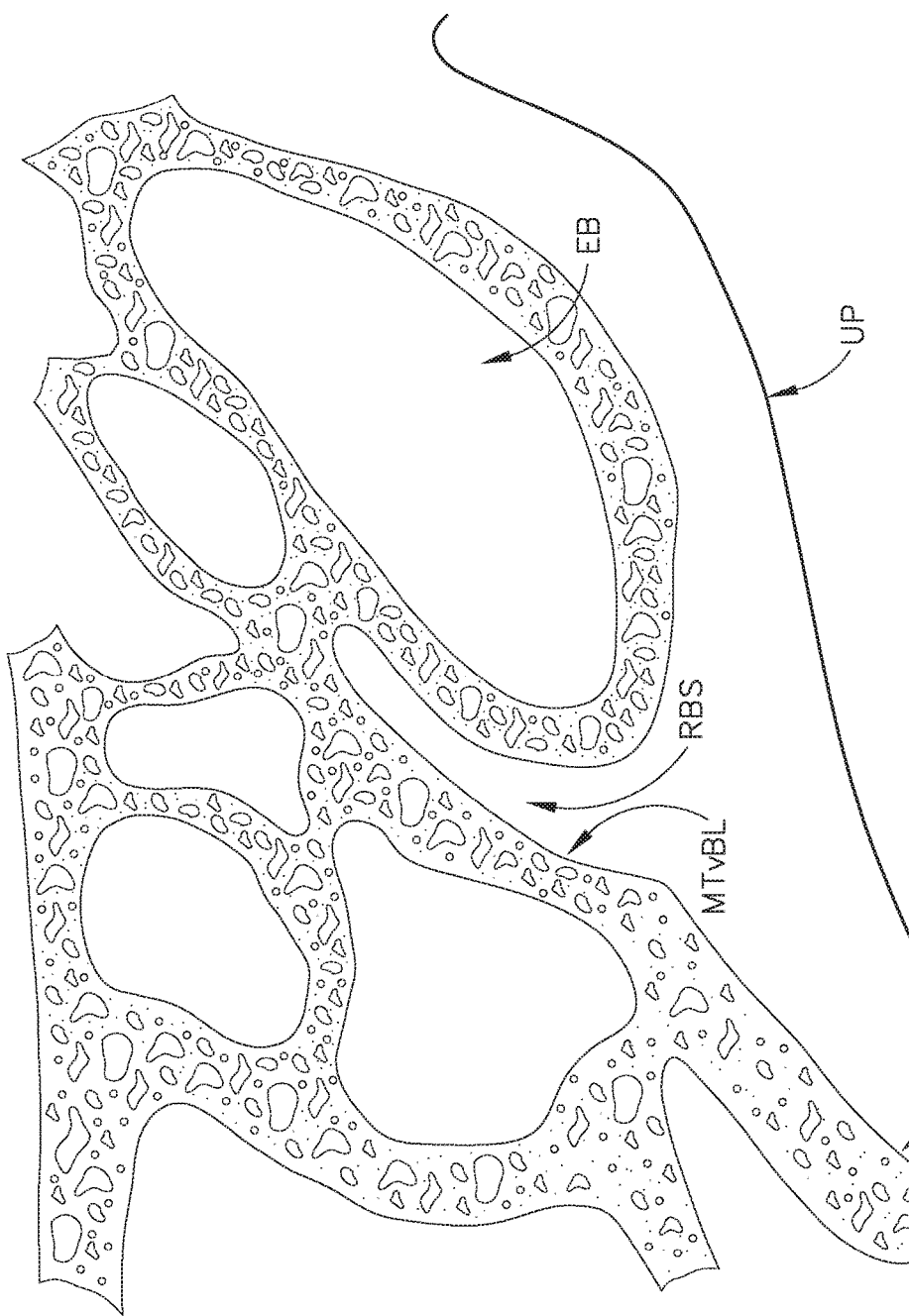
FIG. 19A depicts a left sagittal cross-sectional view of a portion of a human head, showing the retrobullar space in a non-dilated configuration.

As noted above, there may be instances where the configuration of the retrobullar space (RBS) may impede flow through the ostium of the ethmoid bulla (EB). It may therefore be desirable to remodel the retrobullar space (RBS) in order to enlarge the transition zone and thereby improve fluid flow into and out of the ethmoid bulla (EB). FIG. 19A shows an exemplary retrobullar space (RBS) before a remodeling procedure. FIG. 19B shows a guide catheter (1400) positioned at the retrobullar space (RBS) to begin a remodeling procedure. Guide catheter (1400) of this example is similar to guide catheter (30) discussed above. Guide catheter (1400) includes a body (1402) having an open distal end (1406) and a bend (1404) just proximal to distal end (1406). Guide catheter (1400) is positioned such that open distal end (1406) is positioned at retrobullar space (RBS), anterior to the middle turbinate vertical basal lamella (MTvBL) and posterior to the posterior wall of the ethmoid bulla (EB). Endoscope (60) or some other visualization device may be used to assist in positioning of guide catheter (1400).

Figure 19C:
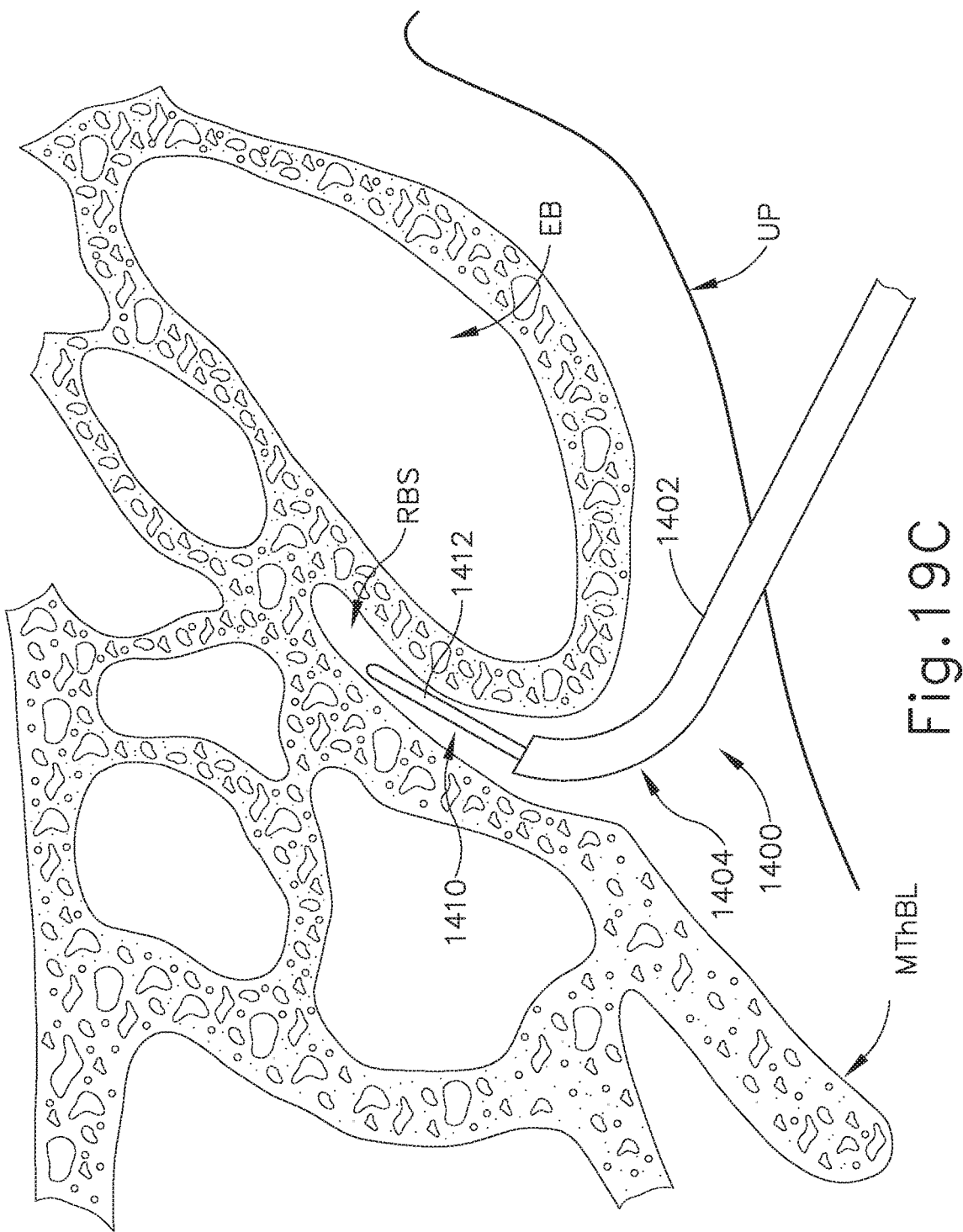
FIG. 19C depicts a left sagittal cross-sectional view of a portion of a human head, with a dilation catheter advanced through the guide catheter of FIG. 19B into the retrobullar space.
Figure 19D:
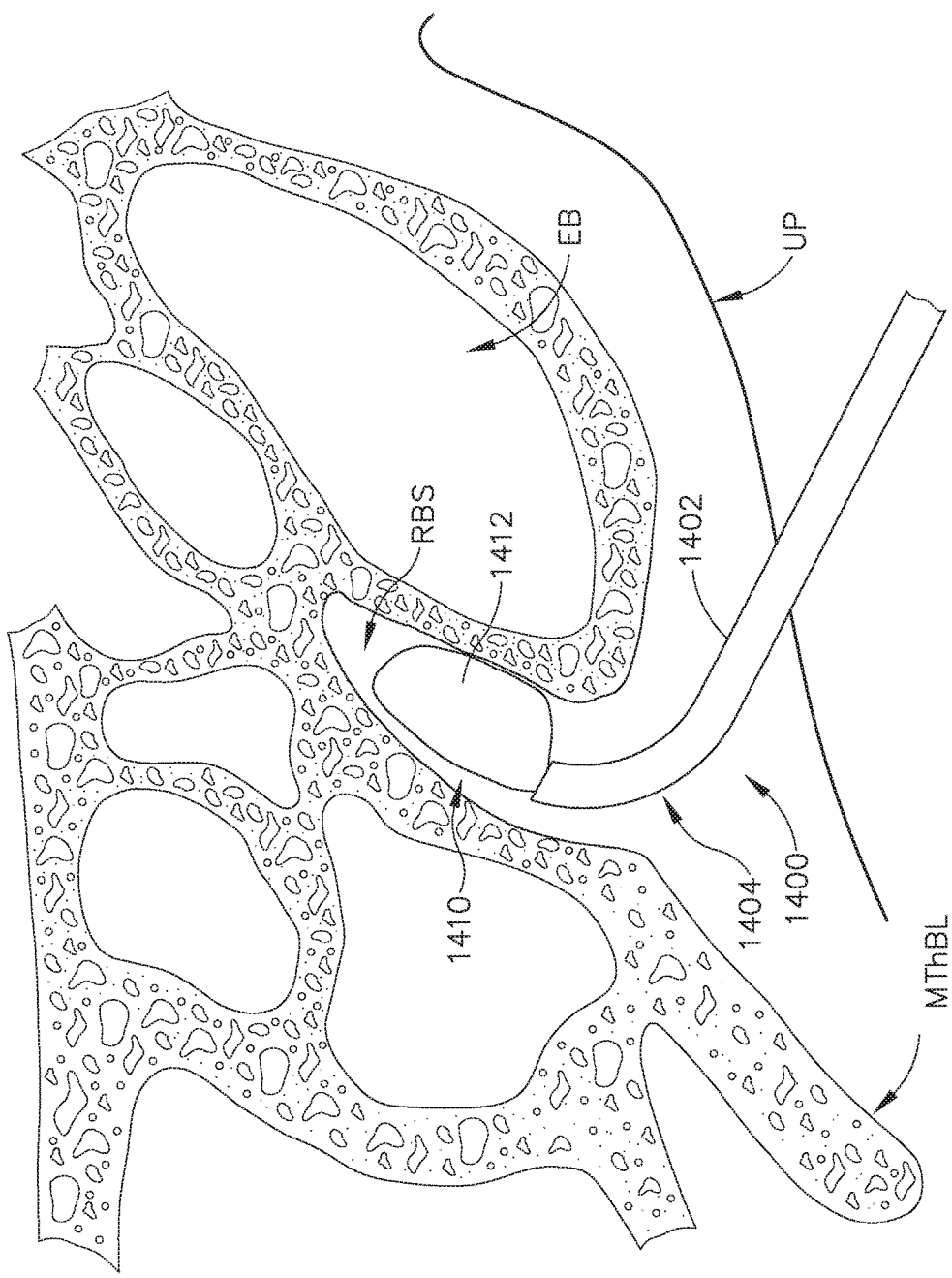
FIG. 19D depicts a left sagittal cross-sectional view of a portion of a human head, with a dilator of the dilation catheter of FIG. 19C in an inflated state in the retrobullar space.

Once guide catheter (1400) has been suitably positioned, a balloon catheter (1410) is advanced through guide catheter (1400) as shown in FIG. 19C. Balloon catheter (1410) has an asymmetrically inflating balloon (1412), which is positioned within the retrobullar space (RBS) at this stage, though balloon (1412) is in a deflated state during advancement and positioning of balloon catheter (1410). While the operator maintains a firm grip on guide catheter (1400) and balloon catheter (1410), balloon (1412) is then inflated as shown in FIG. 19D. In this example, due to the configuration of balloon (1412), rigidity within catheters (1400, 1410), and the operator's firm grip providing a mechanical ground, inflated balloon (1412) only bears anteriorly on the ethmoid bulla (EB) and does not bear posteriorly on the middle turbinate vertical basal lamella (MTvBL). Various suitable ways in which balloon (1412) may be configured to provide such inflation will be apparent to those of ordinary skill in the art in view of the teachings herein. In the present example, inflated balloon (1412) fractures the bone forming the posterior wall of the ethmoid bulla (EB), driving the bone and tissue anteriorly. It should be understood that the fragments formed by fracturing the bone will remain contained within the mucosa, which itself remains intact on both sides of the bone. This is due to the fact that balloon (1412) is an atraumatic device used to move the posterior wall of the ethmoid bulla (EB). A traumatic method of remodeling may cause bone fragments to be released in the nasal cavity, which may require the bone fragments to be carefully removed. Such bone fragment removal may be time consuming and difficult. Thus, using balloon (1412) may make the remodeling process easier and faster than a procedure that uses a traumatic instrument.

Figure 19E:
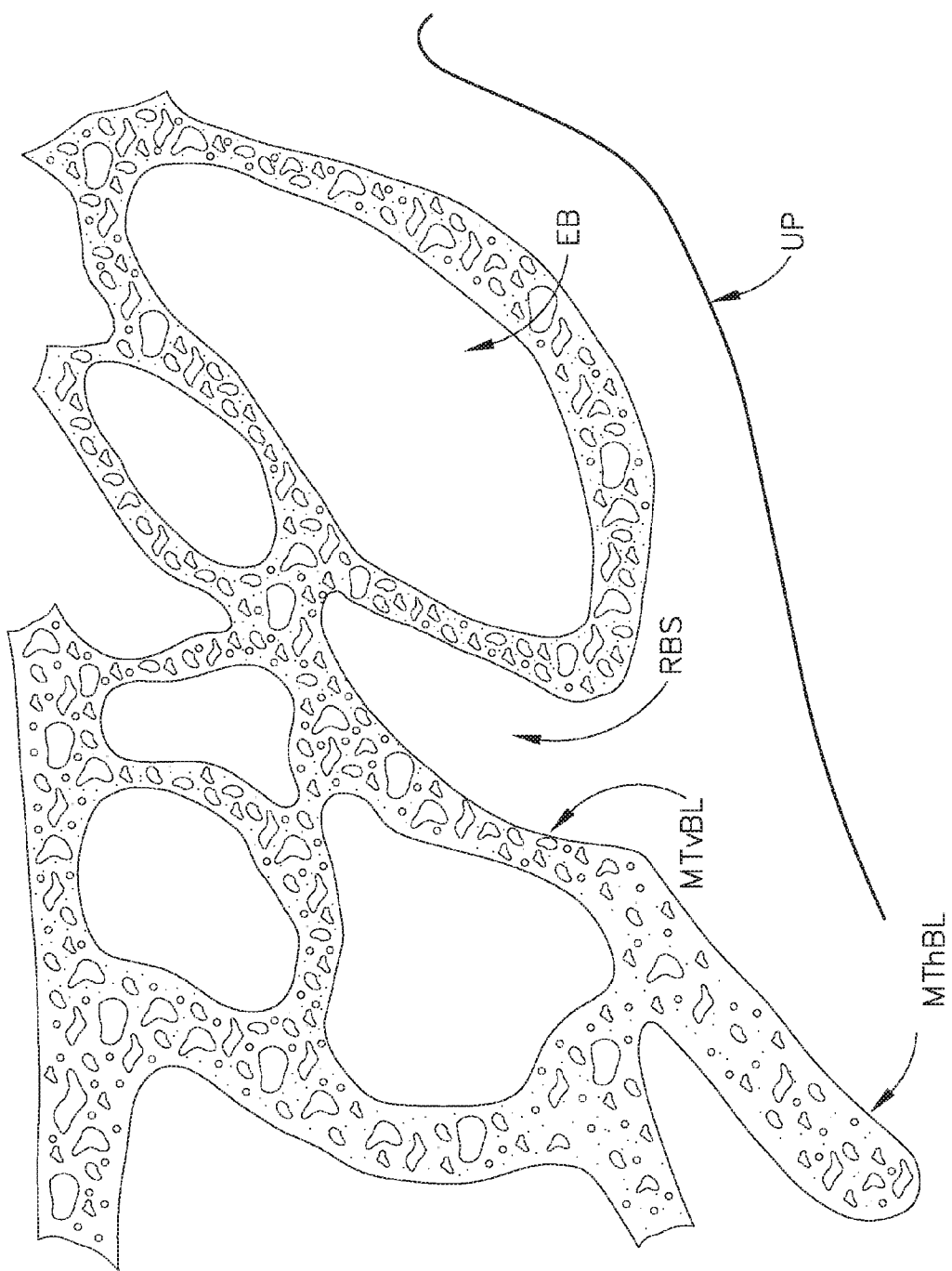
FIG. 19E depicts a left sagittal cross-sectional view of a portion of a human head, showing the retrobullar space in a dilated configuration.

After balloon (1412) has been inflated to the point where balloon (1412) has remodeled the posterior wall of the ethmoid bulla (EB), balloon (1412) is then deflated, and catheters (1400, 1410) are withdrawn from the patient, leaving behind an enlarged retrobullar space (RBS) as shown in FIG. 19E. This enlarged retrobullar space (RBS) shown in FIG. 19E may provide greater fluid communication (e.g., mucus outflow) for ethmoid bulla (EB) than the retrobullar space (RBS) shown in FIG. 19A. In some variations, inflated balloon (1412) bears against the middle turbinate vertical basal lamella (MTvBL) in addition to bearing against the posterior wall of the ethmoid bulla (EB). In some such versions, the strength of the middle turbinate vertical basal lamella (MTvBL) is greater than the strength of the posterior wall of the ethmoid bulla (EB), such that the posterior wall of the ethmoid bulla (EB) is remodeled by inflating balloon (1412) while the middle turbinate vertical basal lamella (MTvBL) is not remodeled by inflating balloon (1412). The vertical basal lamella (MTvBL) may thus provide a mechanical grounding structure for balloon (1412) in some instances.

It should be understood that the retrobullar space (RBS) remodeling procedure described above may be performed in addition to or in lieu of deploying ports and/or wicks as described above. It should also be understood that various other kinds of instruments may be used to perform a retrobullar space (RBS) remodeling procedure. By way of example only, catheters (1400, 1410) or instrument (1500) may be substituted with a dilation instrument as taught in U.S. patent application Ser. No. 13/832,167, entitled "Uncinate Process Support for Ethmoid Infundibulum Illumination," now U.S. Pat. No. 9,615,959, issued on Apr. 11, 2017, the disclosure of which is incorporated by reference herein.

VI. Exemplary Retrobullar Ostium Dilation

Figure 20:
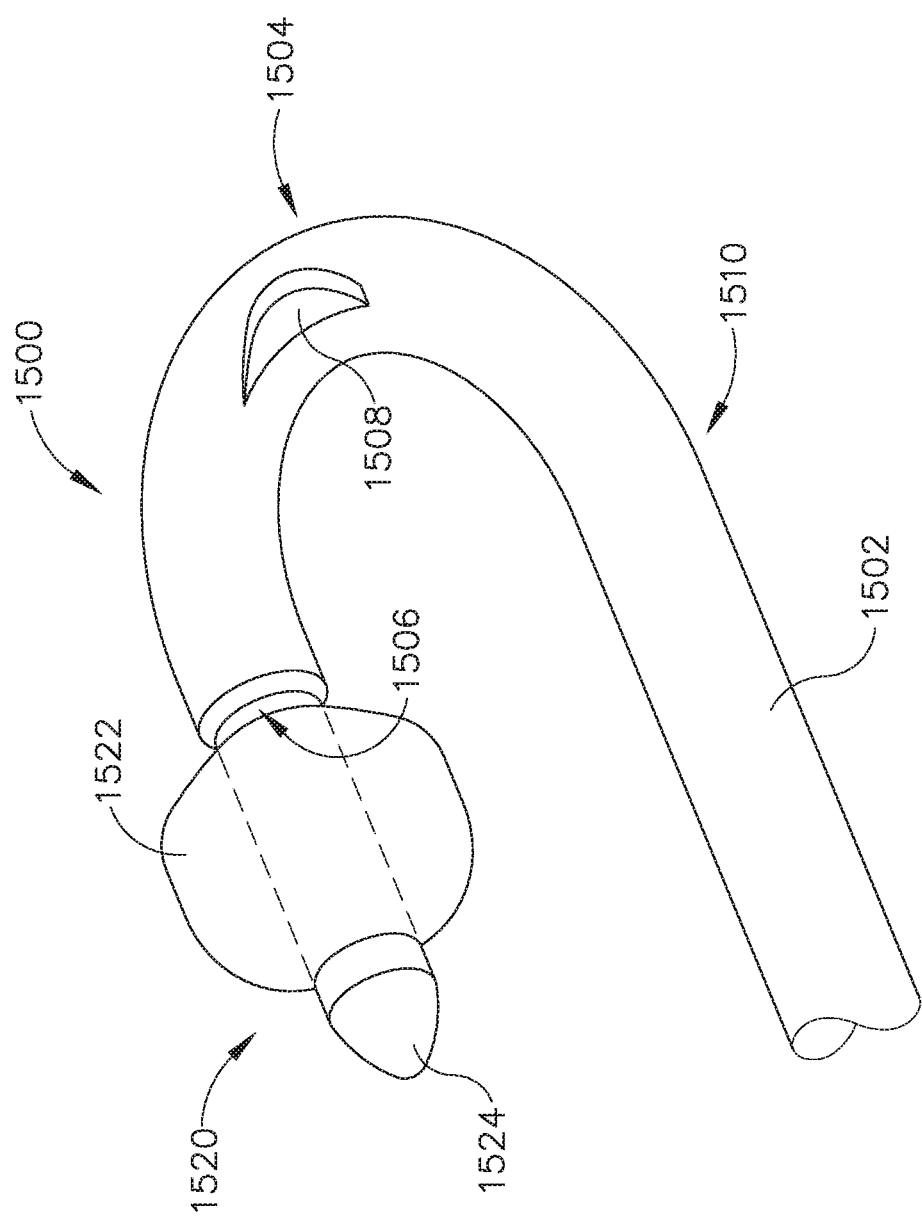
FIG. 20 depicts a perspective view of an exemplary dilation catheter and catheter suitable for dilating an ethmoid bulla ostium.

FIG. 20 shows an exemplary instrument (1500) that may be used to dilate an ostium of the ethmoid bulla (EB) from within the retrobullar space (RBS). Instrument (1500) of this example comprises a guide catheter (1510) and a balloon catheter (1520). Guide catheter (1510) includes a body (1502) having an open distal end (1506) and a bend (1504) just proximal to distal end (1506). While guide catheter (1400) of the example described above reaches the retrobullar space (RBS) from an inferior approach (with distal end (1406) oriented superiorly), guide catheter (1510) of this example reaches the retrobullar space (RBS) from a more medial approach (with distal end (1506) oriented laterally then anteriorly). Bend (1504) of guide catheter (1510) also extends along a greater arc angle than bend (1404) of guide catheter (1400). By way of example only, bend (1504) may extend along an arc angle between approximately 135° and approximately 180°. Bend (1504) is configured to facilitate orienting distal end (1506) directly toward an ostium of the ethmoid bulla (EB) from within the retrobullar space (RBS), anterior to the middle turbinate vertical basal lamella (MT-vBL).

Guide catheter (1510) of this example also includes a transversely extending reflective member (1508). Reflective member (1508) is positioned at bend (1504) and facilitates viewing of the retrobullar space (RBS) using an endoscope such as endoscope (60). In some versions, reflective member (1508) may be selectively advanced or retracted transversely relative to body (1502). Various suitable ways in which reflective member (1508) may be selectively advanced or retracted transversely relative to body (1502) will be apparent to those of ordinary skill in the art in view of the teachings herein.

Balloon catheter (1520) of the present example includes an inflatable balloon (1522) and an atraumatic tip (1524) with a rounded/tapered profile that is configured to facilitate insertion into an ostium of the ethmoid bulla (EB). In some versions, balloon catheter (1520) is configured to drive tip (1524) through an ostium when the effective inner diameter of the ostium is less than the outer diameter of tip (1524). Balloon (1522) may be configured substantially similar to dilator (22) described above. Balloon catheter (1520) may be advanced distally through (1510) to expose balloon (1522) relative to distal end (1506). Balloon (1522) may then be inflated with fluid from a fluid source (e.g., inflator (40), etc.) to expand and thereby dilate an ostium.

In an exemplary use, the operator may position guide catheter (1510) such that distal end (1506) is oriented directly toward an ostium of the ethmoid bulla (EB) from within the retrobullar space (RBS). During this positioning, the operator may direct the line of sight for endoscope (60) (or some other visualization device) at reflective member (1508) to obtain a reflected view of the posterior wall of the ethmoid bulla (EB) to visually locate the ostium. Once the guide catheter (1510) is suitably positioned, the operator may advance balloon catheter (1520) distally through guide catheter (1510) such that the tip (1524) of balloon catheter (1520) passes through the ostium. Again, this may be performed using visualization assistance from reflective member (1508). Once balloon (1522) is positioned in the ostium, balloon (1522) may be inflated with fluid (e.g., from inflator (40)) to dilate the ostium. Balloon (1522) may be held in an inflated state for any suitable duration. Balloon (1522) may be repeatedly inflated and deflated as many times as desired. Once balloon (1522) has been finally deflated, balloon (1522) may be retracted back into guide catheter (1510) and instrument (1500) may be removed from the patient's nasal cavity. It should be understood that the retrobullar ostium dilation procedure described above may be performed in addition to or in lieu of deploying ports and/or wicks as described above; and/or in addition to or in lieu of a retrobullar space (RBS) remodeling procedure as described above.

VII. Exemplary Retrobullar Piercing

In addition to or in lieu of installing a port, installing a wick, and/or enlarging the retrobullar space (RBS) by remodeling the posterior wall of the ethmoid bulla (EB), it may be desirable to drive a piercing element into the posterior wall of the ethmoid bulla (EB). In some instances, this may be done to enlarge the size of the naturally occurring ostium that is located at the posterior wall of the ethmoid bulla (EB). In addition or in the alternative, this may be done to create a new ostium for the ethmoid bulla (EB). Whether enlarging an ostium or creating an ostium, this may improve the flow of air and fluid into and out of the ethmoid bulla (EB). Various examples of instruments and procedures that may be used to pierce the posterior wall of the ethmoid bulla (EB) will be described in greater retail below, while other examples will be apparent to those of ordinary skill in the art in view of the teachings herein.

FIGS. 21A-21C show one merely exemplary instrument (1600) that may be used to pierce the posterior wall of the ethmoid bulla (EB). Instrument (1600) of this example comprises a catheter body (1602) having an atraumatic distal tip (1604), a distal balloon (1606), a proximal balloon (1608), and a transverse opening (1610) located between balloons (1606, 1608). Balloons (1606, 1608) are coupled with a fluid source (1632) via a conduit (1630) such that fluid source (1632) may selectively communicate fluid (e.g., saline) to balloons (1606, 1608). FIG. 21A shows balloons (1606, 1608) in a non-inflated state while FIGS. 21B-21C show balloons (1606, 1608) in an inflated state. In the present example, balloons (1606, 1608) are on the same fluid line and are in fluid communication with each other. In some other versions, balloons (1606, 1608) are on independent fluid lines.

Instrument (1600) of this example further includes a piercing element (1620). Piercing element (1620) is slidably disposed within a passageway (1614) in catheter body (1602). Piercing element (1620) includes a sharp distal tip (1622). Tip (1622) is configured to pierce the wall of the ethmoid bulla (EB) without shattering the wall of the ethmoid bulla (EB). In other words, the wall of the ethmoid bulla (EB) remains intact except for the opening created by piercing element (1620), with such an opening being approximately the same size as the outer diameter of piercing element (1620). Passageway (1614) is fluidly isolated from the fluid path for balloons (1606, 1608). The distal end of passageway includes a ramp (1612) leading to transverse opening (1610). While ramp (1612) is shown as being generally planar, it should be understood that ramp (1612) may instead be curved or have some other configuration. Ramp (1612) is configured to guide piercing element (1620) generally transversely out through transverse opening (1610) when piercing element (1620) is advanced distally relative to catheter body (1602) as shown in FIG. 21C. In some instances, piercing element (1620) is resiliently biased to assume the configuration shown in FIG. 21C. In some other instances, piercing element (1620) is not resiliently biased to assume the configuration shown in FIG. 21C and is instead driven to that configuration by ramp (1612). It should be understood that piercing element (1620) is configured such that tip (1622) may be positioned outside an outer diameter region defined by inflated balloons (1606, 1608). Tip (1622) may thus pass through a tissue wall that is engaged by balloons (1606, 1608), as described below.

Figure 22C:
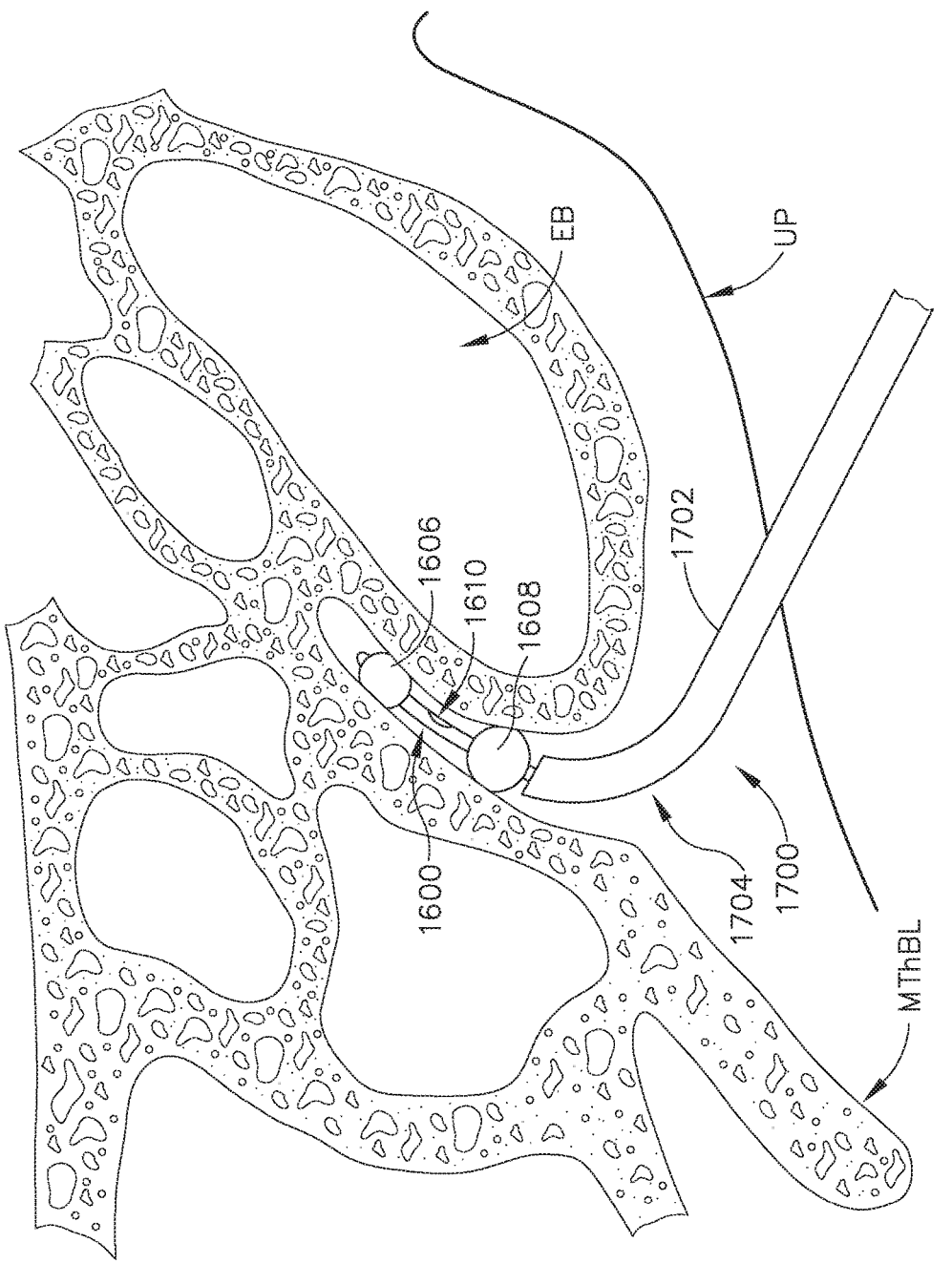
FIG. 22C depicts a left sagittal cross-sectional view of a portion of a human head, with the balloons of the piercing catheter of FIG. 21A in an inflated state in the retrobullar space.

FIGS. 22A-22E show a process where instrument (1600) is used to pierce the posterior wall of the ethmoid bulla (EB). In particular, FIG. 22A shows a guide catheter (1700) positioned at the retrobullar space (RBS). Guide catheter (1700) of this example is substantially identical to guide catheter (1400) discussed above. Guide catheter (1700) includes a body (1702) having an open distal end (1706) and a bend (1704) just proximal to distal end (1706). Guide catheter (1700) is positioned such that open distal end (1706) is positioned at retrobullar space (RBS), anterior to the middle turbinate vertical basal lamella (MTvBL) and posterior to the posterior wall of the ethmoid bulla (EB). Endoscope (60) or some other visualization device may be used to assist in positioning of guide catheter (1700).

Once guide catheter (1700) has been suitably positioned, instrument (1600) is advanced through guide catheter (1700) as shown in FIG. 22B. Balloons (1606, 1608) are both in a deflated state (see also FIG. 21A) during this advancement of instrument (1600). Piercing element (1620) is also in a retracted state during this advancement of instrument (1600). Instrument (1600) is oriented such that transverse opening (1610) faces the posterior wall of the ethmoid bulla (EB). In some instances, this orientation is achieved through direct visualization. In some other instances, this orientation is achieved through complementary features of guide catheter (1700) and instrument (1600). For instance, such complementary features may operate on an assumption that the inner region of bend (1704) is oriented toward the ethmoid bulla (EB). The complementary features may include a visual indicator on guide catheter (1700) that is aligned with the inner region of bend (1705) and a visual indicator on catheter body (1602) that is aligned with transverse opening (1610), such that the operator may rotate catheter body (1602) relative to guide catheter (1700) until these visual indicators are aligned with each other. Alternatively, complementary notch and protrusion may mate when catheter body (1602) is properly oriented relative to guide catheter (1700). As yet another merely illustrative example, catheter body (1602) may be keyed to guide catheter (1700), providing a poka-yoke feature that ensures consistent alignment between transverse opening (1610) and the inner region of bend (1704). Other suitable features will be apparent to those of ordinary skill in the art in view of the teachings herein.

Once instrument (1600) has been suitably positioned, fluid source (1632) is actuated to drive fluid into balloons (1606, 1608), thereby inflating balloons (1606, 1608) as shown in FIG. 22C (see also FIG. 21B). In the present example, balloons (1606, 1608) are only inflated with enough fluid pressure to provide structural support of catheter body (1602) in the retrobullar space (RBS). Balloons (1606, 1608) are not inflated to the point where they remodel the retrobullar space (RBS) by fracturing the middle turbinate vertical basal lamella (MTvBL) or the posterior wall of the ethmoid bulla (EB). In some other instances, though, balloons (1606, 1608) may in fact be inflated to the point where hey remodel the retrobullar space (RBS) by fracturing the middle turbinate vertical basal lamella (MTvBL) and/or the posterior wall of the ethmoid bulla (EB). Piercing element (1620) remains in the retracted position until balloons (1606, 1608) are sufficiently inflated.

Figure 22D:
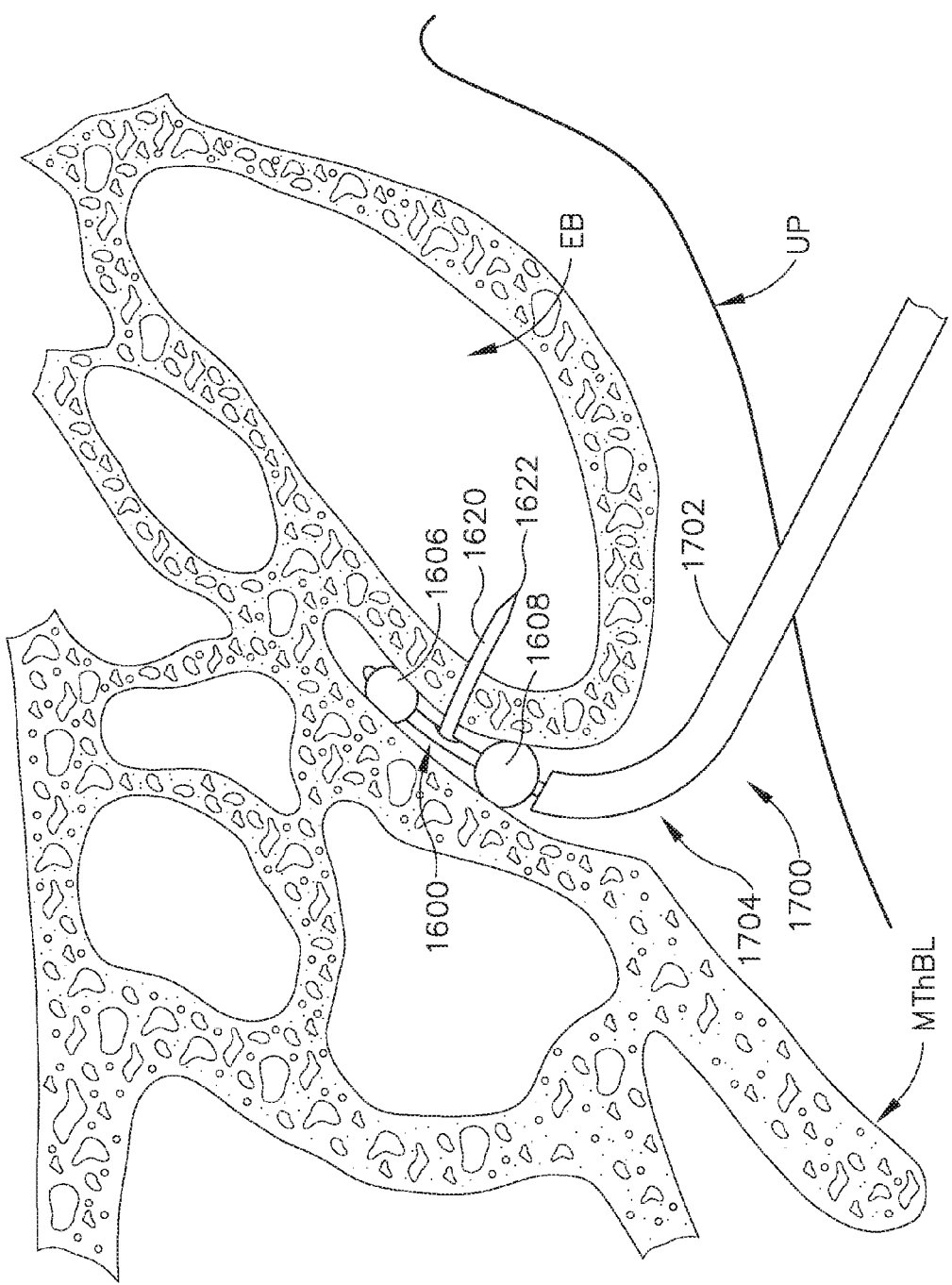
FIG. 22D depicts a left sagittal cross-sectional view of a portion of a human head, with the piercing element of the piercing catheter of FIG. 21A advanced to pierce a posterior wall of the ethmoid bulla.
Figure 22E:
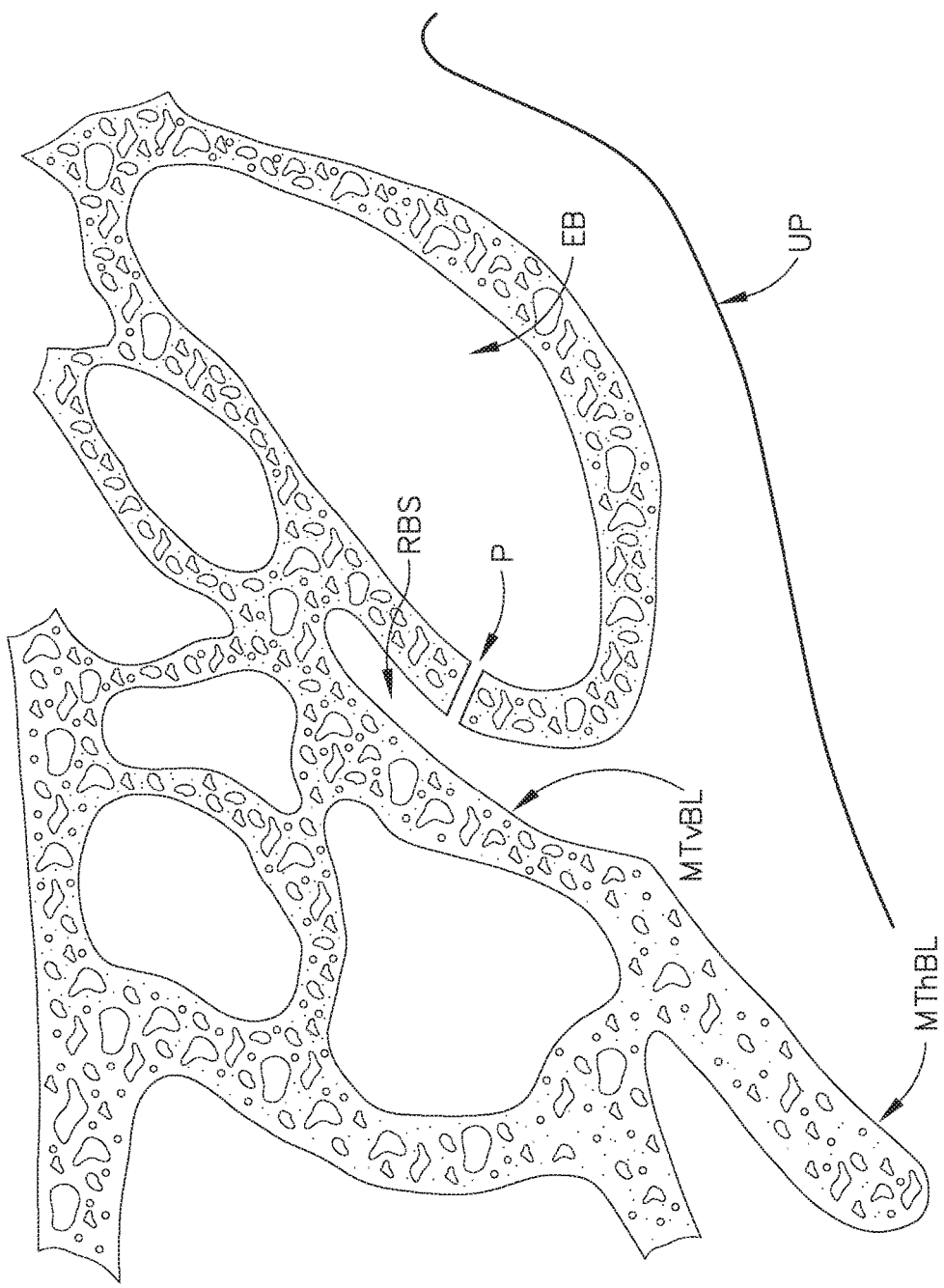
FIG. 22E depicts a left sagittal cross-sectional view of a portion of a human head, showing the pierced posterior wall of the ethmoid bulla.

After balloons (1606, 1608) have been sufficiently inflated, piercing element (1620) is advanced distally as shown in FIG. 22D (see also FIG. 21C). This drives tip (1622) along a generally transverse path such that tip (1622) pierces the posterior wall of the ethmoid bulla (EB). In some instances, a port or wick is deployed in the posterior wall of the ethmoid bulla (EB). In addition or in the alternative, the ethmoid bulla (EB) may be flushed with saline and suction through the opening formed by tip (1622). In the present example, however, piercing element (1620) is simply retracted proximally back into catheter body (1602), balloons (1606, 1608) are deflated, and instrument (1600) and catheter (1700) are removed from the nasal cavity, leaving behind a newly formed passageway (P) in the posterior wall of the ethmoid bulla (EB). This newly formed passageway (P) provides improved fluid communication between the ethmoid bulla (EB) and the transition zone provided by the retrobullar space (RBS). While piercing element (1622) is used to form a new passageway (P) in this example, it should be understood that piercing element (1622) may instead be used to widen an existing ostium or passageway. For instance, piercing element (1622) may be used to widen a naturally occurring ostium or an ostium that has been created using an instrument.

Figure 23:
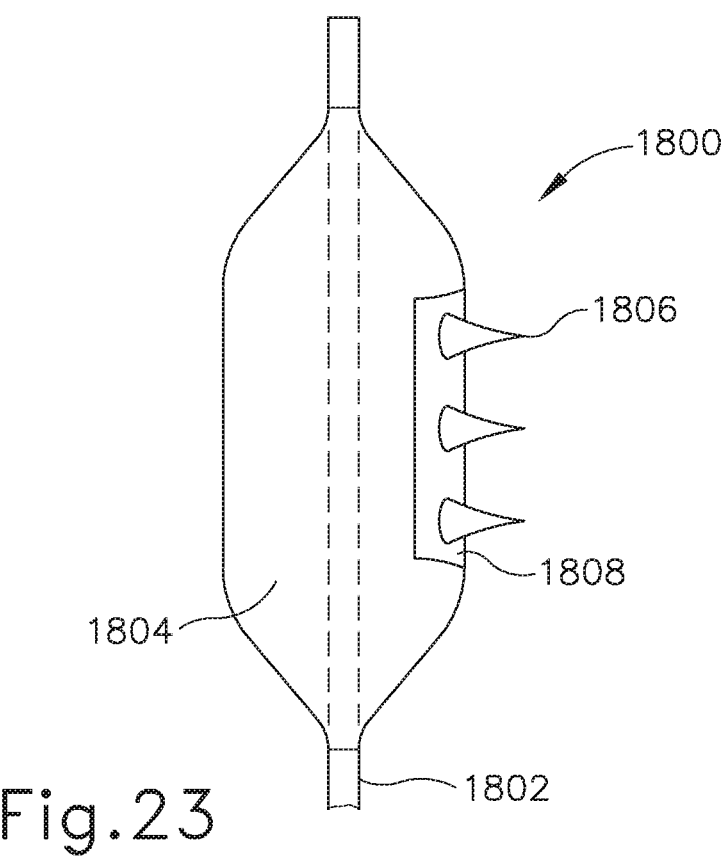
FIG. 23 depicts a side elevational view of an exemplary alternative piercing catheter.

FIG. 23 shows another exemplary instrument (1800) that may be used to pierce the posterior wall of the ethmoid bulla (EB). Instrument (1800) of this example comprises a catheter body (1802), a balloon (1804), and a plurality of spikes (1806) secured to a base (1808). Base (1808) is secured to balloon (1804) such that balloon (1804) will drive spikes (1806) outwardly when balloon (1804) is inflated, with base (1808) providing support for spikes (1806) over a substantial surface area of balloon (1804). Instrument (1800) may be used in place of instrument (1600) described above in order to create new ostia in the posterior wall of the ethmoid bulla (EB). In particular, instrument (1800) may be advanced through guide catheter (1700) while balloon (1804) is in a non-inflated state until balloon (1804) reaches the retrobullar space (RBS). Once balloon (1804) is in the retrobullar space (RBS) and spikes (1806) are pointed toward the posterior wall of the ethmoid bulla (EB), the balloon (1804) is inflated to drive spikes (1806) through the posterior wall of the ethmoid bulla (EB). Balloon (1804) is then deflated and instrument (1800) is removed with guide catheter (1700), leaving behind ostia formed by spikes (1806) in the posterior wall of the ethmoid bulla (EB). In some instances, balloon (1804) is inflated to a point where balloon (1804) remodels the retrobullar space (RBS) by fracturing the middle turbinate vertical basal lamella (MTvBL) or the posterior wall of the ethmoid bulla (EB), though this is of course merely optional.

Figure 24:
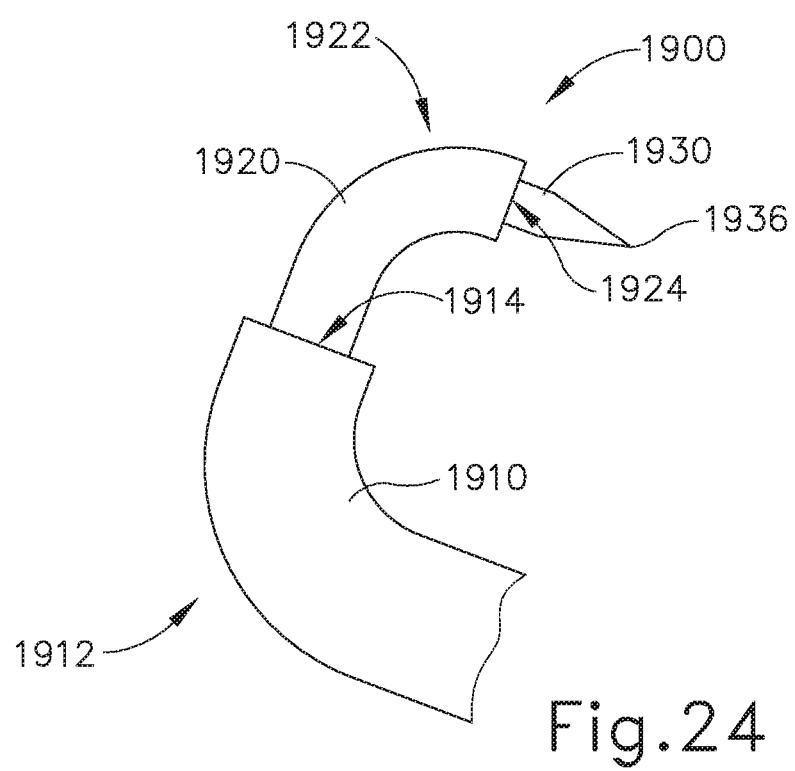
FIG. 24 depicts a side elevational view of another exemplary alternative piercing catheter.

FIG. 24 shows yet another exemplary instrument (1900) that may be used to pierce the posterior wall of the ethmoid bulla (EB). Instrument (1900) of this example comprises a guide catheter (1910) having a bend (1912) and an open distal end (1914). A secondary guide (1920) is slidably disposed in guide catheter (1910) and has another bend (1922) and an open distal end (1924). Secondary guide (1920) is resiliently biased to define bend (1922) but is configured to assume a straight configuration when retracted and confined within guide catheter (1910). A piercing element (1930) is slidably disposed in secondary guide (1920) and has a piercing tip (1936). Piercing element (1930) is flexible enough to slide along the paths formed by bends (1912, 1922) yet has sufficient strength to pierce the posterior wall of the ethmoid bulla (EB). Bend (1912) spans approximately 90 degrees while bend (1922) also spans approximately 90 degrees, such that guide catheter (1910) and secondary guide (1920) together are configured to redirect piercing element (1930) approximately 180 degrees. This may enable piercing element (1930) to readily reach the posterior wall of the ethmoid bulla (EB). In addition to forming a new ostium in the ethmoid bulla (EB), it should be understood that instrument (1900) may also be used to enlarge an ostium that is already present. Such a pre-existing ostium may be a naturally occurring ostium or an ostium that was created by an instrument such as any of the piercing instruments (1600, 1800, 1900) described herein, etc. Piercing element (1930) and secondary guide (1920) may both be retracted relative to guide catheter (1910) during positioning of instrument (1900) in the patient and during removal of instrument (1900) from the patient.

While the foregoing examples are provided in the context of piercing a wall of the ethmoid bulla (EB), it should be understood that similar procedures may be performed elsewhere within the sinus complex, such as in the sphenoid sinus (SS), or in the posterior ethmoid sinus (PES). By way of example only, an instrument may be used to form an opening in the middle turbinate vertical basal lamella (MTvBL), medial to the posterior wall of the ethmoid bulla (EB) but lateral to the lateral wall of the vertical basal lamella (MTvBL). The formed opening may serve to increase ventilation to the posterior ethmoid sinus (PES) cells and allow patient-administered substances to reach the posterior ethmoid sinus (PES) cells. Various ways in which the above described procedures (and in some cases, instruments) may be modified to create ostia for sinus cells other than the ethmoid bulla (EB) will be apparent to those of ordinary skill in the art in view of the teachings herein.

VIII. Exemplary Additional Piercing Variations

As noted above, the wall defining a sinus cavity may be pierced for various purposes, including but not limited to deploying a port, deploying a wick, or simply creating a new ostium. Several examples of instruments that may be used to pierce the wall of a sinus cavity have been described above. It should be understood that sinus wall piercing elements may include trocar type tips, coring tips, and other types of tips. Such tips may be advanced without rotation, advanced with rotation (e.g., in full rotations or angularly reciprocating partial rotations), advanced with longitudinal reciprocation (e.g., in a jackhammering action), or advanced with both rotation and longitudinal reciprocation. Piercing tips may have a sharp edge and/or an abrasive edge. As used herein, the term "piercing" should be understood to include various forms of cutting. For instance, a piercing element may also be configured to cut a slice out of a sinus wall. This may include corner slicing, medial slicing, or other forms of slicing/cutting. In some instances an act of cutting leaves a mucosal flap that can cover over exposed bone. When a cut leaves exposed bone or a tattered tissue edge, the same may be covered with a conformal material and/or curing material. Additional examples of piercing/cutting elements will be described in greater detail below; while further examples will be apparent to those of ordinary skill in the art in view of the teachings herein.

A. Exemplary Piercing Element with Serrated Edge

Figure 25:
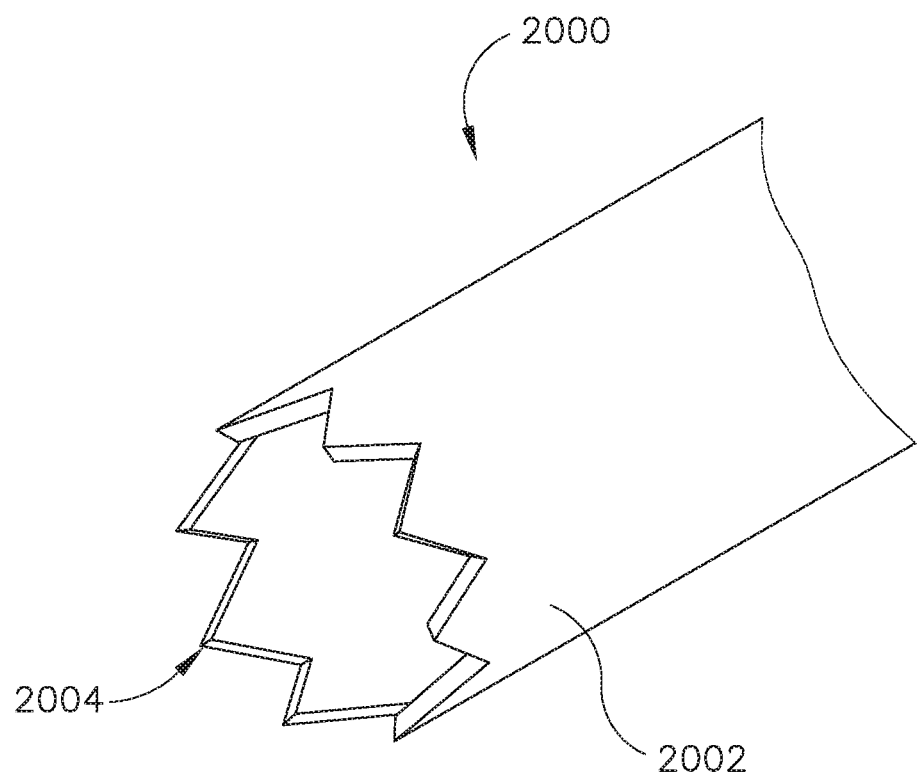
FIG. 25 depicts a perspective view of the distal end of an exemplary alternative sinus wall piercing element.

FIG. 25 shows an exemplary piercing tip (2000) that may be used to form an opening in a lamina wall in the sinus cavity such as a sinus wall. Piercing tip (2000) of this example comprises a tubular portion (2002) with a plurality of sharp points (2004) angularly arrayed about its distal edge. Piercing tip (2000) may be rotated about its longitudinal axis while being advanced along its longitudinal axis to pierce a sinus wall. In some versions where piercing tip (2000) is used to pierce the wall of an ethmoid bulla (EB), piercing tip (2000) is advanced in the posterior direction. In some such versions, a back support (not shown) may be positioned within the retrobullar space (RBS). Such a support may be an integral feature of the instrument that includes piercing tip (2000) or may be part of a separate instrument. In addition or in the alternative, some exemplary uses may include first partially driving sharp points (2004) into the sinus wall without rotating piercing tip (2000) (e.g., stopping advancement as soon as sharp points (2004) have reached the bone), then subsequently initiating rotation and further advancement of piercing tip (2000) to complete the piercing process. Other suitable ways in which piercing tip (2000) may be used will be apparent to those of ordinary skill in the art in view of the teachings herein.

B. Exemplary Piercing Element with Coil

Figure 26D:
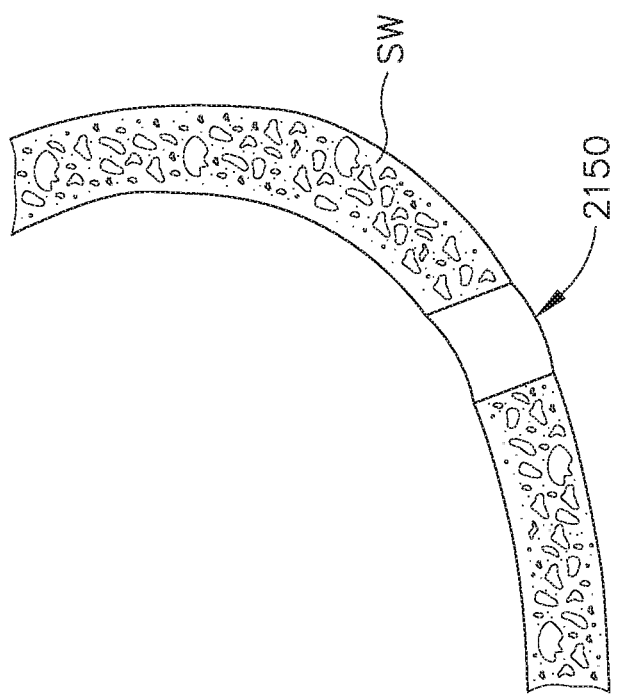
FIG. 26D depicts a cross-sectional view of the sinus wall of FIG. 26A after completion of a procedure with the piercing instrument of FIG. 26A.
Figure 26C:
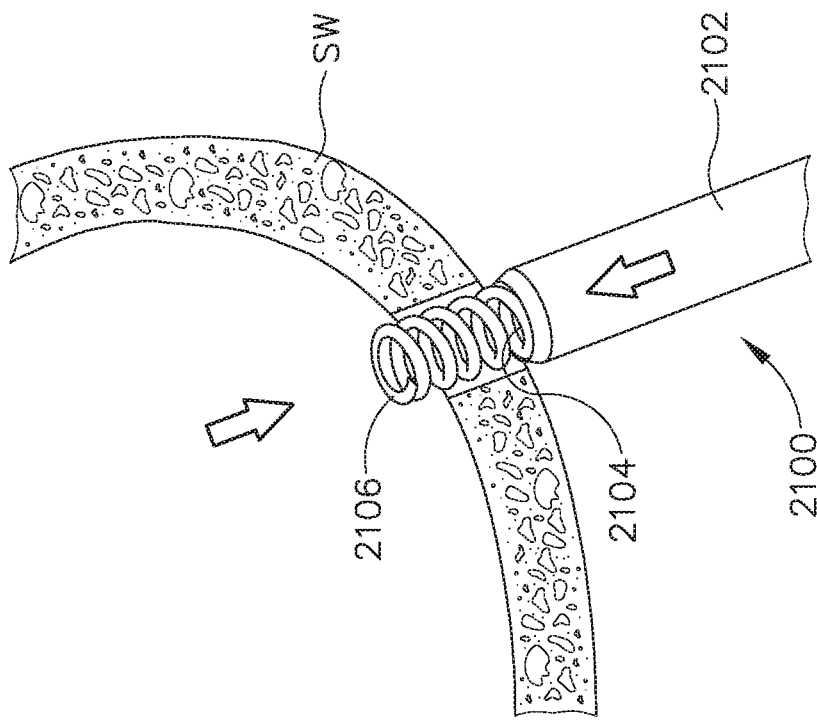
FIG. 26C depicts an elevational view of the distal end of the piercing instrument of FIG. 26A, with the sinus wall in cross section, and with the piercing element being reciprocated in the sinus wall.

FIGS. 26A-26C show another exemplary instrument (2100) that may be used to form an opening in a lamina wall in the sinus cavity such as a sinus wall (SW). The sinus wall (SW) may be a wall of the ethmoid bulla (EB) or the wall of some other sinus cavity. Instrument (2100) of this example comprises a tubular outer sheath (2102) with a distal opening (2104). In some versions, distal opening (2104) is defined by a sharp edge. Instrument (2100) further includes an inner coil member (2106) that has a corkscrew configuration. Inner coil member (2106) is operable to rotate and translate relative to outer sheath (2102). As shown in FIG. 26A, instrument (2100) is positioned such that distal opening (2104) is located at the sinus wall (SW). Inner coil member (2106) is then driven through the sinus wall (SW) while outer sheath (2102) remains stationary, as shown in FIG. 26B. In the present example, inner coil member (2106) rotates as it advances longitudinally. With the inner coil member (2106) disposed in the sinus wall (SW), instrument (2100) is then reciprocated longitudinally as shown in FIG. 26C. In some versions, this reciprocation involves only coil member (2106), while outer sheath (2102) remains stationary. In some other versions, this reciprocation also involves outer sheath (2102), such that the distal edge defining distal opening (2104) is driven through sinus wall (SW). In either case, the reciprocation enlarges the initial opening formed by coil member (2106).

C. Exemplary Piercing Element with Curved Cutting Member

FIGS. 27A-27C and 28A-28C show another exemplary instrument (2200) that may be used to form an opening in a lamina wall in the sinus cavity such as a sinus wall (SW). The sinus wall (SW) may be a wall of the ethmoid bulla (EB) or the wall of some other sinus cavity. Instrument (2200) of this example comprises an elongate member (2202) having a curved distal end terminating in a sharp tip (2204). Instrument (2200) further comprises a cutting member (2206) that is slidably disposed about elongate member (2202). In the present example, cutting member (2206) has a sharp distal edge (2208) and a U-shaped profile. Distal edge (2208) further extends along at least part of the length of cutting member (2206) in the present example. Of course, cutting member (2206) may have various other configurations.

Figure 27B:
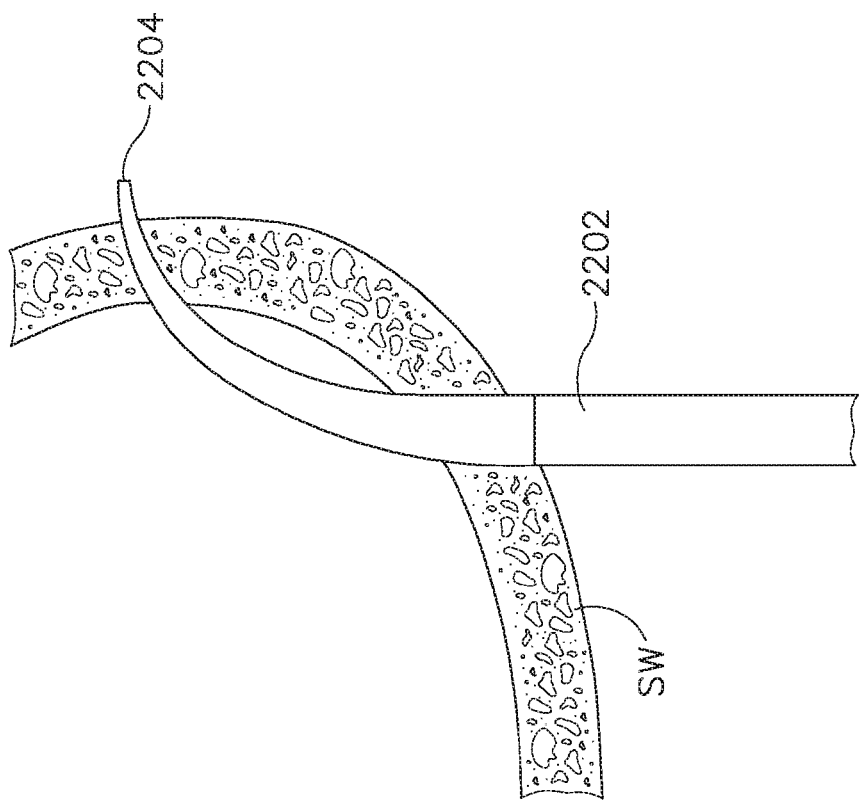
FIG. 27B depicts an elevational view of the distal end of the piercing instrument of FIG. 27A, with the sinus wall in cross section, with the piercing element advanced through the sinus wall, and with the wall cutter retracted out of view.
Figure 27A:
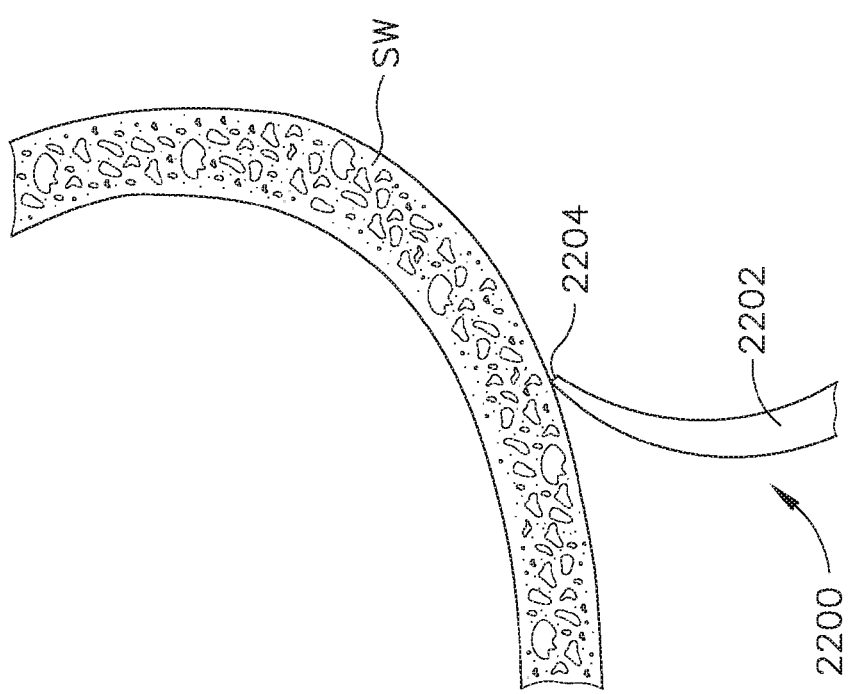
FIG. 27A depicts an elevational view of the distal end of another exemplary alternative sinus wall piercing instrument positioned adjacent to a sinus wall, with the sinus wall in cross section, and with a wall cutter retracted out of view.
Figure 28B:
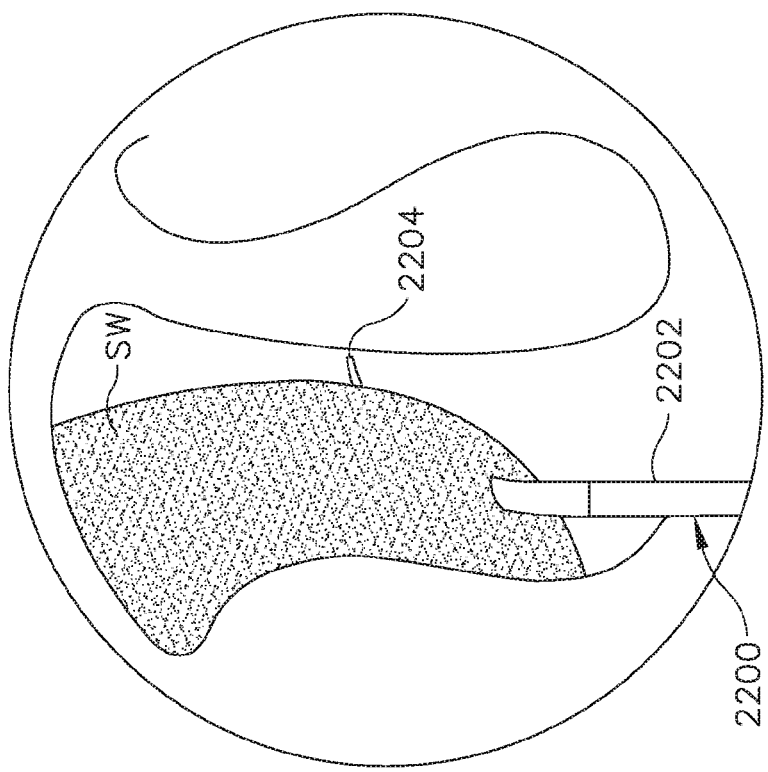
FIG. 28B depicts a perspective view of the distal end of the piercing element of FIG. 27A, with the piercing element advanced through the sinus wall, and with the wall cutter retracted out of view.
Figure 28A:
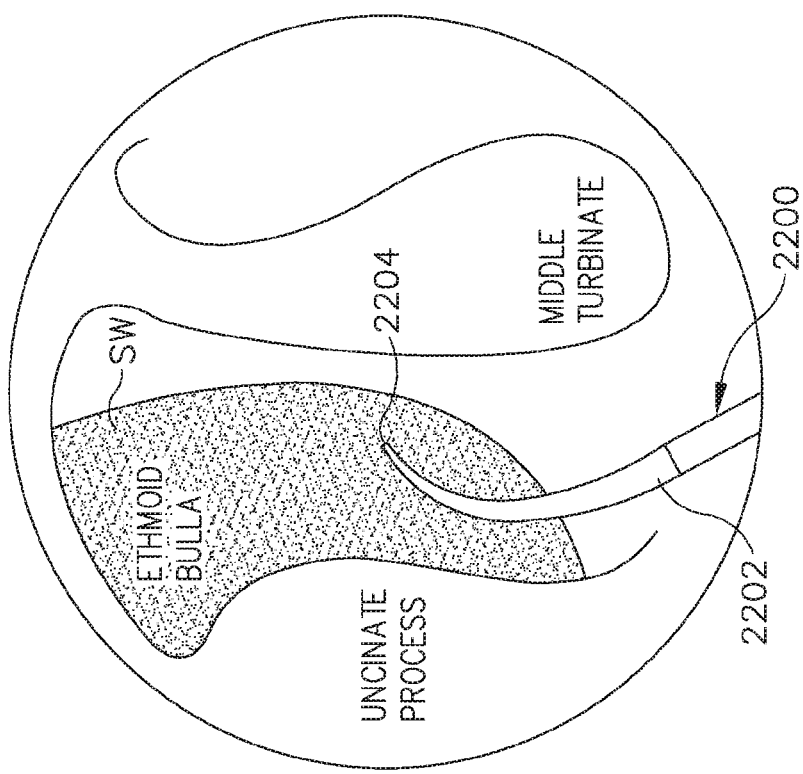
FIG. 28A depicts a perspective view of the distal end of the piercing element of FIG. 27A positioned adjacent to the sinus wall, with the wall cutter retracted out of view.
Figure 28D:
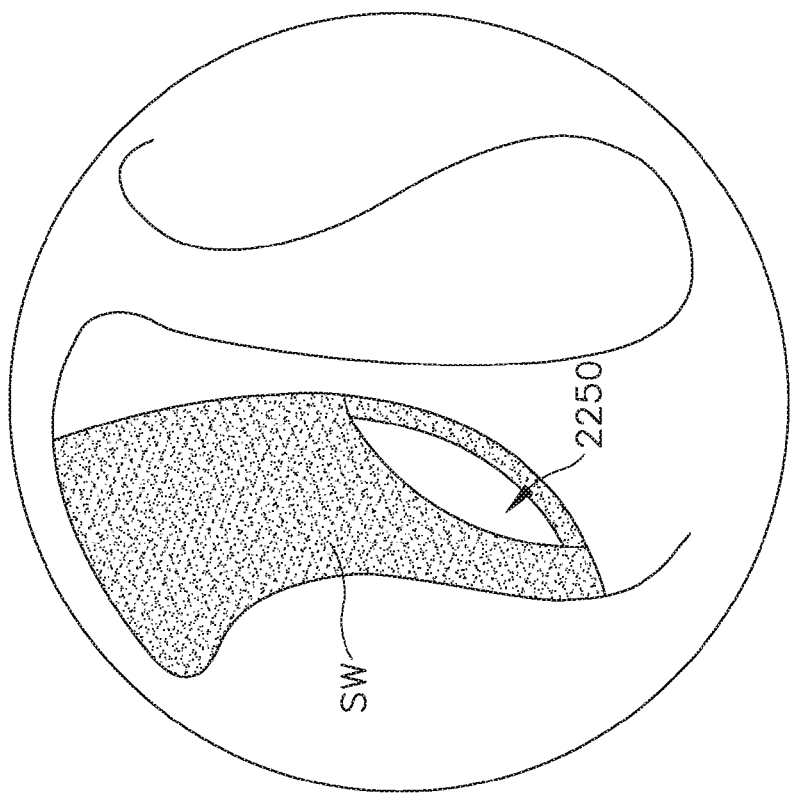
FIG. 28D depicts a perspective view of the sinus wall of FIG. 27A after completion of a procedure with the piercing instrument of FIG. 27A.
Figure 28C:
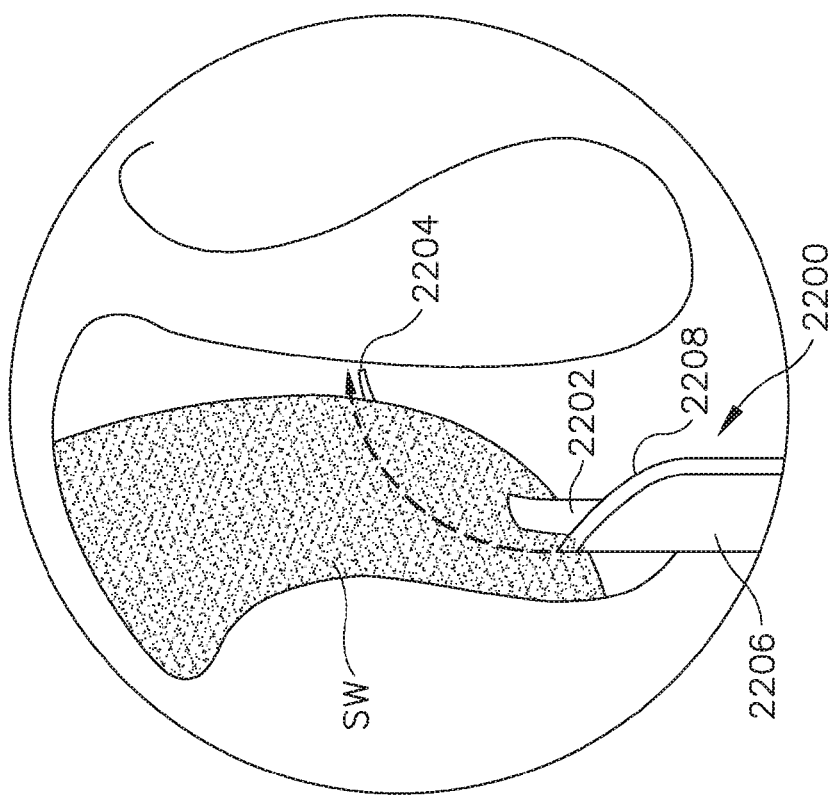
FIG. 28C depicts a perspective view of the distal end of the piercing element of FIG. 27A, with the piercing element advanced through the sinus wall, and with the wall cutter being advanced toward the sinus wall.

As shown in FIGS. 27A and 28A, instrument (2200) may be initially positioned such that tip (2204) is at a sinus wall (SW), with cutting member (2206) in a retracted position (retracted out of view in FIGS. 27A and 28A). Elongate member (2202) is then advanced through the sinus wall (SW), while cutting member (2206) remains in a retracted position. As shown in FIGS. 27B and 28B, tip (2204) has passed through the sinus wall (SW) twice due to the curved configuration of the distal end of elongate member (2202). Next, cutting member (2206) is advanced along elongate member (2202), while elongate member (2202) remains stationary, as shown in FIGS. 27C and 28C. Cutting member (2206) is configured to follow the curved path defined by the distal end of elongate member (2202); and is further configured to travel to a point where sharp distal edge (2208) is positioned by tip (2204). During this advancement, sharp distal edge (2208) cuts through the sinus wall (SW) twice. It should be understood that elongate member (2202) anchors instrument (2200) in the sinus wall (SW) and may further provide structural support to the sinus wall (SW) as cutting member (2206) traverses the sinus wall (SW). Instrument (2200) is then withdrawn from sinus wall (SW), leaving behind an opening (2250) as shown in FIGS. 27D and 28D. Various other suitable features of instrument (2200) and methods of using instrument (2200) will be apparent to those of ordinary skill in the art in view of the teachings herein.

D. Exemplary Piercing Element with Claws

FIGS. 29A-29C and 30A-30C show another exemplary instrument (2300) that may be used to form an opening in a lamina wall in the sinus cavity such as a sinus wall (SW). The sinus wall (SW) may be a wall of the ethmoid bulla (EB) or the wall of some other sinus cavity. Instrument (2300) of this example comprises an elongate shaft (2302) having a plurality of transversely extending sharp-tipped claw members (2304) at its distal end. In the present example, claw members (2304) are selectively retracted and extended relative to shaft (2302). Claw members (2304) are configured to extend and retract along curved paths, such that claw members (2304) on opposing sides of a longitudinally extending transverse plane extend toward each other in a grabbing action as claw members (2304) are advanced to extended positions. Various suitable ways in which claw members (2304) may be selectively retracted and extended relative to shaft (2302) will be apparent to those of ordinary skill in the art in view of the teachings herein.

Figure 29B:
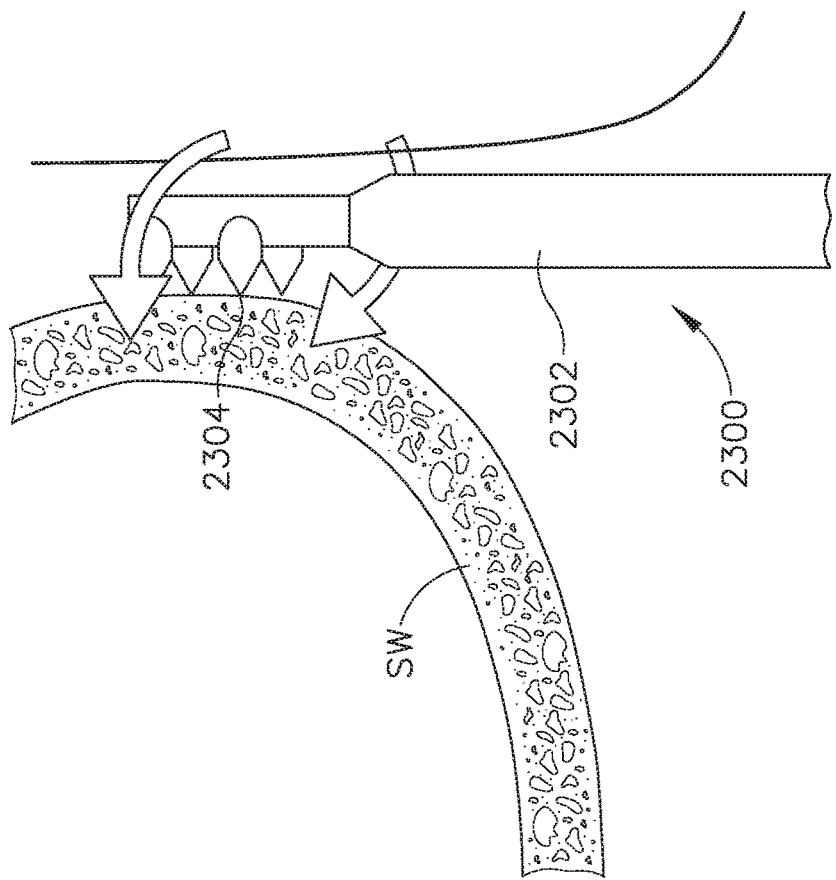
FIG. 29B depicts an elevational view of the distal end of the piercing instrument of FIG. 29A, with the sinus wall in cross section, with piercing elements advanced through the sinus wall.
Figure 29A:
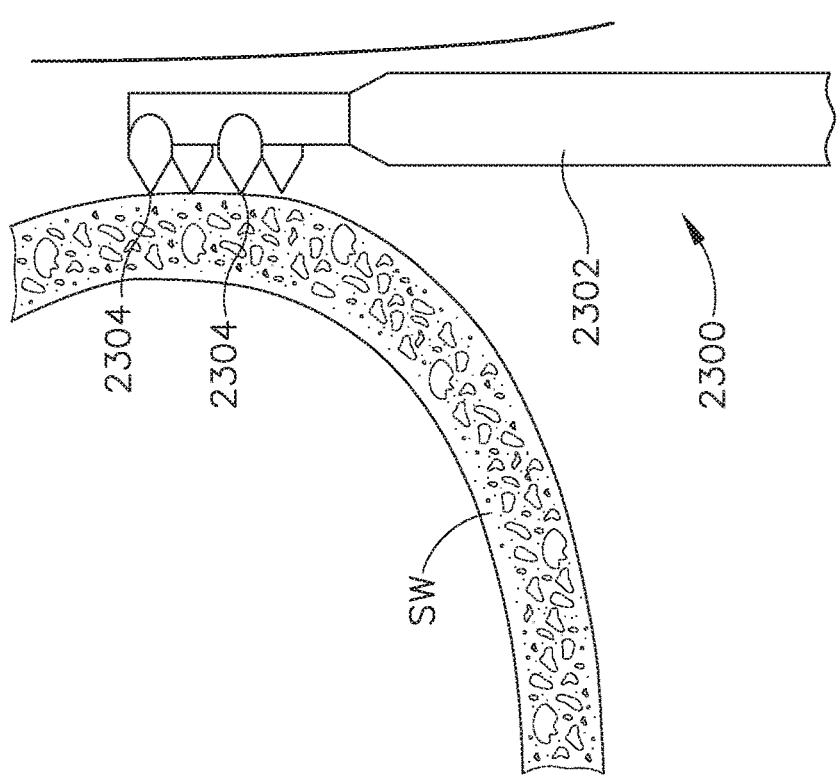
FIG. 29A depicts an elevational view of the distal end of another exemplary alternative sinus wall piercing instrument positioned adjacent to a sinus wall, with the sinus wall in cross section.
Figure 30B:
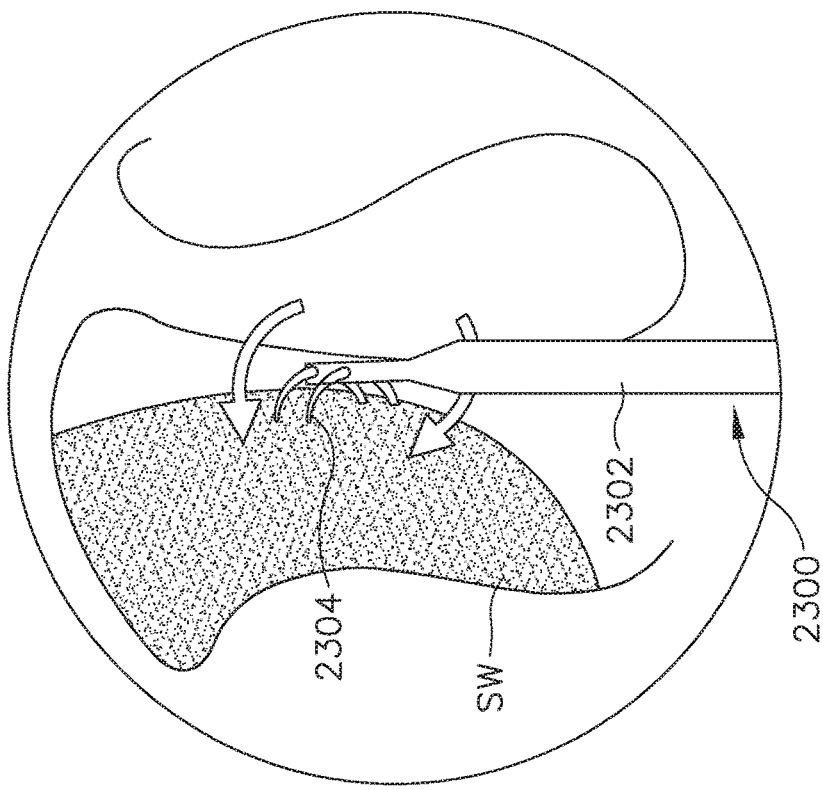
FIG. 30B depicts a perspective view of the distal end of the piercing element of FIG. 29A, with piercing elements advanced through the sinus wall.
Figure 30A:
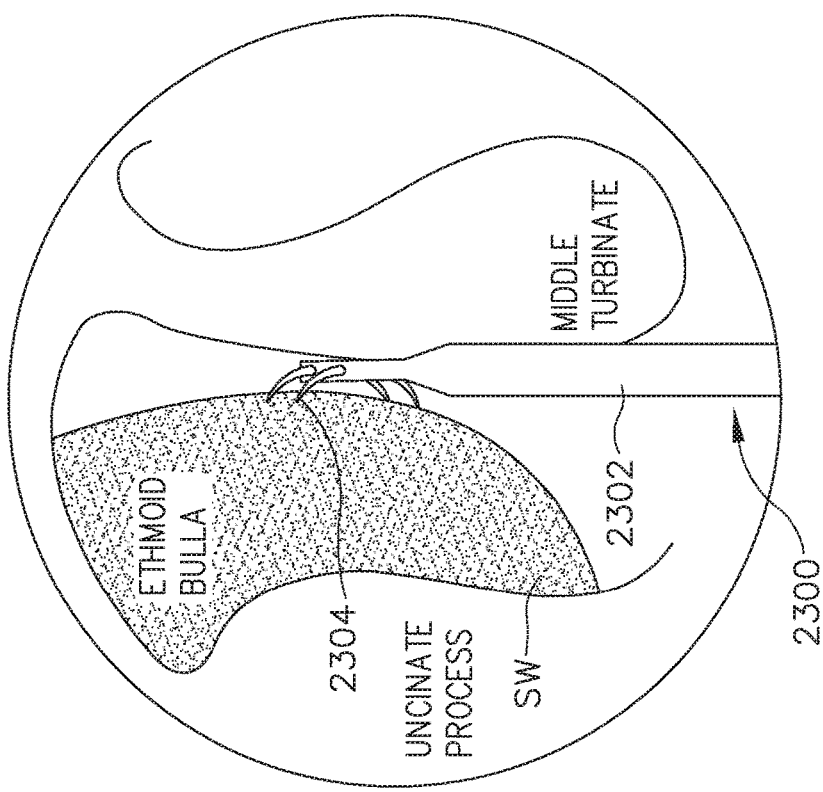
FIG. 30A depicts a perspective view of the distal end of the piercing element of FIG. 29A, with the piercing elements adjacent to the sinus wall.
Figure 30D:
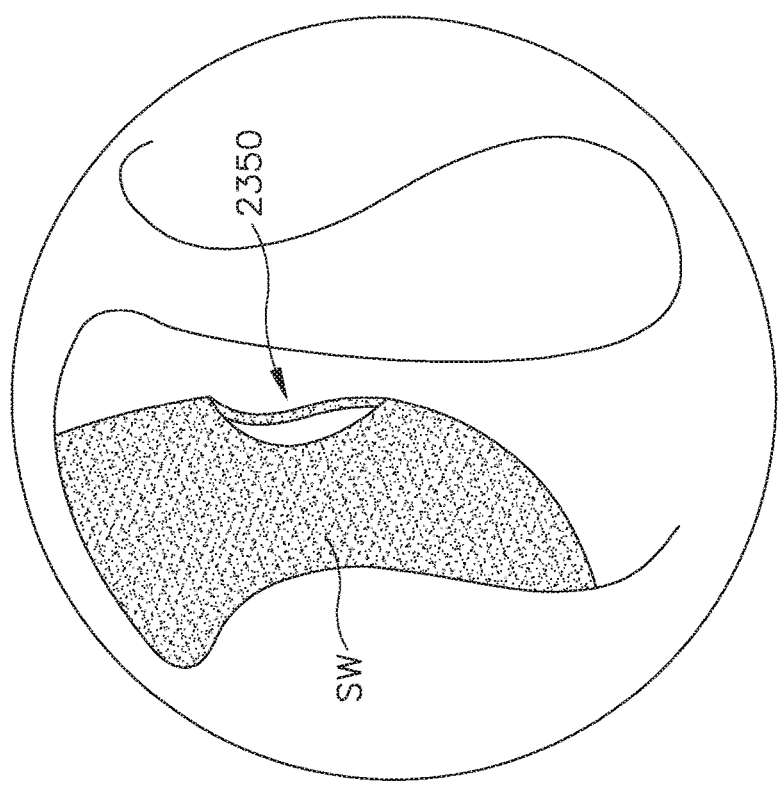
FIG. 30D depicts a perspective view of the sinus wall of FIG. 29A after completion of a procedure with the piercing instrument of FIG. 29A.
Figure 30C:
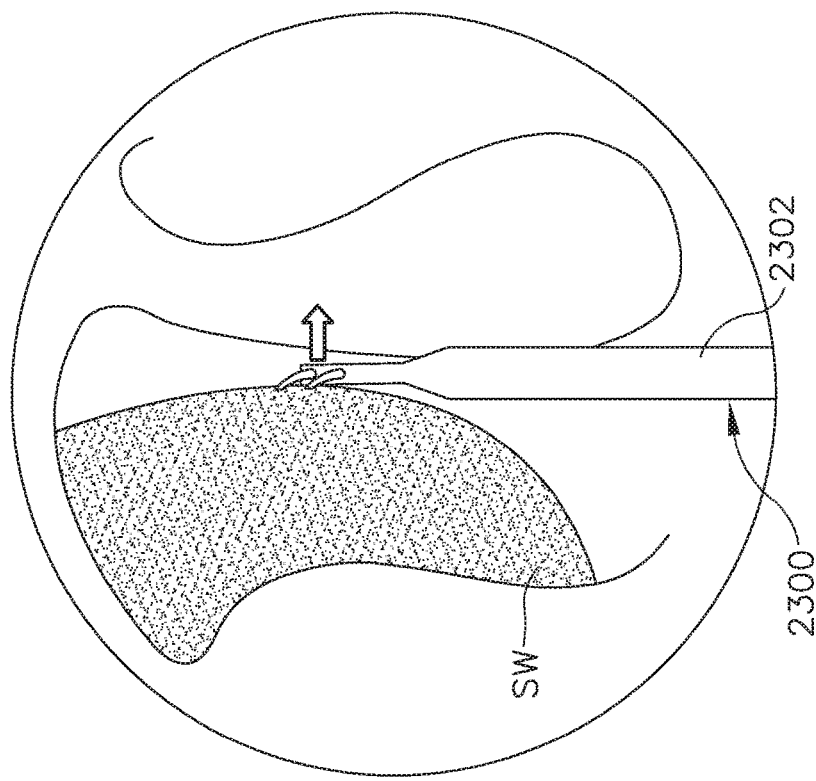
FIG. 30C depicts a perspective view of the distal end of the piercing element of FIG. 29A, with the instrument being pulled away from the sinus wall while the piercing elements are disposed in the sinus wall.

As shown in FIGS. 29A and 30A, instrument (2300) may be initially positioned such that the distal end of shaft (2302) is at a sinus wall (SW) with claw members (2304) in retracted positions. Claw members (2304) are then extended into the sinus wall (SW) while shaft (2302) remains stationary, as shown in FIGS. 29B and 30B. With claw members (2304) disposed in the sinus wall (SW) and held in the extended position, shaft (2302) is then pulled away from the sinus wall (SW), along a path that is generally transverse to the longitudinal axis of shaft (2302), as shown in FIGS. 29C and 30C. This effectively tears away a portion of the sinus wall (SW) that was being grasped by claw members (2304), leaving behind an opening (2350) as shown in FIGS. 29D and 30D. In some versions, the base of each claw member (2304) may be formed into sharp blades extending between claw members (2304), thus allowing the target tissue to be sliced away from the remaining sinus wall (SW) rather than being torn, as claw members (2304) are closed into the positions shown in FIGS. 29C and 30C. Various other suitable features of instrument (2300) and methods of using instrument (2300) will be apparent to those of ordinary skill in the art in view of the teachings herein.

E. Exemplary Piercing Element with Helical Auger

FIGS. 31A-31E show another exemplary instrument (2400) that may be used to form an opening in a lamina wall in the sinus cavity such as a sinus wall (SW). The sinus wall (SW) may be a wall of the ethmoid bulla (EB) or the wall of some other sinus cavity. Instrument (2400) of this example comprises an outer cutting sheath (2402) and an inner auger member (2410). Outer cutting sheath (2402) comprises a tapered distal region (2403) terminating in an opening (2404) that is defined by a sharp annular edge. Auger member (2410) comprises a sharp distal tip (2412) and a helical blade or flight (2414). Helical flight (2414) presents an effective outer diameter that increases along the length of auger member (2410). It should be understood that the depicted version of helical flight (2414) is merely illustrative; and that helical flight (2414) may have any suitable flight pitch. Auger member (2410) is operable to longitudinally advance distally relative to cutting sheath (2402) and also rotate relative to cutting sheath (2402).

Figure 31A:
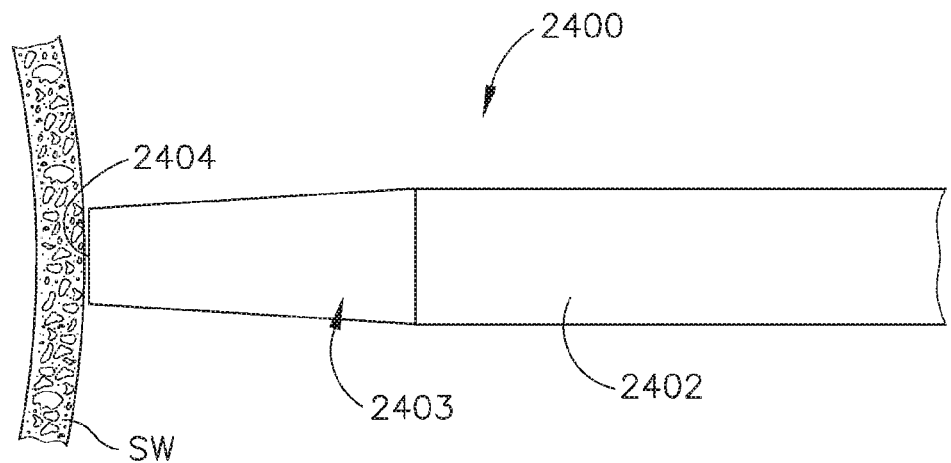
FIG. 31A depicts an elevational view of the distal end of another exemplary alternative sinus wall piercing instrument positioned adjacent to a sinus wall, with the sinus wall in cross section.
Figure 31B:
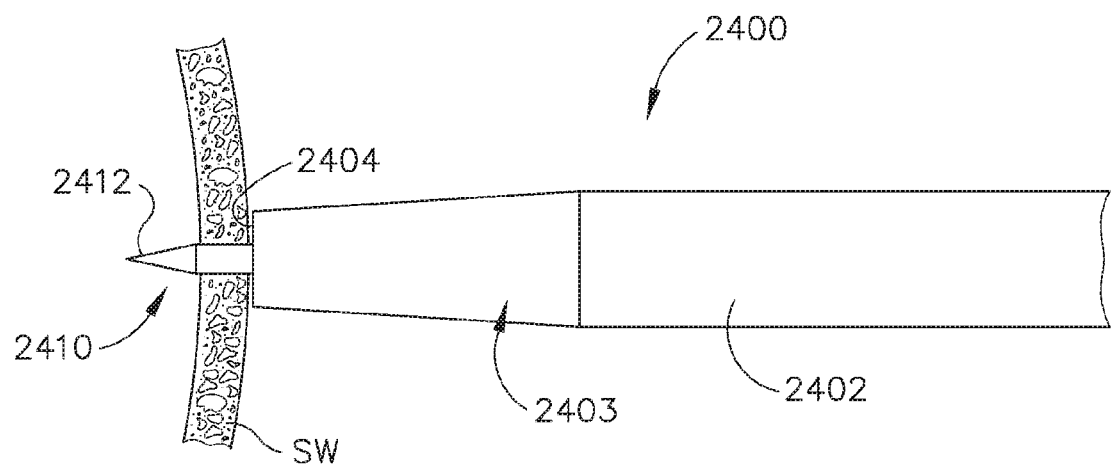
FIG. 31B depicts an elevational view of the distal end of the piercing instrument of FIG. 31A, with the sinus wall in cross section, and with the tip of an auger member disposed in the sinus wall.
Figure 31C:
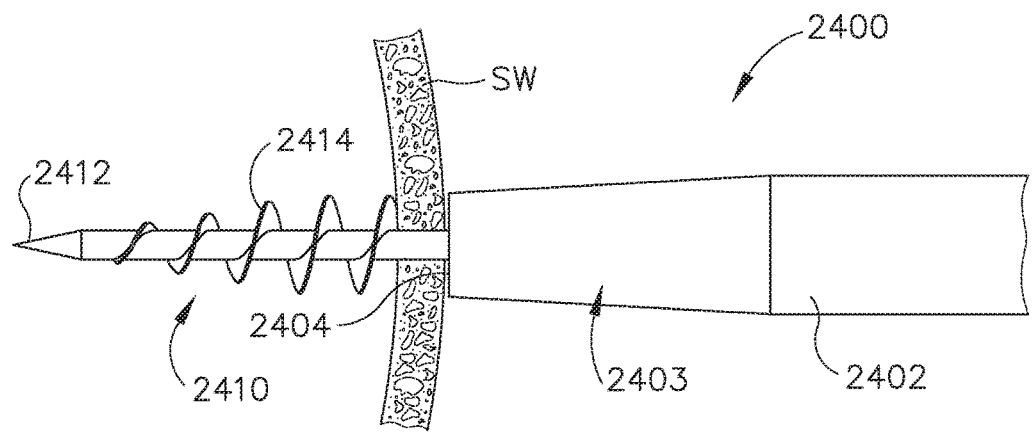
FIG. 31C depicts an elevational view of the distal end of the piercing instrument of FIG. 31A, with the sinus wall in cross section, and with the auger member advanced through the sinus wall.
Figure 31D:
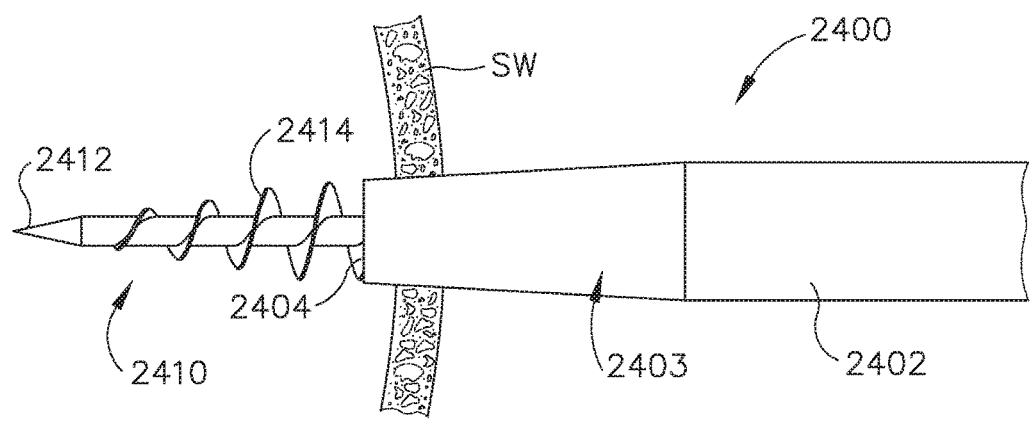
FIG. 31D depicts an elevational view of the distal end of the piercing instrument of FIG. 31A, with the sinus wall in cross section, and with an outer cutter member partially advanced through the sinus wall.
Figure 31E:
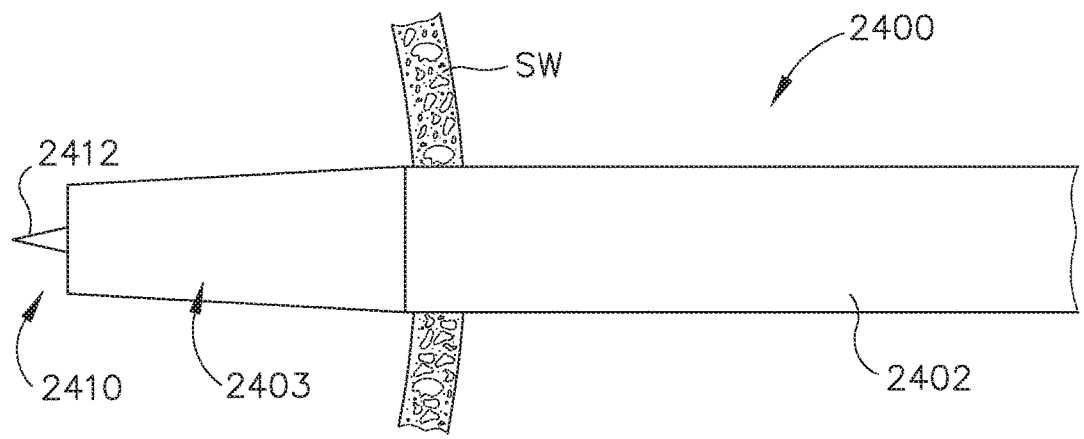
FIG. 31E depicts an elevational view of the distal end of the piercing instrument of FIG. 31A, with the sinus wall in cross section, and with an outer cutter member fully advanced through the sinus wall.
Figure 31F:
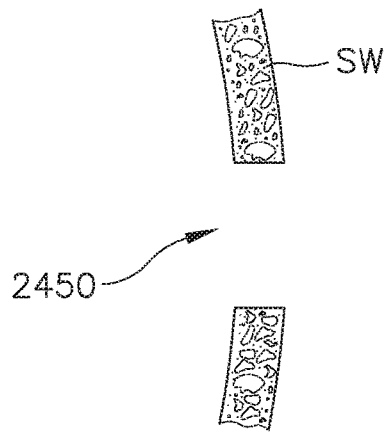
FIG. 31F depicts a cross-sectional view of the sinus wall of FIG. 31A after completion of a procedure with the piercing instrument of FIG. 31A.

As shown in FIG. 31A, instrument (2400) may be initially positioned such that the distal end (2404) of cutting sheath (2402) is at a sinus wall (SW) with auger member (2410) retracted within cutting sheath (2402). Auger member (2410) is then advanced distally such that distal tip (2412) pierces the sinus wall (SW) as shown in FIG. 31B. In some versions, auger member (2410) rotates during this advancement while in other versions it does not. After initially piercing the sinus wall (SW) with distal tip (2412), auger member (2410) continues to advance distally by rotating. This causes helical flight (2414) to drive through the sinus wall (SW) like a screw, as shown in FIG. 31C. To this point, cutting sheath (2402) has remained stationary. However, cutting sheath (2402) now is advanced distally while auger member (2410) remains stationary. In some versions, sheath (2402) rotates while it advances distally; while in other versions it does not. When cutting sheath (2402) advances, the sharp edge defining opening (2404) passes through the sinus wall (SW) such that tapered region (2403) is initially disposed in the sinus wall (SW) as shown in FIG. 31D. During this advancement of cutting sheath (2402), auger member (2410) anchors instrument (2400) in the sinus wall (SW) and may further provide structural support to the sinus wall (SW) as cutting sheath (2402) traverses the sinus wall (SW). Sheath (2402) continues to advance distally (either with or without rotation) while auger member (2410) remains stationary, until tapered region (2403) has fully traversed the sinus wall (SW) as shown in FIG. 31E. Tapered region (2403) thus provides a gradual widening of the opening in the sinus wall (SW). Instrument (2400) is then withdrawn from sinus wall (SW), leaving behind an opening (2450) as shown in FIG. 31F. It should be understood that auger member (2410) and/or sheath (2402) may be driven to any depth desired. For instance, auger member (2410) and sheath (2402) may be driven through two or more sinus walls (SW) (e.g., along the same longitudinal path). Various other suitable features of instrument (2400) and methods of using instrument (2400) will be apparent to those of ordinary skill in the art in view of the teachings herein.

F. Exemplary Instrument with Helical Auger and Retractable Sheath

Figure 32:
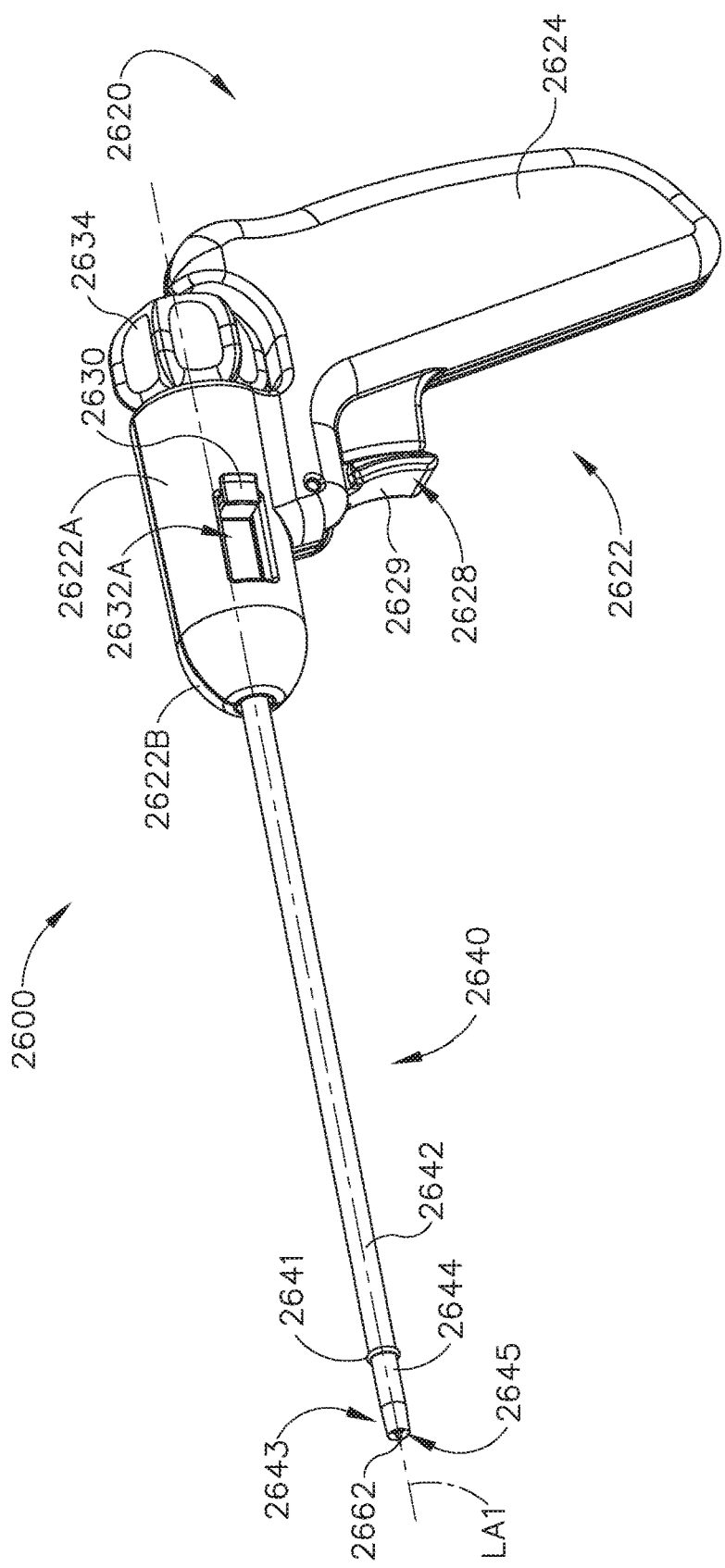
FIG. 32 depicts a perspective view of yet another exemplary alternative sinus wall piercing instrument.
Figure 33:
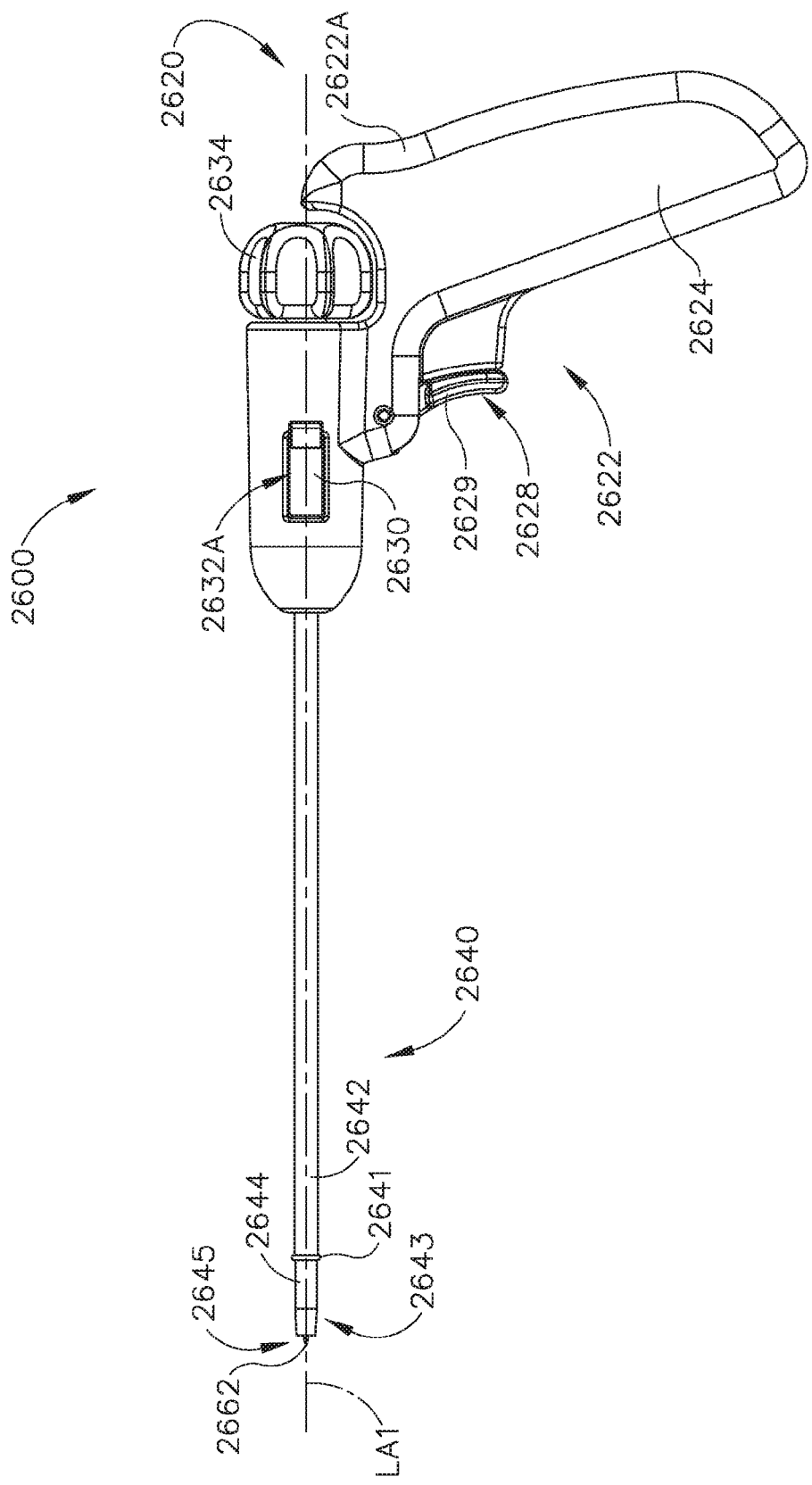
FIG. 33 depicts a side elevational view of the instrument of FIG. 32.
Figure 35:
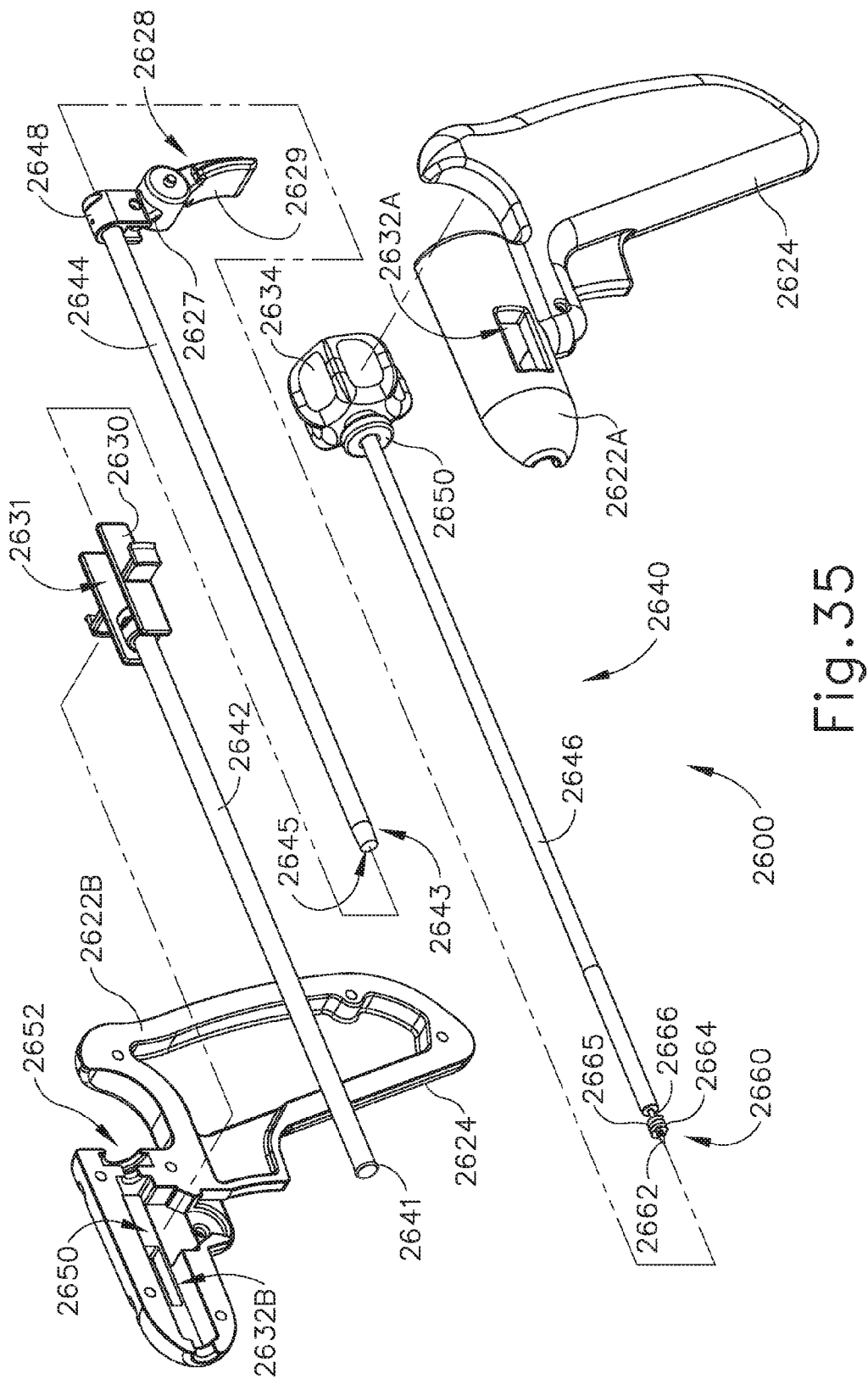
FIG. 35 depicts an exploded perspective view of the instrument of FIG. 32

FIGS. 32-33 and 35 show another exemplary instrument (2600) that may be used to form an opening in a lamina wall in the sinus cavity such as a sinus wall (SW). Instrument (2600) of this example is a merely illustrative variation of instrument (2400) described above. The sinus wall (SW) may be a wall of the ethmoid bulla (EB) (e.g., the anterior face of the ethmoid bulla (EB)) or the wall of some other sinus cavity. Instrument (2600) of the present example comprises a handle assembly (2620) and a shaft assembly (2640). Handle assembly (2620) comprises a first body portion (2622A) and a second body portion (2622B) coupled together to form a body (2622). Of course, handle assembly (2620) may instead be formed of a single body portion or more than two body portions. Body (2622) defines a pistol grip (2624) in the present example, though it should be understood that body (2622) may alternatively provide a variety of alternative grip configurations.

Handle assembly (2620) further includes a pivoting trigger (2628) that is pivotable toward and away from pistol grip (2624). As shown in FIGS. 32-35, pivoting trigger (2628) includes a paddle (2629) extending downwardly from body (2622) such that a user may actuate pivoting trigger (2628) with a finger or thumb of a hand that is grasping pistol grip (2624). As will be discussed in more detail below, actuation of pivoting trigger (2628) causes longitudinal movement of a cutter tube (2644) of shaft assembly (2640). Handle assembly (2620) also includes a sliding trigger (2630) that is longitudinally slidable between a proximal position and a distal position within an internal channel (2650) of body (2622). Portions of sliding trigger (2630) project laterally from a pair of slots (2632A, 2632B) formed respectively in first body portion (2622A) and second body portion (2622B) such that a user may actuate sliding trigger (2630) with a finger or thumb of a hand that is grasping pistol grip (2624). As will be discussed in more detail below, actuation of sliding trigger (2630) causes longitudinal movement of an outer sheath (2642) of shaft assembly (2640). Handle assembly (2620) further includes a rotatable knob (2634) that is rotatable about a longitudinal axis (LA1) defined by shaft assembly (2640). As will be discussed in more detail below, actuation of rotatable knob (2634) cause rotation of a rotatable shaft (2646) of shaft assembly (2640) relative to handle assembly (2620) and relative to other components of shaft assembly (2640).

Figure 36:
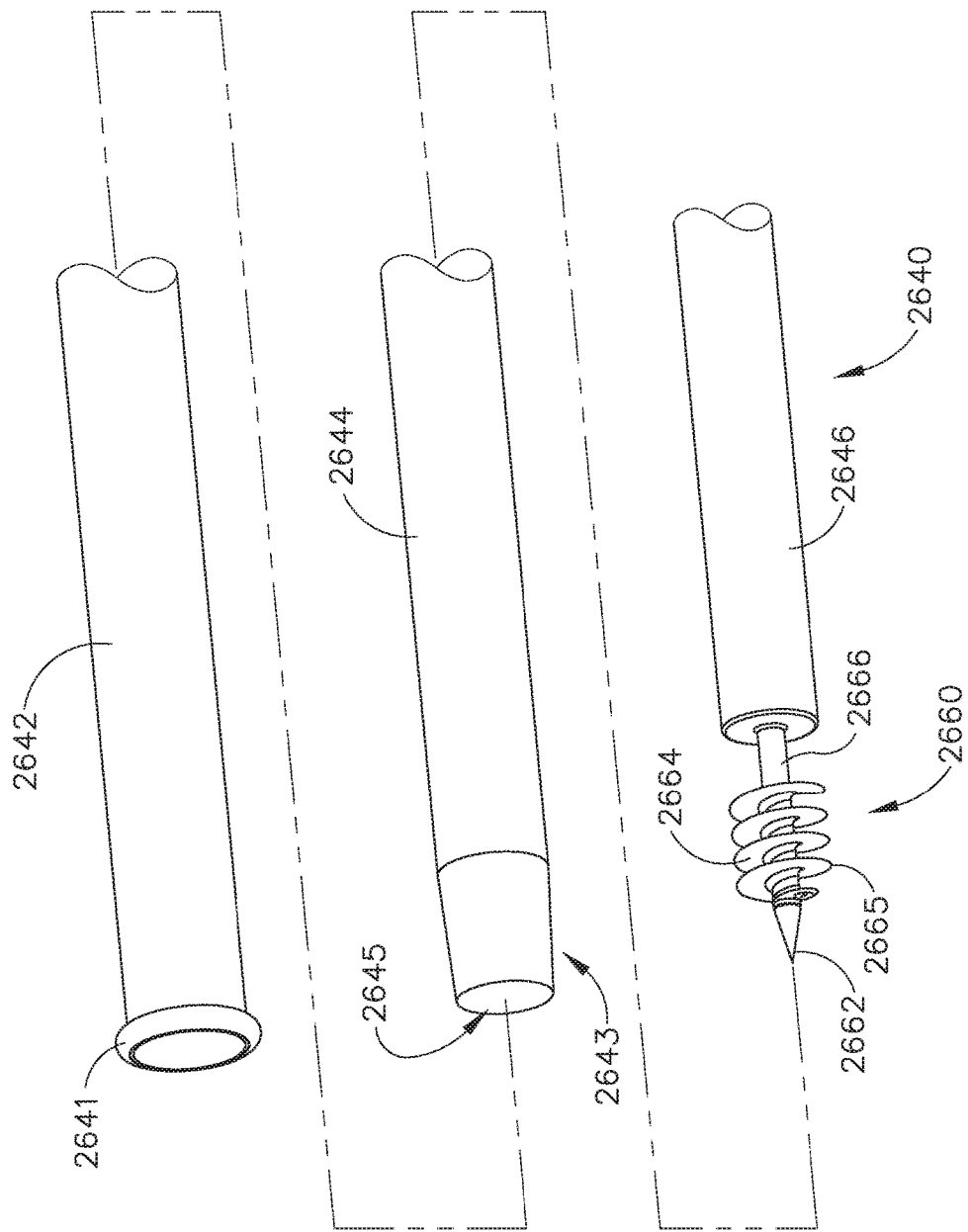
FIG. 36 depicts an exploded perspective view of a shaft assembly of the instrument of FIG. 32.

Shaft assembly (2640) extends distally from handle assembly (2620). As best seen in FIGS. 35-36, shaft assembly (2640) comprises an outer sheath (2642), a cutter tube (2644), and a rotatable shaft (2646). As best seen in FIG. 35, a proximal end of outer sheath (2642) is unitarily coupled with a distal portion of sliding trigger (2630) such that longitudinal movement of siding trigger (2630) causes concurrent longitudinal sliding of outer sheath (2642) along longitudinal axis (LA1). Cutter tube (2644) is slidably disposed within outer sheath (2642) such that cutter tube (2644) and outer sheath (2642) are able to move independently relative to each other along longitudinal axis (LA1).

Figure 34:
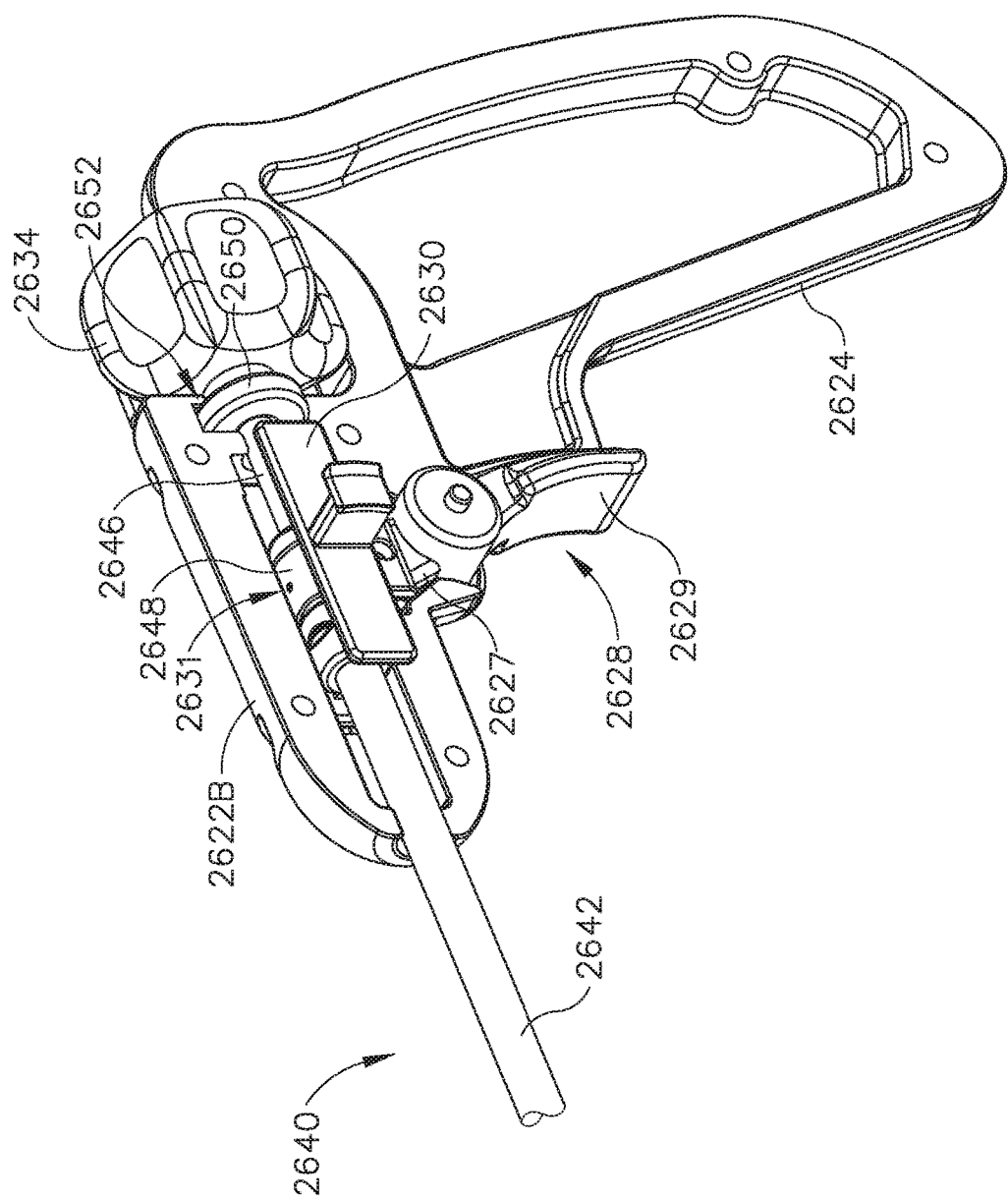
FIG. 34 depicts a detailed perspective view of a handle assembly of the instrument of FIG. 32

A proximal end of cutter tube (2644) is integrally coupled with a sliding member (2648). As best seen in FIG. 34, sliding member (2648) is slidably disposed within a proximal gap (2631) defined by sliding trigger (2630) such that sliding member (2648) slides longitudinally within proximal gap (2631) of sliding trigger (2630); and such that sliding member (2648) and sliding trigger (2630) are able to slide longitudinally independently relative to each other. Sliding member (2648) is pivotably coupled with an arm (2627) extending unitarily from pivoting trigger (2628) in an opposite direction of paddle (2629). It should therefore be understood that pivoting of paddle (2629) toward pistol grip (2624) will cause pivoting of arm (2627) distally, and vice versa. It should further be understood that, distal pivoting of arm (2627) will cause distal longitudinal movement of sliding member (2648) and cutter tube (2644) along longitudinal axis (LA1); and proximal pivoting of arm (2627) will cause proximal longitudinal movement of sliding member (2648) and cutter tube (2644) along longitudinal axis (LA1). In some versions, pivoting trigger (2628) is biased away from pistol grip (2624) by a resilient member (e.g. a torsion spring, leaf spring, etc.) such that cutter tube (2644) is biased toward a proximal position. An operator may thus advance cutter tube (2644) distally relative to handle assembly (2620) by squeezing paddle (2629) toward pistol grip (2624); then retract cutter tube (2644) proximally by releasing paddle (2629).

Rotatable shaft (2646) is rotatably disposed within cutter tube (2644) such that rotatable shaft (2646) rotates independently relative to cutter tube (2644) and such that cutter tube (2644) is capable of moving longitudinally independently relative to rotatable shaft (2646). A proximal end of rotatable shaft (2646) is integrally coupled with rotatable knob (2634) such that rotation of rotatable knob (2634) causes rotation of rotatable shaft (2646) about longitudinal axis (LA1). As best seen in FIG. 35, an annular flange (2652) extends outwardly from a distal portion of rotatable knob (2634) and is rotatably disposed within an annular pocket (2652) that is formed in body (2622), such that rotatable knob (2634) is capable of rotating yet incapable of moving longitudinally relative to longitudinal axis (LA1).

The distal end of outer sheath (2642) includes an outwardly projecting annular bumper (2641). By way of example only, bumper (2641) may be formed of steel, hard plastic, soft plastic, elastomeric material, etc. Alternatively, bumper (2641) may be a unitarily formed feature of outer sheath (2642), with a radiused edge to provide outer sheath (2642) with an atraumatic distal tip. Bumper (2641) may be used to move anatomical structures (e.g., middle turbinate, uncinate process, etc.) without damaging those anatomical structures as the distal end of shaft assembly (2640) is advanced to the sinus wall (SW). Bumper (2641) may also soften any forward force that sheath (2642) might exert on the sinus wall (SW) while shaft assembly (2640) is being positioned. In some versions, bumper (2641) and/or the distal end of outer sheath (2642) may be obliquely angled relative to the longitudinal axis of outer sheath (2642) (e.g., angled from approximately 20° to approximately 70°, etc.), which may facilitate use of bumper (2641) to move tissue. It should also be understood that some versions of bumper (2641) may extend distally past the distal end of outer sheath (2642).

A distal portion of cutter tube (2644) has a tapered distal region (2643) terminating in an opening (2645) that is defined by a sharp annular edge. An auger member (2660) extends distally from a distal end of rotatable shaft (2646) such that as rotatable shaft (2646) rotates, auger member (2660) rotates as well. Auger member (2660) comprises a minor shaft (2666) having a sharp distal tip (2662) and a helical blade or flight (2664) projecting outwardly from minor shaft (2666). Minor shaft of the present example has an outer diameter of between approximately 0.04 inches and approximately 0.06 inches, though it should be understood that any other suitable outer diameter may be used. As will be discussed in more detail below, sharp distal tip (2662) may be used to penetrate the sinus wall (SW). The length of sharp distal tip (2662) may be configured to avoid inadvertent contact with other portions of sinus wall (SW). For instance, sharp distal tip (2662) may have a length of approximately 0.1 inches. Alternatively, any other suitable length may be used.

Figure 37:
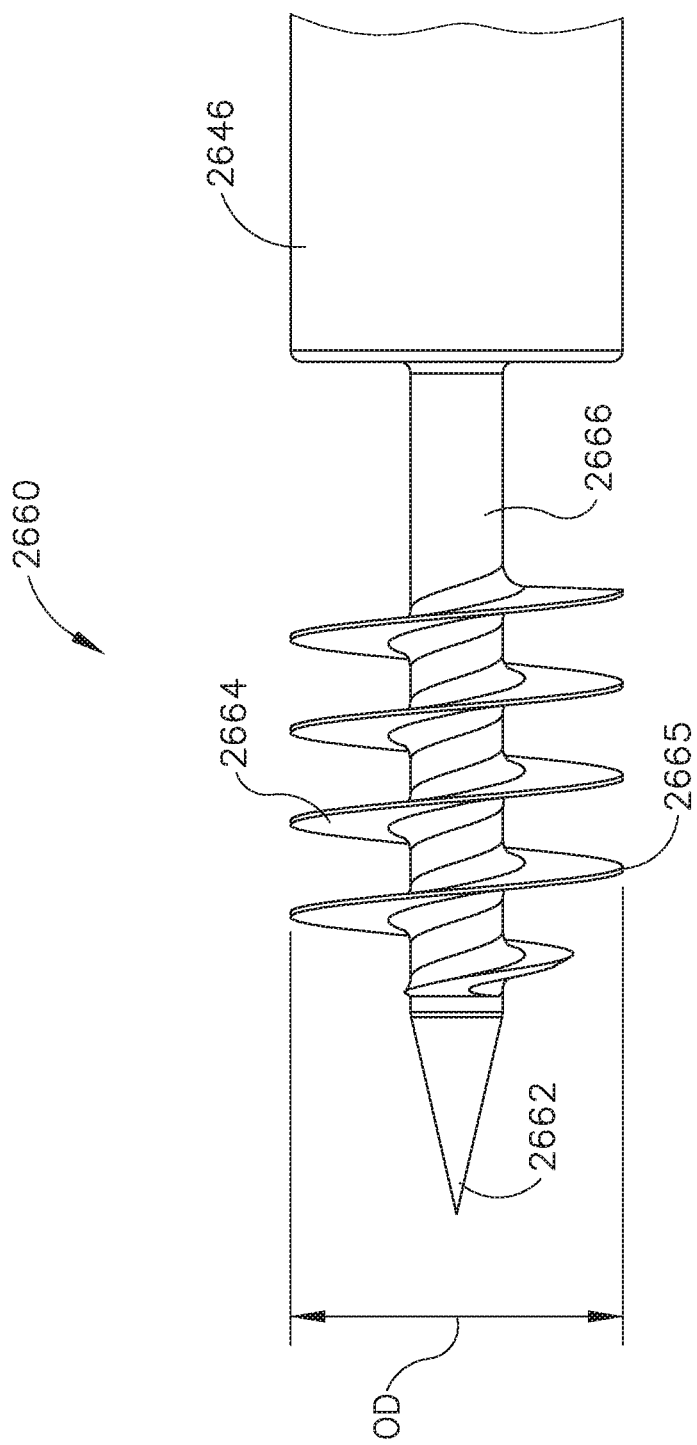
FIG. 37 depicts a detailed side elevational view of an exemplary auger of the shaft assembly of FIG. 36.

Helical flight (2664) presents an effective outer diameter (OD) that is substantially similar to an inner diameter defined by the sharp annular distal edge of cutter tube (2644). By way of example only, the inner diameter defined by the sharp annular distal edge of cutter tube (2644) may define a gap with the effective outer diameter (OD) of helical flight (2664) that is between approximately 0.0005 inches and approximately 0.002 inches. In some versions, the inner diameter defined by the sharp annular distal edge of cutter tube (2644) defines a gap with the effective outer diameter (OD) of helical flight (2664) that is less than approximately 0.005 inches. The inner diameter of cutter tube (2644) thus closely complements the effective outer diameter (OD) of helical flight (2664). Alternatively, any other suitable gap may be provided. In the present example, the gap between the inner diameter defined by the sharp annular distal edge of cutter tube (2644) and the effective outer diameter (OD) of helical flight (2664) is dimensioned to prevent any tissue from getting lodged between the inner diameter defined by the sharp annular distal edge of cutter tube (2644) and the effective outer diameter (OD) of helical flight (2664). In the present example, outer diameter (OD) is approximately 0.144 inches, though any other suitable outer diameter (OD) may be used. Also in the present example, the effective outer diameter (OD) is approximately equal to the outer diameter of major diameter proximal portion (2686). As best seen in FIG. 37, beginning at a distal portion of helical flight (2664), helical flight (2664) gradually projects further from outwardly minor shaft (2666) until reaching outer diameter (OD). In some versions, the distal-most portion of helical flight (2664) begins in a region where tip (2662) slopes inwardly from the outer diameter of minor shaft (2666) (i.e., such that the distal end of helical flight (2664) terminates within the conical tapered region of tip (2662)). It should be understood that the depicted version of helical flight (2664) is merely illustrative; and that helical flight (2664) may have any suitable flight pitch.

Auger member (2660) of the present example also defines a longitudinal gap extending longitudinally between a proximal end of helical flight (2664) and the distal end of rotatable shaft (2646). The gap between the proximal end of helical flight (2664) and the distal end of rotatable shaft (2646) of the present example has a length of approximately 0.040 inches, though it should be understood that the gap may have any other suitable length. An exterior edge of helical flight (2664) in the present example presents a flat surface (2665). Flat surface (2665) of the present example has a width between approximately 0.002 inches and approximately 0.005 inches. Alternatively, any other suitable width may be used. As will be discussed in more detail below, helical flight (2664) is configured to guide and drive auger member (2660) through an opening formed in sinus wall (SW) by sharp distal tip (2662); and to provide a structural anchor for instrument (2600) within sinus wall (SW).

1. Exemplary Operation of Instrument with Helical Auger and Retractable Sheath

Figure 38A:
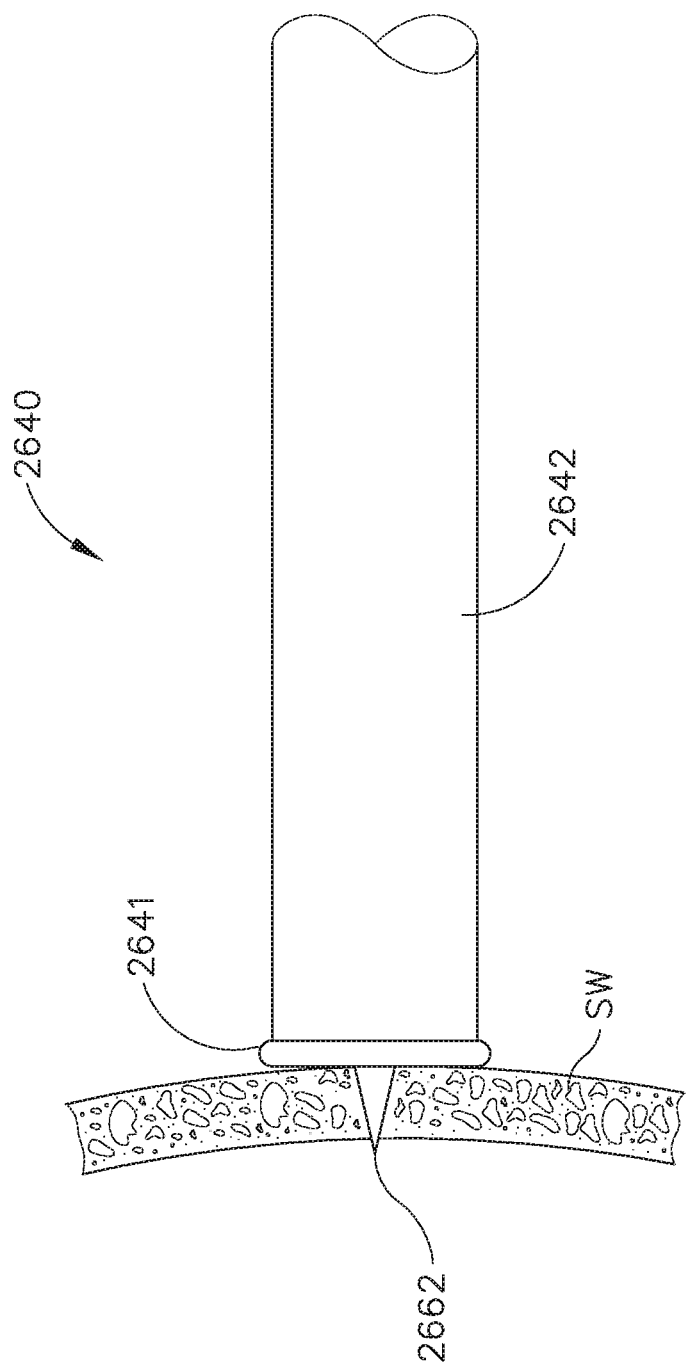
FIG. 38A depicts a side elevational view of the shaft assembly of FIG. 36 in a first longitudinal position, with an outer sheath and a cutter of the shaft assembly also in a first longitudinal position.
Figure 38B:
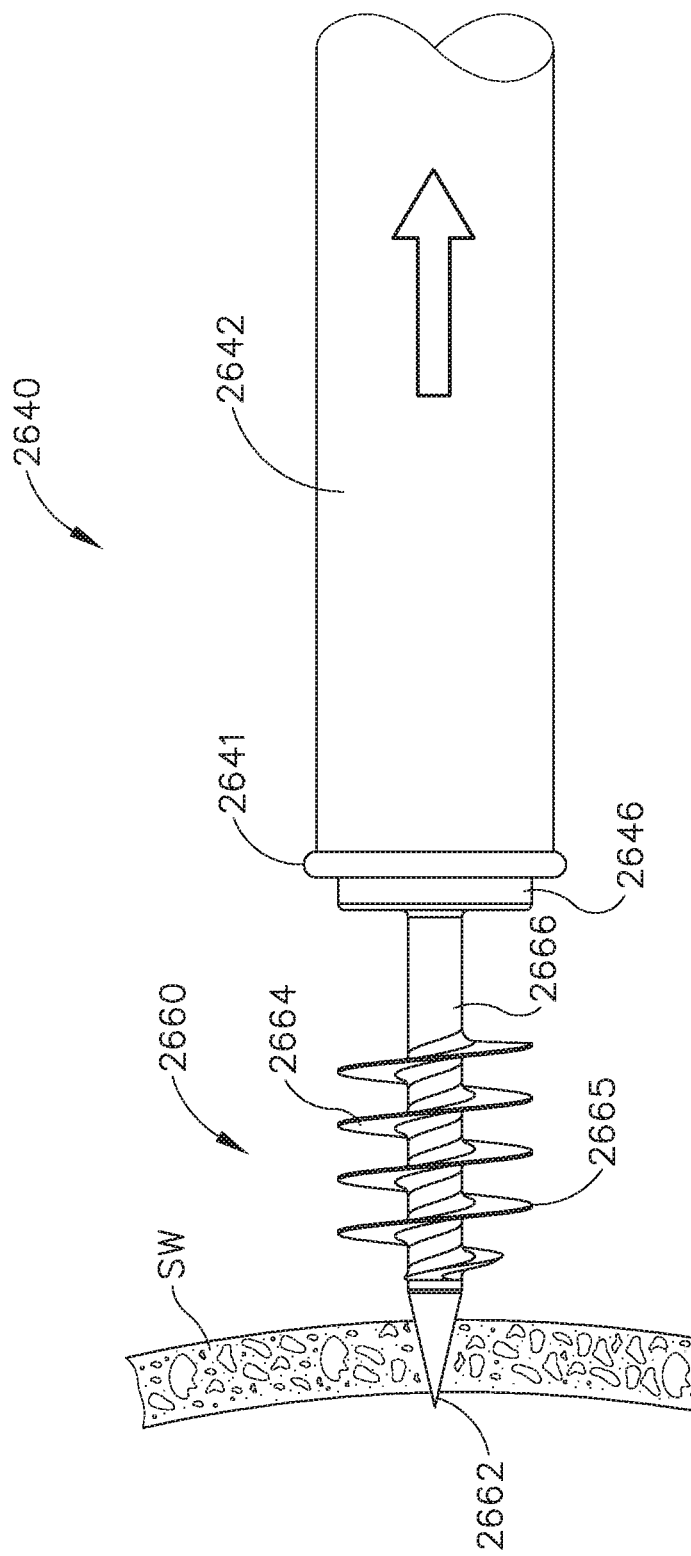
FIG. 38B depicts a side elevational view of the shaft assembly of FIG. 36 in the first longitudinal position, with the outer sheath moved to a second longitudinal position, and with the cutter still in the first longitudinal position.
Figure 38C:
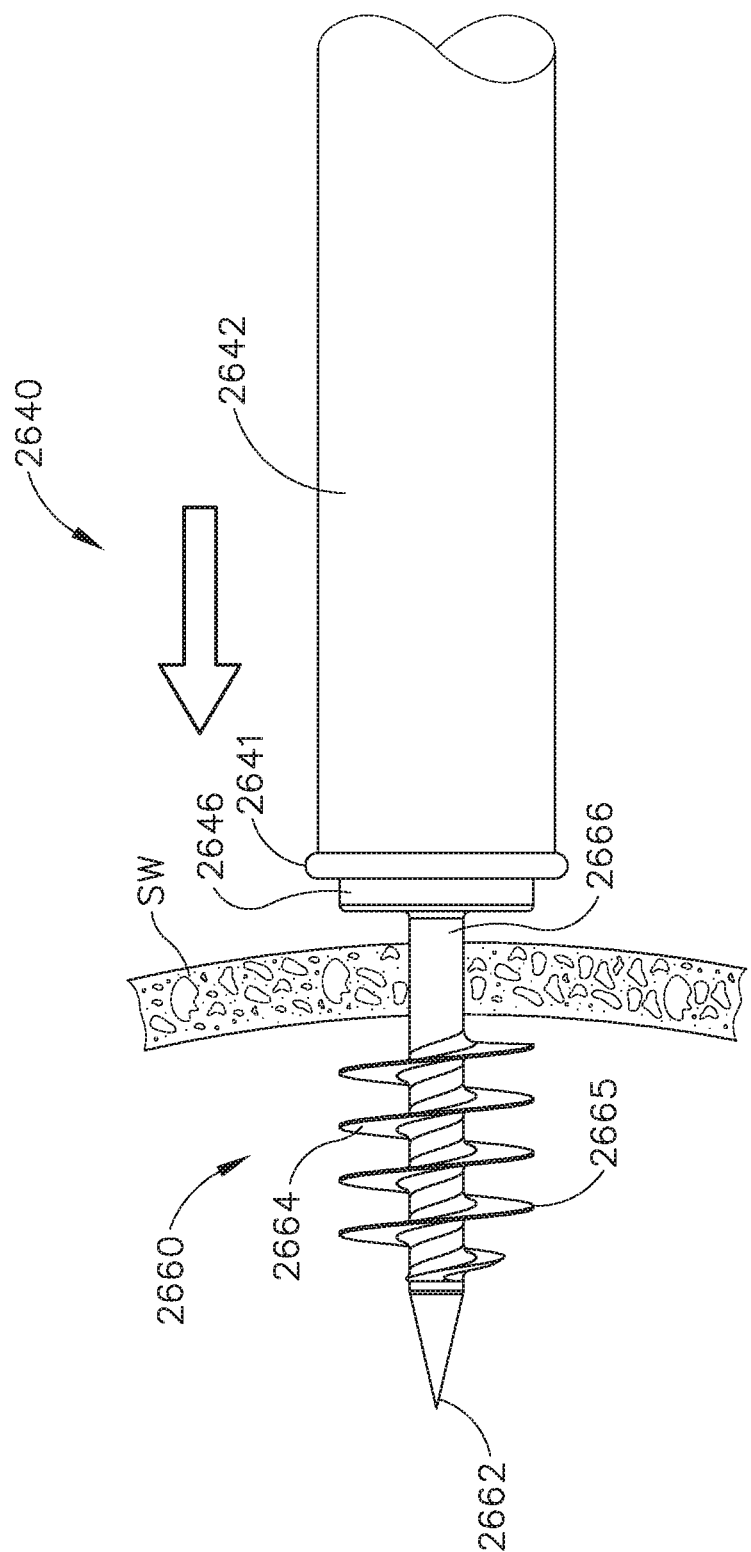
FIG. 38C depicts a side elevational view of the shaft assembly of FIG. 36 moved to a second longitudinal position, with the outer sheath still in the second longitudinal position, and with the cutter still in the first longitudinal position.
Figure 39A:
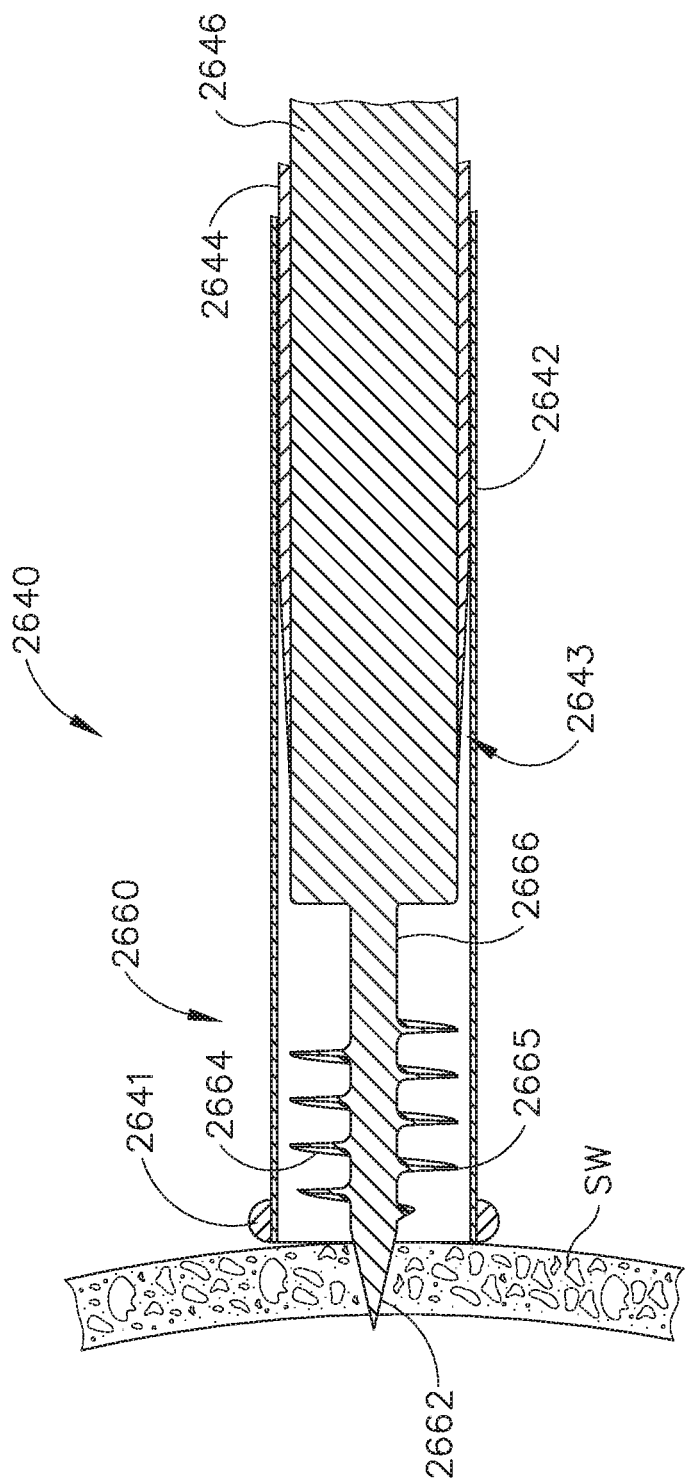
FIG. 39A depicts a side cross-sectional view of the shaft assembly of FIG. 36 in a first longitudinal position, with an outer sheath and a cutter of the shaft assembly also in a first longitudinal position.
Figure 39B:
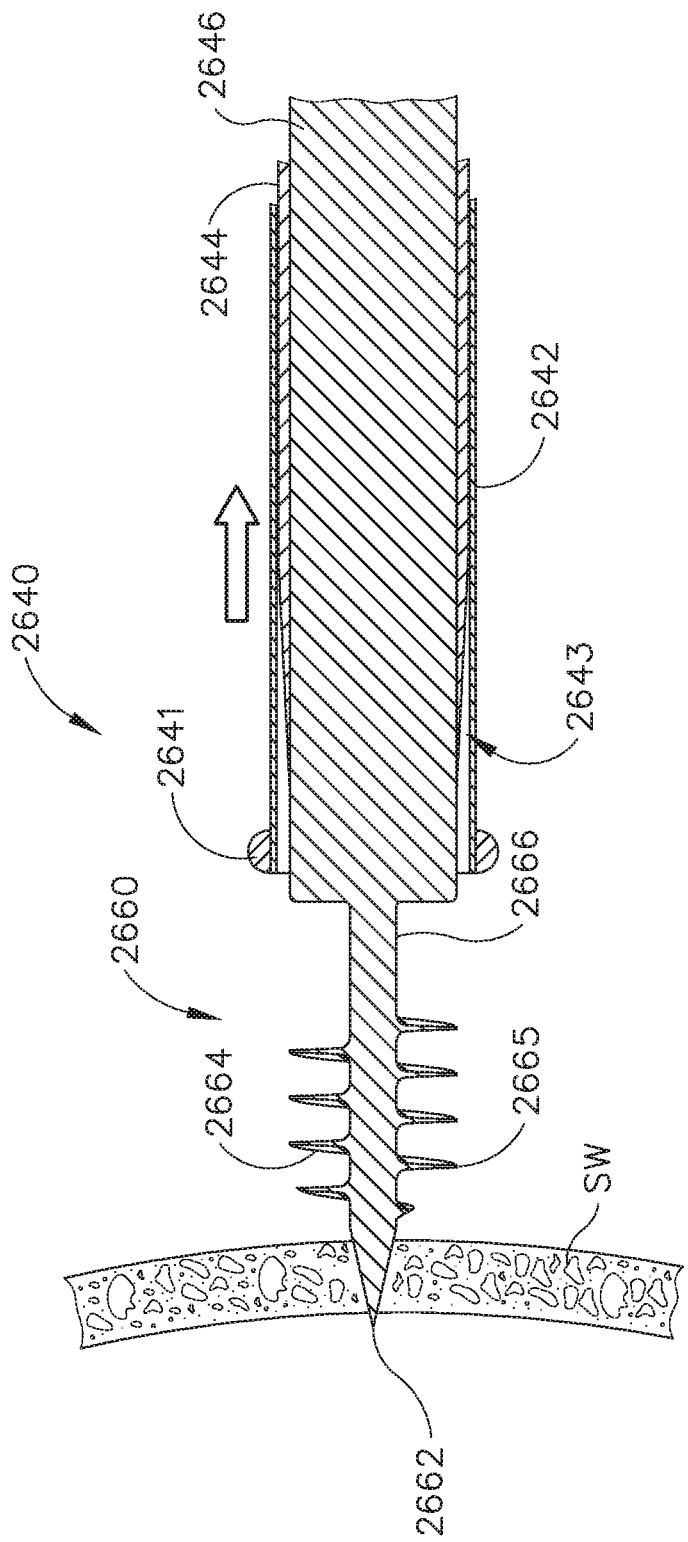
FIG. 39B depicts a side cross-sectional view of the shaft assembly of FIG. 36 in the first longitudinal position, with the outer sheath moved to a second longitudinal position, and with the cutter still in the first longitudinal position.
Figure 39C:
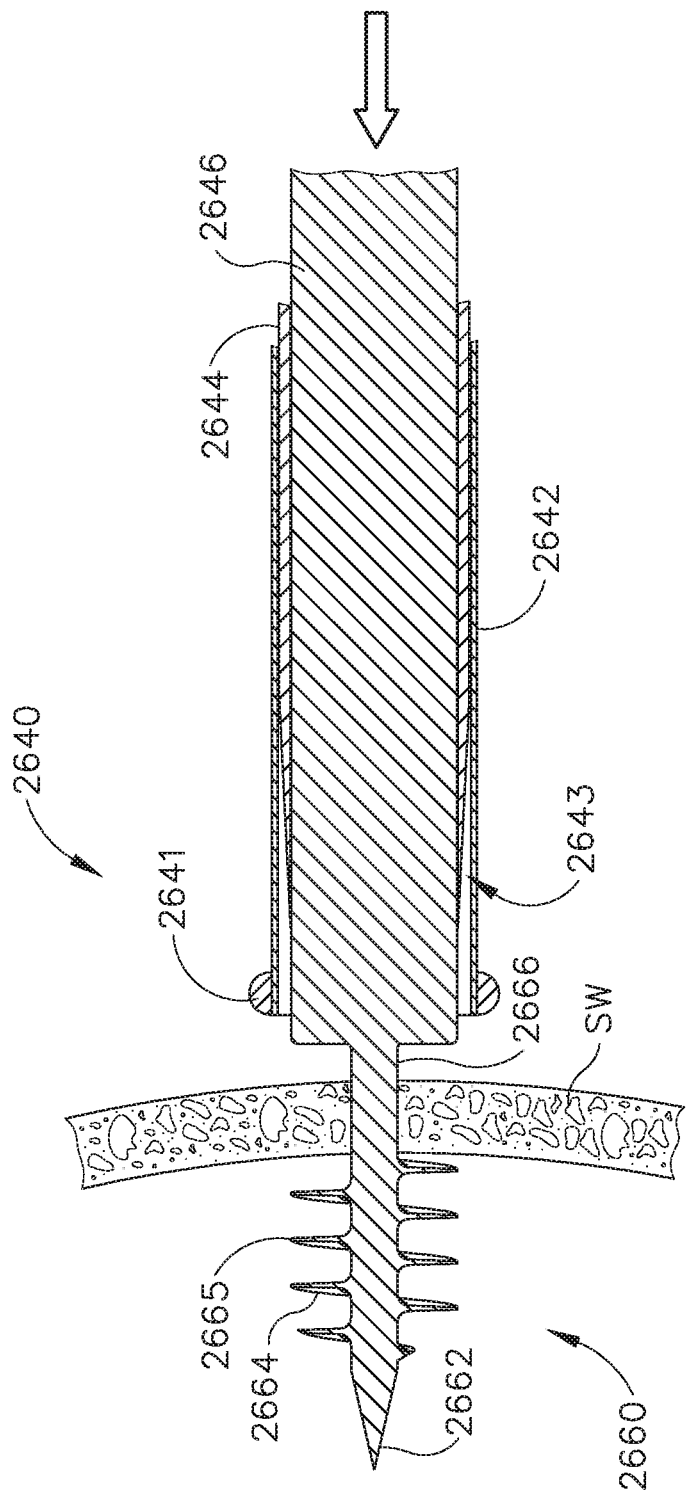
FIG. 39C depicts a side cross-sectional view of the shaft assembly of FIG. 36 moved to a second longitudinal position, with the outer sheath still in the second longitudinal position, and with the cutter still in the first longitudinal position.

As shown in FIGS. 38A and 39A, instrument (2600) may be initially positioned such that the circular bumper (2641) of outer sheath (2642) is at the sinus wall (SW) with outer sheath (2642) partially covering auger member (2660) such that only a distal portion of sharp distal tip (2662) penetrates sinus wall (SW). In some versions, outer sheath (2642) is configured to completely cover sharp distal tip (2662) until the distal end of shaft assembly (2640) reaches sinus wall (SW). Once sharp distal tip (2662) initially pierces sinus wall (SW), outer sheath (2642) is fully retracted proximally by moving sliding trigger (2630) longitudinally proximally, thus completely exposing auger member (2660) as shown in FIGS. 38B and 39B. Auger member (2660) is then rotated and advanced distally by rotating rotatable knob (2634) and advancing instrument (2600) distally. It should be understood that, after initially piercing the sinus wall (SW) with sharp distal tip (2662), auger member (2660) continues to advance distally by rotating due to the helical configuration of flight (2664). In particular, helical flight (2664) is driven through the sinus wall (SW) like a screw until the sinus wall (SW) is positioned within the longitudinal gap between the proximal end of helical flight (2664) and the distal end of rotatable shaft (2646), as shown in FIGS. 38C and 39C. In some other exemplary uses, distal advancement of instrument (2600) ceases before sinus wall (SW) reaches the longitudinal gap between the proximal end of helical flight (2664) and the distal end of rotatable shaft (2646). It should be understood that auger member (2660) may be advanced through the sinus wall (SW) solely due to rotation of auger member (2660), such that the operator need not also press distally on any portion of instrument (2600) as flight (2664) traverses the sinus wall (SW).

Figure 38D:
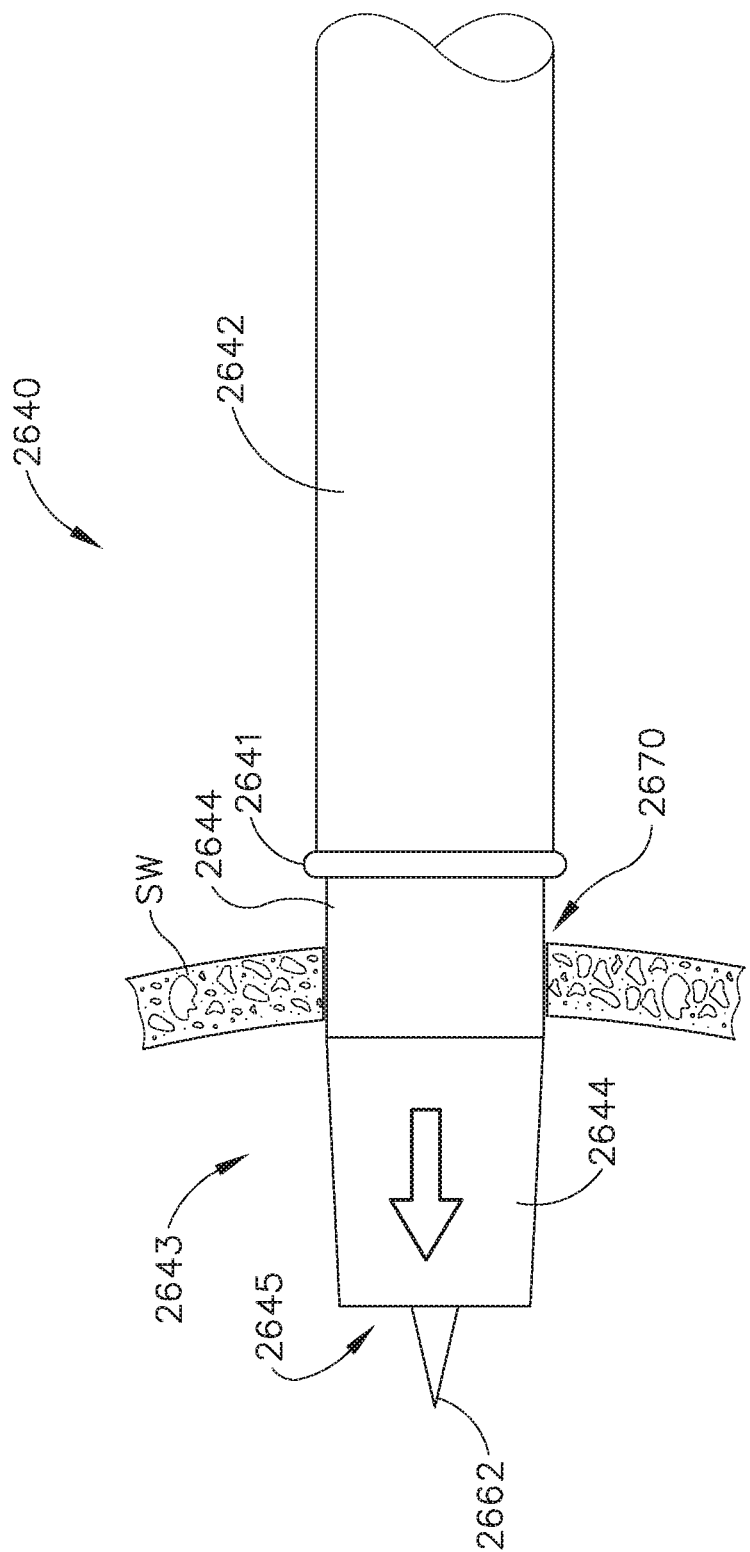
FIG. 38D depicts a side elevational view of the shaft assembly of FIG. 36 in the second longitudinal position, with the outer sheath still in the second longitudinal position, and with the cutter moved to a second longitudinal position.
Figure 39D:
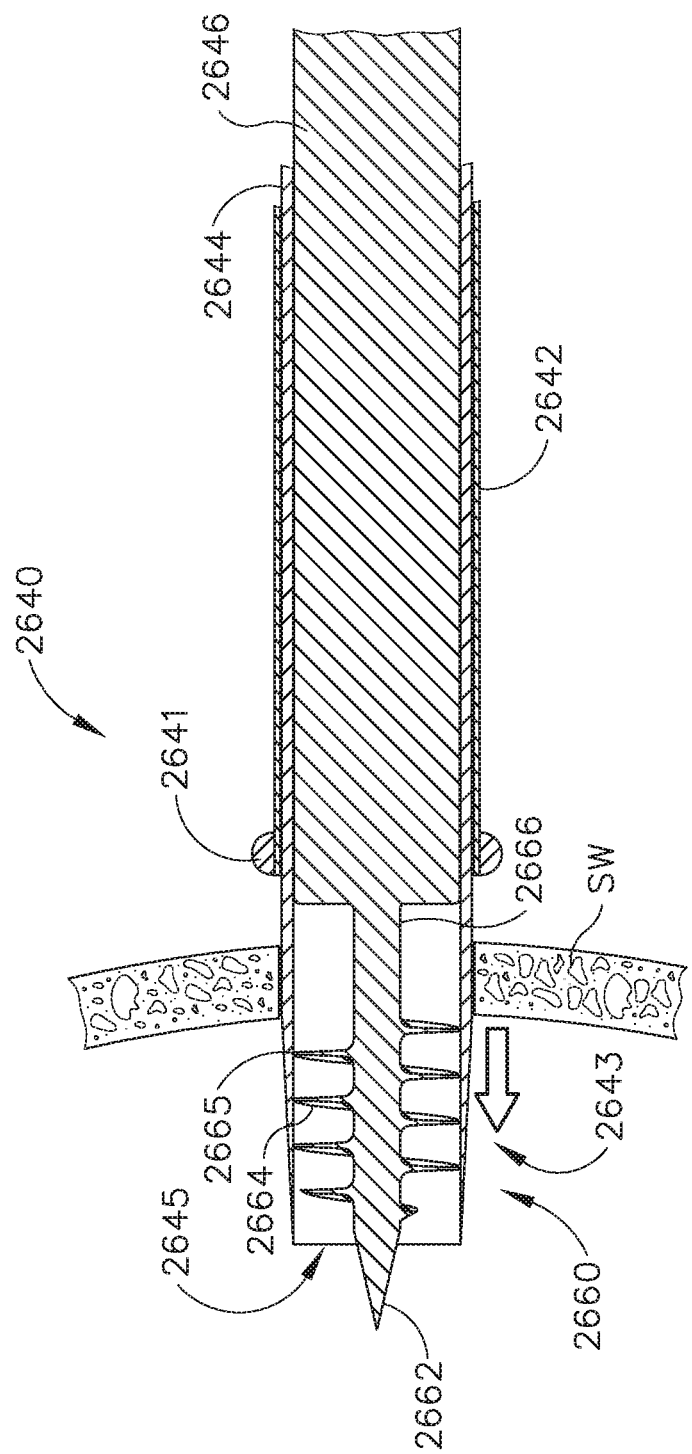
FIG. 39D depicts a side cross-sectional view of the shaft assembly of FIG. 36 in the second longitudinal position, with the outer sheath still in the second longitudinal position, and with the cutter moved to a second longitudinal position.
Figure 40:
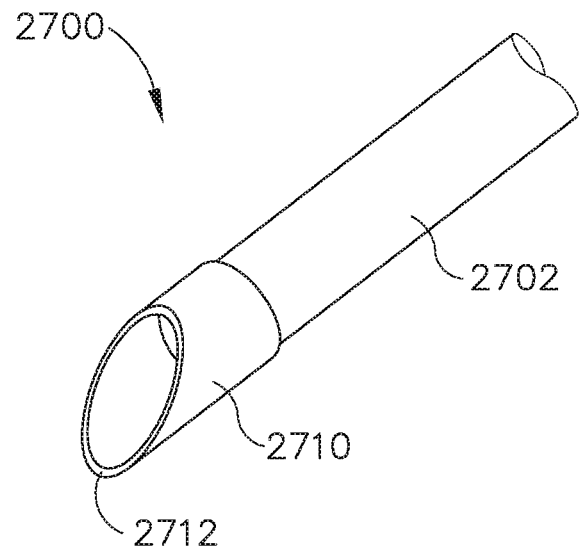
FIG. 40 depicts a perspective view of an exemplary alternative outer sheath assembly that may be used with the instrument of FIG. 32.
Figure 41:
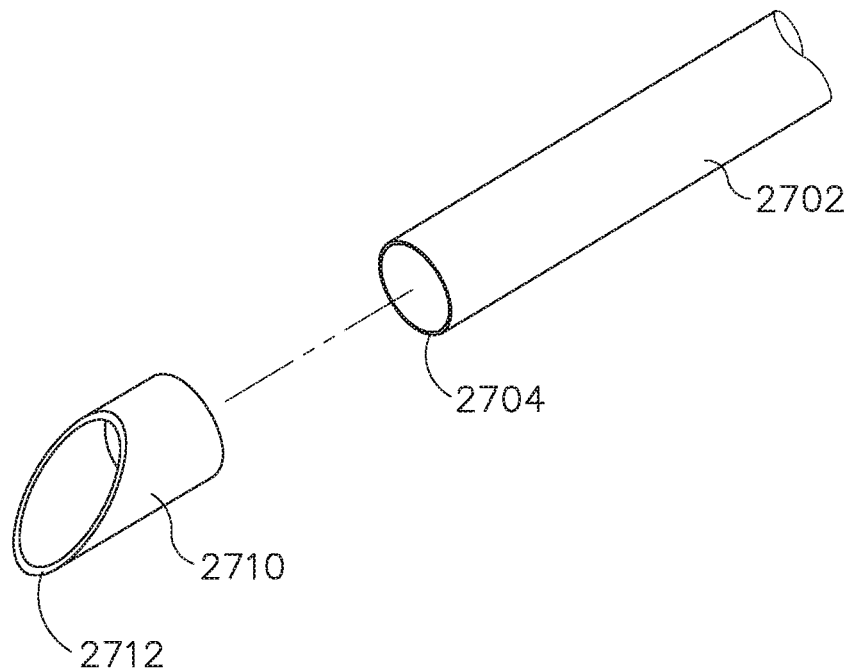
FIG. 41 depicts an exploded view of the outer sheath assembly of FIG. 40.

To the stage shown in FIGS. 38C and 39C, cutter tube (2644) has remained stationary relative to outer sheath (2642). Outer sheath (2642) has thus protected tissue from inadvertent contact with the sharp distal end of cutter tube (2644). However, once auger member (2660) has been driven through sinus wall (SW), cutter tube (2644) is then advanced distally relative to outer sheath (2642) and rotatable shaft (2646) by squeezing of pivoting trigger (2628) toward pistol grip (2624) while auger member (2660) remains stationary. In some versions, cutter tube (2644) rotates while it advances distally; while in other versions it does not. In versions of cutter tube (2644) that rotate, cutter tube (2644) may comprise cutting features—e.g. serrations—along the sharp edge defining opening (2645). When cutter tube (2644) advances distally, the sharp edge defining opening (2645) passes through the sinus wall (SW) until tapered region (2643) has fully traversed the sinus wall (SW) as shown in FIGS. 38D and 39D. During this advancement of cutter tube (2644), auger member (2660) anchors instrument (2600) in the sinus wall (SW) and may further provide structural support to the sinus wall (SW) as cutter tube (2644) traverses the sinus wall (SW). Tapered region (2643) provides a gradual widening of the opening in the sinus wall (SW). Instrument (2600) is then withdrawn from sinus wall (SW), leaving behind an opening (2670). In some instances, the tapered configuration of distal region (2643) drives some adjacent soft tissue away from the bone of sinus wall (SW) as cutter tube (2644) is advanced distally through sinus wall (SW), such that the soft tissue returns to position and covers the edge of the bone at opening (2670) when shaft assembly (2640) is withdrawn from opening (2670).

It should be understood that auger member (2660) and/or cutter tube (2644) may be driven to any depth desired. For instance, auger member (2660) and cutter tube (2644) may be driven through two or more sinus walls (SW) (e.g., along the same longitudinal path) in succession (e.g., forming a first opening in the first sinus wall (SW), then advancing distally to subsequently form a second opening in a second sinus wall (SW) after the first opening is complete, etc.). It should also be understood that, once opening (2670) has been initially formed, the operator may retract cutter tube (2644), position an edge of opening (2670) in a gap defined along the length of minor shaft (2666) between the proximal end of flight (2664) and the distal end of the major diameter portion of rotatable shaft (2646), then advance cutter tube (2644) distally to thereby take a bite out of the edge of opening (2670). This will enlarge the size of opening (2670) and may be repeated as desired in order to provide a selected size and configuration for opening (2670). Various other suitable features of instrument (2600) and methods of using instrument (2600) will be apparent to those of ordinary skill in the art in view of the teachings herein.

Although outer sheath (2642) of the present example is driven by sliding trigger (2360), it should be understood that outer sheath (2642) may be driven by other methods. For instance, outer sheath (2642) may be driven proximally, thus exposing cutter tube (2646), via rotation of rotatable knob (2634). Outer sheath (2642) may also comprise a tapered distal portion that covers auger member (2660) to thereby further facilitate insertion of shaft assembly (2640) into tight places. While sheath (2642) of the present example is rigid (e.g., formed of rigid plastic or stainless steel, etc.), outer sheath (2642) may alternatively be flexible to thereby further facilitate insertion of shaft assembly (2640) into tight places. Such a flexible outer sheath (2642) may comprise a slidable "exoskeleton" to selectively prevent flexibility when rigidity is necessary. Such a flexible outer sheath may further comprise internal features that cause outer sheath (2642) to flex outwardly as cutter tube (2646) is driven distally to avoid cutting of outer sheath (2642). It should also be understood that sheath (2642) may include detent features or similar features that provide some degree of resistance to sliding sheath (2642) when sheath (2642) is in a proximal position and/or when sheath (2642) is in a distal position. Other suitable variations will be apparent to those of ordinary skill in the art in view of the teachings herein.

2. Exemplary Alternative Retractable Sheath

FIGS. 40-43E depict an exemplary alternative sheath assembly (2700) that may be readily incorporated into shaft assembly (2640) of instrument (2600), in place of outer sheath (2642). Sheath assembly (2700) of this example comprises a tube (2702) and a tip member (2710) positioned at the distal end (2704) of tube (2702). Tip member (2710) includes a distal edge (2712) that defines a plane that is oriented at an oblique angle relative to the longitudinal axis of tube (2702). By way of example only, the plane of distal edge (2712) may be oriented at anywhere between approximately 45 degrees and approximately 60 degrees relative to the longitudinal axis of tube (2702). In some instances, the oblique orientation of distal edge (2712) may facilitate navigation of shaft assembly (2640) through the paranasal cavity. For instance, distal edge (2712) may act as a cam, thereby driving anatomical structures out of the way as a lead-in for further insertion of tube (2702).

Tip member (2710) may be formed of a variety of materials, including but not limited to pebax, plastic, metal, etc., including combinations thereof. Various suitable materials that may be used to form tip member (2710) will be apparent to those of ordinary skill in the art in view of the teachings herein. It should also be understood that tip member (2710) may be secured to tube (2702) in a variety of ways, including but not limited to overmolding, interference fitting, snap fitting, adhesives, welding, etc. Various suitable ways in which tip member (2710) may be secured to tube (2702) will be apparent to those of ordinary skill in the art in view of the teachings herein. In some other variations, distal edge (2407) of tube (2702) is formed at an oblique angle. In some such versions, tip member (2710) is omitted.

Figure 42A:
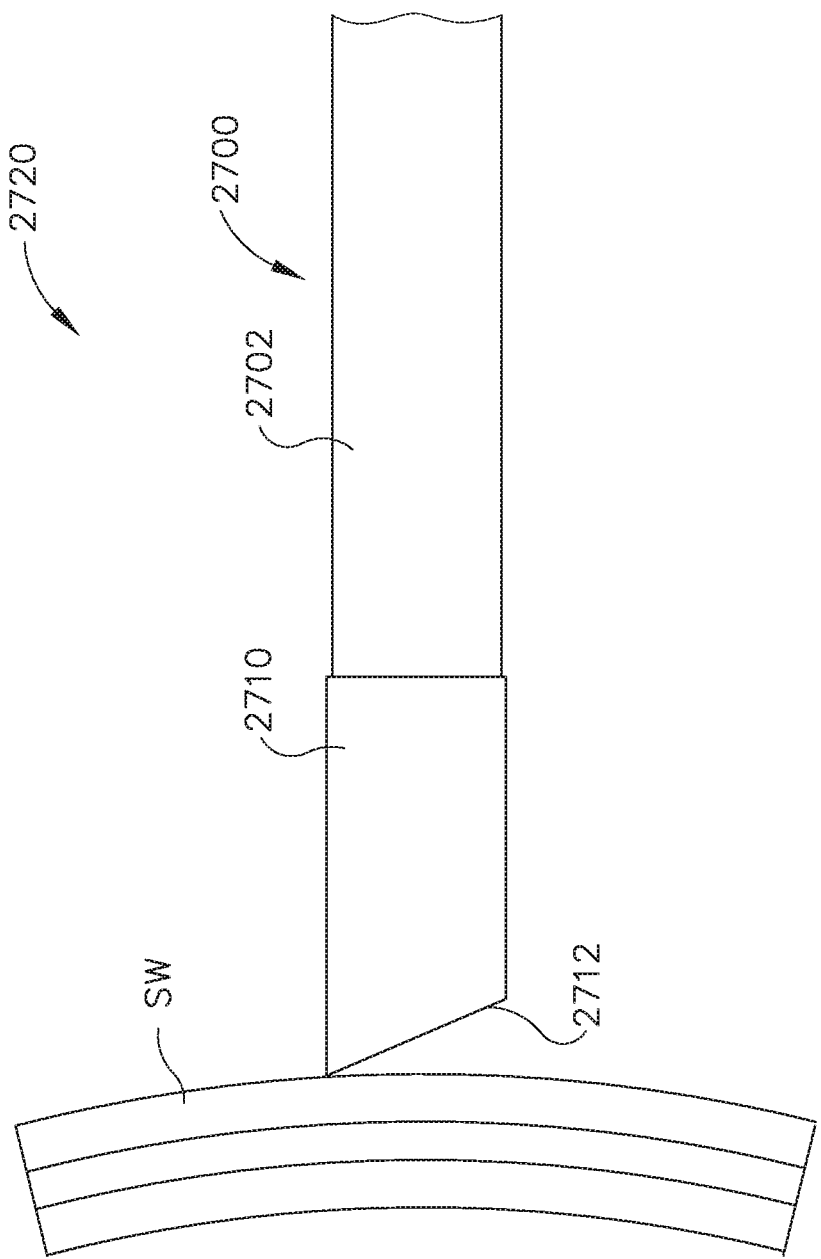
FIG. 42A depicts a side elevational view of the shaft assembly of FIG. 36, incorporating the outer sheath assembly of FIG. 40, with the entire shaft assembly in a first longitudinal position.
Figure 42B:
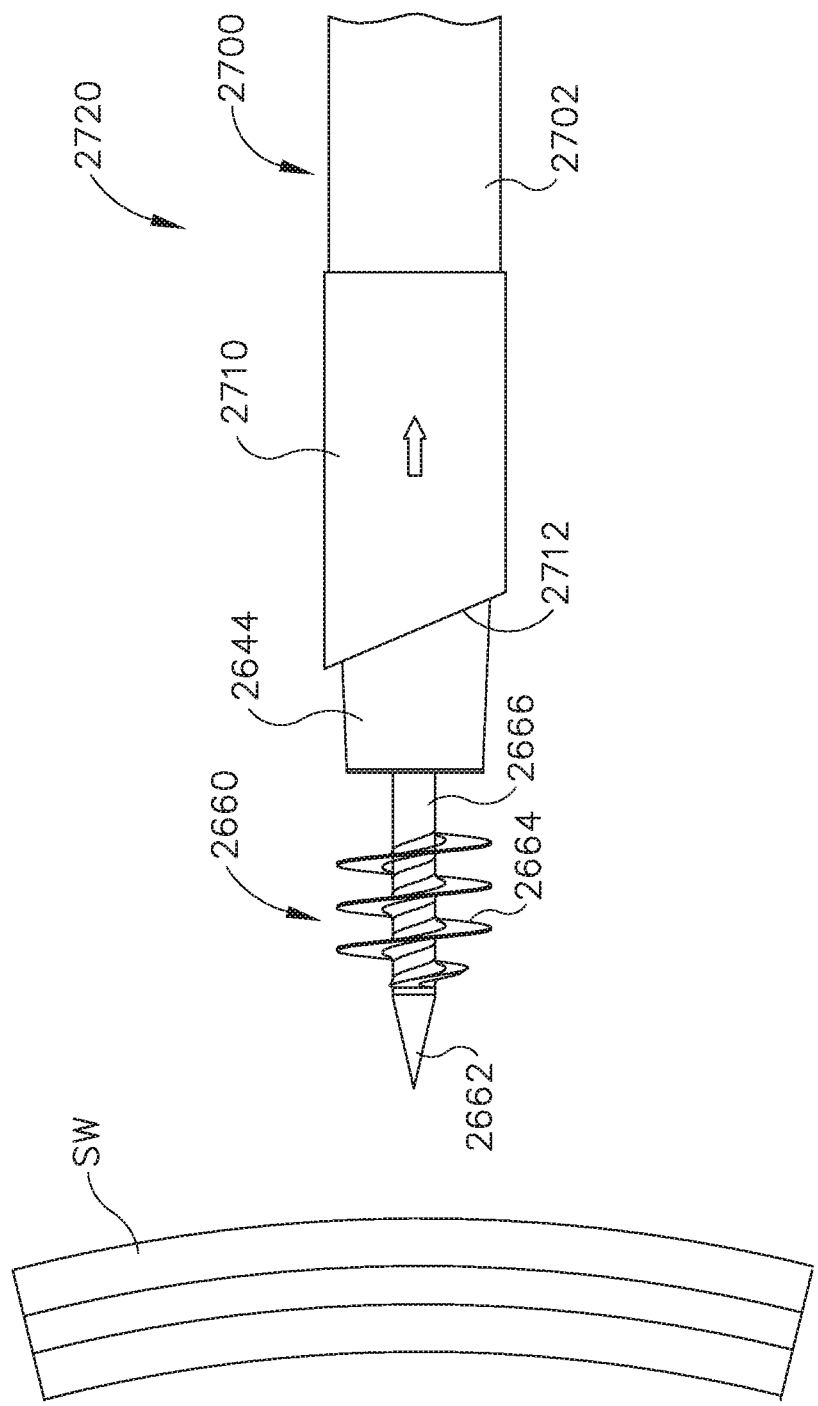
FIG. 42B depicts a side elevational view of the shaft assembly of FIG. 36, incorporating the outer sheath assembly of FIG. 40, with the outer sheath assembly retracted proximally while the rest of the shaft assembly remains in the first longitudinal position.

FIGS. 42A-43E show a shaft assembly (2720) that incorporates sheath assembly (2700), being used to form an opening in a sinus wall (SW). The sinus wall (SW) may be a wall of the ethmoid bulla (EB) (e.g., the anterior face of the ethmoid bulla (EB)) or the wall of some other sinus cavity. In this example, shaft assembly (2720) is identical to shaft assembly (2640), except that shaft assembly (2720) of this example includes sheath assembly (2700) instead of sheath (2642). As shown in FIGS. 42A and 43A, shaft assembly (2720) is initially positioned such that the distal-most portion of distal edge (2712) contacts the sinus wall (SW). Up to this point, auger member (2660) and cutter tube (2644) are covered by sheath assembly (2700). Then, sheath assembly (2700) is retracted proximally (e.g., by moving sliding trigger (2630) longitudinally proximally), thereby revealing auger member (2660) and the distal end of cutter tube (2644) as shown in FIGS. 42B and 43B.

Figure 42C:
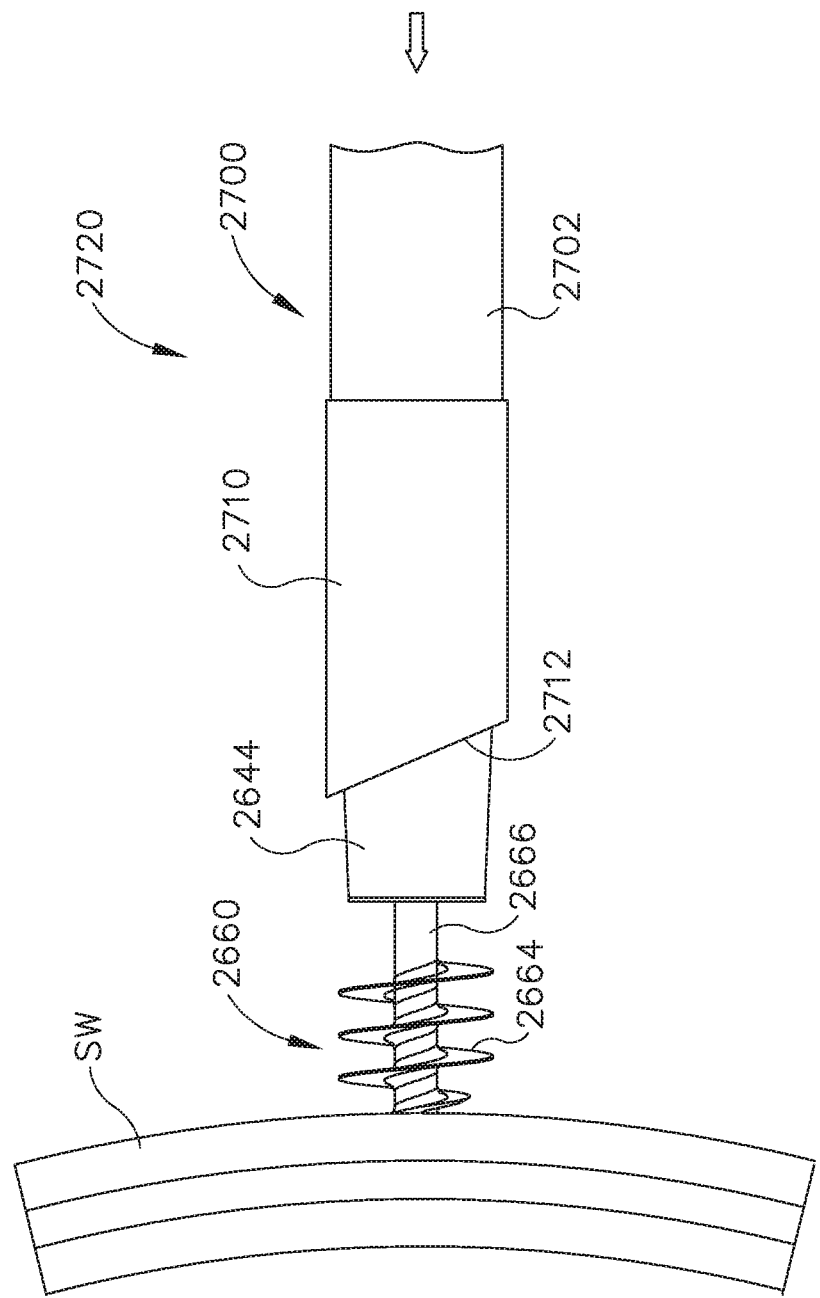
FIG. 42C depicts a side elevational view of the shaft assembly of FIG. 36, incorporating the outer sheath assembly of FIG. 40, with the entire shaft assembly advanced to a second longitudinal position.
Figure 43A:
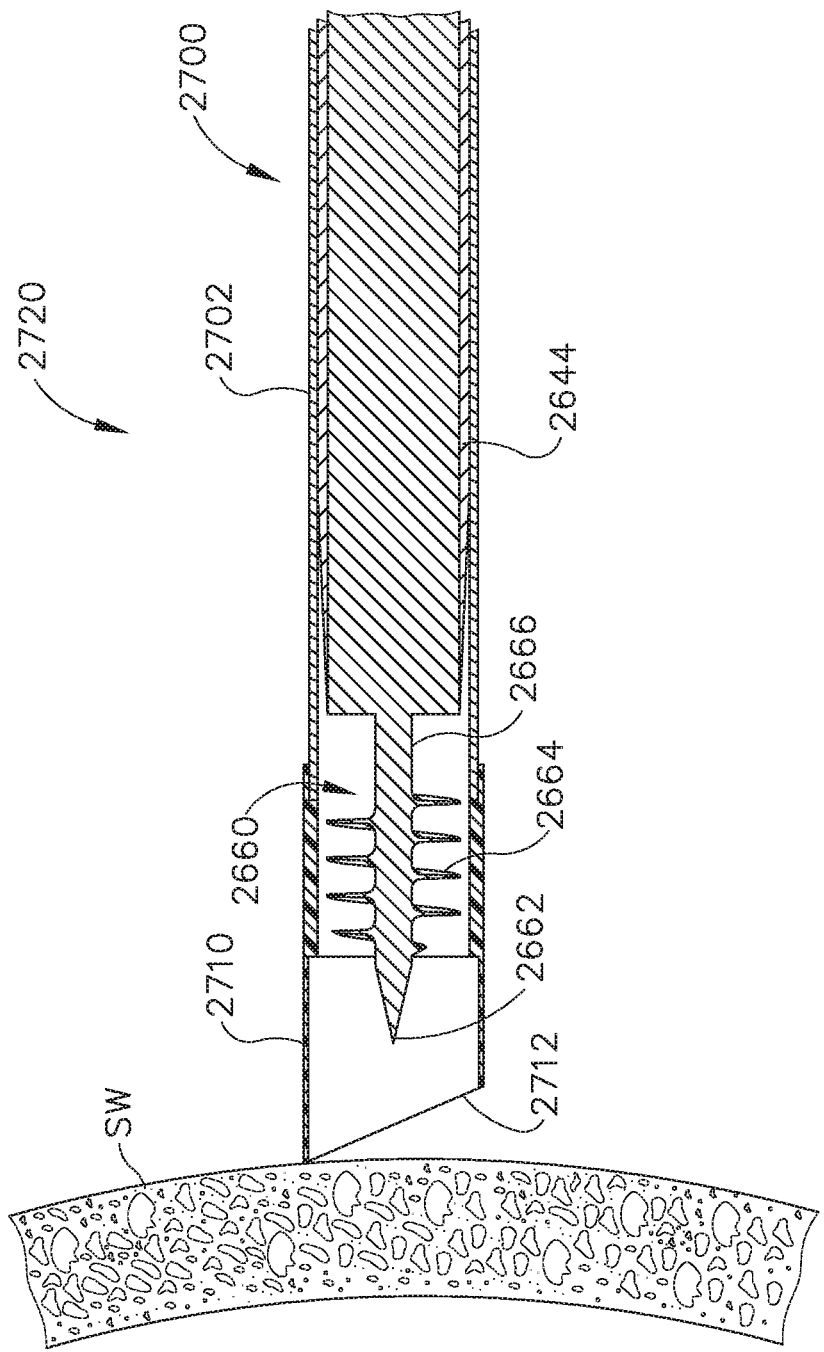
FIG. 43A depicts a side elevational view of the shaft assembly of FIG. 36, incorporating the outer sheath assembly of FIG. 40, with the entire shaft assembly in the first longitudinal position.
Figure 43B:
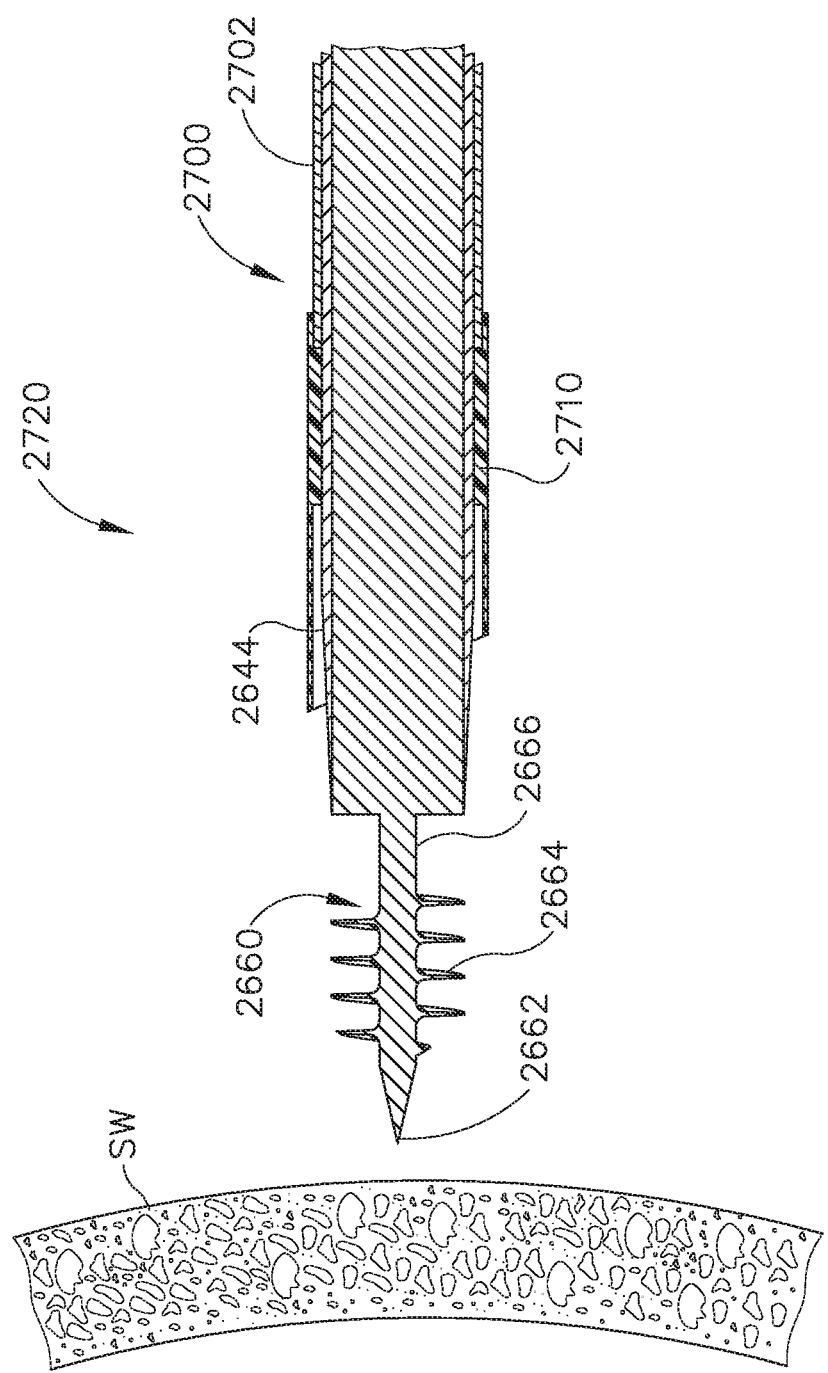
FIG. 43B depicts a side cross-sectional view of the shaft assembly of FIG. 36, incorporating the outer sheath assembly of FIG. 40, with the outer sheath assembly retracted proximally while the rest of the shaft assembly remains in the first longitudinal position.
Figure 43C:
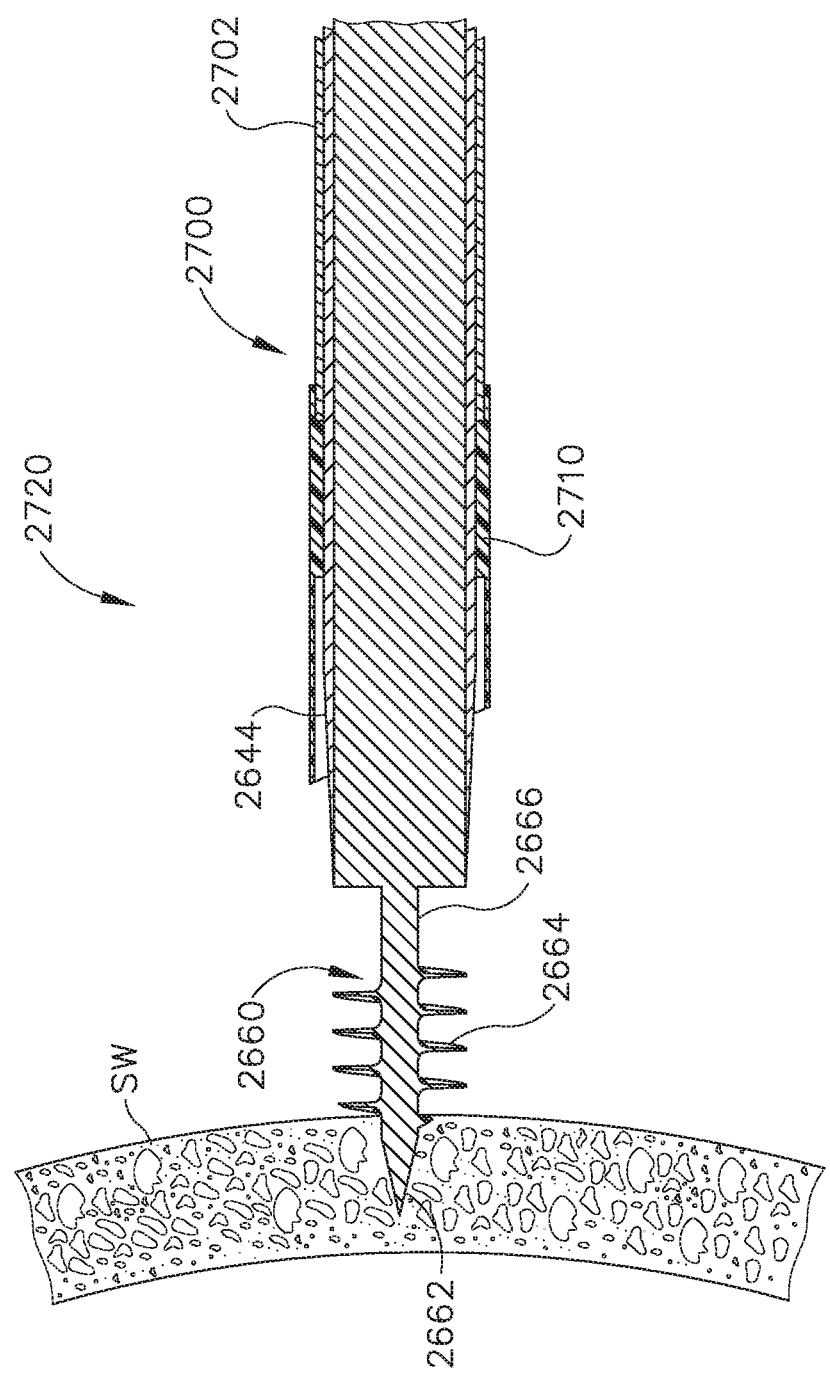
FIG. 43C depicts a side cross-sectional view of the shaft assembly of FIG. 36, incorporating the outer sheath assembly of FIG. 40, with the entire shaft assembly advanced to the second longitudinal position.

With sheath assembly (2700) retracted, the entire shaft assembly (2720) is advanced distally toward the sinus wall (SW), until sharp distal tip (2662) of auger member (2660) pierces the sinus wall (SW) as shown in FIGS. 42C and 43C. With tip (2662) in the sinus wall (SW), the operator continues to advance the entire shaft assembly (2720) while rotating auger member (2660) about the longitudinal axis of shaft assembly (2720) (e.g., by rotating rotatable knob (2634)). It should be understood that, after initially piercing the sinus wall (SW) with sharp distal tip (2662), auger member (2660) continues to advance distally by rotating due to the helical configuration of flight (2664). In particular, helical flight (2664) is driven through the sinus wall (SW) like a screw. Auger member (2660) eventually reaches the position shown in FIGS. 42D and 43D, where flight (2644) is located within sinus wall (SW). In some instances, the operator stops rotating auger member (2660) and stops advancing the entire shaft assembly (2720) at this stage. In other words, the region of minor shaft (2666) proximal to flight (2664) does not reach the sinus wall (SW) in some instances. In some other instances, the operator rotates auger member (2660) and continues to advance the entire shaft assembly (2720) until sinus wall (SW) is positioned about the region of minor shaft (2666) proximal to flight (2664). In either case, it should be understood that auger member (2660) may be advanced through the sinus wall (SW) solely due to rotation of auger member (2660), such that the operator need not also press distally on any portion of instrument (2600) as flight (2664) traverses the sinus wall (SW).

Figure 42E:
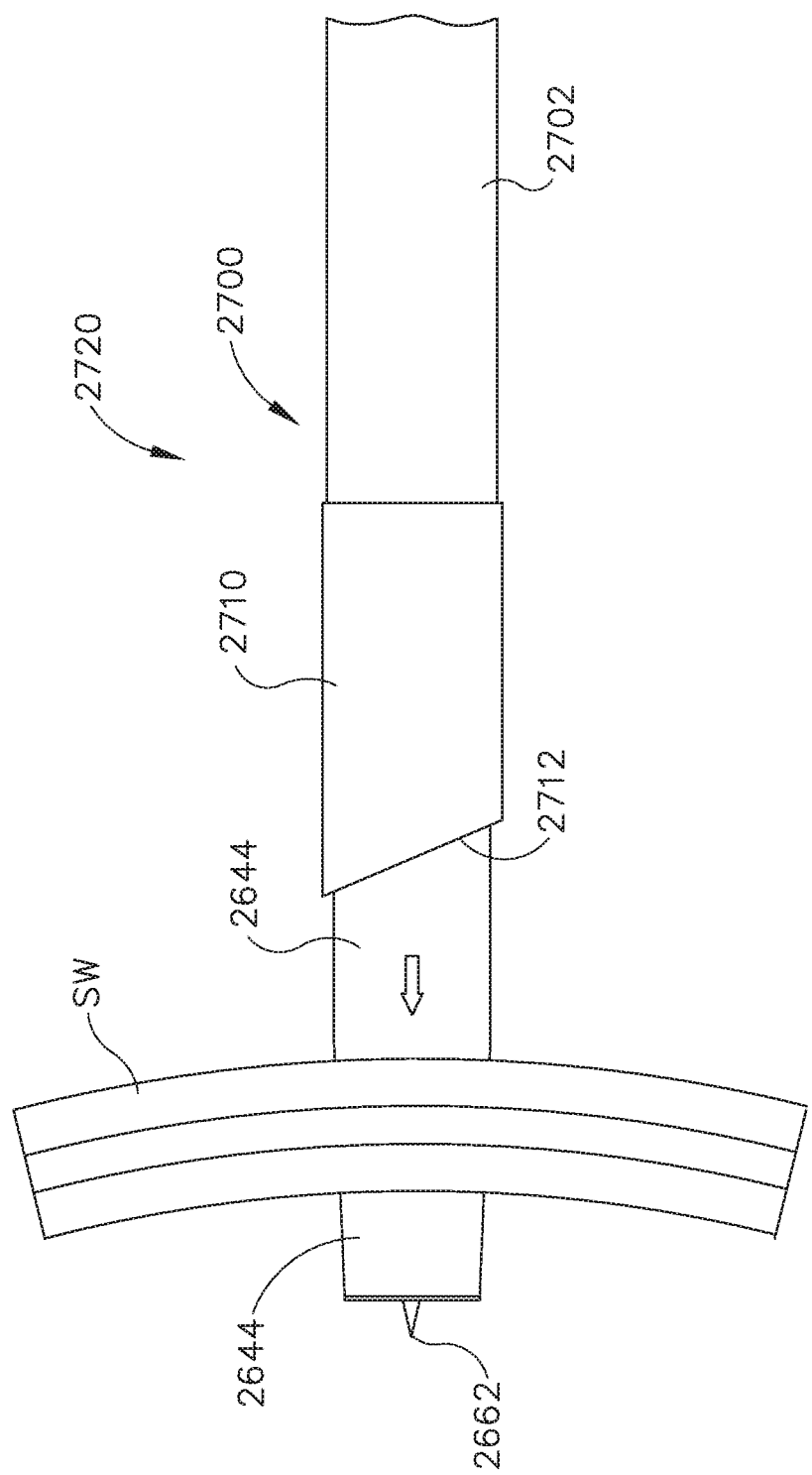
FIG. 42E depicts a side elevational view of the shaft assembly of FIG. 36, incorporating the outer sheath assembly of FIG. 40, with the cutter advanced distally while the rest of the shaft assembly remains in the third longitudinal position.
Figure 43D:
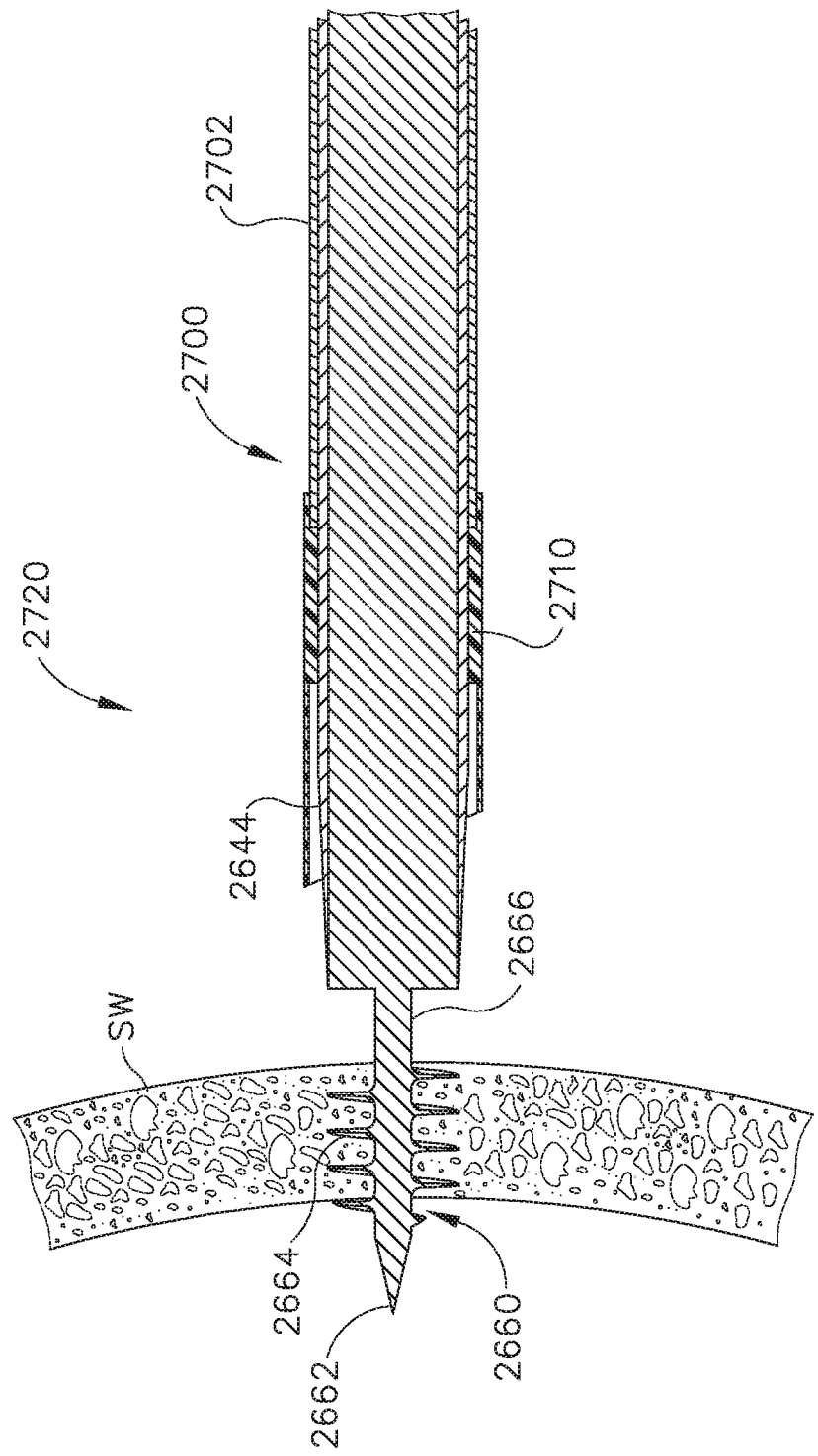
FIG. 43D depicts a side cross-sectional view of the shaft assembly of FIG. 36, incorporating the outer sheath assembly of FIG. 40, with the entire shaft assembly advanced to the third longitudinal position.
Figure 43E:
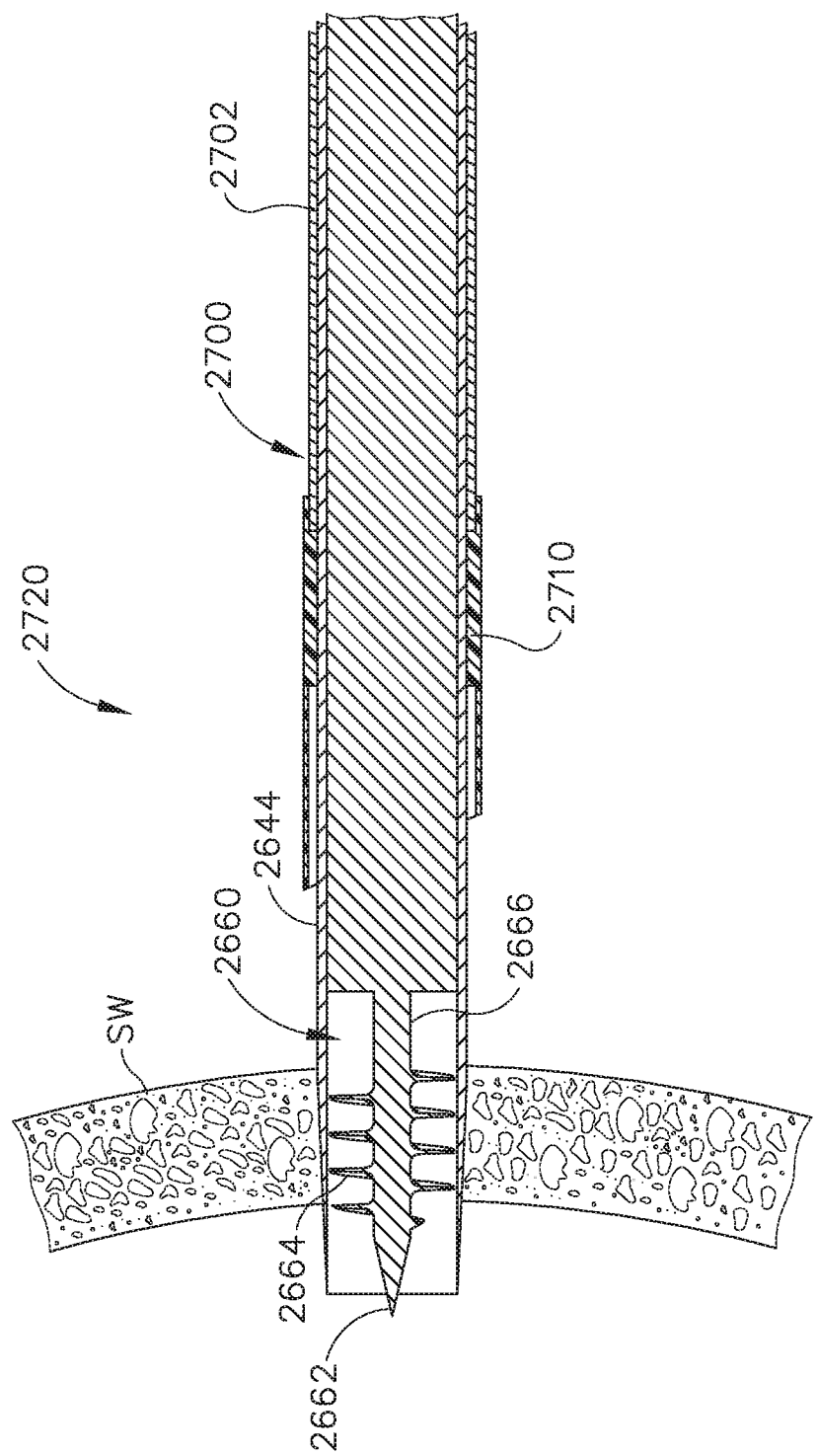
FIG. 43E depicts a side cross-sectional view of the shaft assembly of FIG. 36, incorporating the outer sheath assembly of FIG. 40, with the cutter advanced distally while the rest of the shaft assembly remains in the third longitudinal position.
Figure 43F:
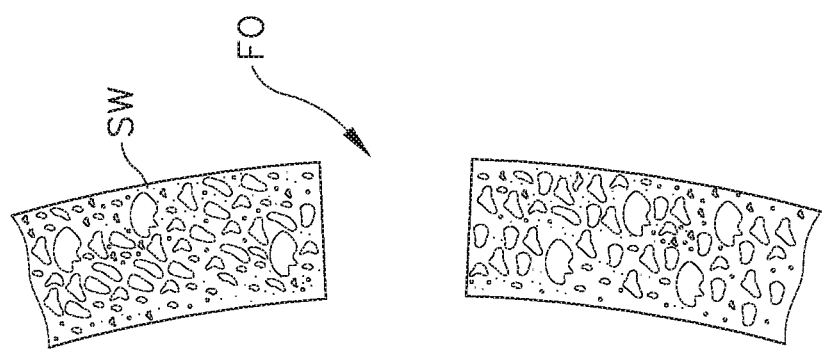
FIG. 43F depicts a side cross-sectional view of a sinus wall with an opening formed by the shaft assembly of FIG. 36.

Having reached the stage shown in FIGS. 42D and 43D, the operator advances cutter tube (2644) distally (e.g., by squeezing of pivoting trigger (2628) toward pistol grip (2624)) while holding the remainder of shaft assembly (2720) stationary. Cutter tube (2644) thereby cuts a circular opening in the sinus wall (SW), slicing through the bone and tissue of the sinus wall (SW), as shown in FIGS. 42E and 43E. During this advancement of cutter tube (2644), auger member (2660) anchors shaft assembly (2720) in the sinus wall (SW) and may further provide structural support to the sinus wall (SW) as cutter tube (2644) traverses the sinus wall (SW). After cutter tube (2644) cuts through the sinus wall (SW), the entire shaft assembly (2720) is retracted proximally to reveal the formed opening (FO) in the sinus wall (SW), as shown in FIG. 43F. Shaft assembly (2720) may then be cleaned, disposed of, or otherwise handled. Merely illustrative ways in which auger member (2660) may be cleaned will be described in greater detail below, while other examples will be apparent to those of ordinary skill in the art in view of the teachings herein.

3. Exemplary Alternative Rotatable Shafts with Helical Augers

FIGS. 44 and 45 show an exemplary alternative rotatable shaft (2680) that may be readily incorporated into instrument. Rotatable shaft (2680) is configured to operate substantially similar to rotatable shaft (2646) discussed above. Rotatable shaft (2680) of this example includes an auger member (2682) at the distal end of rotatable shaft (2680) and a key recess (2687) formed in the proximal end of rotatable shaft (2680). Auger member (2682) includes a sharp distal tip (2683) and a helical blade or flight (2684). Tip (2683) and flight (2664) are substantially identical to tip (2662) and flight (2664) discussed above. A tapered transition (2685) is formed between auger member (2682) and a major diameter proximal portion (2686) of rotatable shaft (2680). Key recess (2687) is configured to receive a distally projecting key feature of a shaft or some other component. Key recess (2687) is configured such that rotatable shaft (2680) will rotate unitarily with the complementary component inserted in key recess (2687). An opening (2688) is formed in major diameter proximal portion (2686) of rotatable shaft (2680) to accommodate a set screw (not shown), which may be used to secure the inserted component in key recess (2687). In the present example, key recess (2687) has a hexagonal cross-sectional profile, though it should be understood that any other suitable configuration may be used.

Rotatable shaft (2680) of this example is formed in a molding process. By way of example only, rotatable shaft (2680) may be formed of molded plastic and/or metal. Other suitable materials and methods of manufacture that may be used to form rotatable shaft (2680) will be apparent to those of ordinary skill in the art in view of the teachings herein.

FIG. 46 shows another exemplary alternative rotatable shaft (2690) that may be readily incorporated into instrument. Rotatable shaft (2690) is configured to operate substantially similar to rotatable shaft (2646) discussed above. Rotatable shaft (2690) of this example includes an auger member (2692) at the distal end of rotatable shaft (2690) and a major diameter proximal portion (2691). Auger member (2692) includes a sharp distal tip (2693) and a helical blade or flight (2694). Tip (2693) and flight (2694) are substantially identical to tip (2662) and flight (2664) discussed above, except that flight (2694) of this example terminates directly in major diameter proximal portion (2691) of shaft (2690). In other words, there is no longitudinal gap between flight (2694) and major diameter proximal portion (2691) of shaft (2690). As with shaft (2680), shaft (2690) of this example may be formed of any suitable material(s) (e.g., plastic, metal, etc.) and using any suitable process(es) (e.g., molding, etc.).

Figure 47:
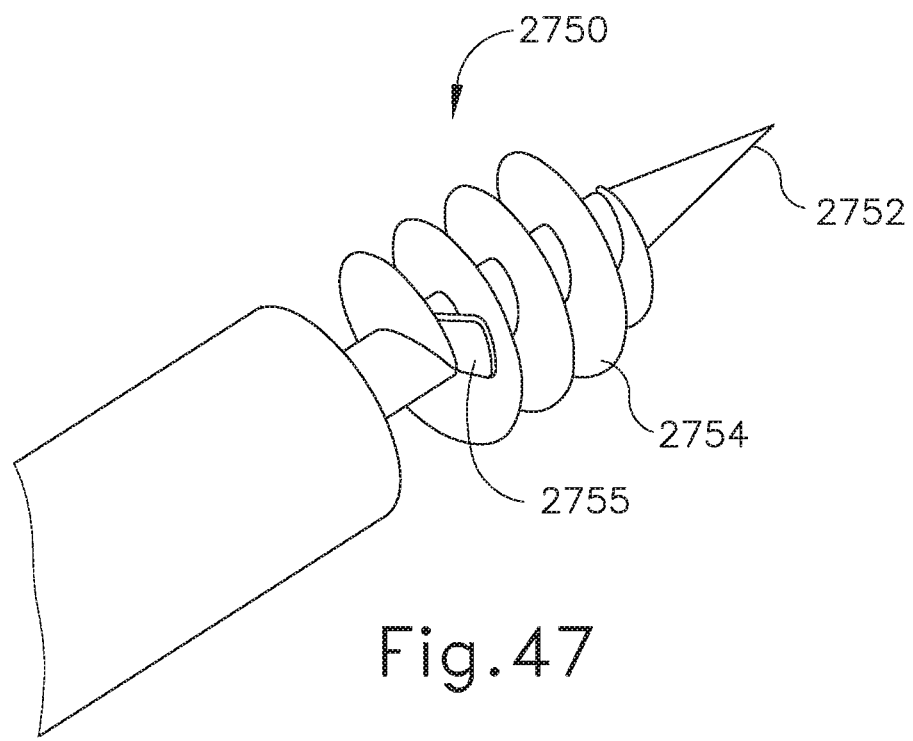
FIG. 47 depicts a perspective view of another exemplary alternative auger shaft that may be used with the instrument of FIG. 32.
Figure 48:
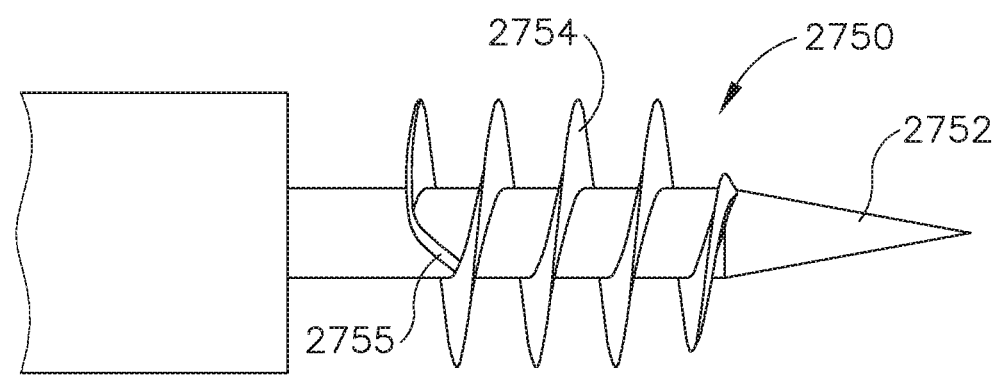
FIG. 48 depicts a side elevational view of the auger of FIG. 47.

FIGS. 47-48 show an exemplary alternative auger member (2750) that may be incorporated into rotatable shaft (2646). Auger member (2750) of this example comprises a sharp distal tip (2752) and a helical flight (2754). Auger member (2750) is substantially identical to auger member (2660) described above, except that the proximal end of flight (2754) includes a bent portion (2755). Bent portion (2755) projects substantially distally from the proximal end of flight (2754), such that bent portion (2755) terminates at the proximal face of region of flight (2754) that is distal to the proximal end of flight (2754). Bent portion (2755) may provide a hard stop for advancement of auger member (2750) into an anatomical structure such as a sinus wall (SW). For instance, as auger member (2750) is driven into a sinus wall (e.g., as shown in the transition from FIG. 38B to FIG. 38C, the transition from FIG. 39B to FIG. 39C, the transition from FIG. 42C to FIG. 42D, and the transition from FIG. 43C to FIG. 43D), auger member (2750) may resist further advancement when bent portion (2755) engages the sinus wall (SW). This resistance may be felt by the operator (e.g., as the operator manually rotates knob (2634)), prompting the operator to advance cutter tube (2644) distally. Thus, in addition to providing a hard stop for advancement of auger member (2750) in the sinus wall (SW), bent portion (2755) may provide tactile feedback to the operator, indicating that auger member (2750) has reached a suitable depth in the sinus wall (SW).

4. Exemplary Devices for Cleaning Helical Augers

Figure 49:
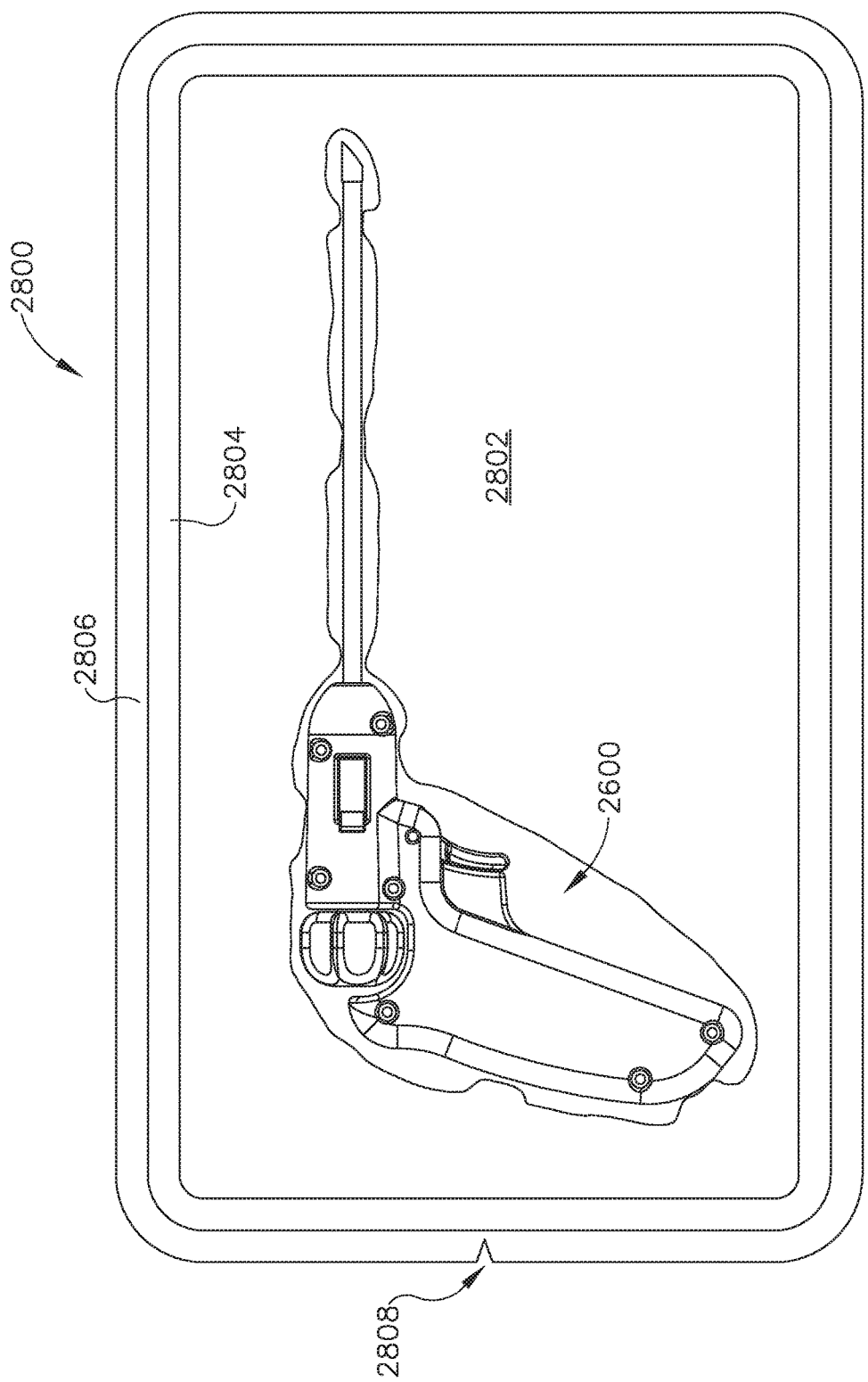
FIG. 49 depicts a top plan view of the instrument of FIG. 32, fitted with the outer sheath assembly of FIG. 40, disposed in an exemplary blister packaging tray.
Figure 50A:
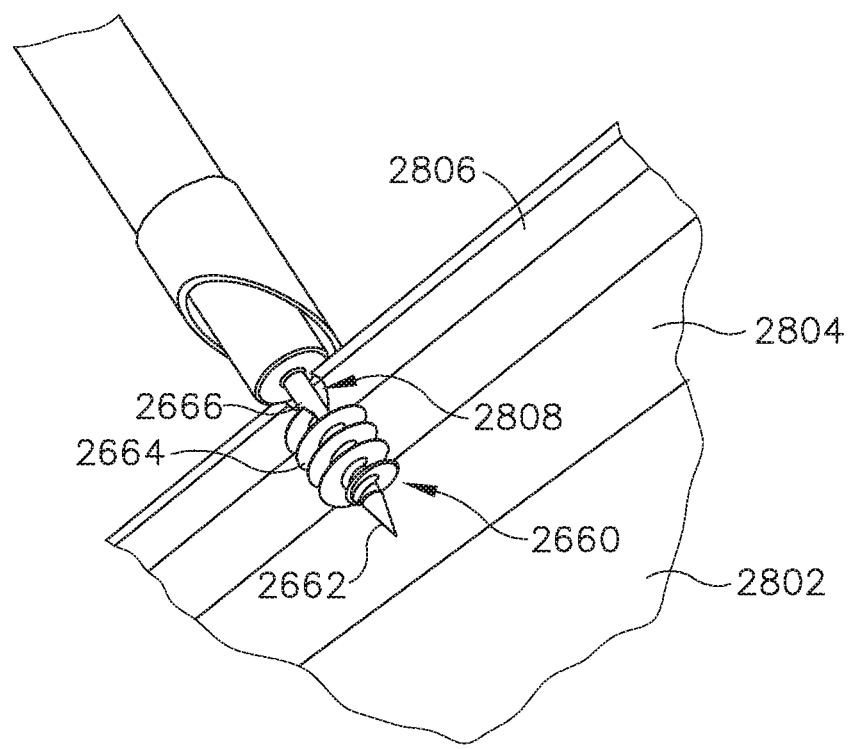
FIG. 50A depicts a perspective view of the auger of FIG. 37 disposed in a notch of the tray of FIG. 49, in a first longitudinal position.
Figure 50B:
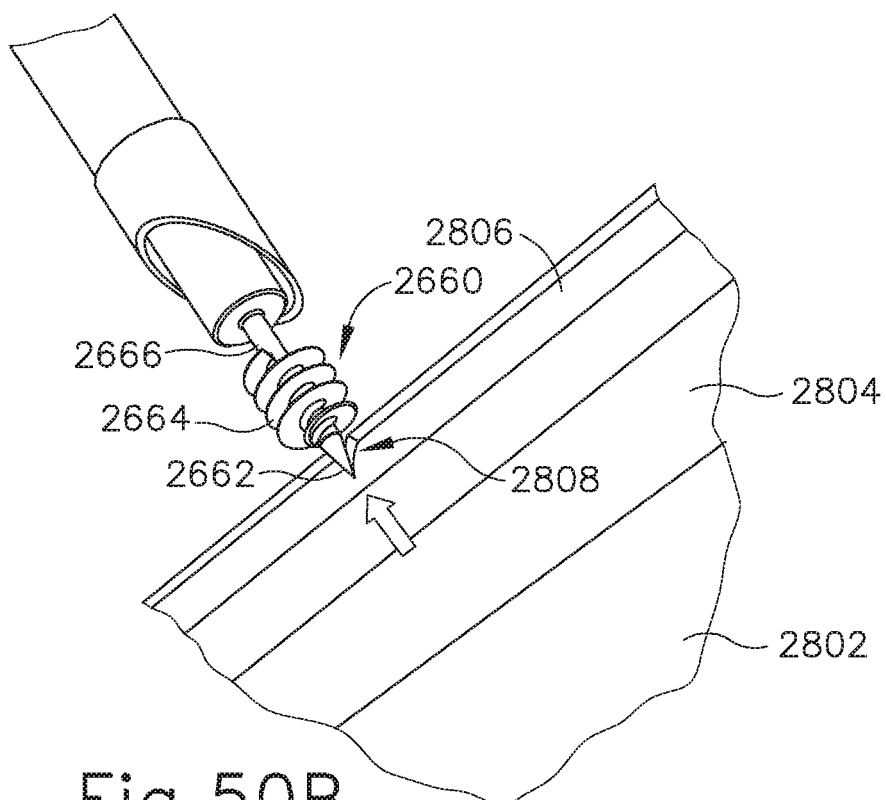
FIG. 50B depicts a perspective view of the auger of FIG. 37 disposed in a notch of the tray of FIG. 49, in a second longitudinal position.

As noted above, auger member (2660) may pick up debris such as fragments of tissue, bone, etc., after auger member (2660) has been used to form an opening (FO) in a sinus wall (SW). In some instances, it may be desirable to clean this debris from auger member (2660). By way of example only, it may be desirable to clean debris from auger member (2660) if auger member is going to be driven through another sinus wall (SW) or another region of the same sinus wall (SW), etc. In addition or in the alternative, it may be desirable to collect such debris in order to provide a tissue specimen for further analysis, as will be described in greater detail below. FIGS. 49-50B show one merely illustrative device that may be used to remove debris from auger member (2660). In particular, FIG. 49 shows a blister packaging tray (2800) that is used to contain instrument (2600) for storage and shipment, etc. Tray (2800) includes an instrument holding region (2802), a cover sealing region (2804), and an outer flange (2808). In the present example, instrument holding region (2802) is vertically offset from cover sealing region (2804). Likewise, flange (2808) is vertically offset from cover sealing region (2804). Cover sealing region (2804) presents a flat surface to which a cover (e.g., film, etc.) may be adhered or otherwise secured, to thereby seal and maintain the sterility of instrument (2600) in instrument holding region (2802).

Flange (2806) of the present example includes a notch (2808). While only one notch (2808) is shown, it should be understood that any other suitable number of notches (2808) may be provided. In the present example, notch (2808) has a "V" shape. In some other versions, notch (2808) has a "U" shape. Other suitable shapes that may be used for notch (2808) will be apparent to those of ordinary skill in the art in view of the teachings herein. As shown in FIGS. 50A-50B, notch (2808) is sized to receive minor shaft (2666) of auger member (2660). In an exemplary use, the operator first inserts the region of minor shaft (2666) proximal to flight (2664) in notch (2808), as shown in FIG. 50A. The operator then rotates auger member (2660) to pass flange (2806) distally along the length of auger member (2660), until flange (2806) reaches tip (2662) of auger member (2660) as shown in FIG. 50B. As auger member (2660) traverses flange (2806), the edges of notch (2808) scrape along minor shaft (2666) and flight (2664), thereby removing debris from minor shaft (2666) and flight (2664). Due to the helical configuration of flight (2664), the debris is urged distally (and/or outwardly) relative to auger member (2660). Once tip (2662) reaches flange (2806), the operator may scrape the sides of tip (2662) along the edges of notch (2808) to remove any remaining debris. If desired (e.g., to provide a tissue specimen), the process depicted in FIGS. 50A-50B may be performed over a receptacle to capture the removed debris for subsequent analysis.

Figure 51:
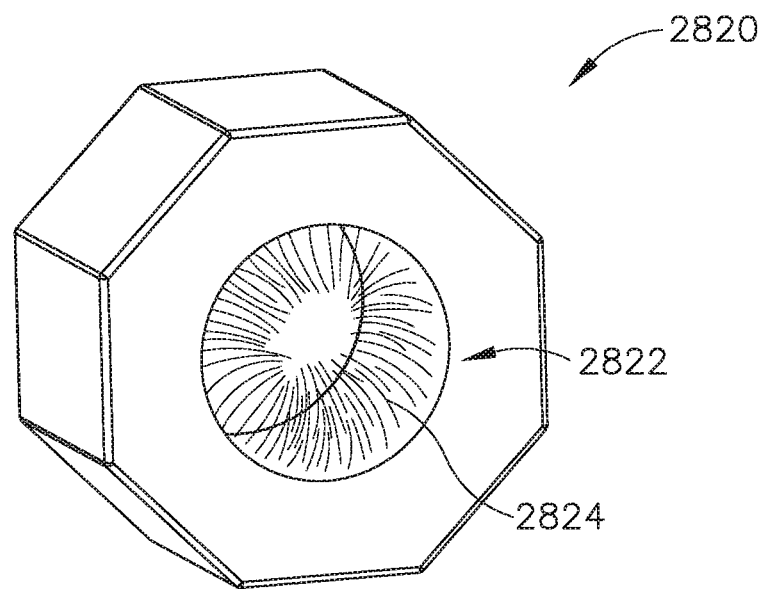
FIG. 51 depicts a perspective view of an exemplary auger cleaning device.

FIG. 51 shows another exemplary instrument (2820) that may be used clean debris from auger member (2660). Instrument (2820) of this example defines a bore (2822) that includes a plurality of inwardly directed bristles (2824). Bristles (2824) may be formed of metal, plastic (e.g., nylon, etc.), and/or various other kinds of materials, including combinations of materials. In use, an operator may insert auger member (2660) into bore (2822) and then rotate and/or reciprocate auger member (2660) within bore (2822). As auger member (2660) rotates and/or reciprocates within bore (2822), bristles (2824) may remove debris from minor shaft (2666) and/or flight (2664). If desired (e.g., to provide a tissue specimen for further analysis), the debris that is removed by bristles (2824) may be picked or flushed from bristles (2824).

In some variations of instrument (2820), a foam material is used in place of bristles (2824). For instance, such a foam material may fill bore (2822), and may define a slit to facilitate insertion of auger member (2660) through the foam. As auger member (2660) rotates and/or reciprocates within bore (2822), the foam may remove debris from minor shaft (2666) and/or flight (2664). If desired (e.g., to provide a tissue specimen for further analysis), the debris that is removed by the foam may be removed from the foam.

Figure 52:
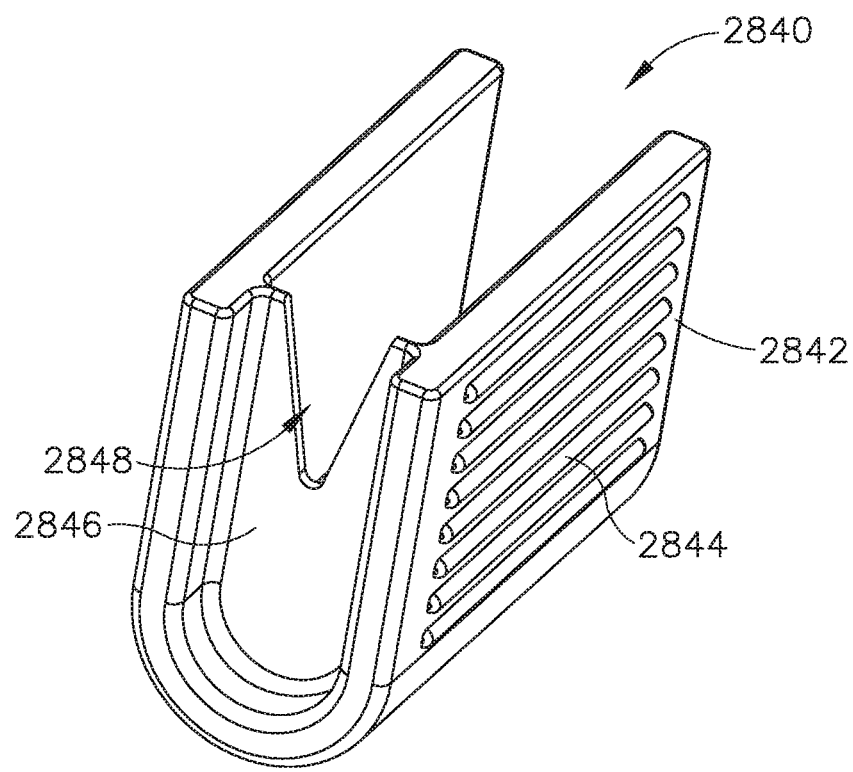
FIG. 52 depicts a perspective view of another exemplary auger cleaning device.
Figure 53A:
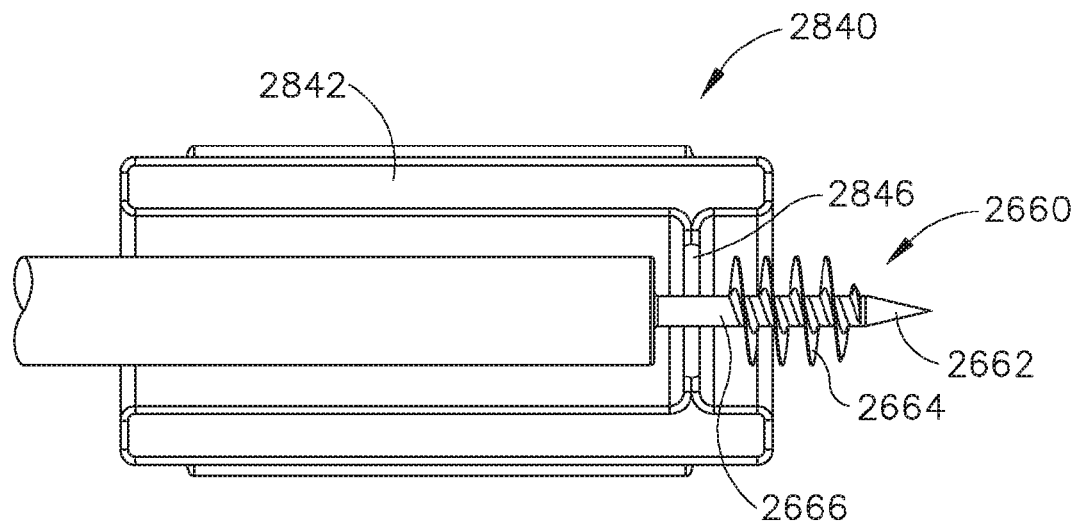
FIG. 53A depicts a top plan view of the auger of FIG. 37 engaged with the auger cleaning device of FIG. 52, in a first longitudinal position.
Figure 53B:
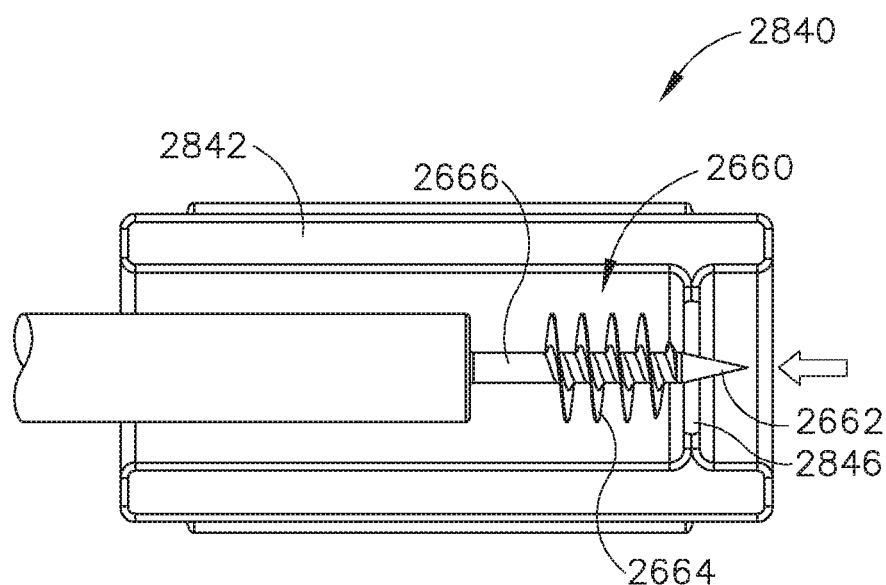
FIG. 53B depicts a top plan view of the auger of FIG. 37 engaged with the auger cleaning device of FIG. 52, in a second longitudinal position.

FIGS. 52-53B show yet another exemplary instrument (2840) that may be used clean debris from auger member (2660). Instrument (2840) of this example includes a body (2842) with an integral web (2846). Body (2842) of this example has a "U" shaped profile and includes gripping regions (2844) on each side. Of course, body (2842) may instead have any other suitable shape. Web (2846) extends transversely across body (2842). Web (2846) includes a notch (2848). In the present example, notch (2848) has a "V" shape. In some other versions, notch (2848) has a "U" shape. Other suitable shapes that may be used for notch (2848) will be apparent to those of ordinary skill in the art in view of the teachings herein.

As shown in FIGS. 53A-53B, notch (2848) is sized to receive minor shaft (2666) of auger member (2660). In an exemplary use, the operator first inserts the region of minor shaft (2666) proximal to flight (2664) in notch (2848), as shown in FIG. 53A. The operator then rotates auger member (2660) to pass web (2846) distally along the length of auger member (2660), until web (2846) reaches tip (2662) of auger member (2660) as shown in FIG. 50B. As auger member (2660) traverses web (2846), the edges of notch (2848) scrape along minor shaft (2666) and flight (2664), thereby removing debris from minor shaft (2666) and flight (2664). Due to the helical configuration of flight (2664), the debris is urged distally (and/or outwardly) relative to auger member (2660). Once tip (2662) reaches web (2846), the operator may scrape the sides of tip (2662) along the edges of notch (2848) to remove any remaining debris. If desired (e.g., to provide a tissue specimen), the process depicted in FIGS. 53A-53B may be performed over a receptacle to capture the removed debris for subsequent analysis.

In the present example, web (2846) is perpendicular to gripping regions (2844), such that web (2846) is perpendicular to the longitudinal axis of auger member (2660). Put another way, web (2846) is perpendicular to a longitudinal axis of body (2842) along two dimensions (e.g., along a vertical transverse dimension and along a horizontal transverse dimension). In some other versions, web (2846) is oriented obliquely relative to gripping regions (2844) and the longitudinal axis of auger member (2660). In some such versions, web (2846) is oriented at an angle that complements the pitch angle of flight (2664). In versions where web (2846) is oriented obliquely, web (2846) may be oriented obliquely along just one dimension or along two dimensions. For instance, web (2846) may be oriented obliquely along just a horizontal transverse dimension while still being perpendicular along a vertical transverse dimension.

As yet another merely illustrative variation, body (2842) may define or otherwise include a receptacle adjacent to web (2846). Such a receptacle may be configured to catch and hold debris that is removed from auger member (2660) as auger member (2660) traverses web (2846). In some such versions, instrument (2840) may also include a cap to selectively cover the receptacle, to thereby contain the debris within the receptacle. Such a cap may be provided as a separate piece that is removably securable to body (2842). Alternatively, such a cap may be integral with body (2842), coupled thereto via a living hinge or strip of flexible material, etc. In versions with a cap (either integral or separate), the cap may include a web feature that complements web (2846) of body (2842). Thus, before auger member (2660) traverses web (2846) of body (2842), the cap may be closed down on auger member (2660) such that the web feature of the cap cooperates with web (2846) of body (2842) to remove debris from auger member (2660). It should also be understood that an instrument (e.g., a clip type of device, etc.) may include complementary pinching features that cooperate to remove debris from auger member (2660) after the pinching features are pinched onto auger member (2660), without necessarily also including a receptacle to capture the removed debris. Other suitable variations will be apparent to those of ordinary skill in the art in view of the teachings herein.

Figure 54:
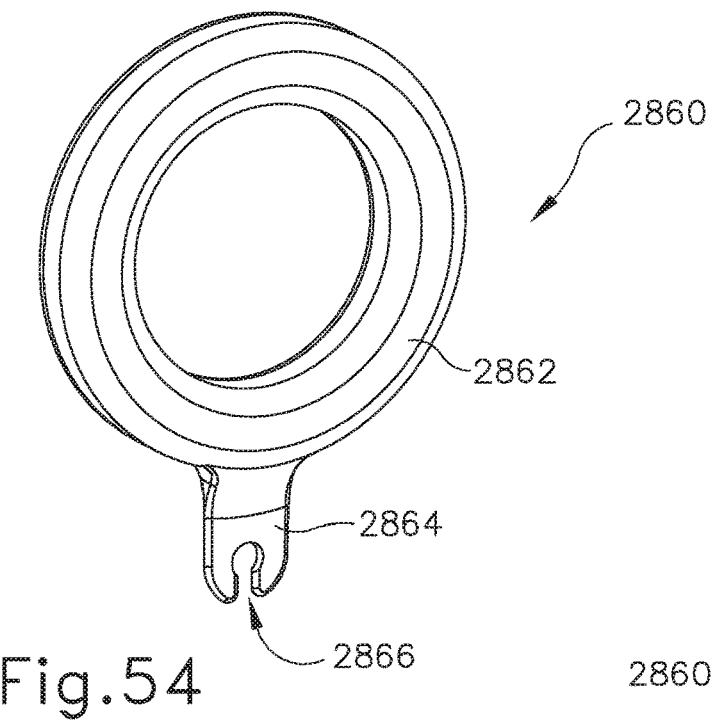
FIG. 54 depicts a perspective view of another exemplary auger cleaning device.
Figure 55:
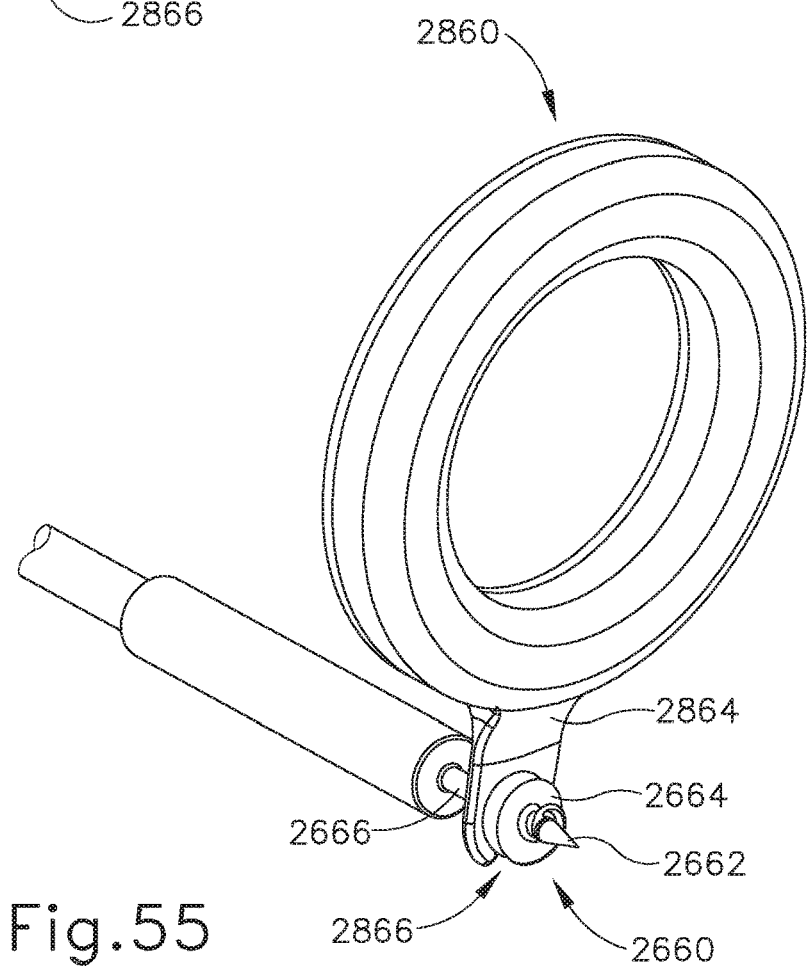
FIG. 55 depicts a perspective view of the auger of FIG. 37 engaged with the auger cleaning device of FIG. 54.

FIGS. 54-55 show yet another exemplary instrument (2860) that may be used clean debris from auger member (2660). Instrument (2860) of this example includes an annular body (2862) with an integral, outwardly extending tab (2864). Tab (2864) includes a notch (2866). In the present example, notch (2866) is shaped like the profile of a conventional incandescent light bulb. In some other versions, notch (2866) has a "V" shape or a "U" shape. Other suitable shapes that may be used for notch (2866) will be apparent to those of ordinary skill in the art in view of the teachings herein. Notch (2866) is sized to receive minor shaft (2666) of auger member (2660), as shown in FIG. 55. It should therefore be understood that tab (2864) may be used to clean debris from auger member (2660) in a manner similar to flange (2806) of tray (2800) and web (2846) of instrument (2840) as described above. It should also be understood that a receptacle may be used to capture debris removed by tab (2864), if desired.

G. Exemplary Dual Piercing Elements

FIGS. 56A-56B show an exemplary instrument (2500) that may be used to form openings in two sinus walls (SW) on opposite sides of the nasal septum (NS) substantially simultaneously. In the present example, the sinus walls (SW) are medial walls of the ethmoid bullae (EB), though it should be understood that instrument (2500) may be used on other sinus walls (SW). Instrument (2500) of this example comprises a shaft (2502) having a pair of longitudinally extending arms (2504). The distal end of each arm (2504) includes an outwardly extending piercing element (2506). While piercing elements (2506) are shown as spikes in the present example, it should be understood that piercing elements (2506) may have various other suitable configurations as will be apparent to those of ordinary skill in the art in view of the teachings herein. For instance, piercing elements (2506) may be selectively retractable relative to arms (2504) (e.g., similar to piercing element (1620) of instrument (1600) described above).

Instrument (2500) is operable to move arms (2504) laterally outwardly from a first position to a second position. In particular, as shown in FIG. 56A, arms (2504) are positioned such that piercing elements (2506) are medial to the sinus walls (SW) when arms (2504) are in the first position. It should be understood that arms (2504) are spaced such that arms (2504) may be simultaneously inserted into respective nostrils when arms (2504) are in the first position. As shown in FIG. 56B, arms (2504) drive piercing elements (2506) laterally into the sinus walls (SW) when arms (2504) are moved to the second position. The sinus walls (SW) may provide inwardly directed counteracting forces on arms (2504) as arms (2504) simultaneously move to the second position. In some other versions, arms (2504) are actuated independently/unilaterally. In some such versions, the stationary arm (2504) bears against the lateral wall of the middle turbinate (MT) for support; while the other arm (2504) is actuated to drive piercing element (2506) into the sinus wall (SW). Arms (2504) may be actuated manually by a mechanical linkage, by direct application of the operator's hand force, by hydraulic/pneumatic means such as a balloon, and/or in any other suitable fashion. In some versions, piercing elements (2506) are replaced with atraumatic tissue contact features (e.g., pads) that are pressed against the sinus walls (SW) to deform the sinus walls and thereby remodel a portion of the paranasal cavity. Various other suitable features of instrument (2500) and methods of using instrument (2500) will be apparent to those of ordinary skill in the art in view of the teachings herein.

In any of the foregoing examples of sinus wall piercing (among other examples), it may be desirable to provide some form of structural support to the sinus wall during interaction between the sinus wall and the instrument, to reduce the risk of the sinus wall shattering to an undesirable degree during such interaction. As noted above with respect to instruments (2200, 2400, 2600), such support may be provided by the instrument itself. While curved elongate member (2202) and auger member (2410, 2660, 2682, 2692) were used in the examples above, other instrument features that may be used to provide structural support to a sinus wall during piercing will be apparent to those of ordinary skill in the art in view of the teachings herein.

In some other versions, a support material may be introduced into the sinus cavity before the act of piercing with an instrument, again to reduce the risk of the sinus wall shattering to an undesirable degree during piercing/cutting of the sinus wall. By way of example only, such support material may include a sand-like material or a hardening liquid. For instance, a hardening polymer fluid may be introduced into the sinus cavity before the act of piercing with an instrument; and may then be removed after the sinus wall has been pierced. As another merely illustrative example, a hardening biocompatible liquid may be removed with irrigation fluid once the sinus wall has been opened with a piercing element. As yet another merely illustrative example, a material that dissolves through bioabsorption or through some other process (dissolving either shortly after the sinus wall has been pierced or some time thereafter) may be used. Other examples of support material will be apparent to those of ordinary skill in the art in view of the teachings herein. Likewise, various suitable ways in which support material may be introduced to the sinus cavity will be apparent to those of ordinary skill in the art in view of the teachings herein.

In addition to or in lieu of providing a support material, the sinus wall may be frozen in order to add structural integrity to the sinus wall. By way of example only, such freezing may be provided through an applicator that is kept cold; or by the injection of a cold liquid (e.g., liquid nitrogen, etc.). As yet another alternative to providing a support material, an instrument may rely on the inertia of the sinus wall to effectively provide structural integrity. For instance, the tip of the piercing element may be advanced (and perhaps also rotated) at such a rapid rate that the inertia of the sinus wall acts as a support.

In addition to or in lieu of injecting a structural supporting material into a sinus cavity, a therapeutic material may be injected into a sinus cavity. Such therapeutic material may be injected through a naturally occurring ostium, through a natural ostium that has been enlarged (e.g., enlarged by a balloon catheter, etc.), or through a created ostium (e.g., created using any of the instruments described herein, etc.). Such a therapeutic material may be injected as a liquid that gellates once it is inside the sinus cavity. By way of example only, the gellation may be triggered by heat, by the mixing of two or more components prior to injection, by the change in shear stress following injection, by a change in pH from a pH value associated with a storage condition to a pH value associated with mucus that the liquid comes in contact with one inside the sinus cavity, and/or by other conditions.

Alternatively, a pregellated gel may be delivered to the sinus cavity. As yet another merely illustrative example, a solid or foam structure may be introduced into the sinus cavity, with a therapeutic substance being contained within the solid or foam structure. Such a solid or foam structure may be bioabsorbable or non-bioabsorbable. The inserted material may be delivered in an as-manufactured shape and size, or it may be trimmed by the surgeon at the time of delivery. In this case, the total dose of the therapeutic agent will be delivered when the as-manufactured inserted material is used; the inserted material will have been manufactured with demarcations to indicate fractional portions of the dose. The inserted material can be formed from Poly(DL-lactide-co-glycolide), such as Lactel, manufactured by Durect Corporation. Other suitable ways in which a therapeutic agent may be delivered to a sinus cavity will be apparent to those of ordinary skill in the art in view of the teachings herein.

IX. Exemplary Tissue Collecting Shaft Assembly

In some instances, a patient may suffer from turbinate hypertrophy (e.g., an enlarged inferior turbinate), which may adversely impact patency through the patient's paranasal cavity. It may be desirable to reduce the size of the hypertrophic turbinate through a turbinoplasty procedure in order to treat this condition. During a turbinoplasty procedure, the operator may remove bone and soft tissue of the turbinate submocosally, in order to minimize removal of the turbinate mucosa or other damage to the turbinate mucosa. Some conventional turbinoplasty procedures may include the use of instruments such as radiofrequency devices or powered microdebriders. Such instruments may require the use of additional capital equipment such as control consoles, suction components, irrigation components, etc., which may increase the cost and complexity of the instrument. Such instruments may also require connections by cable, tube, etc., which may complicate handling of the instrument.

By contrast, it should be understood that a tetherless, self-contained device similar to instrument (2600), with an auger member and a cylindraceous cutter, may also be used to remove bone and soft tissue from a turbinate in a turbinoplasty procedure. It should also be understood that a turbinoplasty procedure may require removal of more bone and/or soft tissue than would be removed in procedures such as those described above, such as where a shaft assembly (2720) is just used to form an opening (FO) through a sinus wall (SW). The bone and soft tissue that is removed in a turbinoplasty procedure may tend to accumulate on the instrument in a way that adversely impacts the efficacy of the instrument or in some other undesirable way. It may therefore be advantageous to provide for the removal of bone and soft tissue from working elements of the instrument. Moreover, it may be desirable to provide such removability of bone and soft tissue from working elements of the instrument without requiring the instrument to be removed from the patient's paranasal cavity. A merely illustrative example of a shaft assembly (3000) that may provide such operability will be described in greater detail below. Other variations and examples will be apparent to those of ordinary skill in the art in view of the teachings herein.

FIGS. 57-59E show an exemplary shaft assembly (3000) that may be incorporated into a variation of instrument (2600). Various suitable modifications that may be made to instrument (2600) in order to accommodate the below describe configurations and operabilities of shaft assembly (3000) will be apparent to those of ordinary skill in the art in view of the teachings herein. Similarly, other kinds of instruments that may incorporate shaft assembly (3000) will be apparent to those of ordinary skill in the art in view of the teachings herein. Shaft assembly (3000) is similar to shaft assemblies (2640, 2720) in numerous ways. In particular, shaft assembly (3000) of this example comprises an outer sheath tube (3010), an outer sheath tip member (3020), a cutter tube (3030), and an auger member (3050). Tip member (3020) is secured to the distal end of sheath tube (3010), and the combination of tip member (3020) and sheath tube (3010) are configured to translate longitudinally relative to cutter tube (3030) and auger member (3050). Like tip member (2710) described above, tip member (3020) of this example has an obliquely angled distal edge (3022). Of course, distal edge (3022) may instead be oriented perpendicular to the longitudinal axis of shaft assembly (3000) or have any other suitable orientation. It should also be understood that tip member (3020) is merely optional and may be omitted.

Cutter tube (3030) is configured to translate relative to auger member (3050) and relative to the combination of tip member (3020) and sheath tube (3010). Like cutter tube (2644) described above, cutter tube (3030) of the present example has a sharp, annular distal edge (3032). Unlike cutter tube (2644) described above, cutter tube (3030) of the present example includes a neck-down transition (3034) where the inner diameter and the outer diameter of cutter tube (3030) step down to a smaller size. In particular, the inner diameter and the outer diameter of cutter tube (3030) are reduced along the length of cutter tube (3030) that is distal to neck-down transition (3034). This reduced inner diameter of cutter tube (3030) corresponds to an effective outer diameter defined by flight (3054) of auger member (3050). Also unlike cutter tube (2644) described above, cutter tube (3030) of the present example includes a pair of fins (3040, 3042), which will be described in greater detail below. Fins (3040, 3042) are located proximal to neck-down transition (3034), in a tissue collection region (3036) of cutter tube (3030) as will also be described in greater detail below.

Auger member (3050) is configured to rotate and translate relative to cutter tube (3030) and relative to the combination of tip member (3020) and sheath tube (3010). Like auger member (2660) described above, auger member (3050) of this example comprises a minor shaft (3056) and a major shaft (3058). Minor shaft (3056) has a sharp distal tip (3052) and a helical blade or flight (3054) projecting outwardly from minor shaft (3056). Minor shaft (3056) is substantially longer than minor shaft (2666) described above, such that major shaft (3058) is located substantially further from tip (3052) of auger member (3050) than the corresponding major shaft is from tip (2662) of auger member (2660). The additional length of minor shaft (3056) corresponds with tissue collection region (3036) of cutter tube (3030).

Figure 57:
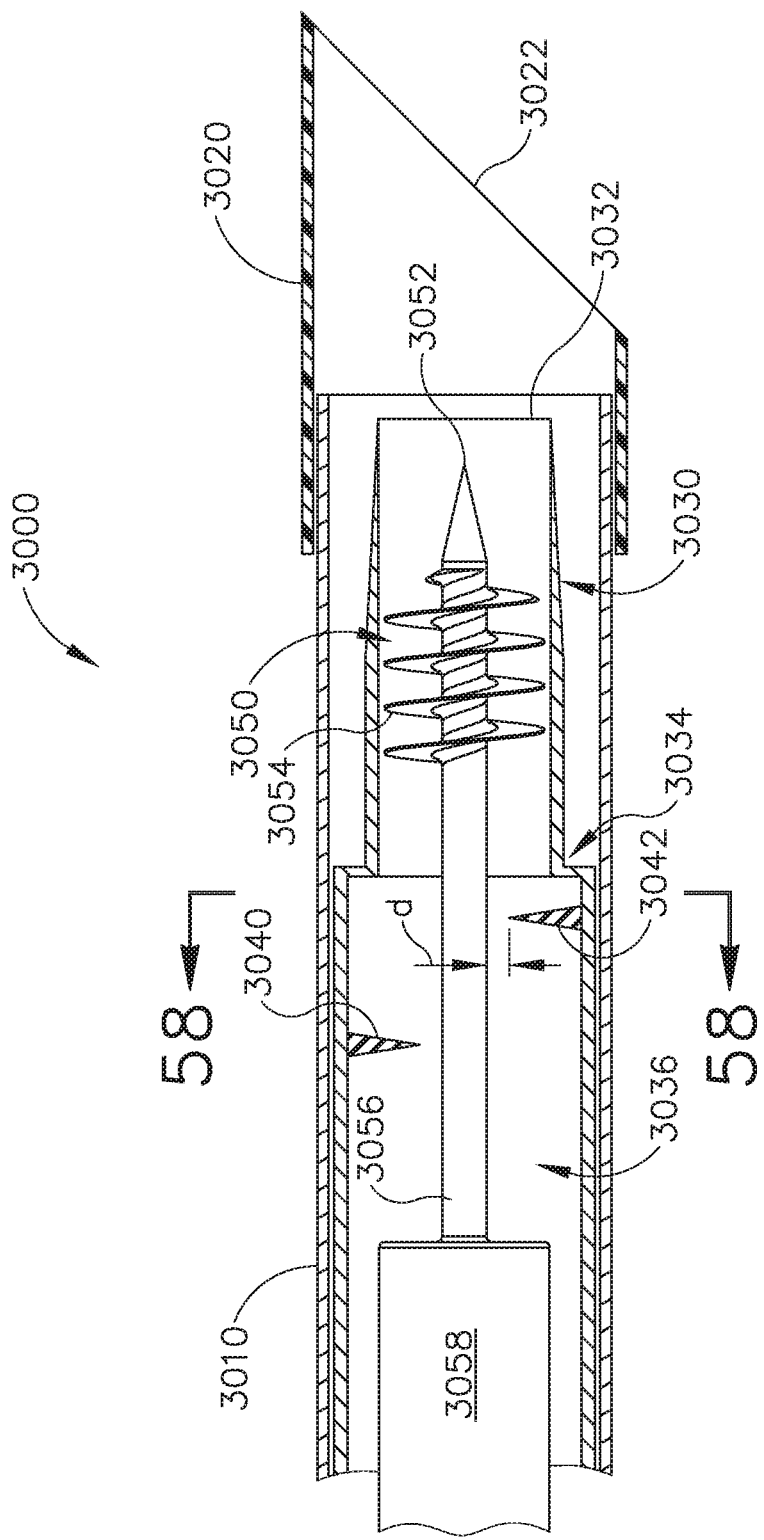
FIG. 57 depicts a side cross-sectional view of an exemplary alternative shaft assembly that may be used with a variation of the instrument of FIG. 32.
Figure 58:
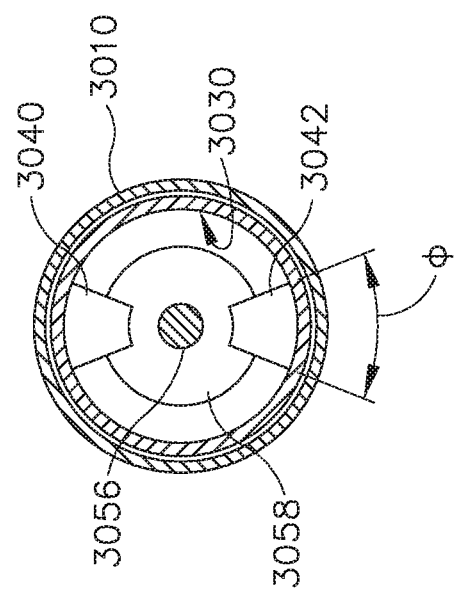
FIG. 58 depicts an end cross-sectional view of the shaft assembly of FIG. 57, taken along line 58-58 of FIG. 57.

As shown in FIGS. 57-58, fins (3040, 3042) extend inwardly from the inner diameter of cutter tube (3030), such that fins (3040, 3042) are oriented toward minor shaft (3056) of auger member (3050). In some versions, the base of each fin (3040) is fixedly secured to the inner diameter of cutter tube (3030). In some other versions, the base of each fin (3040, 3042) is hingedly secured to the inner diameter of cutter tube (3030), such as by a living hinge, a pinned hinge, etc. Regardless of how fins (3040, 3042) are secured to the inner diameter of cutter tube (3030), fins (3040, 3042) may be configured to deflect proximally within cutter tube (3030); yet may further be resiliently biased to assume the transverse orientations shown in FIG. 57.

As shown, each fin (3040, 3042) terminates before reaching the outer diameter of minor shaft (3056), such that the terminal edge of each fin (3040, 3042) is spaced at a gap distance (d) from the outer diameter of minor shaft (3056). Various suitable values that may be used for gap distance (d) will be apparent to those of ordinary skill in the art in view of the teachings herein. In some versions, the innermost edges of fins (3040, 3042) contact the outer diameter of minor shaft (3056), such that the gap distance (d) is zero. As best seen in FIG. 58, each fin (3040) extends through an angular range ($\phi$). By way of example only, the angular range ($\phi$) may be approximately 30°, approximately 45°, approximately 60°, approximately 90°, approximately 180°, approximately 270°, or even approximately 360°. Of course, any other suitable value may be used for the angular range ($\phi$).

In some versions, fins (3040, 3042) are formed of a rigid material, yet fins (3040, 3042) are configured to deflect relative to cutter tube (3030), such as through a hinged coupling or otherwise deformable coupling. In some other versions, fins (3040, 3042) are formed of a semi-rigid material. In still other versions, fins (3040, 3042) are formed of a flexible material (e.g., rubber, silicone, etc.). In some such versions, fins (3040, 3042) may be configured to flex along paths that are parallel to the longitudinal axis of shaft assembly (3000); yet fins (3000, 3042) may be relatively non-flexible along angular paths about the longitudinal axis of shaft assembly (3000). Other suitable properties that may be incorporated into fins (3040, 3042) will be apparent to those of ordinary skill in the art in view of the teachings herein. Similarly, other suitable relationships between fins (3040, 3042) and cutter tube (3030) will be apparent to those of ordinary skill in the art in view of the teachings herein.

While two fins (3040, 3042) are shown in the present example, any other suitable number of fins (3040, 3042) may be provided. For instance, cutter tube (3030) may have just one fin (3040 or 3042), three or more fins (3040, 3042), etc. In addition, while fins (3040, 3042) are located at different longitudinal positions along the length of shaft assembly (3000) in the present example, fins (3040, 3042) may instead be located at the same longitudinal position along the length of shaft assembly (3000). While fins (3040, 3042) are shown as being angularly offset from each other by approximately 180°, any other suitable angular offset may be used. It should therefore be understood that cutter tube (3030) may include any suitable number of fins (3040, 3042) at any suitable longitudinal position(s) and at any suitable angular position(s).

As noted above, shaft assembly (3000) may be used to remove soft tissue and bone from a turbinate (e.g., inferior turbinate) in a patient's paranasal cavity. It should be understood that this may be accomplished using a procedure like the one shown in FIGS. 42A-43E and described above, where the components of shaft assembly (3000) are operated in the same kind of sequence as shaft assembly (2720), except with the target anatomy being a turbinate instead of a sinus wall (SW). The steps of this sequence will therefore not be described in detail, in order to avoid repetition. Once a first sequence is completed, shaft assembly (3000) may appear similar to shaft assembly (3000) as shown in FIG. 59A. In particular, tissue (T) that was severed by severed by cutter tube (3030) may be trapped in flight (3054) of auger member (3050); and elsewhere between minor shaft (3056) and the inner diameter of cutter tube (3030). It should be understood that bone fragments may also be trapped with tissue (T). After completing a first sequence of actuating shaft assembly (3000) to remove tissue (T) from a patient's turbinate and reaching the state shown in FIG. 59A, the operator may wish to repeat the sequence of actuating shaft assembly (3000) to remove additional tissue (T) from the patient's turbinate. However, the presence of trapped tissue (T) in the location shown in FIG. 59A may prevent shaft assembly (3000) from actuating through another sequence to remove additional tissue (T) from the patient's turbinate in an effective manner.

Figure 59B:
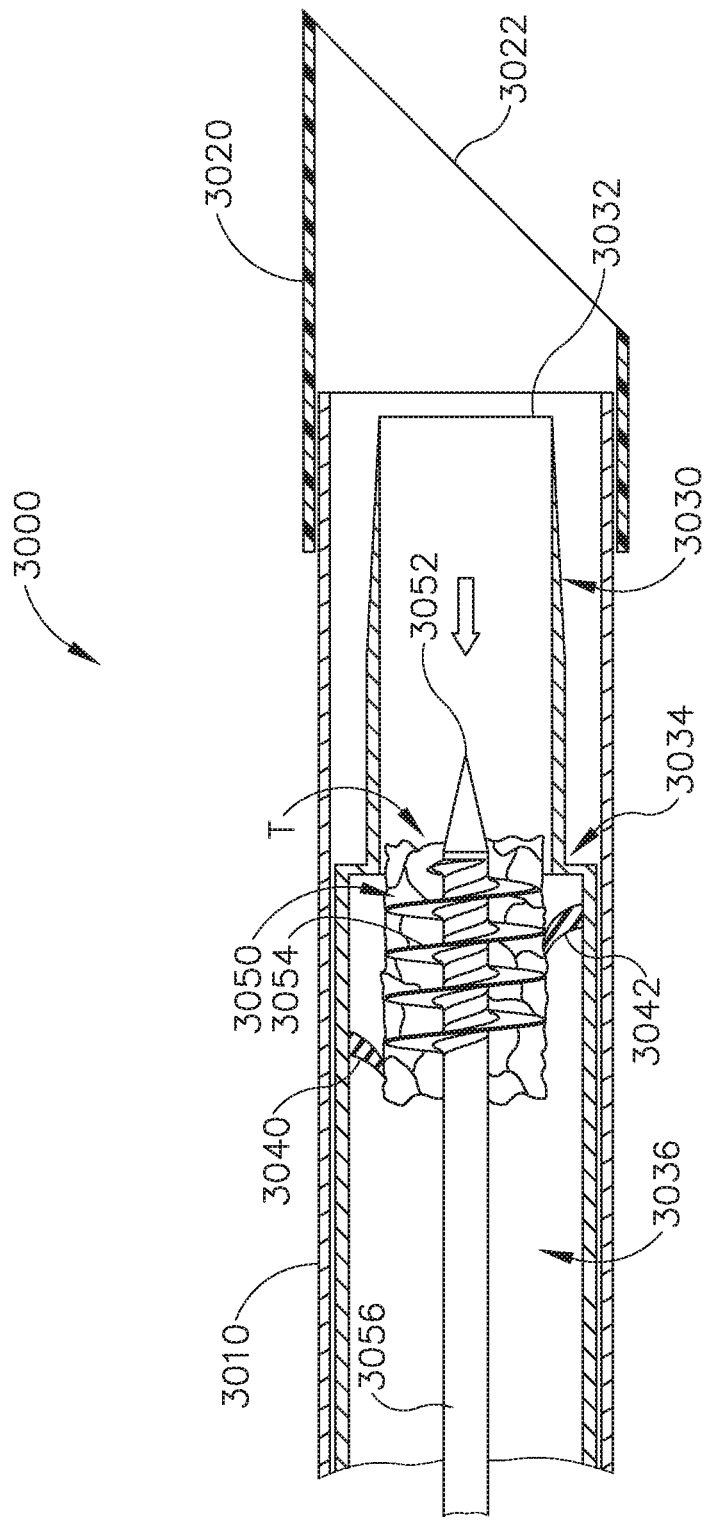
FIG. 59B depicts a side cross-sectional view of the shaft assembly of FIG. 57, with the trapped tissue on the auger member passing between fins as the auger member retracts toward a proximal position.
Figure 59C:
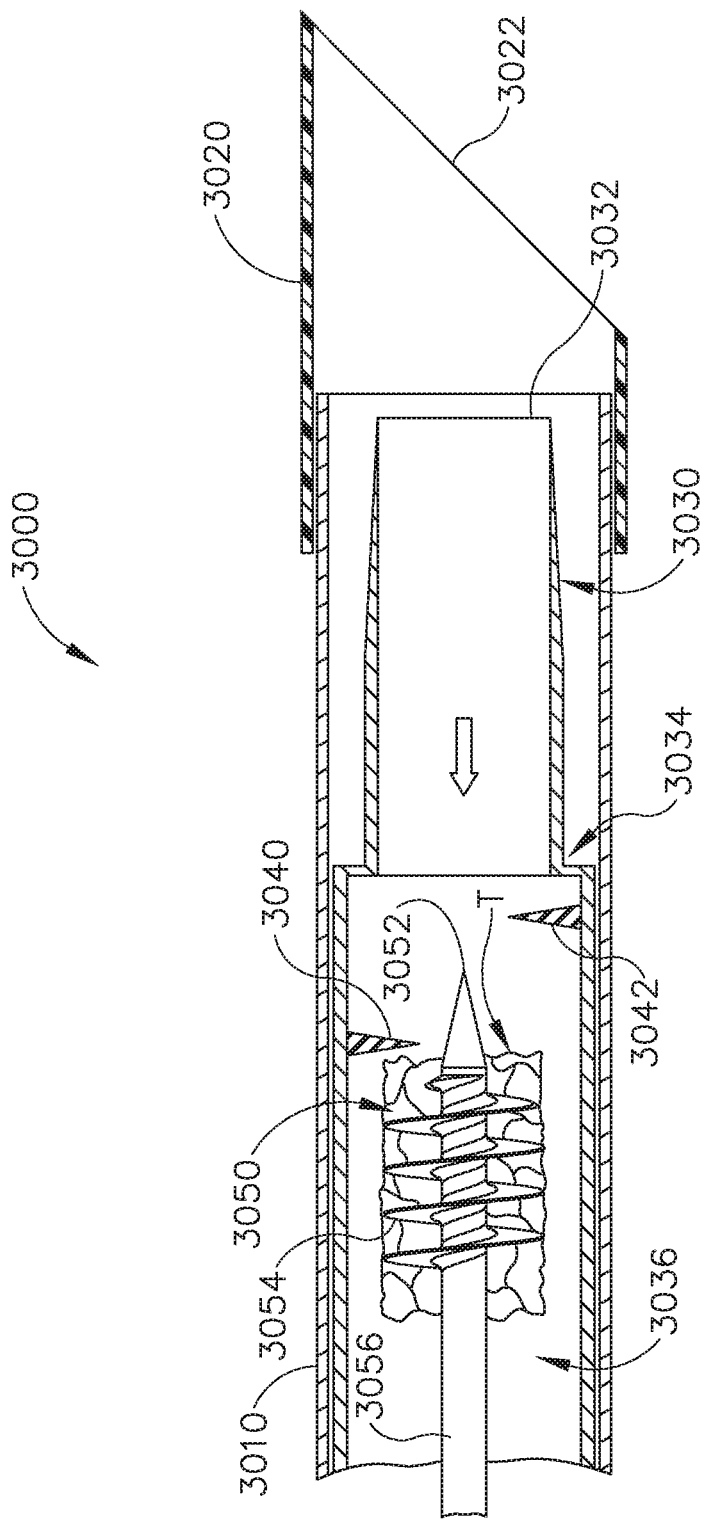
FIG. 59C depicts a side cross-sectional view of the shaft assembly of FIG. 57, with the trapped tissue on the auger member located proximal to the fins, and with the auger member in the proximal position.

In order to remove the trapped tissue from auger member (3050), the operator may retract auger member (3050) proximally within shaft assembly (3000). In the present example, auger member (3050) is not rotated during this proximal retraction. As shown in FIG. 59B, fins (3040, 3042) deflect proximally along paths that are generally parallel to the longitudinal axis of shaft assembly (3000) as auger member (3050) is retracted proximally. In particular, the tissue (T) and flight (3054) bear against fins (3040, 3042) to cause this deflection. Once auger member (3050) reaches a fully proximal position as shown in FIG. 59C, the resilient bias of fins (3040, 3042) causes fins (3040, 3042) to return to their original transverse orientations. In versions where fins (3040, 3042) are rigid yet hingedly coupled with the inner diameter of cutter tube (3030), the resilient bias may be provided at the hinged coupling. In versions where fins (3040, 3042) are flexible yet fixedly coupled with the inner diameter of cutter tube (3030), the resilient bias may be provided by the material forming the body of each fin (3040, 3042). It should also be understood that the instrument in which shaft assembly (3000) is incorporated may be configured to provide some form of audible, tactile, and/or visual feedback (e.g., through a detent, hard stop, etc.) to indicate to the operator that auger member (3050) has reached the fully proximal position shown in FIG. 59C.

Figure 59D:
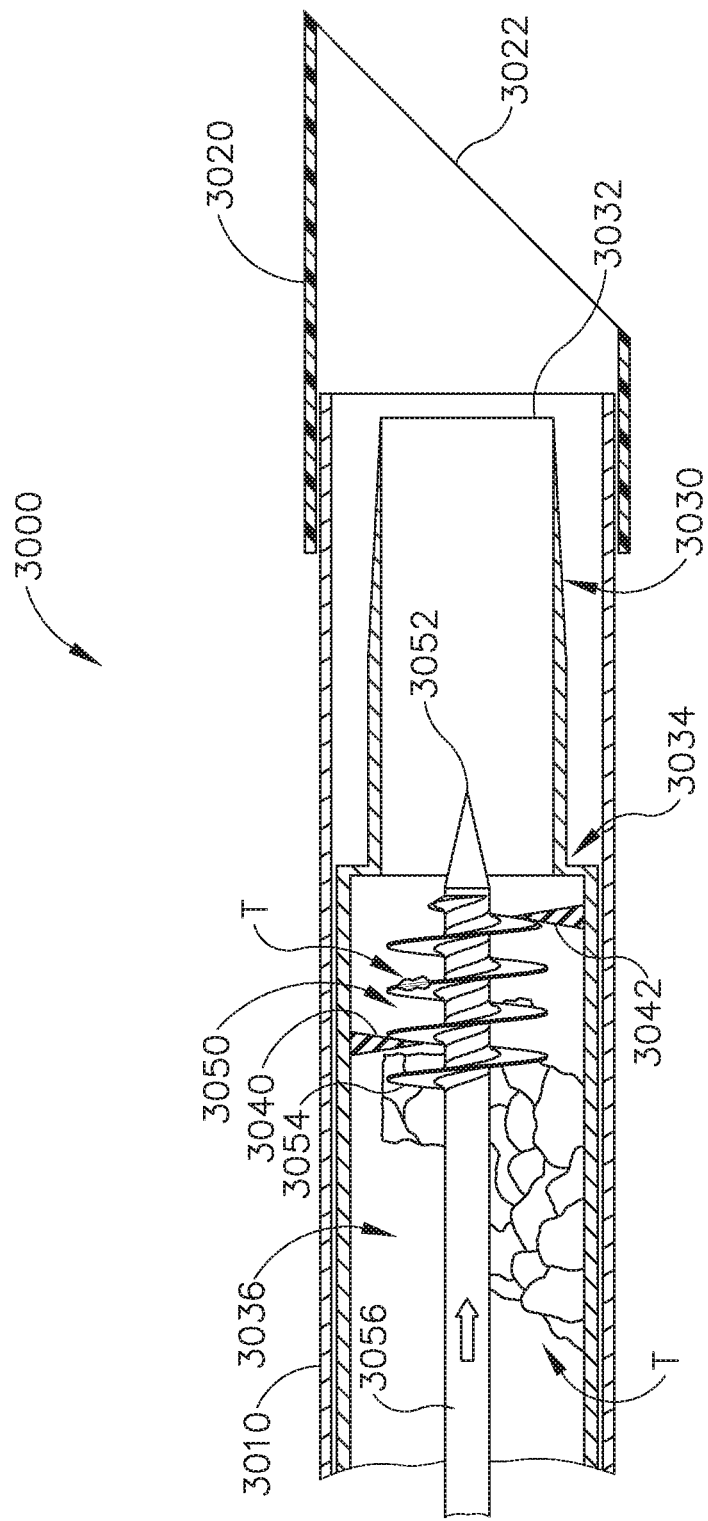
FIG. 59D depicts a side cross-sectional view of the shaft assembly of FIG. 57, with the trapped tissue being cleared from the auger member by the fins as the auger member rotatably advances back toward the distal position.
Figure 59E:
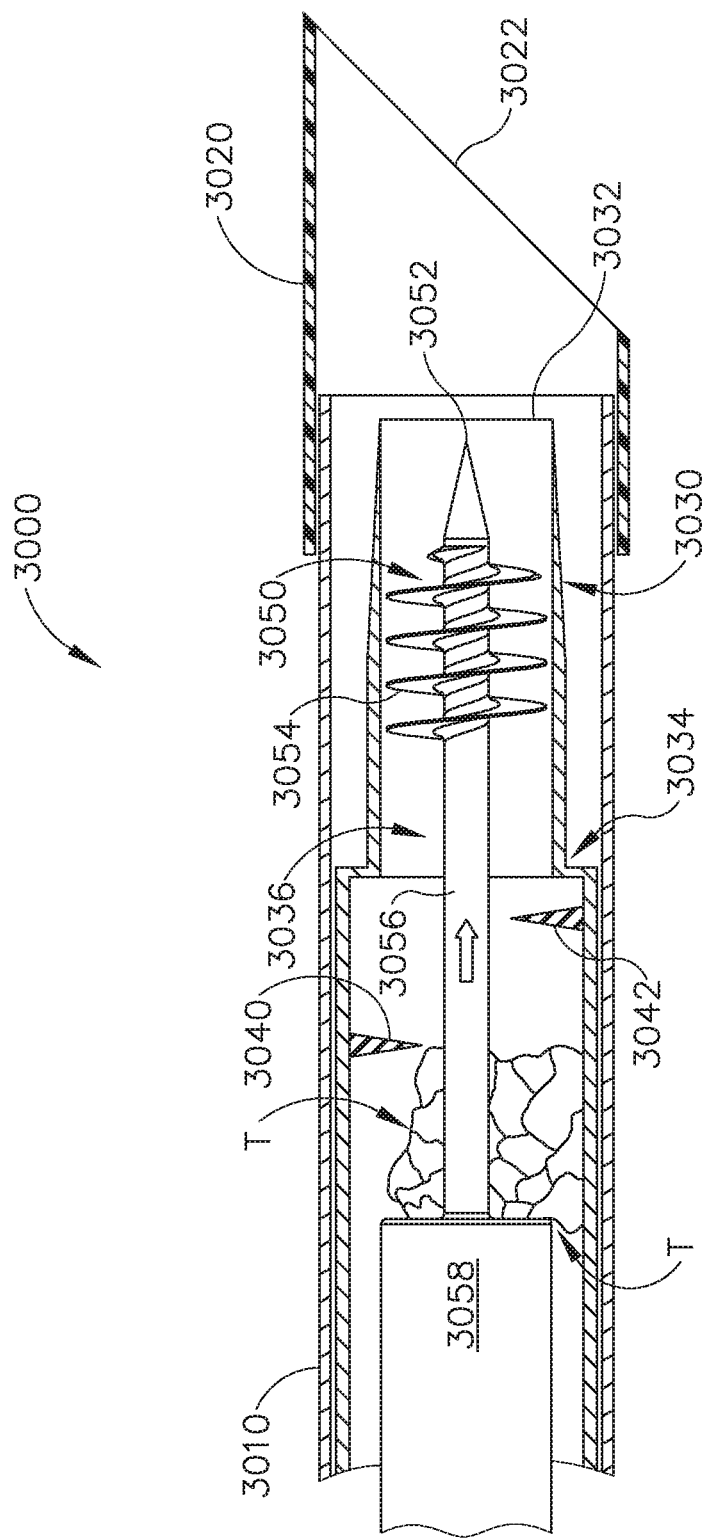
FIG. 59E depicts a side cross-sectional view of the shaft assembly of FIG. 57, with the trapped tissue cleared from the auger member and deposited in a tissue collection region, and with the auger member returned to the distal position.

After reaching the fully proximal position shown in FIG. 59C, the operator then advances auger member (3050) back toward the distal position. In the present example, auger member (3050) rotates about the longitudinal axis of shaft assembly (3000) as auger member (3050) translates along the longitudinal axis of shaft assembly (3000) toward the distal position. In particular, the operator may rotate auger member (3050) in the same angular direction (e.g., clockwise) in which the operator rotated auger member (3050) in order to anchor shaft assembly (3000) in the turbinate before advancing cutter tube (3030) to sever/capture the tissue (T) from the turbinate. As shown in FIG. 59D, fins (3040, 3042) dislodge the tissue (T) from flight (3054) and minor shaft (3056) as auger member (3050) advances distally. In particular, fin (3040) dislodges substantially all of the tissue (T), while fin (3042) at least some of the remaining bits of the tissue (T). The dislodged tissue (T) falls into tissue collection region (3036) of cutter tube (3030). By the time auger member (3050) reaches the distal position again as shown in FIG. 59E, flight (3054) and the associated region of minor shaft (3056) are substantially if not completely free of tissue (T). Shaft assembly (3000) may then be used in another sequence to remove more soft tissue and bone from the turbinate.

It should be understood from the foregoing that shaft assembly (3000) may be operated in two modes—a tissue removal mode in a sequence similar to that shown in FIGS. 42A-43E and described above; and a tissue clearing mode in a sequence as shown in FIGS. 59A-59E and described above. Shaft assembly (3000) may be used in a procedure that sequentially alternates between these two modes in a repeating fashion until the desired amount of soft tissue and bone has been removed from the turbinate, with the removed tissue (T) building up in tissue collection region (3036) of cutter tube (3030). It should also be understood that shaft assembly (3000) may be used in a procedure that sequentially alternates between these two modes in a repeating fashion without needing to remove the distal end of shaft assembly (3000) from the patient's paranasal cavity until the desired amount of soft tissue and bone has been removed from the turbinate. In other words, shaft assembly (3000) does not need to be removed from the patient's paranasal cavity in order to clean the tissue (T) from auger member (3050) between each tissue cutting sequence.

While shaft assembly (3000) is described above as being used in a turbinoplasty procedure, it should be understood that shaft assembly (3000) may also be used in other kinds of procedures within a patient. Other suitable procedures in which shaft assembly (3000) may be used will be apparent to those of ordinary skill in the art in view of the teachings herein.

X. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc, should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
    (a) a rotating member, wherein the rotating member includes:
        (i) a shaft defining a longitudinal axis,
        (ii) a helical blade arranged distally of the shaft, and
        (iii) a tip arranged at a distal end of the helical blade, wherein the tip extends distally and coaxially along the longitudinal axis; and
    (b) a translating member positioned coaxially about the rotating member, wherein a distal end of the translating member includes a cutting edge,
    wherein the rotating member is configured to rotate relative to the translating member, and the translating member is configured to translate proximally and distally relative to the rotating member,
    wherein the helical blade, the tip, and the cutting edge are sized to be received within a nasal cavity of a patient and are configured to advance through a sinus wall of the patient.

2. The apparatus of claim 1, wherein the translating member includes a tapered distal portion, wherein the cutting edge of the translating member is arranged at a distal end of the tapered distal portion.

3. The apparatus of claim 1, wherein the translating member comprises a tubular member.

4. The apparatus of claim 3, wherein at least a distal portion of the tubular member extends axially with a uniform inner diameter and a non-uniform outer diameter.

5. The apparatus of claim 1, wherein the cutting edge of the translating member comprises an annular edge.

6. The apparatus of claim 1, wherein the cutting edge of the translating member defines a plane that extends transversely relative to the longitudinal axis.

7. The apparatus of claim 1, wherein a proximal end of the helical blade is spaced distally from a distal end of the shaft.

8. The apparatus of claim 1, wherein the rotating member is operatively coupled with a first user-engageable feature, wherein the translating member is operatively coupled with a second user-engageable feature, wherein the first and second user-engageable features are selectively operable independently of one another.

9. The apparatus of claim 1, further comprising an outer sheath positioned coaxially about the translating member, wherein the outer sheath is configured to translate proximally and distally relative to the translating member and the rotating member.

10. The apparatus of claim 9, wherein a distal end of the outer sheath has an enlarged diameter relative to the remainder of the outer sheath.

11. The apparatus of claim 9, wherein the rotating member is operatively coupled with a first user-engageable feature, wherein the translating member is operatively coupled with a second user-engageable feature, wherein the outer sheath is operatively coupled with a third user-engageable feature, wherein the user-engageable features are selectively operable independently of one another.

12. The apparatus of claim 11, wherein the first user-engageable feature comprises a rotatable member, wherein the rotatable member is configured to rotate about the longitudinal axis.

13. The apparatus of claim 12, wherein the second user-engageable feature comprises a translatable member, wherein the translatable member is configured to translate along the longitudinal axis.

14. The apparatus of claim 13, wherein the third user-engageable feature comprises a pivotable member, wherein the pivotable member is configured to pivot about a pivot axis that extends transversely relative to the longitudinal axis.

15. A system comprising:
    (a) the apparatus of claim 1; and
    (b) a cleaning member configured to clean the apparatus, wherein the cleaning member includes a notch having a cleaning edge, wherein the notch defines an opening that is smaller than an outer diameter of the helical blade, wherein the notch is configured to receive a portion of the rotating member and permit the rotating member to rotate relative to the notch such that the cleaning edge scrapes along the helical blade to remove tissue debris from the helical blade.

16. An apparatus comprising:
    (a) a rotating member, wherein the rotating member includes:
        (i) a major shaft defining a longitudinal axis,
        (ii) a minor shaft extending distally from a distal end of the major shaft, and
        (iii) a helical blade arranged on the minor shaft, wherein a proximal end of the helical blade is spaced axially from a distal end of the major shaft; and
    (b) a translating member positioned coaxially about the rotating member, wherein a distal end of the translating member includes a cutting edge, wherein the rotating member is configured to rotate freely relative to the translating member, and the translating member is configured to translate proximally and distally relative to the rotating member, wherein the helical blade, the tip, and the cutting edge are configured to advance through a sinus wall of a patient.

17. The apparatus of claim 16, wherein the major shaft is formed with a first diameter and the minor shaft is formed with a second diameter smaller than the first diameter.

18. The apparatus of claim 16, wherein the rotating member further includes a tip arranged at a distal end of the minor shaft.

19. An apparatus comprising:
(a) a rotating member, wherein the rotating member includes:
  (i) a shaft defining a longitudinal axis,
  (ii) a tip arranged at a distal end of the shaft, and
  (iii) a helical blade arranged distally of the shaft and proximally of the tip, wherein the helical blade tapers distally toward the tip;
(b) a translating member positioned coaxially about the rotating member, wherein a distal end of the translating member includes a cutting edge; and
(c) an outer sheath positioned coaxially about the translating member, wherein the outer sheath is retractable proximally relative to the rotating member to expose a distal end of the rotating member, wherein the rotating member is rotatable about the longitudinal axis to advance the helical blade distally through a sinus wall of a patient, wherein the translating member is translatable distally along the longitudinal axis relative to the rotating member to advance the cutting edge through the sinus wall and thereby form an opening in the sinus wall.

20. The apparatus of claim 19, wherein a distal end of the outer sheath includes a radially projecting element that defines a maximum outer diameter of the retractable sheath.

* * * * *